(12) United States Patent
Samajdar et al.

(10) Patent No.: US 11,174,232 B2
(45) Date of Patent: *Nov. 16, 2021

(54) SUBSTITUTED HETEROCYCLYL DERIVATIVES AS CDK INHIBITORS

(71) Applicant: Aurigene Discovery Technologies Limited, Bangalore (IN)

(72) Inventors: Susanta Samajdar, Bangalore (IN); Ramulu Poddutoori, Karimnagar (IN); Chetan Pandit, Bangalore (IN); Subhendu Mukherjee, Hooghly (IN); Rajeev Goswami, Deharadun (IN)

(73) Assignee: Aurigene Discovery Technologies Limited, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/867,761

(22) Filed: May 6, 2020

(65) Prior Publication Data

US 2020/0262793 A1 Aug. 20, 2020

Related U.S. Application Data

(63) Continuation of application No. 15/579,246, filed as application No. PCT/IB2016/053267 on Jun. 3, 2016, now Pat. No. 10,689,347.

(30) Foreign Application Priority Data

Jun. 4, 2015 (IN) .............................. 2803/CHE/2015
Nov. 18, 2015 (IN) .............................. 6214/CHE/2015

(51) Int. Cl.

| C07D 231/40 | (2006.01) |
| A61K 45/06 | (2006.01) |
| C07D 403/12 | (2006.01) |
| C07D 401/14 | (2006.01) |
| C07D 231/56 | (2006.01) |
| C07D 401/04 | (2006.01) |
| C07D 401/12 | (2006.01) |
| C07D 413/12 | (2006.01) |
| C07D 471/04 | (2006.01) |
| A61K 31/415 | (2006.01) |
| A61K 31/4155 | (2006.01) |
| A61K 31/416 | (2006.01) |
| A61K 31/4439 | (2006.01) |
| A61K 31/454 | (2006.01) |
| A61K 31/4545 | (2006.01) |
| A61K 31/4725 | (2006.01) |
| A61K 31/496 | (2006.01) |
| A61K 31/497 | (2006.01) |
| A61K 31/5377 | (2006.01) |

(52) U.S. Cl.
CPC .......... *C07D 231/40* (2013.01); *A61K 31/415* (2013.01); *A61K 31/416* (2013.01); *A61K 31/4155* (2013.01); *A61K 31/4439* (2013.01); *A61K 31/454* (2013.01); *A61K 31/4545* (2013.01); *A61K 31/4725* (2013.01); *A61K 31/496* (2013.01); *A61K 31/497* (2013.01); *A61K 31/5377* (2013.01); *A61K 45/06* (2013.01); *C07D 231/56* (2013.01); *C07D 401/04* (2013.01); *C07D 401/12* (2013.01); *C07D 401/14* (2013.01); *C07D 403/12* (2013.01); *C07D 413/12* (2013.01); *C07D 471/04* (2013.01)

(58) Field of Classification Search
CPC ....................................................... C07D 231/40
USPC ....................................................... 514/236.5
See application file for complete search history.

(56) References Cited

U.S. PATENT DOCUMENTS

| 6,218,418 B1 | 4/2001 | Pevarello et al. |
| 6,455,559 B1 | 9/2002 | Pevarello et al. |
| 7,034,049 B1 | 4/2006 | Pevarello et al. |
| 8,404,718 B2 | 3/2013 | Curry et al. |
| 9,725,465 B2 | 8/2017 | Holladay et al. |
| 10,689,347 B2 * | 6/2020 | Samajdar ............. A61K 31/415 |
| 2011/0002879 A1 | 1/2011 | Curry et al. |
| 2011/0269740 A1 * | 11/2011 | Abraham ................ A61P 37/06 514/210.21 |

(Continued)

FOREIGN PATENT DOCUMENTS

| EP | 1202733 A1 | 5/2002 |
| WO | 2000047553 A2 | 8/2000 |
| WO | 2001012189 A1 | 2/2001 |

(Continued)

OTHER PUBLICATIONS

Venkatesh et al., J. Pharm. Sci. 89, 145-54 (2000).*

(Continued)

*Primary Examiner* — Nizal S Chandrakumar
(74) *Attorney, Agent, or Firm* — Honigman LLP; Heidi M. Berven; Andrew S. Chipouras

(57) ABSTRACT

The present invention provides substituted heterocyclylderivatives of formula (I), which are therapeutically useful, particularly as selective transcriptional CDK inhibitors including CDK7, CDK9, CDK12, CDK13 and CDK18, more particularly transcriptional CDK7 inhibitors. These compounds are useful in the treatment and prevention of diseases and/or disorders associated with selective transcriptional CDKs in a mammal. The present invention also provides preparation of the compounds and pharmaceutical formulations comprising at least one of the substituted heterocyclyl derivatives of formula (I) or a pharmaceutically acceptable salt or a stereoisomer thereof.

14 Claims, No Drawings

(56) References Cited

U.S. PATENT DOCUMENTS

2012/0107836 A1* 5/2012 Rauh .................. C12N 9/12
                                                     435/7.6
2012/0184557 A1   7/2012 Meijer et al.

FOREIGN PATENT DOCUMENTS

| WO | 2002048114 | A1 | 6/2002 |
| WO | 2006070195 | A1 | 7/2006 |
| WO | 2006070198 | A1 | 7/2006 |
| WO | 2006077425 | A1 | 7/2006 |
| WO | 2010075376 | A2 | 7/2010 |
| WO | 2013/074986 | A1 | 5/2013 |
| WO | 2014063068 | A1 | 4/2014 |
| WO | 2015031613 | A1 | 3/2015 |
| WO | 2015061247 | A2 | 4/2015 |
| WO | 2015154022 | A1 | 10/2015 |
| WO | 2016105528 | A2 | 6/2016 |

OTHER PUBLICATIONS

J. G. Cannon, Chapter Nineteen in Burger's Medicinal Chemistry and Drug Discovery, Fifth Edition, vol. I: Principles and Practice, Wiley-lnterscience 1995, pp. 783-802, 784.*

Dorwald F. A. Side Reactions in Organic Synthesis, 2005, Wiley: VCH, Weinheim p. IX of Preface p. 1-15.*

J. G. Cannon, Chapter Nineteen in Burger's Medicinal Chemistry and Drug Discovery, Fifth Edition, vol. I: Principles and Practice, Wiley-Interscience 1995, pp. 783-802, 784.

Pevarello et al., 3-Aminopyrazole Inhibitors of CDK2/Cyclin A as Antitumor Agents. 1.Lead Finding, J. Med. Chem. 2004, 47, 3367-3380.

* cited by examiner

SUBSTITUTED HETEROCYCLYL DERIVATIVES AS CDK INHIBITORS

This application is a continuation under 35 U.S.C. § 120 of pending application U.S. Ser. No. 15/579,246, filed Dec. 4, 2017, which is a national stage application under 35 U.S.C. § 371 of International Application No. PCT/IB2016/053267, filed Jun. 3, 2016, now abandoned, which claims the benefit of Indian provisional application numbers 2803/CHE/2015, filed on Jun. 4, 2015, now abandoned, and 6214/CHE/2015, filed on Nov. 18, 2015, now abandoned; the specifications of which are hereby incorporated by reference in their entirety.

FIELD OF THE INVENTION

This invention pertains to compounds which inhibit the activity of selective transcriptional cyclin dependent kinases (CDKs) including CDK7, CDK9, CDK12, CDK13 and CDK18, more particularly transcriptional cyclin dependent kinase-7 (CDK7). The invention also provides pharmaceutically acceptable compositions comprising compounds of the present invention and methods of using said compositions in the treatment of diseases or disorder associated with selective transcriptional CDKs.

BACKGROUND OF THE INVENTION

One of the most important and fundamental processes in biology is the division of cells mediated by the cell cycle. This process ensures the controlled production of subsequent generations of cells with defined biological function. It is a highly regulated phenomenon and responds to a complex set of cellular signals both within the cell and from external sources. A complex network of tumor promoting and suppressing gene products are key components of this cellular signalling process. Over-expression of tumor-promoting components or the subsequent loss of the tumor-suppressing products will lead to unregulated cellular proliferation and the generation of tumors (Pardee, *Science* 246:603-608, 1989).

Kinases are important cellular enzymes that perform essential cellular functions such as regulating cell division and proliferation, and also appear to play a decisive role in many disease states that are characterized by uncontrolled proliferation and differentiation of cells. These disease states encompass a variety of cell types and maladies such as cancer, atherosclerosis, restenosis and other proliferative disorders (Kris M G et al., *JAMA* 290 (16): 2149-58, 2003).

Cyclin-dependent kinases (CDKs) are relatively small proteins, with molecular weights ranging from 34 to 40 kDa, and contain little more than the kinase domain. CDK binds a regulatory protein called a cyclin. Without cyclin, CDK has little kinase activity; only the cyclin-CDK complex is an active kinase. CDKs phosphorylate their substrates on serines and threonines, so they are serine-threonine kinases (Morgan, D. O., *Cell Division*, 2:27, 2007).

The members of the cyclin-dependent kinase (CDK) family play critical regulatory roles in cell proliferation. There are currently 20 known mammalian CDKs. While CDK7-13 and 18 have been linked to transcription, only CDK1, 2, 4 and 6 show demonstrable association with the cell cycle. Unique among the mammalian CDKs, CDK7 has consolidated kinase activities, regulating both the cell cycle and transcription. In the cytosol, CDK7 exists as a heterotrimeric complex and is believed to function as a CDK1/2-activating kinase (CAK), whereby phosphorylation of conserved residues in CDK1/2 by CDK7 is required for full catalytic CDK activity and cell cycle progression (Desai et al., *Mol. Cell Biol.* 15, 345-350, 1995).

CDK7, which complexes with cyclin H and MAT1, phosphorylates the cell cycle CDKs in the activation of T-loop, to promote their activities (Fisher et al., *Cell., August* 26; 78(4):713-24, 1994). As such, it has been proposed that inhibiting CDK7 would provide a potent means of inhibiting cell cycle progression, which may be especially relevant given that there is compelling evidence from gene knockout studies in mice for lack of an absolute requirement for CDK2, CDK4 and CDK6 for the cell cycle, at least in most cell types (Malumbres et al., *Nature Cell Biology,* 11, 1275-1276, 2009), whilst different tumors appear to require some, but be independent of other interphase CDKs (CDK2, CDK4, CDK6). Recent genetic and biochemical studies have confirmed the importance of CDK7 for cell cycle progression (Larochelle et al., *Mol Cell.*, March 23; 25(6): 839-50. 2007; Ganuza et al., *EMBO J.*, May 30; 31(11): 2498-510, 2012).

Cyclin-dependent kinase 7 (CDK7) activates cell cycle CDKs and is a member of the general Transcription factor II Human (TFIIH). CDK7 also plays a role in transcription and possibly in DNA repair. The trimeric Cak complex CDK7/CyclinH/MAT1 is also a component of TFIIH, the general transcription/DNA repair factor IIH (Morgan, D. O., *Annu. Rev. Cell Dev. Biol.* 13, 261-91, 1997). As a TFIIH subunit, CDK7 phosphorylates the CTD (Carboxy-Terminal-Domain) of the largest subunit of RNA polymerase II (pol II). The CTD of mammalian pol II consists of 52 heptad repeats with the consensus sequence $^1$YSPTSPS$^7$ and the phosphorylation status of the Ser residues at positions 2 and 5 has been shown to be important in the activation of RNAP-II indicating that it is likely to have a crucial role in the function of the CTD. CDK7, which primarily phosphorylates Ser-5 (PS5) of RNAP-II at the promoter as part of transcriptional initiation (Gomes et al., Genes Dev. 2006 Mar. 1; 20(5):601-12, 2006), incontrast with CDK9, which phosphorylates both Ser-2 and Ser-5 of the CTD heptad (Pinhero et al., *Eur. J. Biochem.,* 271, pp. 1004-1014, 2004).

In addition to CDK7, other CDKs have been reported to phosphorylate and regulate RNA pol (II) CTD. The other CDKs include, Cdk9/Cyclin T1 or T2 that constitute the active form of the positive transcription elongation factor (P-TEFb) (Peterlin and Price, *Mol Cell.*, August 4; 23(3): 297-305,2006) and Cdk12/Cyclin K and Cdk13/Cyclin K as the latest members of RNAPII CTD kinases (Bartkowiak et al., *Genes Dev.*, October 15; 24(20):2303-16, 2010; Blazek et al., *Genes Dev.* October 15; 25(20):2158-72, 2011).

Disruption of RNAP II CTD phosphorylation has been shown to preferentially effect proteins with short half-lives, including those of the anti-apoptotic BCL-2 family. (Konig et al., *Blood,* 1, 4307-4312, 1997; The transcriptional non-selective cyclin-dependent kinase inhibitor flavopiridol induces apoptosis in multiple myeloma cells through transcriptional repression and down-regulation of Ml-1; (Gojoet al., *Clin. Cancer Res.* 8, 3527-3538, 2002).

This suggests that the CDK7 enzyme complexes are involved in multiple functions in the cell: cell cycle control, transcription regulation and DNA repair. It is surprising to find one kinase involved in such diverse cellular processes, some of which are even mutually exclusive. It also is puzzling that multiple attempts to find cell cycle dependent changes in CDK7 kinase activity remained unsuccessful. This is unexpected since activity and phosphorylation state of its substrate, CDC2, fluctuate during the cell cycle. In fact, it is shown that cdk7 activity is required for the activation of bothCdc2/Cyclin A and Cdc2/Cyclin B complexes, and for cell division. (Larochelle, S. et al. *Genes Dev* 12,370-81, 1998). Indeed, flavopiridol, a non-selective pan-CDK inhibitor that targets CTD kinases, has demonstrated efficacy for the treatment of chronic lymphocytic leukemia (CLL), but suffers from a poor toxicity profile (Lin et al., *J. Clin. Oncol.* 27, 6012-6018, 2009; Christian et al., *Clin. Lymphoma Myeloma, 9, Suppl.* 3, S179-S185, 2009).

In-vitro studies revealed substrate preferences for the different CDK7 complexes, indicating that CDK7 may form different complexes with different substrate specificity and presumably different in-vivo functions (Frit, P. et al., *Biochimie* 81, 27-38, 1999; Schutz, P. et al. *Cell* 102, 599-607, 2000).

Thus in view of the role transcriptional CDKs play in the regulation of cell cycle, there is a need of compounds to treat diseases and/or disorder associated with selective transcriptional CDKs including CDK7, CDK9, CDK12, CDK13 and CDK18; more particularly CDK7. It is, therefore, an object of this invention to provide compounds useful in the treatment and/or prevention or amelioration of such diseases and/or disorder.

SUMMARY OF THE INVENTION

Provided herein are substituted heterocyclylderivativesand pharmaceutical compositions thereof, which are capable of suppressing and/or inhibiting cyclin dependent kinase-7 signalling pathway.

In one aspect of the present invention, it comprises compounds of formula (I):

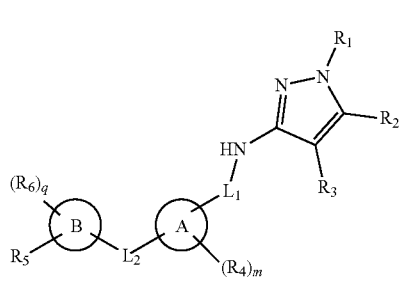

or a pharmaceutically acceptable salt or a stereoisomer thereof;
wherein,
ring A is cycloalkyl, aryl, heteroaryl or heterocyclyl;
ring B is aryl, cycloalkyl, heterocyclyl or absent;
$R_1$ is hydrogen or alkyl;
$R_2$ is hydrogen, alkyl or cycloalkyl;
$R_3$ is hydrogen, alkyl or heteroaryl;
alternatively, $R_2$ together with $R_1$ or $R_3$ along with the ring atoms to which they are attached forms a 5-7 membered ring;
$R_4$ at each occurrence is halo, alkyl, hydroxy, alkoxy, amino, nitro, cyano or haloalkyl;
$R_5$ is

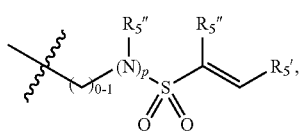

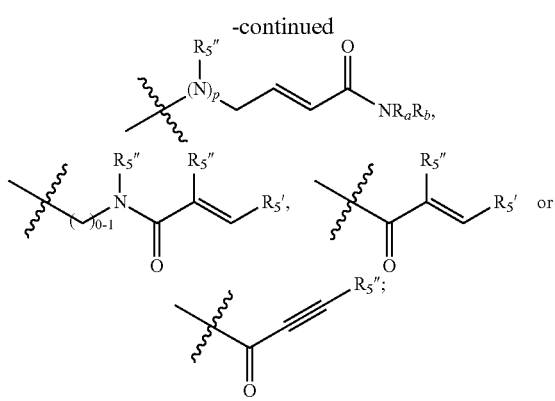

wherein $R_5'$ is hydrogen, halo, alkyl, alkoxy, alkoxyalkyl or —$(CH_2)_{1-3}$—$NR_aR_b$; $R_5''$ is H or alkyl;
$R_a$ and $R_b$ are each independently hydrogen, alkyl, alkoxy or alkoxyalkyl; alternatively, $R_a$ and $R_b$ together with the nitrogen atom to which they are attached form an optionally substituted ring containing 0-2 additional heteroatoms independently selected from N, O or S; wherein the optional substituent is one or more halo, alkyl, acyl, hydroxy, cyano, cyanoalkyl, haloalkyl, alkoxy, alkoxyalkyl, —COOH or —COO-alkyl;
$R_6$ at each occurrence is halo, alkyl, hydroxy, alkoxy, amino, nitro, cyano or haloalkyl;
$L_1$ is *—$CR_cR_d$—$C(O)$—, *—$NR_eC(O)$— or absent;
wherein * is point of attachment with ring A;
$R_c$ and $R_d$ independently are hydrogen, alkyl or haloalkyl; alternatively, $R_c$ and $R_d$ together with the carbon to which they are attached form a cycloalkyl ring;
$R_e$ is hydrogen or alkyl;
$L_2$ is —$C(O)NH$—, —$C(O)O$— or absent;
m is 0, 1 or 2;
p is 0 or 1; and
q is 0 to 3.

In yet another aspect, the present invention provides a pharmaceutical composition comprising a compound of formula (I) or a pharmaceutically acceptable salt thereof and at least one pharmaceutically acceptable excipient (such as a pharmaceutically acceptable carrier or diluent).

In yet another aspect, the present invention relates to the preparation of compounds of formula (I).

In yet another aspect of the present invention, provided herein are substituted heterocyclyl derivatives of formula (I), which are capable of inhibiting CDK7 and therapeutic use thereof.

DETAILED DESCRIPTION OF THE INVENTION

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

As used herein, unless otherwise defined the term "alkyl" alone or in combination with other term(s) means saturated aliphatic hydrocarbon chains, including $C_1$-$C_{10}$ straight or $C_3$-$C_{10}$ branched alkyl groups. Examples of "alkyl" include but are not limited to methyl, ethyl, propyl, isopropyl, butyl, isobutyl, sec-butyl, tert-butyl, isopentyl or neopentyl and the like.

As used herein, the term "halo" or "halogen" alone or in combination with other term(s) means fluorine, chlorine, bromine or iodine.

As used herein, the term "haloalkyl" means alkyl substituted with one or more halogen atoms, wherein the alkyl groups are as defined above. The term "halo" is used herein interchangeably with the term "halogen" means F, Cl, Br or I. Examples of "haloalkyl" include but are not limited to fluoromethyl, difluoromethyl, chloromethyl, trifluoromethyl, 2,2,2-trifluoroethyl and the like.

As used herein, the term "hydroxy" or "hydroxyl" alone or in combination with other term(s) means —OH.

As used herein, the term "alkoxy" refers to the group alkyl-O— or —O-alkyl, where alkyl groups are as defined above. Exemplary alkoxy-groups include but are not limited to methoxy, ethoxy, n-propoxy, n-butoxy, t-butoxy and the like. An alkoxy group can be unsubstituted or substituted with one or more suitable groups.

As used herein, the term "alkoxyalkyl" refers to the group alkyl-O-alkyl-, wherein alkyl and alkoxy groups are as defined above. Exemplary alkoxyalkyl-groups include but are not limited to methoxymethyl, ethoxymethyl, methoxyethyl, isopropoxymethyl and the like.

As used herein, the term "cyano" refers to —CN; and the term "cyanoalkyl" refers to alkyl substituted with —CN; wherein the alkyl groups are as defined above.

As used herein, the term "amino" refers to —NH$_2$;

As used herein, the term "nitro" refers to —NO$_2$;

As used herein, the term "acyl" refers to the group —C(O)-alkyl, wherein alkyl groups are as defined above. Exemplary alkoxy-groups include but are not limited to acetyl, propanoyl and acrylyl. An alkoxy group can be unsubstituted or substituted with one or more suitable groups.

As used herein the term "cycloalkyl" alone or in combination with other term(s) means —C$_3$-C$_{10}$ saturated cyclic hydrocarbon ring. A cycloalkyl may be a single ring, which typically contains from 3 to 7 carbon ring atoms. Examples of single-ring cycloalkylsincludebut are not limited to cyclopropyl, cyclobutyl, cyclopentyl, cyclohexyl, cycloheptyl and the like. A cycloalkyl may alternatively be polycyclic or contain more than one ring. Examples of polycyclic cycloalkyls include bridged, fused and spirocyclyls and the like.

As used herein, the term "aryl" is optionally substituted monocyclic, bicyclic or polycyclic aromatic hydrocarbon ring system of about 6 to 14 carbon atoms. Examples of a C$_6$-C$_{14}$ aryl group include, but are not limited to phenyl, naphthyl, anthryl, tetrahydronaphthyl, fluorenyl, indanyl, biphenylenyl and acenaphthyl. Aryl group which can be unsubstituted or substituted with one or more suitable groups.

The term "heterocycloalkyl" refers to a non-aromatic, saturated or partially saturated monocyclic or polycyclic ring system of 3 to 15 members having at least one heteroatom or heterogroup selected from O, N, S, S(O), S(O)$_2$, NH or C(O) with the remaining ring atoms being independently selected from the group consisting of carbon, oxygen, nitrogen and sulfur. A monocyclic heterocycloalkyl may typically contain 4 to 7 ring atoms. Examples of "Heterocycloalkyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, oxapiperazinyl, oxapiperidinyl, tetrahydrofuryl, tetrahydropyranyl, tetrahydrothiophenyl, dihydropyranyl, indolinyl, indolinylmethyl, azepanyl and N-oxides thereof. Attachment of a heterocycloalkyl substituent can occur via either a carbon atom or a heteroatom. A heterocycloalkyl group can be optionally substituted with one or more suitable groups by one or more aforesaid groups.

As used herein, the term "heteroaryl" alone or in combination with other term(s) means a completely unsaturated ring system containing a total of 5 to 14 ring atoms. At least one of the ring atoms is a heteroatom (i.e., oxygen, nitrogen, or sulfur), with the remaining ring atoms/groups being independently selected from the group consisting of carbon, oxygen, nitrogen or sulfur. A heteroaryl may be a single-ring (monocyclic) or polycyclic ring system. Examples of "heteroaryl" include but are not limited to pyridyl, indolyl, benzimidazolyl, benzothiazolyl and the like.

As used herein, the term "heterocyclyl" alone or in combination with other term(s) includes both "heterocycloalkyl" and "heteroaryl" groups which are as defined above.

The term "heteroatom" as used herein designates a sulfur, nitrogen or oxygen atom.

As used in the above definitions, the term "optionally substituted" or "substituted" or "optionally substituted with suitable groups" refers to replacement of one or more hydrogen radicals in a given structure with a radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl and heteroaryl. It is understood that the substituent may be further substituted.

As used herein, the term 'compound(s)' comprises the compounds disclosed in the present invention.

As used herein, the term "comprise" or "comprising" is generally used in the sense of include, that is to say permitting the presence of one or more features or components.

As used herein, the term "or" means "and/or" unless stated otherwise.

As used herein, the term "including" as well as other forms, such as "include", "includes" and "included" is not limiting.

As used herein, the term "composition" is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

As used herein, the term "treat", "treating" and "treatment" refer to a method of alleviating or abrogating a disease and/or its attendant symptoms.

As used herein, the term "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

As used herein, the term "therapeutically effective amount" refers to that amount of the compound being administered sufficient to prevent development of or alleviate to some extent one or more of the symptoms of the condition or disorder being treated.

"Pharmaceutically acceptable" means that, which is useful in preparing a pharmaceutical composition that is generally safe, non-toxic and neither biologically nor otherwise undesirable and includes that which is acceptable for veterinary as well as human pharmaceutical use.

The term "stereoisomers" refers to any enantiomers, diastereoisomers, or geometrical isomers of the compounds of Formula (I), (IA), (IB), (IC), (ID), (IE), (IF) and (IG), wherever they are chiral or when they bear one or more double bonds. When the compounds of the formula (I), (IA), (IB), (IC), (ID), (IE), (IF) and (IG) are chiral, they can exist in racemic or in optically active form. It should be understood that the invention encompasses all stereochemical isomeric forms, including diastereomeric, enantiomeric and epimeric forms, as well as d-isomers and l-isomers and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E) and zusammen (Z) isomers as well as the appropriate mixtures thereof.

The present invention provides substituted heterocyclylderivatives of formula (I), which are useful for the inhibition of CDK7.

The present invention further provides pharmaceutical compositions comprising the said substituted heterocyclyl compounds of formula (I) and their derivatives as therapeutic agents.

In first embodiment, the present invention provides compounds of formula (I),

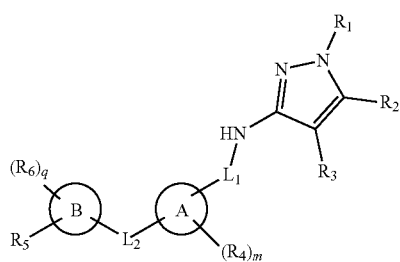

(I)

or a pharmaceutically acceptable salt or a stereoisomer thereof,
wherein,
ring A is cycloalkyl, aryl, heteroaryl or heterocyclyl;
ring B is aryl, cycloalkyl, heterocyclyl or absent;
$R_1$ is hydrogen or alkyl;
$R_2$ is hydrogen, alkyl or cycloalkyl;
$R_3$ is hydrogen, alkyl or heteroaryl;
alternatively, $R_2$ together with $R_1$ or $R_3$ along with the ring atoms to which they are attached forms a 5-7 membered ring;

$R_4$ at each occurrence is halo, alkyl, hydroxy, alkoxy, amino, nitro, cyano or haloalkyl;
$R_5$ is

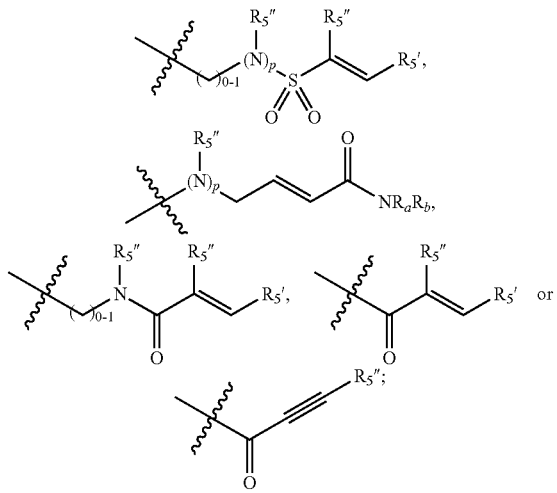

wherein $R_5'$ is hydrogen, halo, alkyl, alkoxy, alkoxyalkyl or —$(CH_2)_{1-3}$—$NR_aR_b$; $R_5''$ is H or alkyl;
$R_a$ and $R_b$ are each independently hydrogen, alkyl, alkoxy or alkoxyalkyl; alternatively, $R_a$ and $R_b$ together with the nitrogen atom to which they are attached form an optionally substituted ring containing 0-2 additional heteroatoms independently selected from N, O or S; wherein the optional substituent is one or more halo, alkyl, acyl, hydroxy, cyano, cyanoalkyl, haloalkyl, alkoxy, alkoxyalkyl, —COOH or —COO-alkyl;
$R_6$ at each occurrence is halo, alkyl, hydroxy, alkoxy, amino, nitro, cyano or haloalkyl;
$L_1$ is *—$CR_cR_d$—$C(O)$—, *—$NR_eC(O)$— or absent; wherein * is point of attachment with ring A;
$R_c$ and $R_d$ independently are hydrogen, alkyl or haloalkyl; alternatively, $R_c$ and $R_d$ together with the carbon to which they are attached form a cycloalkyl ring;
$R_e$ is hydrogen or alkyl;
$L_2$ is —C(O)NH—, —C(O)O— or absent;
m is 0, 1 or 2;
p is 0 or 1; and
q is 0 to 3.

In another embodiment of the present invention, it provides compounds of formula (IA),

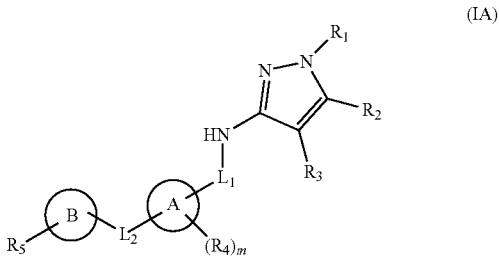

(IA)

or a pharmaceutically acceptable salt thereof or a stereoisomer thereof; wherein,
ring A is cycloalkyl, aryl, heteroaryl or heterocyclyl;
ring B is aryl, cycloalkyl, heterocyclyl or absent;

$R_1$ is hydrogen or alkyl;
$R_2$ is hydrogen, alkyl or cycloalkyl;
$R_3$ is hydrogen, alkyl or heteroaryl;
alternatively, $R_2$ together with $R_1$ or $R_3$ along with the ring atoms to which they are attached forms a 5-7 membered ring;
$R_4$ at each occurrence is halo, alkyl, hydroxy or alkoxy;
$R_5$ is

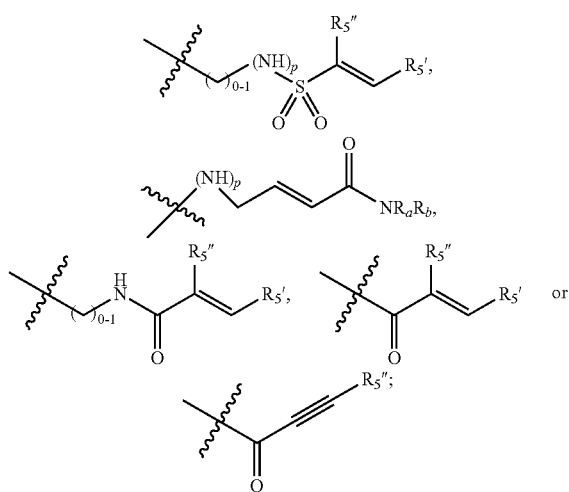

wherein $R_5'$ is hydrogen, halo, alkyl, alkoxy, alkoxyalkyl or $-(CH_2)_{1-3}-NR_aR_b$; $R_5''$ is H or alkyl;
$R_a$ and $R_b$ are each independently hydrogen or alkyl; alternatively, $R_a$ and $R_b$ together with the nitrogen atom to which they are attached form an optionally substituted ring containing 0-2 additional heteroatoms independently selected from N, O or S; wherein the optional substituent is one or more halo, alkyl, hydroxy, haloalkyl or alkoxy;
$L_1$ is *—$CR_cR_d$—C(O)—, *—$NR_eC(O)$— or absent; wherein * is point of attachment with ring A;
$R_c$ and $R_d$ independently are hydrogen, alkyl or haloalkyl; alternatively, $R_c$ and $R_d$ together with the carbon to which they are attached form a cycloalkyl ring;
$R_e$ is hydrogen or alkyl;
$L_2$ is —C(O)NH—, —C(O)O— or absent;
m is 0, 1 or 2; and
p is 0 or 1.

In another embodiment of the present invention, it provides compounds of formula (IA), or a pharmaceutically acceptable salt thereof or a stereoisomer thereof; wherein,
ring A is cycloalkyl, aryl, heteroaryl or heterocyclyl;
ring B is aryl, cycloalkyl, heterocyclyl or absent;
$R_1$ is hydrogen or alkyl;
$R_2$ is hydrogen, alkyl or cycloalkyl;
$R_3$ is hydrogen, alkyl or heteroaryl;
alternatively, $R_2$ together with $R_1$ or $R_3$ along with the ring atoms to which they are attached forms a 5-7 membered ring;
$R_4$ at each occurrence is halo, alkyl, hydroxy or alkoxy;
$R_5$ is —$(NH)_p$—$S(O)_2$—CH=$CH_2$, —NH—$CH_2$—CH=CH—C(O)—$NR_aR_b$,

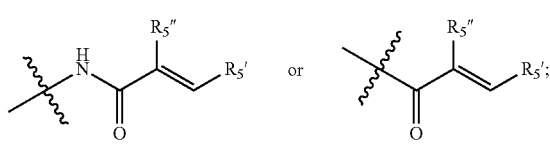

wherein $R_5'$ is hydrogen, halo, alkyl, alkoxyalkyl or —$CH_2$—$NR_aR_b$; $R_5''$ is H or alkyl;
$R_a$ and $R_b$ are each independently hydrogen or alkyl; alternatively, $R_a$ and $R_b$ together with the Nitrogen to which they are attached form an optionally substituted ring containing 0-2 additional heteroatoms independently selected from N, O or S; wherein the optional substituent is one or more halo, alkyl, hydroxy, haloalkyl or alkoxy;
$L_1$ is *—$CR_cR_d$—C(O)—, *—$NR_eC(O)$— or absent; wherein * is point of attachment with ring A;
$R_c$ and $R_d$ independently are hydrogen, alkyl or haloalkyl; alternatively, $R_c$ and $R_d$ together with the carbon to which they are attached form a cycloalkyl ring;
$R_e$ is hydrogen or alkyl;
$L_2$ is —C(O)NH—, —C(O)O— or absent;
m is 0, 1 or 2; and
p is 0 or 1.

In another embodiment of the present invention, it provides compounds of formula (IB),

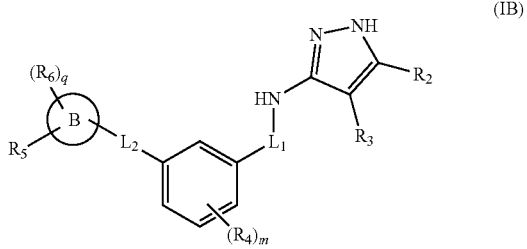

or a pharmaceutically acceptable salt thereof or a stereoisomer thereof;
wherein, ring B, $L_1$, $L_2$, $R_2$, $R_3$, $R_4$, $R_5$, $R_6$, m and q are same as defined in compounds of formula (I).

In yet another embodiment of the present invention, it provides compounds of formula (IC),

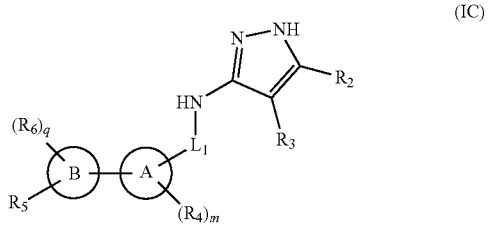

or a pharmaceutically acceptable salt thereof or a stereoisomer thereof;
wherein, ring A, ring B, $L_1$, $R_2$, $R_3$, $R_4$, $R_5$, $R_6$, m and q are same as defined in compounds of formula (I).

In yet another embodiment of the present invention, it provides compounds of formula (ID),

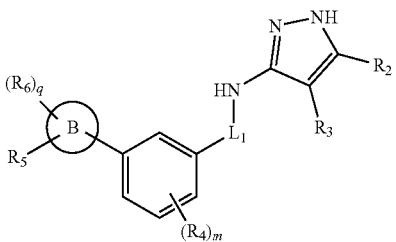

(ID)

or a pharmaceutically acceptable salt thereof or a stereoisomer thereof;
wherein, ring B, $L_1$, $R_2$, $R_3$, $R_4$, $R_5$, $R_6$, m and q are same as defined in compounds of formula (I).

In yet another embodiment of the present invention, it provides compounds of formula (IE),

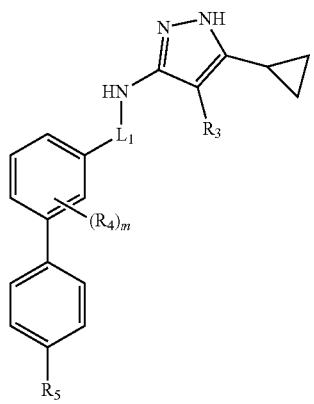

(IE)

or a pharmaceutically acceptable salt thereof or a stereoisomer thereof;
wherein, $L_1$ is *—$CR_cR_d$—C(O)— or *—$NR_eC(O)$—; wherein * is point of attachment with phenyl; $R_3$, $R_4$, $R_5$ and m are same as defined in compounds of formula (I).

In yet another embodiment of the present invention, it provides compounds of formula (IF),

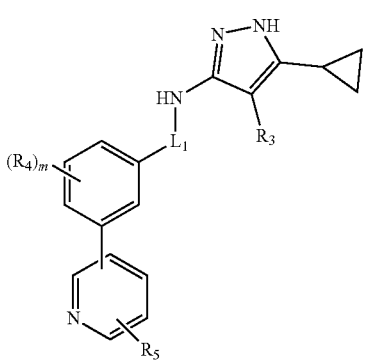

(IF)

or a pharmaceutically acceptable salt thereof or a stereoisomer thereof;
wherein, $L_1$ is *—$CR_cR_d$—C(O)— or *—$NR_eC(O)$—; wherein * is point of attachment with phenyl; $R_3$, $R_4$, $R_5$ and m are same as defined in compounds of formula (I).

In yet another embodiment of the present invention, it provides compounds of formula (IG),

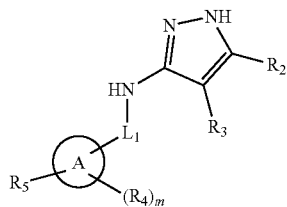

(IG)

or a pharmaceutically acceptable salt thereof or a stereoisomer thereof;
wherein, ring A, $L_1$, $R_2$, $R_3$, $R_4$, $R_5$ and m are same as defined in compounds of formula (I).

The embodiments below are illustrative of the present invention and are not intended to limit the claims to the specific embodiments exemplified.

According to one embodiment, specifically provided are compounds of formula (I), wherein ring A is aryl; preferably the said aryl is phenyl.

According to another embodiment, specifically provided are compounds of formula (I), wherein ring B is aryl; preferably the said aryl is phenyl.

According to yet another embodiment, specifically provided are compounds of formula (I), wherein ring B is heterocyclyl; preferably the said heterocylcyl is piperidinyl, pyridinyl, piperazinyl, pyrazolyl, morpholinyl, indoninyl or pyrrolidinyl.

According to yet another embodiment, specifically provided are compounds of formula (I), wherein ring B is absent.

According to yet another embodiment, specifically provided are compounds of formula (I), wherein ring B and $L_2$ are absent so that $R_5$ is directly linked to ring A.

According to yet another embodiment, specifically provided are compounds of formula (I), wherein $L_1$ is *—$CR_c R_d$—C(O)— wherein * is the point of attachment with ring A.

According to the preceding embodiment, specifically provided are compounds of formula (I), wherein $R_c$ and $R_d$ are independently hydrogen or alkyl, wherein the said alkyl is methyl, ethyl or isopropyl.

According to yet another embodiment, specifically provided are compounds of formula (I), wherein $L_2$ is *—C(O)NH—, *—C(O)O—, or absent; wherein * is point of attachment with ring B.

According to yet another embodiment, specifically provided are compounds of formula (I), wherein when $L_1$ is present, $L_2$ is absent.

According to yet another embodiment, specifically provided are compounds of formula (I), wherein $R_2$ is alkyl or cycloalkyl; preferably the said alkyl is ethyl and the said cycloalkyl is cyclopropyl, cyclobutyl or cyclopentyl.

According to yet another embodiment, specifically provided are compounds of formula (I), wherein $R_3$ is hydrogen and alkyl; wherein the said alkyl is methyl.

According to yet another embodiment, specifically provided are compounds of formula (I), wherein $R_4$ is halo; preferably the said halo is fluoro.

According to yet another embodiment, specifically provided are compounds of formula (I), wherein m is 0 or 1.

According to yet another embodiment, specifically provided are compounds of formula (I), wherein $R_5$ is

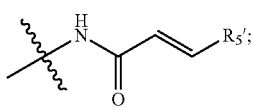

wherein $R_5'$ is hydrogen or —$CH_2$—$NR_aR_b$.

According to yet another embodiment, specifically provided are compounds of formula (I), wherein $R_5$ is

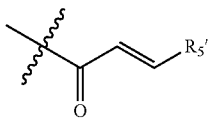

when $R_5$ is attached to hetero atom of ring B; $R_5'$ is hydrogen or —$CH_2$—$NR_aR_b$.

According to the preceding two embodiments, specifically provided are compounds of formula (I), wherein the said $R_a$ and $R_b$ are each independently hydrogen or alkyl; preferably the said alkyl is methyl.

According to the preceding embodiment, specifically provided are compounds of formula (I), wherein the said $R_a$ and $R_b$ together with the nitrogen to which they are attached form an optionally substituted ring containing 0-2 additional heteroatoms independently selected from N, O or S; wherein the optional substituent is one or more halo, hydroxy, haloalkyl or alkoxy.

According to yet another embodiment, specifically provided are compounds of formula (I), wherein n is 1 or 2.

In certain embodiments of formula (I), ring A is aryl or heteroaryl; in another embodiment, the said aryl is phenyl.

In certain embodiments of formula (I), ring A is meta-substituted with respect to $L_1$ and $L_2$.

In certain embodiments of formula (I), ring B is monocyclic or bicyclic cycloalkyl, aryl, heterocycloalkyl or heteroaryl.

In certain embodiments of formula (I), ring B is heterocyclyl; in another embodiment the said heterocylcyl is piperidinyl, pyridinyl, 1,2,3,6-tetrahydropyridinyl, piperazinyl, pyrazinyl, pyrazolyl, morpholinyl, indolinyl or pyrrolidinyl.

In certain embodiments of formula (I), ring B is absent.

In certain embodiments of formula (I), wherein ring B and $L_2$ are absent so that $R_5$ is directly linked to ring A.

In certain embodiments of formula (I), $R_2$ is cycloalkyl; in another embodiment, the said cycloalkyl is cyclopropyl, cyclobutyl or cyclopentyl.

In certain embodiments of formula (I), $R_2$ and $R_1$ together with the atoms to which they are attached form a 5 or 6 membered ring.

In certain embodiments of formula (I), $R_2$ and $R_3$ together with the atoms to which they are attached form a 5 or 6 membered ring.

In certain embodiments of formula (I), $R_2$ and $R_3$ together with the atoms to which they are attached form a 6 membered aromatic ring.

In certain embodiments of formula (I), $R_5$ is,

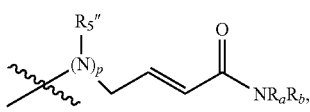

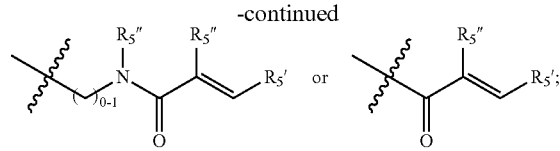

wherein $R_5'$ and $R_5''$ are as defined in formula (I).

In certain embodiments of formula (I), $R_5$ is,

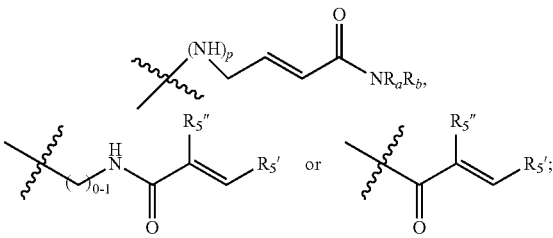

wherein $R_5'$ and $R_5''$ are as defined in formula (I).

In certain embodiments of formula (I), $R_5$ is

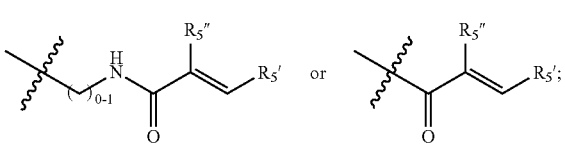

wherein $R_5'$ and $R_5''$ are as defined in formula (I).

In certain embodiments of formula (I), $R_5$ is

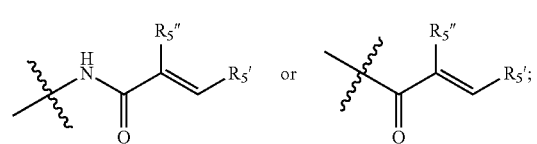

wherein $R_5'$ is hydrogen, halo, alkyl, alkoxy or alkoxyalkyl; and $R_5''$ is H or alkyl.

In certain embodiments of formula (I), $R_5$ is

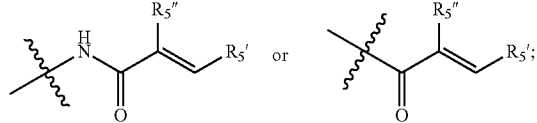

wherein $R_5'$ is —$CH_2$—$NR_aR_b$; $R_5''$ is H or alkyl; $R_a$ and $R_b$ are each independently hydrogen, alkyl, alkoxy or alkoxyalkyl.

In certain embodiments of formula (I), $R_5$ is

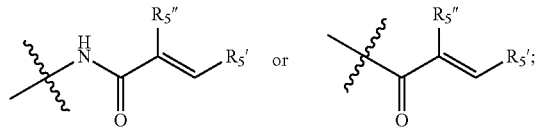

wherein $R_5'$ is —$CH_2$—$NR_aR_b$; $R_5''$ is H or alkyl; $R_a$ and $R_b$ together with the nitrogen atom to which they are attached form an optionally substituted 4-7 membered heterocyclyl ring containing 0-2 additional heteroatoms independently selected from N, O or S; wherein the optional substituent is one or more halo, alkyl, acyl, hydroxy, cyano, cyanoalkyl, haloalkyl, alkoxy, alkoxyalkyl, —COOH or —COO-alkyl.

In certain embodiments of formula (I), R$_5$ is

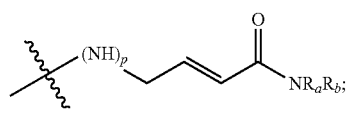

wherein p, R$_a$ and R$_b$ are as defined in formula (I).

In certain embodiments of formula (I), R$_5$ is,

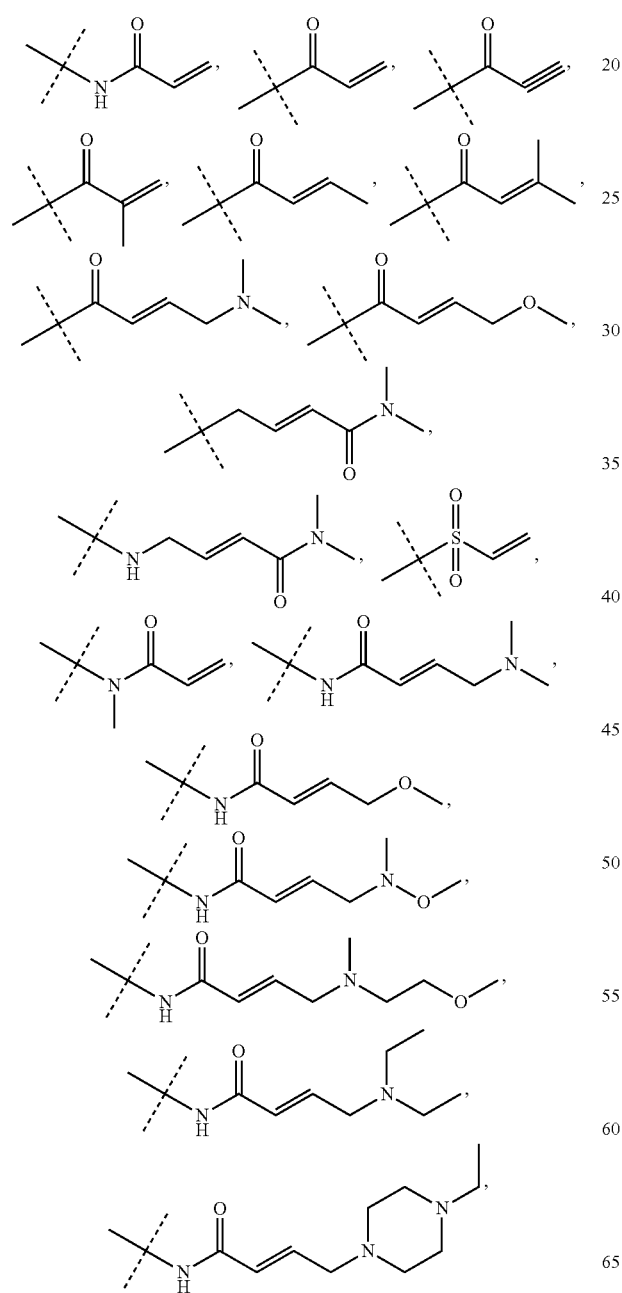

-continued

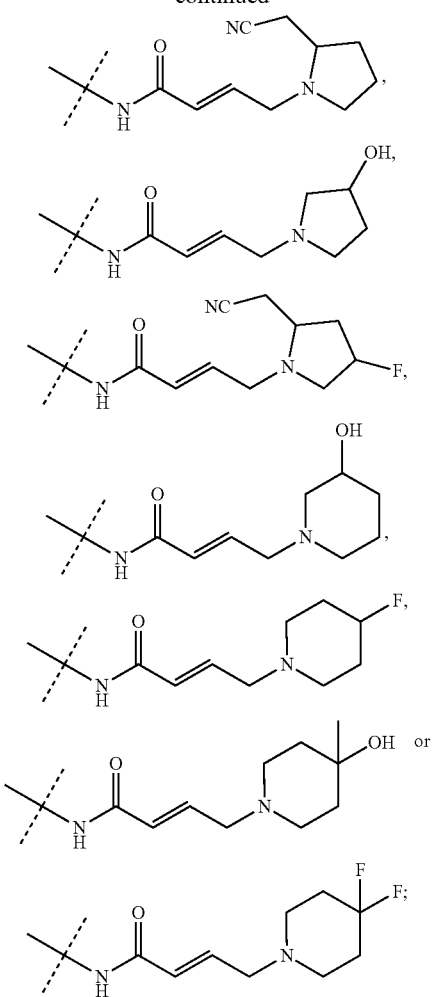

wherein ⌇ is a point of attachment.

In certain embodiments of formula (I), $R_5'$ is —$(CH_2)_{1-3}$—$NR_aR_b$; wherein $R_a$ and $R_b$ are as defined in formula (I).

In certain embodiments of formula (I), $R_a$ and $R_b$ together with the nitrogen atom to which they are attached form an optionally substituted heterocyclic ring having 0-2 additional heteroatoms selected from O, S or N; wherein the optional substituent is one or more halo, alkyl, acyl, hydroxy, cyano, cyanoalkyl, haloalkyl, alkoxy, alkoxyalkyl, —COOH or —COO-alkyl.

In certain embodiments of formula (I), $L_1$ is *—$CR_cR_d$—C(O)—; wherein * is the point of attachment with ring A; and $R_c$ and $R_d$ are as defined in claim 1.

In certain embodiments of formula (I), $L_2$ is —C(O)NH— or —C(O)O—.

In certain embodiments of formula (I), $L_2$ is *—C(O)NH— or *—C(O)O—; wherein * is the point of attachment with ring B.

In certain embodiments of formula (I), when $L_1$ is —$CR_cR_d$—C(O)— or —$NR_eC(O)$—, $L_2$ is absent.

In certain embodiments, the present invention provides a compound selected from the group consisting of:

| Compound No. | IUPAC name |
|---|---|
| 1. | (E)-N-(3'-(1-((5-cyclopropyl-1H-pyrazol-3-yl)amino)-1-oxopropan-2-yl)-[1,1'-biphenyl]-4-yl)-4-(dimethylamino)but-2-enamide; |
| 2. | (E)-N-(3'-(1-((5-cyclopropyl-1H-pyrazol-3-yl)amino)-1-oxopropan-2-yl)-[1,1'-biphenyl]-4-yl)-4-(dimethylamino)but-2-enamide (Isomer-1 of compound-1); |
| 3. | (E)-N-(3'-(1-((5-cyclopropyl-1H-pyrazol-3-yl)amino)-1-oxopropan-2-yl)-[1,1'-biphenyl]-4-yl)-4-(dimethylamino)but-2-enamide (Isomer-2 of compound-1); |
| 4. | (E)-N-(5'-(1-((5-cyclopropyl-1H-pyrazol-3-yl)amino)-1-oxopropan-2-yl)-2'-fluoro-[1,1'-biphenyl]-4-yl)-4-(dimethylamino)but-2-enamide; |
| 5. | (E)-N-(3'-(1-((5-cyclopropyl-1H-pyrazol-3-yl)amino)-1-oxopropan-2-yl)-4'-fluoro-[1,1'-biphenyl]-4-yl)-4-(dimethylamino)but-2-enamide; |
| 6. | (E)-N-(3'-(1-((5-cyclopropyl-1-methyl-1H-pyrazol-3-yl)amino)-1-oxopropan-2-yl)-[1,1'-biphenyl]-4-yl)-4-(dimethylamino)but-2-enamide; |
| 7. | (E)-N-(3'-(2-((5-cyclopropyl-1H-pyrazol-3-yl)amino)-2-oxoethyl)-[1,1'-biphenyl]-4-yl)-4-(dimethylamino)but-2-enamide; |
| 8. | (E)-4-(dimethylamino)-N-(3'-(1-((5-ethyl-1H-pyrazol-3-yl)amino)-1-oxopropan-2-yl)-[1,1'-biphenyl]-4-yl)but-2-enamide; |
| 9. | (E)-N-(3'-(1-((5-(tert-butyl)-1H-pyrazol-3-yl)amino)-1-oxopropan-2-yl)-[1,1'-biphenyl]-4-yl)-4-(dimethylamino)but-2-enamide; |
| 10. | (E)-N-(5-(3-(1-((5-cyclopropyl-1H-pyrazol-3-yl)amino)-1-oxopropan-2-yl)phenyl)pyridin-2-yl)-4-morpholinobut-2-enamide; |
| 11. | (E)-N-(5-(3-(1-((5-cyclopropyl-1H-pyrazol-3-yl)amino)-1-oxopropan-2-yl)phenyl)pyridin-2-yl)-4-morpholinobut-2-enamide (Isomer-1 of compound-10); |
| 12. | (E)-N-(5-(3-(1-((5-cyclopropyl-1H-pyrazol-3-yl)amino)-1-oxopropan-2-yl)phenyl)pyridin-2-yl)-4-morpholinobut-2-enamide (Isomer-2 of compound-10); |
| 13. | (E)-N-(3'-(1-((5-cyclopropyl-1H-pyrazol-3-yl)amino)-1-oxobutan-2-yl)-[1,1'-biphenyl]-4-yl)-4-(dimethylamino)but-2-enamide; |
| 14. | (E)-N-(3'-(1-((5-cyclopropyl-1H-pyrazol-3-yl)amino)-1-oxopropan-2-yl)-3-fluoro-[1,1'-biphenyl]-4-yl)-4-(dimethylamino)but-2-enamide; |
| 15. | (E)-N-(3'-(1-((5-cyclobutyl-1H-pyrazol-3-yl)amino)-1-oxopropan-2-yl)-[1,1'-biphenyl]-4-yl)-4-(dimethylamino)but-2-enamide; |
| 16. | (E)-N-(6-(3-(1-((5-cyclopropyl-1H-pyrazol-3-yl)amino)-1-oxopropan-2-yl)phenyl)pyridin-3-yl)-4-(dimethylamino)but-2-enamide; |
| 17. | (E)-N-(3'-(1-((5-cyclopropyl-1H-pyrazol-3-yl)amino)-1-oxopropan-2-yl)-2-fluoro-[1,1'-biphenyl]-4-yl)-4-(dimethylamino)but-2-enamide; |
| 18. | N-(3'-(1-((5-cyclopropyl-1H-pyrazol-3-yl)amino)-1-oxopropan-2-yl)-[1,1'-biphenyl]-4-yl)acrylamide; |
| 19. | N-(3'-(1-((5-cyclopropyl-1H-pyrazol-3-yl)amino)-1-oxopropan-2-yl)-3-fluoro-[1,1'-biphenyl]-4-yl)acrylamide; |
| 20. | N-(5-(3-(1-((5-cyclopropyl-1H-pyrazol-3-yl)amino)-1-oxopropan-2-yl)phenyl)pyridin-2-yl)acrylamide; |

| Compound No. | IUPAC name |
|---|---|
| 21. | N-(5-(3-(1-((5-cyclopropyl-1H-pyrazol-3-yl)amino)-1-oxopropan-2-yl)phenyl)pyridin-2-yl)acrylamide (Isomer-1 of compound-20); |
| 22. | N-(5-(3-(1-((5-cyclopropyl-1H-pyrazol-3-yl)amino)-1-oxopropan-2-yl)phenyl)pyridin-2-yl)acrylamide (Isomer-2 of compound-20); |
| 23. | N-(5'-(1-((5-cyclopropyl-1H-pyrazol-3-yl)amino)-1-oxopropan-2-yl)-2',3-difluoro-[1,1'-biphenyl]-4-yl)acrylamide; |
| 24. | N-(6-(3-(1-((5-cyclopropyl-1H-pyrazol-3-yl)amino)-1-oxopropan-2-yl)phenyl)pyridin-3-yl)acrylamide; |
| 25. | 2-(4'-acrylamido-3'-fluoro-[1,1'-biphenyl]-3-yl)-N-(5-cyclopropyl-1H-pyrazol-3-yl)-3-methylbutanamide; |
| 26. | 2-(3-(5-acrylamidopyridin-2-yl)phenyl)-N-(5-cyclopropyl-1H-pyrazol-3-yl)butanamide; |
| 27. | 2-(4'-acrylamido-3'-fluoro-[1,1'-biphenyl]-3-yl)-N-(5-cyclopropyl-1H-pyrazol-3-yl)butanamide; |
| 28. | (E)-N-(3'-(1-((5-cyclopentyl-1H-pyrazol-3-yl)amino)-1-oxopropan-2-yl)-3-fluoro-[1,1'-biphenyl]-4-yl)-4-(dimethylamino)but-2-enamide; |
| 29. | (E)-N-(5-cyclopropyl-1H-pyrazol-3-yl)-2-(3-(1-(4-(dimethylamino)but-2-enoyl)indolin-5-yl)phenyl)propanamide; |
| 30. | N-(3'-(1-((5-cyclopropyl-4-methyl-1H-pyrazol-3-yl)amino)-1-oxopropan-2-yl)-[1,1'-biphenyl]-4-yl)acrylamide; |
| 31. | (E)-N-(3'-(1-((5-cyclopropyl-1H-pyrazol-3-yl)amino)-1-oxobutan-2-yl)-3-fluoro-[1,1'-biphenyl]-4-yl)-4-(dimethylamino)but-2-enamide; |
| 32. | (E)-N-(3'-(1-((5-cyclopropyl-1H-pyrazol-3-yl)amino)-1-oxopropan-2-yl)-3-fluoro-[1,1'-biphenyl]-4-yl)-4-(diethylamino)but-2-enamide; |
| 33. | (E)-N-(3'-(1-((5-cyclopropyl-1H-pyrazol-3-yl)amino)-1-oxopropan-2-yl)-3-fluoro-[1,1'-biphenyl]-4-yl)-4-(pyrrolidin-1-yl)but-2-enamide; |
| 34. | (E)-N-(3'-(1-((5-cyclopropyl-1H-pyrazol-3-yl)amino)-1-oxopropan-2-yl)-3-fluoro-[1,1'-biphenyl]-4-yl)-4-morpholinobut-2-enamide; |
| 35. | (E)-N-(6-(3-(1-((5-cyclopropyl-1H-pyrazol-3-yl)amino)-1-oxopropan-2-yl)phenyl)pyridin-3-yl)-4-morpholinobut-2-enamide; |
| 36. | (E)-N-(6-(3-(1-((5-cyclopropyl-1H-pyrazol-3-yl)amino)-3-methyl-1-oxobutan-2-yl)phenyl)pyridin-3-yl)-4-(dimethylamino)but-2-enamide; |
| 37. | (E)-4-((6-(3-(1-((5-cyclopropyl-1H-pyrazol-3-yl)amino)-1-oxopropan-2-yl)phenyl)pyridin-3-yl)amino)-N,N-dimethylbut-2-enamide; |
| 38. | (E)-N-(6-(3-(1-((5-cyclopropyl-1H-pyrazol-3-yl)amino)-1-oxopropan-2-yl)phenyl)-2-fluoropyridin-3-yl)-4-(dimethylamino)but-2-enamide; |
| 39. | (E)-N-(6-(3-(1-((5-cyclopropyl-1H-pyrazol-3-yl)amino)-1-oxopropan-2-yl)phenyl)pyridin-3-yl)-4-(piperidin-1-yl)but-2-enamide; |
| 40. | (E)-N-(5-(3-(1-((5-cyclopropyl-1H-pyrazol-3-yl)amino)-1-oxopropan-2-yl)phenyl)pyridin-2-yl)-4-(piperidin-1-yl)but-2-enamide; |
| 41. | (E)-N-(5-(3-(1-((5-cyclopropyl-1H-pyrazol-3-yl)amino)-1-oxopropan-2-yl)phenyl)pyridin-2-yl)-4-methoxybut-2-enamide; |
| 42. | (E)-N-(5-(3-(1-((5-cyclopropyl-1H-pyrazol-3-yl)amino)-1-oxopropan-2-yl)phenyl)pyridin-2-yl)-4-(dimethylamino)but-2-enamide; |
| 43. | (E)-N-(3'-(1-((5-cyclopropyl-1H-pyrazol-3-yl)amino)-3-methyl-1-oxobutan-2-yl)-3-fluoro-[1,1'-biphenyl]-4-yl)-4-(dimethylamino)but-2-enamide; |
| 44. | (E)-N-(5-(3-(1-((5-cyclopropyl-1H-pyrazol-3-yl)amino)-3-methyl-1-oxobutan-2-yl)phenyl)pyridin-2-yl)-4-morpholinobut-2-enamide; |
| 45. | (E)-N-(5-(3-(1-((5-cyclopropyl-1H-pyrazol-3-yl)amino)-1-oxopropan-2-yl)phenyl)pyridin-2-yl)-4-(3-fluoropyrrolidin-1-yl)but-2-enamide; |
| 46. | (E)-N-(5-(3-(1-((5-cyclopropyl-1H-pyrazol-3-yl)amino)-1-oxopropan-2-yl)phenyl)pyridin-2-yl)-4-((S)-3-fluoropyrrolidin-1-yl)but-2-enamide; |
| 47. | (E)-N-(5-(3-(1-((5-cyclopropyl-1H-pyrazol-3-yl)amino)-1-oxopropan-2-yl)phenyl)pyridin-2-yl)-4-((S)-3-fluoropyrrolidin-1-yl)but-2-enamide (Isomer-1 of compound-46); |
| 48. | E)-N-(5-(3-(1-((5-cyclopropyl-1H-pyrazol-3-yl)amino)-1-oxopropan-2-yl)phenyl)pyridin-2-yl)-4-((S)-3-fluoropyrrolidin-1-yl)but-2-enamide (Isomer-2 of compound-46); |
| 49. | (E)-N-(5-(3-(1-((5-cyclopropyl-1H-pyrazol-3-yl)amino)-1-oxopropan-2-yl)phenyl)pyridin-2-yl)-4-((R)-3-fluoropyrrolidin-1-yl)but-2-enamide |
| 50. | (E)-N-(5-(3-(1-((5-cyclopropyl-1H-pyrazol-3-yl)amino)-1-oxopropan-2-yl)phenyl)pyridin-2-yl)-4-((R)-3-fluoropyrrolidin-1-yl)but-2-enamide (Isomer-1 of compound-49); |
| 51. | (E)-N-(5-(3-(1-((5-cyclopropyl-1H-pyrazol-3-yl)amino)-1-oxopropan-2-yl)phenyl)pyridin-2-yl)-4-((R)-3-fluoropyrrolidin-1-yl)but-2-enamide (Isomer-2 of compound-49); |
| 52. | (E)-N-(5-(3-(1-((5-cyclopropyl-1H-pyrazol-3-yl)amino)-1-oxopropan-2-yl)phenyl)pyridin-2-yl)-4-(pyrrolidin-1-yl)but-2-enamide; |
| 53. | (E)-N-(5-(3-(1-((5-cyclopropyl-1H-pyrazol-3-yl)amino)-1-oxopropan-2-yl)phenyl)pyridin-2-yl)-4-(pyrrolidin-1-yl)but-2-enamide (Isomer-1 of compound-52); |
| 54. | (E)-N-(5-(3-(1-((5-cyclopropyl-1H-pyrazol-3-yl)amino)-1-oxopropan-2-yl)phenyl)pyridin-2-yl)-4-(pyrrolidin-1-yl)but-2-enamide (Isomer-2 of compound-52); |
| 55. | (E)-N-(5-(3-(1-((5-cyclopropyl-1H-pyrazol-3-yl)amino)-1-oxopropan-2-yl)phenyl)pyridin-2-yl)-4-(diethylamino)but-2-enamide; |
| 56. | (E)-N-(5-(3-(1-((5-cyclopropyl-1H-pyrazol-3-yl)amino)-3-methyl-1-oxobutan-2-yl)phenyl)pyridin-2-yl)-4-(dimethylamino)but-2-enamide; |
| 57. | (E)-N-(5-(3-(1-((5-cyclopropyl-1H-pyrazol-3-yl)amino)-1-oxopropan-2-yl)phenyl)pyridin-2-yl)-4-(3-fluoropiperidin-1-yl)but-2-enamide; |
| 58. | (E)-N-(6-(3-(1-((5-cyclopropyl-1H-pyrazol-3-yl)amino)-1-oxopropan-2-yl)phenyl)-2-fluoropyridin-3-yl)-4-morpholinobut-2-enamide; |

| Compound No. | IUPAC name |
|---|---|
| 59. | (E)-N-(5-(3-(1-((5-cyclopropyl-1H-pyrazol-3-yl)amino)-1-oxopropan-2-yl)phenyl)-6-fluoropyridin-2-yl)-4-morpholinobut-2-enamide; |
| 60. | (E)-N-(5-(3-(1-((5-cyclopropyl-1H-pyrazol-3-yl)amino)-1-oxopropan-2-yl)phenyl)pyridin-3-yl)-4-morpholinobut-2-enamide; |
| 61. | (E)-N-(3'-(1-((5-cyclopropyl-1H-pyrazol-3-yl)amino)-1-oxopropan-2-yl)-[1,1'-biphenyl]-3-yl)-4-morpholinobut-2-enamide; |
| 62. | (E)-N-(5-(3-(1-((5-cyclopropyl-1H-pyrazol-3-yl)amino)-1-oxopropan-2-yl)phenyl)pyridin-2-yl)-4-(methoxy(methyl)amino)but-2-enamide; |
| 63. | (E)-N-(5-(3-(1-((5-cyclopropyl-1H-pyrazol-3-yl)amino)-1-oxopropan-2-yl)phenyl)-3-fluoropyridin-2-yl)-4-morpholinobut-2-enamide; |
| 64. | (E)-N-(6-(3-(1-((5-cyclopropyl-1H-pyrazol-3-yl)amino)-1-oxopropan-2-yl)phenyl)-2-fluoropyridin-3-yl)-4-(3-fluoropyrrolidin-1-yl)but-2-enamide; |
| 65. | N-(3'-(1-((5-cyclopropyl-1H-pyrazol-3-yl)amino)-1-oxopropan-2-yl)-3-methoxy-[1,1'-biphenyl]-4-yl)acrylamide; |
| 66. | N-(3'-(1-((5-cyclopropyl-1H-pyrazol-3-yl)amino)-1-oxopropan-2-yl)-3-methyl-[1,1'-biphenyl]-4-yl)acrylamide; |
| 67. | N-(3'-(1-((5-cyclopropyl-1H-pyrazol-3-yl)amino)-1-oxopropan-2-yl)-3,5-dimethyl-[1,1'-biphenyl]-4-yl)acrylamide; |
| 68. | (E)-N-(5-(3-(1-((5-cyclopropyl-1H-pyrazol-3-yl)amino)-1-oxopropan-2-yl)phenyl)pyridin-2-yl)-4-((2-methoxyethyl)(methyl)amino)but-2-enamide; |
| 69. | (E)-N-(5-(3-(1-((5-cyclopropyl-1H-pyrazol-3-yl)amino)-1-oxopropan-2-yl)phenyl)pyridin-2-yl)-4-(1H-imidazol-1-yl)but-2-enamide; |
| 70. | (E)-N-(5-(3-(1-((5-cyclopropyl-1H-pyrazol-3-yl)amino)-1-oxopropan-2-yl)phenyl)pyridin-2-yl)-4-((S)-2-(methoxymethyl)pyrrolidin-1-yl)but-2-enamide; |
| 71. | (E)-N-(5-(3-(1-((5-cyclopropyl-1H-pyrazol-3-yl)amino)-1-oxopropan-2-yl)phenyl)pyridin-2-yl)-4-((S)-2-(methoxymethyl)pyrrolidin-1-yl)but-2-enamide (Isomer-1 of compound-70); |
| 72. | (E)-N-(5-(3-(1-((5-cyclopropyl-1H-pyrazol-3-yl)amino)-1-oxopropan-2-yl)phenyl)pyridin-2-yl)-4-((S)-2-(methoxymethyl)pyrrolidin-1-yl)but-2-enamide (Isomer-2 of compound-70); |
| 73. | N-(3'-(1-((5-cyclopropyl-1H-pyrazol-3-yl)amino)-1-oxopropan-2-yl)-2-methoxy-[1,1'-biphenyl]-4-yl)acrylamide; |
| 74. | N-((5-(3-(1-((5-cyclopropyl-1H-pyrazol-3-yl)amino)-1-oxopropan-2-yl)phenyl)pyridin-2-yl)methyl)acrylamide; |
| 75. | N-(3'-(1-((5-cyclopropyl-1H-pyrazol-3-yl)amino)-1-oxopropan-2-yl)-2-methyl-[1,1'-biphenyl]-4-yl)acrylamide; |
| 76. | 2-(3-(1-acryloylindolin-5-yl)phenyl)-N-(5-cyclopropyl-1H-pyrazol-3-yl)propanamide; |
| 77. | (E)-N-(5-(3-(1-((5-cyclopropyl-1H-pyrazol-3-yl)amino)-1-oxopropan-2-yl)phenyl)pyridin-2-yl)-4-((2S,4S)-4-fluoro-2-(methoxymethyl)pyrrolidin-1-yl)but-2-enamide; |
| 78. | (E)-4-(3-cyanopyrrolidin-1-yl)-N-(5-(3-(1-((5-cyclopropyl-1H-pyrazol-3-yl)amino)-1-oxopropan-2-yl)phenyl)pyridin-2-yl)but-2-enamide; |
| 79. | N-(6-(3-(1-((5-cyclopropyl-1H-pyrazol-3-yl)amino)-1-oxopropan-2-yl)phenyl)pyrazin-2-yl)acrylamide; |
| 80. | (E)-N-(3'-(1-((5-cyclopropyl-1H-pyrazol-3-yl)amino)-1-oxopropan-2-yl)-3-fluoro-[1,1'-biphenyl]-4-yl)-4-((S)-3-fluoropyrrolidin-1-yl)but-2-enamide; |
| 81. | methyl ((E)-4-((5-(3-(1-((5-cyclopropyl-1H-pyrazol-3-yl)amino)-1-oxopropan-2-yl)phenyl)pyridin-2-yl)amino)-4-oxobut-2-en-1-yl)-L-prolinate; |
| 82. | (E)-4-((S)-2-(cyanomethyl)pyrrolidin-1-yl)-N-(5-(3-(1-((5-cyclopropyl-1H-pyrazol-3-yl)amino)-1-oxopropan-2-yl)phenyl)pyridin-2-yl)but-2-enamide; |
| 83. | 4-acrylamido-N-(3-(5-ethyl-1H-pyrazol-3-yl)amino)phenyl)benzamide; |
| 84. | (E)-N-(5-cyclopropyl-1H-pyrazol-3-yl)-2-(3-(1-(4-(dimethylamino)but-2-enoyl)-1,2,3,6-tetrahydropyridin-4-yl)phenyl)propanamide; |
| 85. | (E)-N-(5-cyclopropyl-1H-pyrazol-3-yl)-2-(3-(1-(4-(dimethylamino)but-2-enoyl)piperidin-4-yl)phenyl)propanamide; |
| 86. | N-(3'-(2-((5-methyl-1H-pyrazol-3-yl)amino)-2-oxoethyl)-[1,1'-biphenyl]-4-yl)acrylamide; |
| 87. | N-(3'-(1-((5-ethyl-1H-pyrazol-3-yl)amino)-1-oxopropan-2-yl)-[1,1'-biphenyl]-4-yl)acrylamide; |
| 88. | N-(3'-(1-((5-(tert-butyl)-1H-pyrazol-3-yl)amino)-1-oxopropan-2-yl)-[1,1'-biphenyl]-4-yl)acrylamide; |
| 89. | (E)-N-(3-((1H-indazol-3-yl)amino)phenyl)-4-(4-(dimethylamino)but-2-enamido)benzamide; |
| 90. | N-(3'-(1-((1H-indazol-3-yl)amino)-1-oxopropan-2-yl)-[1,1'-biphenyl]-4-yl)acrylamide; |
| 91. | (E)-N-(3'-(1-((1H-indazol-3-yl)amino)-1-oxopropan-2-yl)-[1,1'-biphenyl]-4-yl)-4-(dimethylamino)but-2-enamide; |
| 92. | (E)-N-(6-(3-(1-((5-cyclopropyl-1H-pyrazol-3-yl)amino)-1-oxopropan-2-yl)phenyl)pyrazin-2-yl)-4-(pyrrolidin-1-yl)but-2-enamide; |
| 93. | (S,E)-N-(5-(3-(1-((5-cyclopropyl-1H-pyrazol-3-yl)amino)-1-oxopropan-2-yl)phenyl)pyridin-2-yl)-4-morpholinobut-2-enamide; |
| 94. | (E)-N-(5-cyclopropyl-1H-pyrazol-3-yl)-1-(3-(6-(4-(pyrrolidin-1-yl)but-2-enamido)pyridin-3-yl)phenyl)cyclopropane-1-carboxamide; and |
| 95. | (E)-N-(5-(3-(1-((5-cyclopropyl-1H-pyrazol-3-yl)amino)-2-methyl-1-oxopropan-2-yl)phenyl)pyridin-2-yl)-4-(pyrrolidin-1-yl)but-2-enamide; | or a pharmaceutically acceptable salt or a stereoisomer thereof.

In certain embodiments, the present invention provides a compound selected from the group consisting of:

| Compound No. | IUPAC name |
|---|---|
| 96. | (E)-N-(5-(3-(1-((5-cyclopropyl-1H-pyrazol-3-yl)amino)-3-methyl-1-oxobutan-2-yl)phenyl)pyridin-2-yl)-4-(pyrrolidin-1-yl)but-2-enamide; |
| 97. | (E)-N-(5-(3-(1-((5-cyclopropyl-1H-pyrazol-3-yl)amino)-3-methyl-1-oxobutan-2-yl)phenyl)pyridin-2-yl)-4-(3-fluoropyrrolidin-1-yl)but-2-enamide; |
| 98. | (E)-N-(5-(3-(1-((5-cyclopropyl-1H-pyrazol-3-yl)amino)-3-methyl-1-oxobutan-2- |

| Compound No. | IUPAC name |
|---|---|
| | yl)phenyl)pyridin-2-yl)-4-(3-hydroxypyrrolidin-1-yl)but-2-enamide; |
| 99. | (E)-N-(5-(3-(1-((5-cyclopropyl-1H-pyrazol-3-yl)amino)-3-methyl-1-oxobutan-2-yl)phenyl)pyridin-2-yl)-4-(piperidin-1-yl)but-2-enamide; |
| 100. | (E)-N-(5-(3-(1-((5-cyclopropyl-1H-pyrazol-3-yl)amino)-3-methyl-1-oxobutan-2-yl)phenyl)pyridin-2-yl)-4-(3-fluoropiperidin-1-yl)but-2-enamide; |
| 101. | (E)-N-(5-(3-(1-((5-cyclopropyl-1H-pyrazol-3-yl)amino)-3-methyl-1-oxobutan-2-yl)phenyl)pyridin-2-yl)-4-(3-hydroxypiperidin-1-yl)but-2-enamide; |
| 102. | (E)-N-(5-(3-(1-((5-cyclopropyl-1H-pyrazol-3-yl)amino)-3-methyl-1-oxobutan-2-yl)phenyl)pyridin-2-yl)-4-(4-fluoropiperidin-1-yl)but-2-enamide; |
| 103. | (E)-N-(5-(3-(1-((5-cyclopropyl-1H-pyrazol-3-yl)amino)-3-methyl-1-oxobutan-2-yl)phenyl)pyridin-2-yl)-4-(4-hydroxy-4-methylpiperidin-1-yl)but-2-enamide; |
| 104. | (E)-N-(5-(3-(1-((5-cyclopropyl-1H-pyrazol-3-yl)amino)-3-methyl-1-oxobutan-2-yl)phenyl)pyridin-2-yl)-4-(4,4-difluoropiperidin-1-yl)but-2-enamide; |
| 105. | (E)-N-(5-(3-(1-((5-cyclopropyl-1H-pyrazol-3-yl)amino)-3-methyl-1-oxobutan-2-yl)phenyl)pyridin-2-yl)-4-(diethylamino)but-2-enamide; |
| 106. | (E)-N-(1-(3-(1-((5-cyclopropyl-1H-pyrazol-3-yl)amino)-1-oxopropan-2-yl)phenyl)piperidin-4-yl)-4-(dimethylamino)but-2-enamide; |
| 107. | (E)-N-(3-(1-((5-cyclopropyl-1H-pyrazol-3-yl)amino)-1-oxopropan-2-yl)phenyl)-1-methyl-1H-pyrazol-5-yl)-4-(dimethylamino)but-2-enamide; |
| 108. | (E)-N-(5-cyclopropyl-1H-pyrazol-3-yl)-2-(3-(4-(4-(dimethylamino)but-2-enoyl)piperazin-1-yl)phenyl)propanamide; |
| 109. | 3-(1-((5-cyclopropyl-1H-pyrazol-3-yl)amino)-1-oxopropan-2-yl)phenyl (E)-4-(4-(dimethylamino)but-2-enoyl)piperazine-1-carboxylate; |
| 110. | (E)-4-((S)-2-cyanopyrrolidin-1-yl)-N-(5-(3-((S)-1-((5-cyclopropyl-1H-pyrazol-3-yl)amino)-1-oxopropan-2-yl)phenyl)pyridin-2-yl)but-2-enamide; |
| 111. | (E)-4-((2S,4S)-2-(cyanomethyl)-4-fluoropyrrolidin-1-yl)-N-(5-(3-((S)-1-((5-cyclopropyl-1H-pyrazol-3-yl)amino)-1-oxopropan-2-yl)phenyl)pyridin-2-yl)but-2-enamide; |
| 112. | (E)-N-(3'-((S)-1-((5-cyclopropyl-1H-pyrazol-3-yl)amino)-1-oxopropan-2-yl)-3-fluoro-[1,1'-biphenyl]-4-yl)-4-((S)-2-(methoxymethyl)pyrrolidin-1-yl)but-2-enamide; |
| 113. | (E)-N-(3-(1-((5-cyclopropyl-1H-pyrazol-3-yl)amino)-1-oxopropan-2-yl)phenyl)-4-(4-(dimethylamino)but-2-enoyl)morpholine-2-carboxamide; |
| 114. | (E)-N-(3-(1-((5-cyclopropyl-1H-pyrazol-3-yl)amino)-1-oxopropan-2-yl)phenyl)-4-(4-(dimethylamino)but-2-enamido)tetrahydro-2H-pyran-3-carboxamide; |
| 115. | (E)-N-(3-(1-((5-cyclopropyl-1H-pyrazol-3-yl)amino)-1-oxopropan-2-yl)phenyl)-1-(4-(dimethylamino)but-2-enoyl)pyrrolidine-2-carboxamide; |
| 116. | (E)-N-(3-(1-((5-cyclopropyl-1H-pyrazol-3-yl)amino)-1-oxopropan-2-yl)phenyl)-1-(4-(dimethylamino)but-2-enoyl)piperidine-2-carboxamide; |
| 117. | (E)-N-(3-(1-((5-cyclopropyl-1H-pyrazol-3-yl)amino)-1-oxopropan-2-yl)phenyl)-1-(4-(dimethylamino)but-2-enoyl)piperidine-3-carboxamide; |
| 118. | (E)-N-(3-(1-((5-cyclopropyl-1H-pyrazol-3-yl)amino)-1-oxopropan-2-yl)phenyl)-4-(dimethylamino)but-2-enamide; |
| 119. | (E)-N-(4-(1-((5-cyclopropyl-1H-pyrazol-3-yl)amino)-1-oxopropan-2-yl)phenyl)-4-(dimethylamino)but-2-enamide; |
| 120. | (E)-N-(2-(1-((5-cyclopropyl-1H-pyrazol-3-yl)amino)-1-oxopropan-2-yl)phenyl)-4-(dimethylamino)but-2-enamide; |
| 121. | 2-(1-((5-cyclopropyl-1H-pyrazol-3-yl)amino)-1-oxopropan-2-yl)phenyl (E)-4-(4-(dimethylamino)but-2-enoyl)piperazine-1-carboxylate; |
| 122. | 4-(1-((5-cyclopropyl-1H-pyrazol-3-yl)amino)-1-oxopropan-2-yl)phenyl (E)-4-(4-(dimethylamino)but-2-enoyl)piperazine-1-carboxylate; |
| 123. | (E)-N-(5-(3-(1-((5-cyclopropyl-1H-pyrazol-3-yl)amino)-1-oxopropan-2-yl)phenyl)-6-fluoropyridin-2-yl)-4-(dimethylamino)but-2-enamide; |
| 124. | (E)-N-(3-(1-((5-cyclopropyl-1H-pyrazol-3-yl)amino)-1-oxopropan-2-yl)phenyl)pyridin-4-yl)-4-morpholinobut-2-enamide; |
| 125. | (E)-N-(3'-(1-((5-cyclopropyl-1H-pyrazol-3-yl)amino)-1-oxopropan-2-yl)-[1,1'-biphenyl]-2-yl)-4-morpholinobut-2-enamide; |
| 126. | (E)-N-(3-(1-((5-cyclopropyl-1H-pyrazol-3-yl)amino)-1-oxopropan-2-yl)phenyl)-4-(4-(dimethylamino)but-2-enoyl)piperazine-1-carboxamide; |
| 127. | (E)-N-(6-(3-((S)-1-((5-cyclopropyl-1H-pyrazol-3-yl)amino)-1-oxopropan-2-yl)phenyl)pyridin-2-yl)-4-((S)-3-fluoropyrrolidin-1-yl)but-2-enamide; |
| 128. | (E)-N-(6-(3-((S)-1-((5-cyclopropyl-1H-pyrazol-3-yl)amino)-1-oxopropan-2-yl)phenyl)pyrazin-2-yl)-4-((S)-3-fluoropyrrolidin-1-yl)but-2-enamide; |
| 129. | (E)-N-(5-(3-((S)-1-((5-cyclopropyl-1H-pyrazol-3-yl)amino)-1-oxopropan-2-yl)phenyl)pyridin-2-yl)-4-((S)-3-(trifluoromethyl)pyrrolidin-1-yl)but-2-enamide; |
| 130. | (E)-4-((2S,4S)-2-cyano-4-fluoropyrrolidin-1-yl)-N-(5-(3-((S)-1-((5-cyclopropyl-1H-pyrazol-3-yl)amino)-1-oxopropan-2-yl)phenyl)pyridin-2-yl)but-2-enamide; |
| 131. | (E)-4-((S)-2-cyanopyrrolidin-1-yl)-N-(5-(3-((S)-1-((5-cyclopropyl-1H-pyrazol-3-yl)amino)-1-oxopropan-2-yl)phenyl)pyridin-2-yl)but-2-enamide; |
| 132. | (S,E)-N-(3'-(1-((5-cyclopropyl-1H-pyrazol-3-yl)amino)-1-oxopropan-2-yl)-3-fluoro-[1,1'-biphenyl]-4-yl)-4-(diethylamino)but-2-enamide; |
| 133. | (E)-N-(4-(3-((5-cyclopropyl-1H-pyrazol-3-yl)amino)-4-methylisoquinolin-6-yl)phenyl)-4-(dimethylamino)but-2-enamide; |
| 134. | (E)-N-(4-(4-(1-((5-cyclopropyl-1H-pyrazol-3-yl)amino)-1-oxopropan-2-yl)pyridin-2-yl)phenyl)-4-(dimethylamino)but-2-enamide; |
| 135. | (E)-N-(4-(3-(1-((5-cyclopropyl-1H-pyrazol-3-yl)amino)-1-oxopropan-2-yl)phenyl)cyclohexyl)-4-(dimethylamino)but-2-enamide; |
| 136. | (E)-N-(3-(3-(1-((5-cyclopropyl-1H-pyrazol-3-yl)amino)-1-oxopropan-2-yl)phenyl)cyclohexyl)-4-(dimethylamino)but-2-enamide; |

-continued

| Compound No. | IUPAC name |
|---|---|
| 137. | (E)-4-(dimethylamino)-N-(3'-(1-oxo-1-(pyrazolo[1,5-a]pyridin-2-ylamino)propan-2-yl)-[1,1'-biphenyl]-4-yl)but-2-enamide; |
| 138. | (E)-N-(3'-(3-((5-cyclopropyl-1H-pyrazol-3-yl)amino)-1,1,1-trifluoro-3-oxopropan-2-yl)-[1,1'-biphenyl]-4-yl)-4-(dimethylamino)but-2-enamide; |
| 139. | (E)-N-(3'-(1-((5-cyclopentyl-1H-pyrazol-3-yl)amino)-1-oxopropan-2-yl)-[1,1'-biphenyl]-4-yl)-4-(dimethylamino)but-2-enamide; |
| 140. | (E)-N-(3'-(1-((5-cyclohexyl-1H-pyrazol-3-yl)amino)-1-oxopropan-2-yl)-[1,1'-biphenyl]-4-yl)-4-(dimethylamino)but-2-enamide; |
| 141. | (E)-N-(3'-(1-((5-cyclopropyl-4-methyl-1H-pyrazol-3-yl)amino)-1-oxopropan-2-yl)-[1,1'-biphenyl]-4-yl)-4-(dimethylamino)but-2-enamide; |
| 142. | (E)-N-(3'-(1-((5-cyclopropyl-4-(pyridin-2-yl)-1H-pyrazol-3-yl)amino)-1-oxopropan-2-yl)-[1,1'-biphenyl]-4-yl)-4-(dimethylamino)but-2-enamide; and |
| 143. | (E)-N-(3'-(3-(5-cyclopropyl-1H-pyrazol-3-yl)-1-methylureido)-[1,1'-biphenyl]-4-yl)-4-(dimethylamino)but-2-enamide; | or a pharmaceutically acceptable salt or a stereoisomer thereof.

In certain embodiments, when $R_1$ is hydrogen, the compounds of the present invention are known to rapidly equilibrate, in solution, as admixtures of both tautomers:

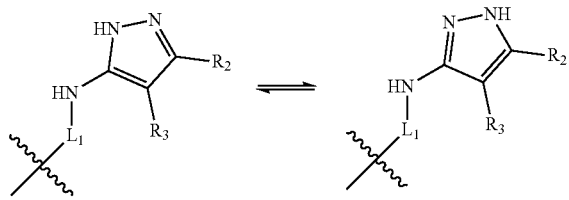

Accordingly, in the present invention, where only one tautomer is indicated for the compounds of formula (I), is also within the scope of the present invention, unless specifically noted otherwise.

In certain embodiments, the present invention provides a pharmaceutical composition comprising a compound of formula (I), or a pharmaceutically acceptable salt thereof or a stereoisomer thereof as described herein and at least one pharmaceutically acceptable excipient (such as a pharmaceutically acceptable carrier or diluent). Preferably, the pharmaceutical composition comprises a therapeutically effective amount of at least one compound described herein. The compounds described in the present invention may be associated with a pharmaceutically acceptable excipient (such as a carrier or a diluent) or be diluted by a carrier or enclosed within a carrier which can be in the form of a capsule, sachet, paper or other container.

In yet another embodiment, the compounds of the present invention are kinase inhibitors. In certain embodiments, the compounds of the present invention are selective CDK inhibitors (e.g., being more active in inhibiting a CDK than a non-CDK kinase). In certain embodiments, the compounds of the present invention are selective CDK7 inhibitors (e.g., being more active in inhibiting CDK7 than a non-CDK7 kinase).

In another embodiment, the present invention provides pharmaceutical composition for use in treating and/or preventing a disease and/or disorder associated with aberrant activity of selective transcritptional CDKs.

In another embodiment, the present invention provides pharmaceutical composition for use in treating a subject suffering from diseases and/or disorder associated with aberrant activity of selective transcriptional CDKs.

In another embodiment, the present invention provides a method of inhibiting selective transcriptional CDKs in a subject, comprising administering to the subject in need thereof a therapeutically effective amount of a compound of the present invention.

In another embodiment, the present invention provides a method of treating diseases and/or disorder mediated by selective transcriptional CDKs in a subject comprising administering to the subject in need thereof a therapeutically effective amount of a compound of the present invention.

In an embodiment, the present invention provides pharmaceutical composition comprising the compound of formula (I), for use in treating a subject suffering from a disease or condition associated with aberrant activity of selective transcriptional CDKs. In another embodiment, the present invention provides pharmaceutical composition comprising the compound of formula (I), for use in treating a subject suffering from diseases and/or disorder associated with aberrant activity of transcriptional CDK9, CDK12, CDK13 or CDK18.

In another embodiment, the present invention provides pharmaceutical composition comprising the compound of formula (I), for use in treating a subject suffering from diseases and/or disorder associated with aberrant activity of transcriptional CDK7.

In yet another embodiment, the present invention provides a method of treating disorders and/or diseases or condition mediated by selective transcriptional CDKs (CDK9, CDK12, CDK13 or CDK18) in a subject comprising administering a therapeutically effective amount of a compound of the present invention.

In yet another embodiment, the present invention provides a method of treating disorders and/or diseases or condition mediated by transcriptional CDK7 in a subject comprising administering a therapeutically effective amount of a compound of the present invention.

In yet another embodiment, the present invention provides a method of inhibiting selective transcriptional CDKs. In another embodiment, the present invention provides a method of inhibiting particularly transcriptional CDK7, CDK9, CDK12, CDK13 or CDK18; more particularly CDK7, in a subject in need thereof by administering to the subject one or more compounds described herein in the amount effective to cause inhibition of such receptor/kinase.

In another aspect, the present invention relates to methods of inhibiting the activity of a kinase in a biological sample or subject. In certain embodiments, the kinase is a selective transcriptional CDK. In another embodiment, the selective transcriptional CDK is CDK9, CDK12, CDK13 or CDK18. In yet another embodiment, the selective transcriptional CDK is particularly CDK7.

In certain embodiments, the inhibition of the activity of the kinase is irreversible. In other embodiments, the inhibition of the activity of the kinase is reversible.

In certain embodiments, the present invention provides compounds of formula (I) as covalent inhibitors of selective transcriptional CDKs. In yet another embodiment, the present invention provides compounds of formula (I) as covalent inhibitors of transcriptional CDK9, CDK12, CDK13 or CDK18. In yet another embodiment, the present invention provides compounds of formula (I) as covalent inhibitors of transcriptional CDK7.

The compounds of the invention are typically administered in the form of a pharmaceutical composition. Such compositions can be prepared using procedures well known in the pharmaceutical art and comprise at least one compound of the present invention. The pharmaceutical composition of the present invention comprises one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents, solvents and the like.

The pharmaceutical composition can be administered by oral, parenteral or inhalation routes. Examples of the parenteral administration include administration by injection, percutaneous, transmucosal, transnasal and transpulmonary administrations.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters and polyoxyethylene.

The pharmaceutical composition may also include one or more pharmaceutically acceptable auxiliary agents, wetting agents, suspending agents, preserving agents, buffers, sweetening agents, flavouring agents, colorants or any combination of the foregoing.

The pharmaceutical compositions may be in conventional forms, for example, tablets, capsules, solutions, suspensions, injectables or products for topical application. Further, the pharmaceutical composition of the present invention may be formulated so as to provide desired release profile.

Administration of the compounds of the invention, in pure form or in an appropriate pharmaceutical composition, can be carried out using any of the accepted routes of administration of pharmaceutical compositions. The route of administration may be any route which effectively transports the active compound of the present invention to the appropriate or desired site of action. Suitable routes of administration include, but are not limited to, oral, nasal, buccal, dermal, intradermal, transdermal, parenteral, rectal, subcutaneous, intravenous, intraurethral, intramuscular or topical.

Solid oral formulations include, but are not limited to, tablets, capsules (soft or hard gelatin), dragees (containing the active ingredient in powder or pellet form), troches and lozenges.

Liquid formulations include, but are not limited to, syrups, emulsions and sterile injectable liquids, such as suspensions or solutions.

Topical dosage forms of the compounds include ointments, pastes, creams, lotions, powders, solutions, eye or ear drops, impregnated dressings and may contain appropriate conventional additives such as preservatives, solvents to assist drug penetration.

The pharmaceutical compositions of the present invention may be prepared by conventional techniques known in literature.

Suitable doses of the compounds for use in treating the diseases or disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. Mode of administration, dosage forms and suitable pharmaceutical excipients can also be well used and adjusted by those skilled in the art. All changes and modifications are envisioned within the scope of the present invention.

In one embodiment, the compounds as disclosed in the present invention are formulated for pharmaceutical administration.

Yet another embodiment of the present invention provides use of the compounds as disclosed in the present invention in the treatment and prevention of diseases and/or disorder associated with the aberrant activity of selective transcriptional CDKs, particularly the selective transcriptional CDK is CDK7, CDK9, CDK12, CDK13 or CDK18; more particularly CDK7.

Yet another embodiment of the present invention provides use of the compound or a pharmaceutically acceptable salt thereof, in treating and/or preventing a disease for which the symptoms thereof are treated, improved, diminished and/or prevented by inhibition of selective transcriptional CDKs, particularly the selective transcriptional CDK is CDK7, CDK9, CDK12, CDK13 or CDK18; more particularly CDK7.

According to yet another embodiment, the selective transcriptional CDK mediated disorder and/or disease or condition is proliferative disease or disorder or condition.

In yet another embodiment, the diseases and/or disorder mediated by selective transcriptional CDKs is selected from, but not limited to the group consisting of a cancer, an inflammatory disorder, an auto-inflammatory disorder or an infectious disease.

In other embodiments, the proliferative disease to be treated or prevented using the compounds of formula (I) will typically be associated with aberrant activity of CDKs, more particularly with CDK7, CDK9, CDK12, CDK13 or 18. Aberrant activity of CDK7, CDK9, CDK12, CDK13 or CDK18 may be an elevated and/or an inappropriate (e.g., abnormal) activity of CDK7, CDK9, CDK12, CDK13 or CDK18. In certain embodiments, CDK7, CDK9, CDK12, CDK13 or CDK18 are not overexpressed, and the activity of CDK7, CDK9, CDK12, CDK13 or CDK18 are elevated and/or inappropriate. In certain other embodiments, CDK7, CDK9, CDK12, CDK13 or CDK18 are overexpressed, and the activity of CDK7, CDK9, CDK12, CDK13 or CDK18 are elevated and/or inappropriate. The compounds of formula (I), and pharmaceutically acceptable salts or stereoisomers, and compositions thereof, inhibit the activity of CDK7, CDK9, CDK12, CDK13 or CDK18 and have been useful in treating and/or preventing proliferative diseases.

According to yet another embodiment, the compounds of the present invention are expected to be useful in the therapy of proliferative diseases such as viral diseases, fungal diseases, neurological/neurodegenerative disorders, autoimmune, inflammation, arthritis, anti-proliferative (e.g., ocular retinopathy), neuronal, alopecia and cardiovascular diseases.

According to yet another embodiment, the compounds of the present invention are useful in the treatment of a variety of cancers, including but not limited to carcinoma, including that of the breast, liver, lung, colon, kidney, bladder, including small cell lung cancer, non-small cell lung cancer, head and neck, thyroid, esophagus, stomach, pancreas, ovary, gall bladder, cervix, prostate and skin, including squamous cell carcinoma; hematopoietic tumors of lymphoid lineage, including leukemia, acute lymphoblastic leukemia, acute lymphocytic leukemia, Hodgkins lymphoma, non-Hodgkins lymphoma, B-cell lymphoma, T-cell lymphoma, hairy cell lymphoma, myeloma, mantle cell lymphoma and Burkett's lymphoma; hematopoietic tumors of myeloid lineage, including acute and chronic myelogenous leukemias, myelodysplastic syndrome and promyelocytic leukemia; tumors of masenchymal origin, including fibrosarcoma and rhabdomyosarcoma; tumors of the central and peripheral nervous system, including astrocytoma, neuroblastoma, glioma and schwannomas; and other tumors, including seminoma, melanoma, osteosarcoma, teratocarcinoma, keratocanthoma, xenoderoma pigmentosum, thyroid follicular cancer and Kaposi's sarcoma.

According to yet another embodiment, the subject is a mammal including human.

According to yet another embodiment, the present invention provides compounds or pharmaceutically acceptable salts or stereoisomers thereof, for use as a medicament.

According to yet another embodiment, the invention provides the use of the compounds of the present invention in the manufacture of a medicament.

According to yet another embodiment, the present invention provides compounds or pharmaceutically acceptable salts or stereoisomers thereof, for use in the treatment of cancer.

According to yet another embodiment, the invention provides the use of the compounds of the present invention in the manufacture of a medicament for the treatment of diseases and/or disorder associated with the aberrant activity of selective transcriptional CDKs.

In yet another embodiment, the invention provides the use of the compounds of the present invention in the manufacture of a medicament for the treatment of cancer.

According to yet another embodiment, the present invention provides compounds for use as a medicament for treating a subject suffering from diseases and/or disorder associated with aberrant activity of selective transcriptional CDKs.

According to yet another embodiment, the present invention comprises administering to the subject in need thereof a therapeutically effective amount of a compound of the present invention along with one or more additional chemotherapeutic agents independently selected from anti-proliferative agents, anti-cancer agents, immunosuppressant agents and pain-relieving agents.

The method(s) of treatment of the present invention comprises administering a safe and effective amount of a compound according to formula (I) or a pharmaceutically acceptable salt thereof to a patient (particularly a human) in need thereof.

Compounds of the invention are indicated both in the therapeutic and/or prophylactic treatment of the above-mentioned conditions. For the above-mentioned therapeutic uses the dosage administered will, of course, vary with the compound employed, the mode of administration, the treatment desired and the disorder or disease indicated.

The compounds of the present invention may be used as single drug or as a pharmaceutical composition in which the compound is mixed with various pharmacologically acceptable materials.

According to one embodiment, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, 36Cl, $^{123}$I and $^{125}$I. Isotopically labeled compounds of the present invention can generally be prepared by following procedures analogous to those disclosed in the schemes and/or in the examples herein below, by substituting an isotopically labeled reagent for a non-isotopically labeled reagent.

The following abbreviations refer respectively to the definitions herein:LDA (Lithium diisopropylamide); $K_2CO_3$ (Potassium carbonate); KOAc (Potassium acetate); EtOH (Ethanol); $NH_3$ solution (Ammonia solution); Prep TLC (Preparative Thin layer Chromatography); rt (Retention time); RT (Room temperature); DMF (Dimethylformamide); h (hour); NaOH (Sodium hydroxide); HATU (1-[Bis(dimethylamino)methylene]-1H-1,2,3-triazolo[4,5-b]pyridinium 3-oxid-hexafluorophosphate); LC-MS (Liquid chromatography mass spectroscopy); HCl (Hydrochloric acid); THF (tetrahydrofuran); DCM (Dichloromethane); TFA (Trifluoroacetic acid); TLC (Thin layer chromatography); DIPEA (Diisopropyl Ethyl amine); $Na_2SO_4$ (Sodium sulphate); $ACN/CH_3CN$ (Acetonitrile); $PdCl_2$(dppf)-DCM (1,1'-Bis(diphenylphosphino)ferrocene]dichloropalladium (II).dichloromethane complex); $Bpin_2$ (Bis(pinacolato)diboron); DMSO-$d_6$ (Dimethyl sulfoxide-d); $Boc_2O$ (Ditertbutyl dicarbonate); HPLC (High pressure liquid chromatography); $NaHCO_3$ (Sodium bicarbonate); $Pd_2(dba)_3$ (Tris(dibenzylideneacetone)dipalladium(0)); TEA (triethyl amine), $Cs_2CO_3$ (Cesium carbonate); MHz (mega hertz); s (singlet); m (multiplet); and d (doublet).

General Modes of Preparation:

Following general guidelines apply to all experimental procedures described here. Until otherwise stated, experiments are performed under positive pressure of nitrogen, temperature described are the external temperature (i.e. oil bath temperature). Reagents and solvents received from vendors are used as such without any further drying or purification. Molarities mentioned here for reagents in solutions are approximate as it was not verified by a prior titration with a standard. All reactions are stirred under magnetic stir bar. Cooling to minus temperature was done by acetone/dry ice or wet ice/salts. Magnesium sulfate and sodium sulfate were used as solvent drying agent after reaction work up and are interchangeable. Removing of solvents under reduced pressure or under vacuummeans distilling of solvents in rotary evaporator.

Compounds of this invention may be made by synthetic chemical processes, examples of which are shown herein. It is meant to be understood that the order of the steps in the processes may be varied, that reagents, solvents and reaction conditions may be substituted for those specifically mentioned and that vulnerable moieties may be protected and deprotected, as necessary.

The specifics of the process for preparing compounds of the present invention are detailed in the experimental section.

The present invention shall be illustrated by means of some examples, which are not construed to be viewed as limiting the scope of the invention.

EXPERIMENTAL

Unless otherwise stated, work-up includes distribution of the reaction mixture between the organic and aqueous phases, separation of layers and drying the organic layer over anhydrous sodium sulphate, filtration and evaporation of the solvent. Purification, unless otherwise mentioned, includes purification by silica gel chromatographic techniques, generally using ethyl acetate/petroleum ether mixture of a suitable polarity as the mobile phase.

Analysis for the compounds of the present invention unless mentioned, was conducted in general methods well known to a person skilled in the art. Having described the invention with reference to certain preferred embodiments, other embodiments will become apparent to one skilled in the art from consideration of the specification. The invention is further defined by reference to the following examples, describing in detail the analysis of the compounds of the invention.

It will be apparent to those skilled in the art that many modifications, both to materials and methods, may be practiced without departing from the scope of the invention. Some of the intermediates were taken to next step based on TLC results, without further characterization, unless otherwise specified.

Synthesis of Intermediates

Synthesis of 2-(3-bromophenyl)propanoic Acid

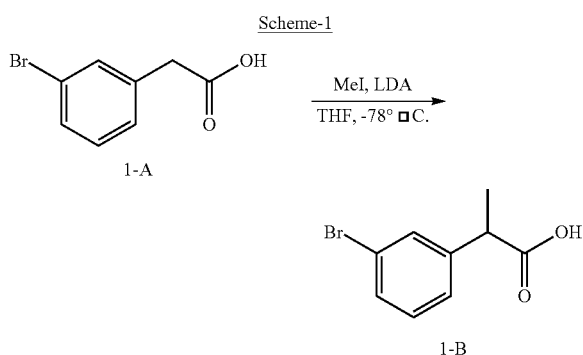

2-(3-bromophenyl)acetic acid (3 g, 13.95 mmol) in THF (15 mL) was added to a solution of 2M LDA (22 mL, 41.8 mmol) at −78° C. over a period of 10 min. The reaction mass was stirred for 1 h at −78° C. followed by the drop wise addition of methyl iodide (6.3 g, 44.6 mmol) over a period of 10 min. The reaction mass was stirred at room temperature for overnight. The reaction mass was quenched with 2N HCl and concentrated under reduced pressure to remove excess amount of THF. The residue was diluted with ether, washed twice with 2N HCl, extracted the ether layer with 10% NaOH. The combined NaOH layer was acidified with 6N HCl, extracted the compound to ether. The ether layer was washed with water followed by brine, dried and concentrated under reduced pressure to afford the crude compound (2.5 g, 78%). LCMS: m/z=229.1 (M+H)$^+$.

Synthesis of 5-cyclopropyl-1-methyl-1H-pyrazol-3-amine

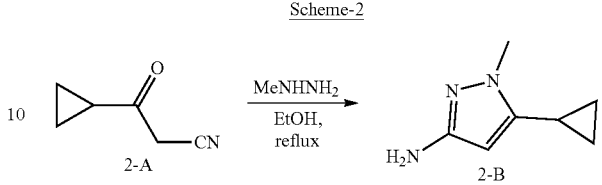

Methyl hydrazine (1 mL) was added to a solution of 3-cyclopropyl-3-oxopropanenitrile (1 g, 9.17 mmol) in ethanol (15 mL). The resulting reaction mass was heated to reflux for 12 h. The reaction mass was quenched with ice cold water and extracted with ethyl acetate. The organic layer was washed with brine, dried over anhydrous sodium sulphate and concentrated under reduced pressure to afford the title compound (1.1 g, 97%) LCMS: m/z=138 (M+H)$^+$.

Synthesis of (E)-N-(5-bromopyridin-2-yl)-4-morpholinobut-2-enamide

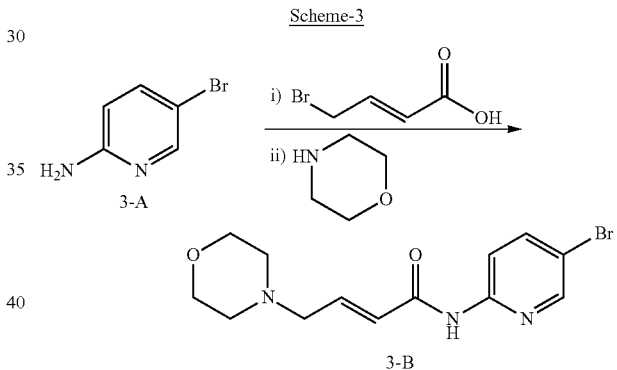

Step-i: (E)-4-bromobut-2-enoic acid (4.5 g, 27.7 mmol) was taken in DCM (30 mL) with catalytic amount of DMF followed by the addition of oxalyl chloride (5 mL). The reaction mass was allowed to stir for 1.5 h at RT, evaporated the solvent under vacuum. The residue was dissolved in DCM and was added to the pre cooled solution of 5-bromopyridin-2-amine (3.0 g, 17.34 mmol) in acetonitrile (50 mL) and DIPEA (11.0 mL, 69.36 mmol) at 0° C. The resulting reaction mixture was stirred for 2 h, added water and extracted with DCM. The combined organic phase was washed with brine, dried over anhydrous Na$_2$SO$_4$, filtered and concentrated under vacuum. The crude was purified by silica gel column chromatography by eluting with 10% methanol in DCM to afford (E)-4-bromo-N-(5-bromopyridin-2-yl)but-2-enamide (1.25 g, 40%), LCMS: m/z=320.9 (M+H)$^+$.

Step-ii: To a stirred solution of (E)-4-bromo-N-(5-bromopyridin-2-yl)but-2-enamide (1.0 g, 3.13 mmol) in acetonitrile (20 mL) was added potassium carbonate (1.0 g, 7.83 mmol) and morpholine (0.39 g, 4.7 mmol) at room temperature. The reaction mixture was heated to 60° C. for about 2 h, concentrated the reaction mixture under vaccum. The crude was purified by neutral alumina column chromatography using 10% methanol in DCM to afford the title compound (0.8 g, 60%), LCMS: m/z=326.1 (M+H)⁺.

Synthesis of 4-acrylamidobenzoic Acid

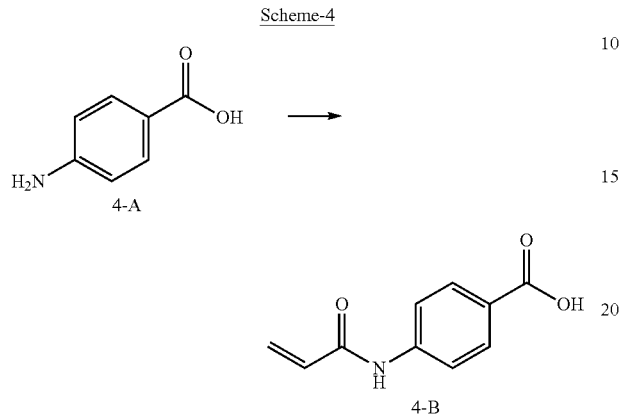

A solution of 4-aminobenzoic acid (1.40 g, 10 mmol) in DMF (10 mL) and pyridine (0.5 ml) was cooled to 0° C. To this solution was added acryloyl chloride (0.94 g, 10 mmol) and the resulting mixture was stirred for 3 hours at RT. The mixture was poured into 200 ml of water and the white solid obtained was filtered, washed with water and ether, dried to afford the title compound which was used in the next step without purification (1.8 g) LCMS: m/z=192.1 (M+H)⁺.

Synthesis of N-(5-bromopyridin-2-yl)acrylamide

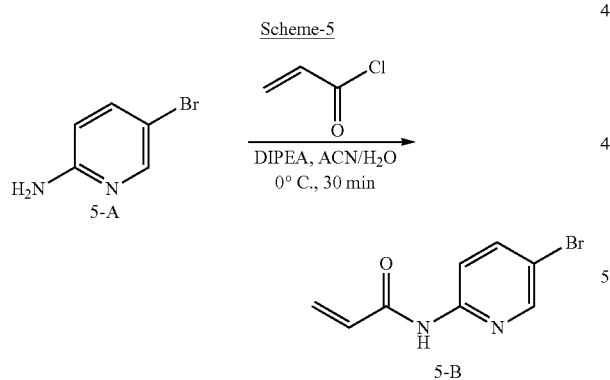

To a solution of of 5-bromopyridin-2-amine (0.5 g, 2.92 mmol) in ACN (20 mL) was added water (2 mL), DIPEA (0.75 g, 5.84 mmol) and acryloyl chloride (0.26 g, 2.92 mmol) at 0° C. After 30 min, the reaction mixture was quenched with ice-water and diluted with EtoAc. The aqueous layer was separated and extracted with EtOAc (2×25 mL). The combined organic phase was washed with brine, dried over Na$_2$SO$_4$, filtered and concentrated. The crude residue was purified by silica gel column by eluting with 10%-30% ethyl acetate-hexane system to afford the title compound (0.3 g, 48%) LCMS: m/z=227.8 (M+H)⁺.

Synthesis of 1-(5-bromoindolin-1-yl)prop-2-en-1-one

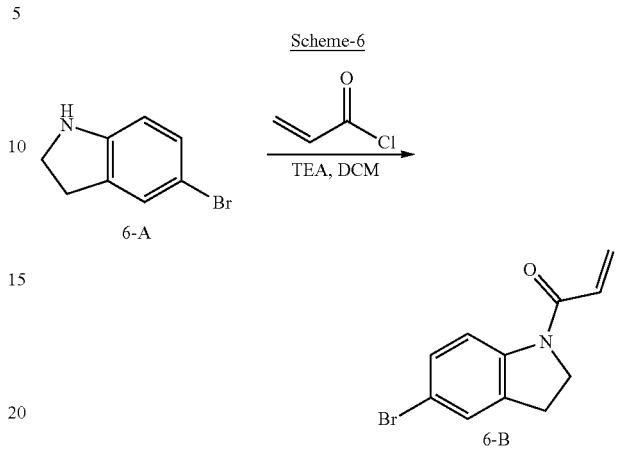

To a solution of 5-bromoindoline (0.5 g, 2.51 mmol) in DCM (5 mL) was added TEA (0.63 mL, 5.02 mmol) and acryloyl chloride (0.23 g, 2.51 mmol) at 0° C. After 30 min, the reaction mixture was quenched with ice-water and diluted with EtOAc. The aqueous layer was separated and extracted with EtOAc (2×25 mL). The combined organic phase was washed with brine, dried over Na$_2$SO$_4$, filtered and concentrated. The crude residue was purified by silica gel column by eluting with 10%-30% ethyl acetate-hexane system to afford the title compound (0.4 g, 63%) LCMS: m/z=253.8 (M+H)⁺.

Synthesis of N-((5-bromopyridin-2-yl)methyl)acrylamide

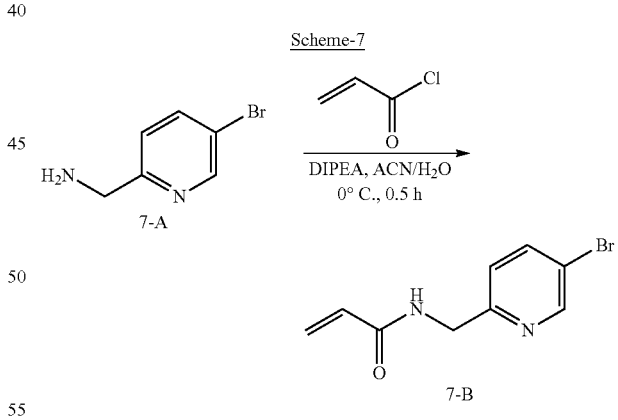

To a solution of (5-bromopyridin-2-yl)methanamine (0.5 g, 2.7 mmol) in ACN (20 mL) was added water (2 mL), DIPEA (0.94 mL, 5.4 mmol) and acryloyl chloride (0.24 g, 2.7 mmol) at 0° C. After 30 min, the reaction mixture was quenched with ice-water and diluted with EtoAc. The aqueous layer was separated and extracted with EtOAc (2×25 mL). The combined organic phase was washed with brine, dried over Na$_2$SO$_4$, filtered and concentrated. The crude residue was purified by silica gel column chromatography by eluting with 0-5% MeOH-DCM to afford the title compound (0.3 g, 46%) LCMS: m/z=240.9 (M+H)⁺.

EXAMPLES

General Synthetic Scheme

Scheme-8

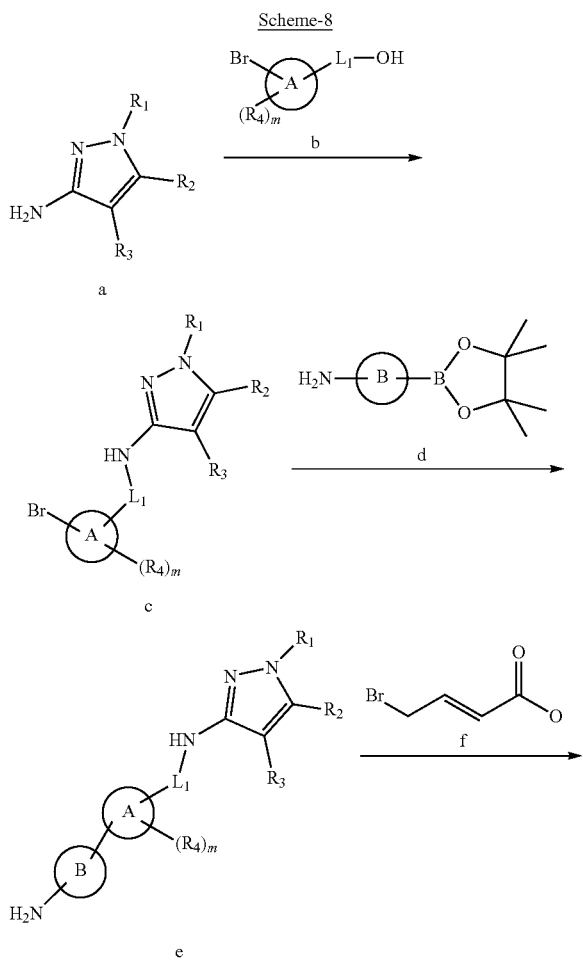

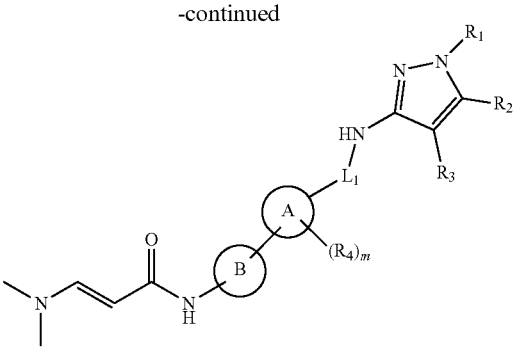

wherein, ring A, ring B, $R_1$, $R_2$, $R_3$, $R_4$, $L_1$ and m are as defined in formula (I);

Some compounds of the present invention may be generally synthesized utilizing the process outlined in Scheme-8. The commercially available or synthesized intermediate-b was converted to corresponding acid chloride in presence of suitable reagents and solvents (DCM, catalytic DMF, oxalyl chloride, RT, 1.5 h) which upon reacting with intermediate-a in presence of suitable reagents and solvents (pyridine, 0° C.-RT, 12 h; or DCM, TEA, 0° C.-RT, 12 h) afforded intermediate-c. Treatment of intermediate-c with intermediate-d (boronic acid or boronate ester) by Suzuki coupling conditions in presence of suitable catalyst such as Pd(dppf)$Cl_2$.DCM or $PdCl_2(PPh_3)_2$, suitable base such as potassium carbonate or cesium carbonate and in the presence of suitable solvent(s) such as 1,4-dioxane and/or water gave intermediate-e. This intermediate-e upon reaction with corresponding acid chloride of intermediate-f for 1 hour at room temperature followed by reaction with 2M N,N-dimethylamine in THF in presence of DIPEA and suitable solvent such as ACN afforded the product of interest.

The present invention is further exemplified, but not limited, by the following examples that illustrate the preparation of compounds according to the invention.

Example-1: Synthesis of (E)-N-(3'-(1-((5-cyclopropyl-1H-pyrazol-3-yl)amino)-1-oxopropan-2-yl)-[1,1'-biphenyl]-4-yl)-4-(dimethylamino)but-2-enamide (Compound-1)

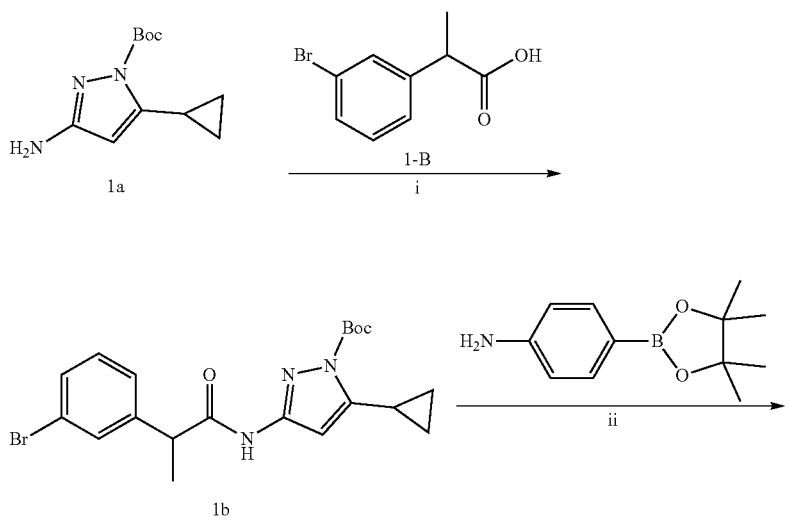

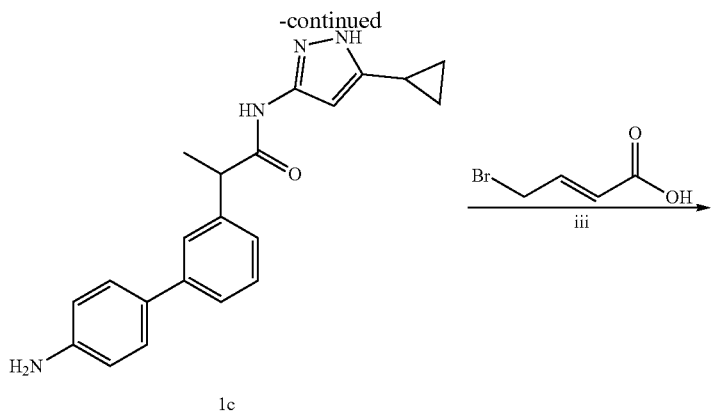

1c

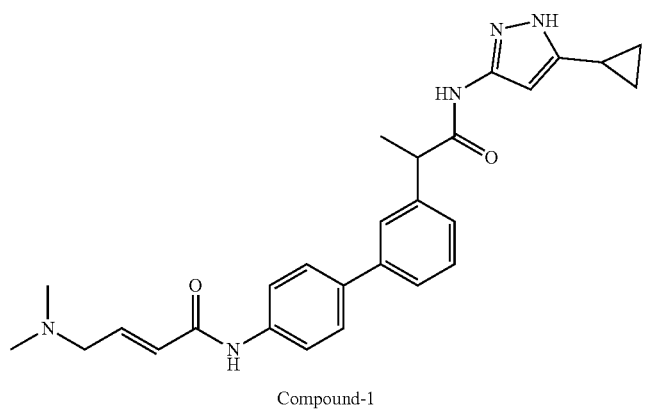

Compound-1

Step-i: Synthesis of tert-butyl 3-(2-(3-bromophenyl)propanamido)-5-cyclopropyl-1H-pyrazole-1-carboxylate 2-(3-bromophenyl)propanoic acid (1 g, 4.36 mmol) was taken in DCM at 0° C. with catalytic amount of DMF and added oxalyl chloride (1.1 g, 8.7 mmol). The reaction mass was stirred at room temperature for 1.5 h. The reaction mass was concentrated under reduced pressure. Re-dissolved the residue in DCM and added to the cooled solution of tert-butyl 3-amino-5-cyclopropyl-1H-pyrazole-1-carboxylate (0.876 g, 3.93 mmol) (synthesis carried outas described in reference *Tetrahedron Letters*, 2005, vol. 46, #6p. 933-935) in pyridine (20 mL) at 0° C. The resultant reaction mass was stirred at room temperature for 12 h. The reaction mass was concentrated under reduced pressure and the residue was dissolved in DCM, washed with saturated $NaHCO_3$ solution and brine. The organic layer was dried over anhydrous sodium sulphate and concentrated under reduced pressure and the crude was purified by silica gel column chromatography by eluting with 15% ethyl acetate-hexane to afford the title compound (0.5 g, 26.45%) LCMS: m/z=336.1 (M-Boc+3).

Step-ii: Synthesis of 2-(4'-amino-[1,1'-biphenyl]-3-yl)-N-(5-cyclopropyl-1H-pyrazol-3-yl)propanamide To a degassed solution of tert-butyl 3-(2-(3-bromophenyl)propanamido)-5-cyclopropyl-1H-pyrazole-1-carboxylate (0.5 g, 1.15 mmol) and 4-(4,4,5,5-tetramethyl-1,3,2-dioxaborolan-2-yl)aniline (0.378 g, 1.72 mmol) in 1,4-dioxane (20 mL) and water (4 mL), added $Cs_2CO_3$ (1.12 g, 3.44 mmol). The reaction mass was stirred for 10 minutes and degassed further for 10 min and added $PdCl_2(dppf).DCM$ (0.046 g, 0.057 mmol). The reaction mass was heated for 12 h at 110° C. in a sealed tube. The reaction mass was cooled to room temperature and diluted with water and ethyl acetate. The separated organic layer was dried over anhydrous sodium sulphate and concentrated under reduced pressure. The residue was purified by silica gel column chromatography by eluting with 15% ethyl acetate-hexane to afford the title compound (0.2 g, 50%) LCMS: m/z=347.2 $(M+H)^+$.

Step-iii: Synthesis of (E)-N-(3'-(1-((5-cyclopropyl-1H-pyrazol-3-yl)amino)-1-oxopropan-2-yl)-[1,1'-biphenyl]-4-yl)-4-(dimethylamino)but-2-enamide (E)-4-bromobut-2-enoic acid (0.14 g, 0.86 mmol) was taken in DCM (5 mL) with catalytic amount of DMF followed by the addition of oxalyl chloride (0.121 g, 0.95 mmol). Stirred the reaction mass for 1.5 h, evaporated the reaction mass under reduced pressure to residue. Re dissolved the reaction mass in DCM (2 mL) and was added at 0° C. to a mixture of 2-(4'-amino-[1,1'-biphenyl]-3-yl)-N-(5-cyclopropyl-1H-pyrazol-3-yl)propanamide (0.15 g, 0.43 mmol) in acetonitrile (10 mL) and DIPEA (0.4 mL, 2.16 mmol). The resulting reaction mixture was stirred for 10 minutes at 0° C. and after completion of the reaction, a solution of N, N-dimethylamine (2M in THF, 1 mL, 2.16 mmol) was added and then allowed to stir at room temperature for 12 h. The reaction mixture was quenched with saturated $NaHCO_3$ solution and diluted with DCM. The aqueous layer was separated and extracted with DCM (2×25 mL). The combined organic phase was washed with brine, dried over Na₂SO₄, filtered and concentrated under reduced pressure and purified the residue with silica gelcolumn chromatography by eluting with 10% methanol-DCM to afford the title compound (0.015 g, 7.57%). ¹HNMR (DMSO-d₆, 400 MHz): δ 12.0 (s, 1H), 10.28 (d, 2H), 7.77 (d, 2H), 7.62 (t, 3H), 7.49 (s, 1H), 7.30-7.39 (m, 2H), 6.74-6.81 (m, 1H), 6.41 (d, 1H), 6.13 (s, 1H), 3.89 (dd, 1H), 3.56-3.58 (m, 2H), 2.70 (s, 6H), 1.77-1.84 (m, 1H), 1.41 (d, 2H), 1.25-1.28 (m, 1H), 0.87 (d, 2H), 0.60 (d, 2H); LCMS: m/z=458.3 (M+H)⁺; HPLC: 98.15%, rt: 6.54 min.

Racemic (E)-N-(3'-(1-((5-cyclopropyl-1H-pyrazol-3-yl)amino)-1-oxopropan-2-yl)-[1,1'-biphenyl]-4-yl)-4-(dimethylamino)but-2-enamide (0.1 g, Compound-1) was separated by using chiral prep HPLC column. (Method: Column: Lux 5µ Cellulose-4(10.0×250 mm), Elution: isocratic (95:5), A=ACN, B=0.1% DEA in EtOH) to afford the pure Isomer-1 (0.04 g) and Isomer-2 (0.04 g).

Isomer-1 (Compound-2): ¹HNMR (DMSO-d₆, 400 MHz): δ 12.0 (brs, 1H), 10.42 (s, 1H), 10.17 (s, 1H), 7.75 (d, 2H), 7.58-7.64 (m, 3H), 7.48 (d, 1H), 7.36 (t, 1H), 7.30 (d, 1H), 6.72-6.76 (m, 1H), 6.28 (d, 1H), 6.12 (s, 1H), 3.87-3.89 (m, 1H), 3.05 (d, 2H), 2.17 (s, 6H), 1.80 (brs, 1H), 1.40 (d, 3H), 0.87 (dd, 2H), 0.60 (d, 2H). LCMS: m/z=458.35 (M+H)⁺; HPLC: 97.98%, rt: 6.06 min.; Chiral HPLC: 97.67%, rt: 6.88 min.

Isomer-2 (Compound-3): ¹HNMR (DMSO-d₆, 400 MHz): δ 12.0 (brs, 1H), 10.42 (s, 1H), 10.17 (s, 1H), 7.75 (d, 2H), 7.58-7.64 (m, 3H), 7.48 (d, 1H), 7.36 (t, 1H), 7.30 (d, 1H), 6.72-6.76 (m, 1H), 6.28 (d, 1H), 6.12 (s, 1H), 3.87-3.89 (m, 1H), 3.05 (d, 2H), 2.17 (s, 6H), 1.80 (brs, 1H), 1.40 (d, 3H), 0.87 (dd, 2H), 0.60 (d, 2H). LCMS: m/z=458.35 (M+H)⁺; HPLC: 96.64%, rt: 6.05 min; Chiral HPLC: 98.74%, rt: 10.16 min.

The compounds listed in the below table-1 were prepared by procedure similar to the one described in Example-1 with appropriate variations in reactants, quantities of reagents, protections and deprotections, solvents and reaction conditions. The characterization data of the compounds are also summarized herein the table-1.

TABLE 1

| Comp. No. | Structure | Characterization data |
|---|---|---|
| 4 | 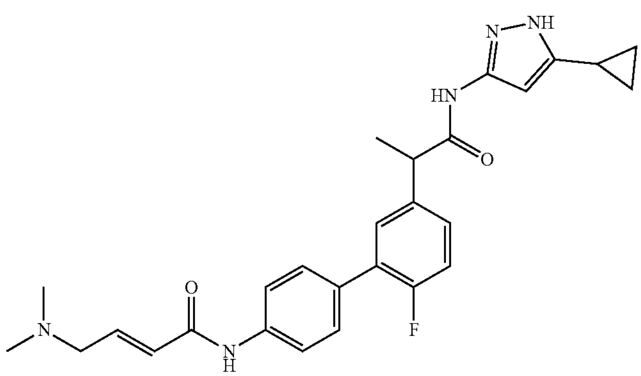 [SMILES: CC(C(=O)Nc1cc(C2CC2)[nH]n1)c1ccc(F)c(-c2ccc(NC(=O)/C=C/CN(C)C)cc2)c1] | ¹HNMR (DMSO-d₆, 400 MHz): δ 10.46 (d, 2H), 9.75 (s, 1H), 7.78 (d, 2H), 7.48-7.52 (m, 3H), 7.32-7.35 (m, 1H), 7.21-7.26 (m, 1H), 6.74-6.78 (m, 1H), 6.47 (d, 1H), 6.11 (s, 1H), 3.96 (t, 2H), 3.85-3.90 (m, 1H), 2.81 (d, 6H), 1.79-1.82 (m, 1H), 1.39 (d, 3H), 0.86 (dd, 2H), 0.60 (dd, 2H); LCMS: m/z = 476.1 (M + H)⁺; HPLC: 93.72%, rt: 6.20 min. |
| 5 | 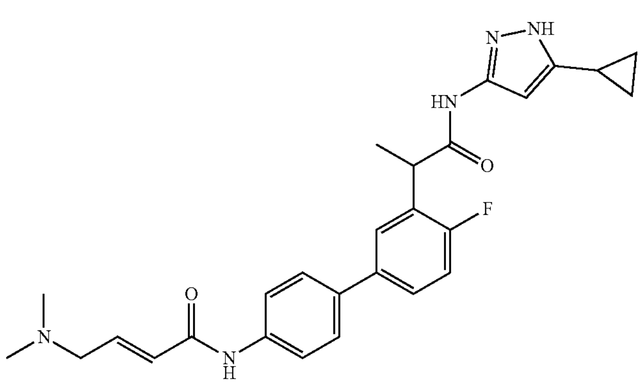 [SMILES: CC(C(=O)Nc1cc(C2CC2)[nH]n1)c1cc(-c2ccc(NC(=O)/C=C/CN(C)C)cc2)ccc1F] | ¹HNMR (DMSO-d₆, 400 MHz): δ 10.46 (d, 2H), 9.75 (s, 1H), 7.76 (d, 2H), 7.65 (d, 1H), 7.58 (dd, 2H), 7.52-7.60 (m, 1H), 7.22 (t, 1H), 6.71-6.78 (m, 1H), 6.46 (d, 1H), 6.12 (s, 1H), 4.14 (d, 1H), 3.34-3.39 (d, 2H), 2.81 (s, 6H), 1.46-1.83 (m, 1H), 1.45 (d, 3H), 0.85-0.88 (m, 2H), 0.59-0.63 (m, 2H); LCMS: m/z = 476.1 (M + H)⁺; HPLC: 94.10%, rt: 10.18 min. |

TABLE 1-continued

| Comp. No. | Structure | Characterization data |
|---|---|---|
| 6 | 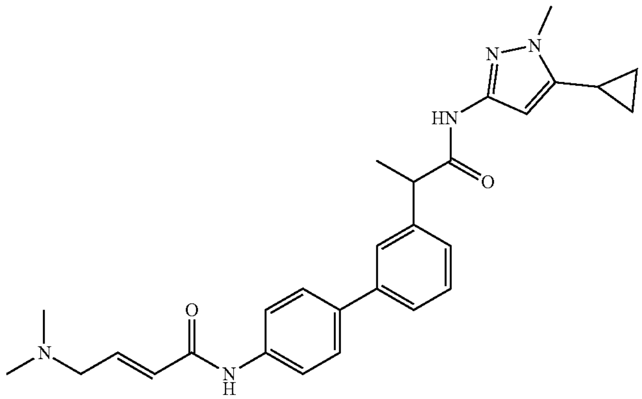 [SMILES: CC(C(=O)Nc1cc(C2CC2)n(C)n1)c1cccc(-c2ccc(NC(=O)/C=C/CN(C)C)cc2)c1] | ¹HNMR (DMSO-d₆, 400 MHz): δ 10.14 (s, 1H), 9.92 (s, 1H), 7.72 (d, 2H), 7.56-7.60 (m, 3H), 7.49 (d, 1H), 7.37 (t, 1H), 7.28 (d, 1H), 6.68-6.74 (m, 1H), 6.24 (d, 1H), 5.81 (s, 1H), 3.88-3.93 (m, 1H), 3.41 (s, 3H), 3.03 (d, 2H), 2.14 (s, 6H), 1.67-1.73 (m, 1H), 1.41 (d, 3H), 0.71-0.76 (m, 2H), 0.49-0.53 (m, 2H); LCMS: m/z = 472.2 (M + H)⁺; HPLC: 97.67%, rt: 6.72 min. |
| 7 | 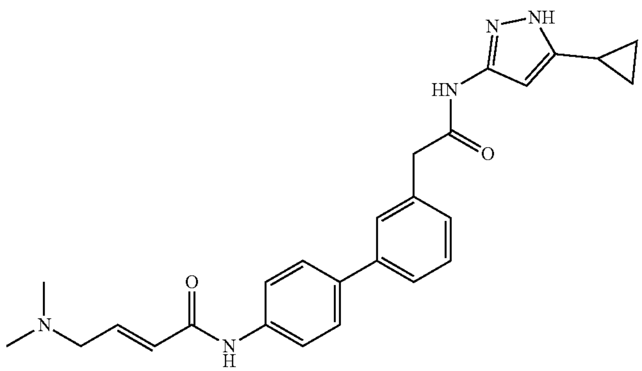 [SMILES: CN(C)C/C=C/C(=O)Nc1ccc(-c2cccc(CC(=O)Nc3cc(C4CC4)[nH]n3)c2)cc1] | ¹HNMR (DMSO-d₆, 400 MHz): δ 12.01 (s, 1H), 10.56 (s, 1H), 10.18 (s, 1H), 7.75 (d, 2H), 7.59 (d, 2H), 7.50 (d, 1H), 7.36 (t, 1H), 7.25 (d, 1H), 6.72-6.76 (m, 1H), 6.26-6.30 (m, 1H), 6.10 (s, 1H), 3.62 (s, 2H), 3.33-3.38 (m, 1H), 3.05 (d, 2H), 2.17 (s, 6H), 1.78-1.81 (m, 1H), 0.86 (dd, 2H), 0.61 (d, 2H); LCMS: m/z = 444.0 (M + H)⁺; HPLC: 95.97%, rt: 5.90 min. |
| 8 | 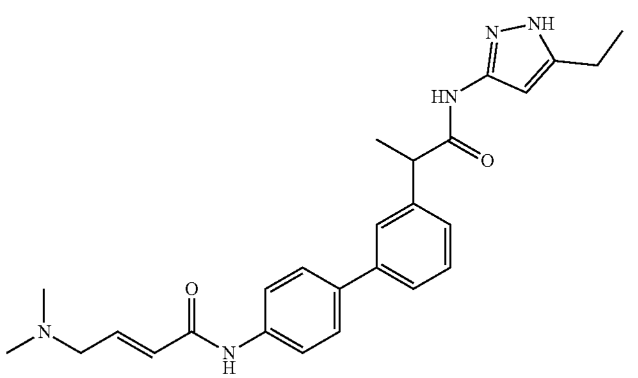 [SMILES: CCc1cc(NC(=O)C(C)c2cccc(-c3ccc(NC(=O)/C=C/CN(C)C)cc3)c2)n[nH]1] | ¹HNMR (DMSO-d₆, 400 MHz): δ 12.0 (s, 1H), 10.42 (s, 1H), 10.21 (s, 1H), 7.74 (d, 2H), 7.64 (s, 1H), 7.59 (d, 2H), 7.49 (d, 1H), 7.37 (t, 1H), 7.31 (d, 1H), 6.71-6.77 (m, 1H), 6.24-6.49 (m, 2H), 3.84-3.89 (m, 2H), 3.76-3.78 (m, 1H), 3.07 (d, 2H), 2.18 (s, 6H), 1.41 (d, 3H), 1.12 (t, 3H). LCMS: m/z = 446.35 (M + H)⁺; HPLC: 93.28%, rt: 5.99 min. |
| 9 | 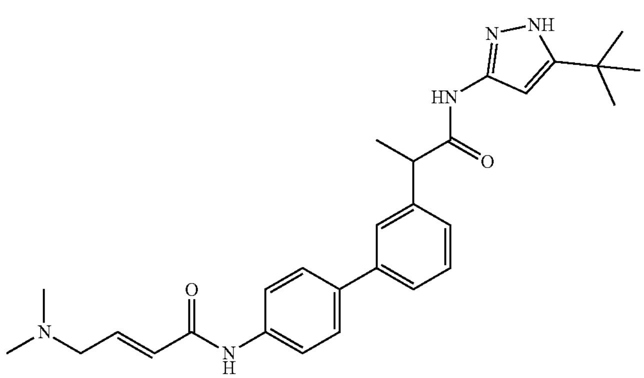 [SMILES: CC(C(=O)Nc1cc(C(C)(C)C)[nH]n1)c1cccc(-c2ccc(NC(=O)/C=C/CN(C)C)cc2)c1] | ¹HNMR (DMSO-d₆, 400 MHz): δ 12.01 (s, 1H), 10.46 (s, 1H), 10.18 (s, 1H), 7.77 (d, 2H), 7.66 (s, 1H), 7.60 (d, 2H), 7.51 (d, 1H), 7.40 (t, 1H), 7.31 (d, 1H), 6.77-6.72 (m, 1H), 6.29 (d, 2H), 3.90 (d, 1H), 3.08 (d, 2H), 2.49 (s, 6H), 1.42 (d, 3H), 1.21 (s, 9H); LCMS: m/z = 474.35 (M + H)⁺; HPLC: 94.08%, rt: 3.22 min. |

General Synthetic Scheme

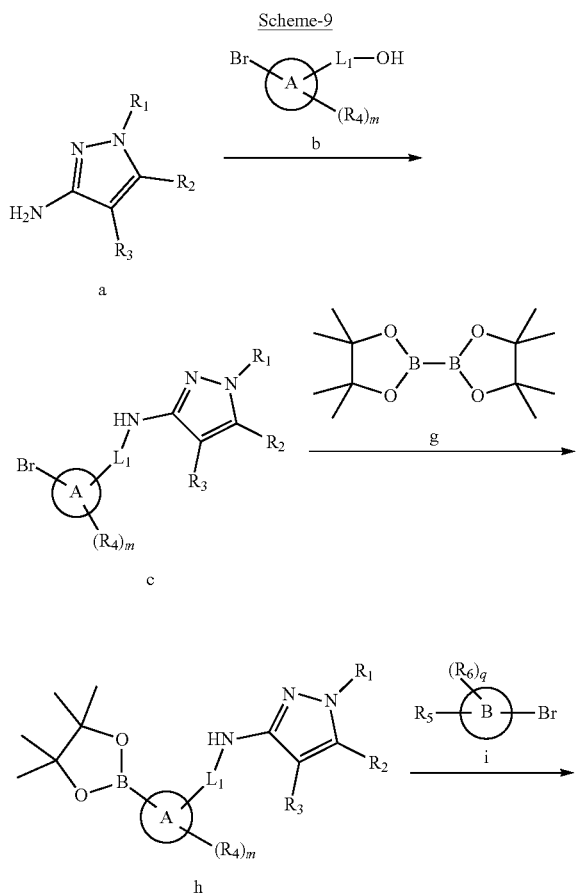

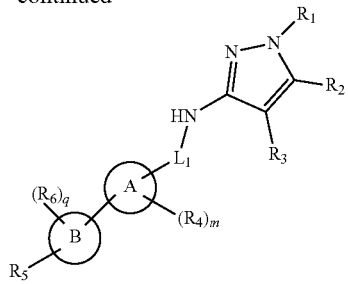

wherein, ring A, ring B, $R_1$, $R_2$, $R_3$, $R_4$, $R_5$, $L_1$ and m are as defined in formula (I);

Some compounds of the present invention can be generally synthesized utilizing the process outlined in this scheme. The commercially available or synthesized intermediate-b was converted to corresponding acid chloride in presence of suitable reagents and solvents (DCM, catalytic DMF, oxalyl chloride, RT, ~1.5 h) which upon reacting with intermediate-a in presence of suitable reagents and solvents (pyridine, 0° C.-RT, 12 h; or DCM, TEA, 0° C.-RT, 12 h) afforded intermediate-c. Treatment of intermediate-c with intermediate-g (4,4,4',4',5,5,5',5'-octamethyl-2,2'-bi(1,3,2-dioxaborolane)) under suitable reagents and conditions (1,4-Dioxane, potassium acetate, Pd(dppf)Cl$_2$.DCM or PdCl$_2$(PPh$_3$)$_2$, 12 h, 100° C.) gave intermediate-h. Treatment of intermediate-h with intermediate-i by Suzuki coupling conditions in presence of suitable catalyst such as Pd(dppf)Cl$_2$.DCM or PdCl$_2$(PPh$_3$)$_2$, suitable base such as potassium carbonate or cesium carbonate and in the presence of suitable solvent(s) such as 1,4-dioxane and/or water afforded the product of interest.

Example-2: Synthesis of (E)-N-(5-(3-(1-((5-cyclopropyl-1H-pyrazol-3-yl)amino)-1-oxopropan-2-yl)phenyl)pyridin-2-yl)-4-morpholinobut-2-enamide (Compound-10)

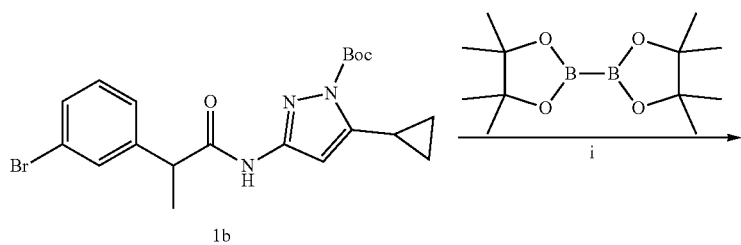

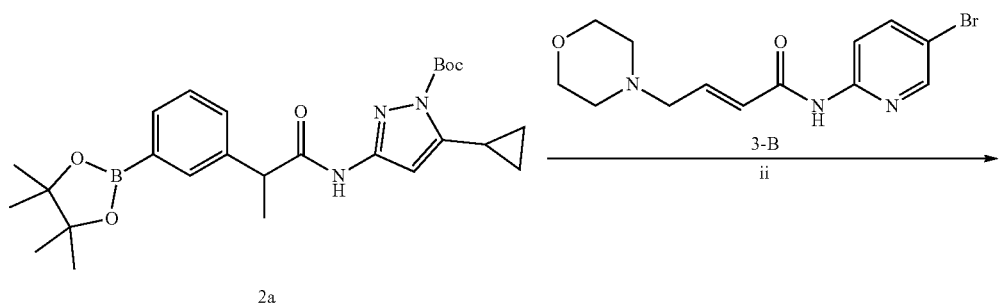

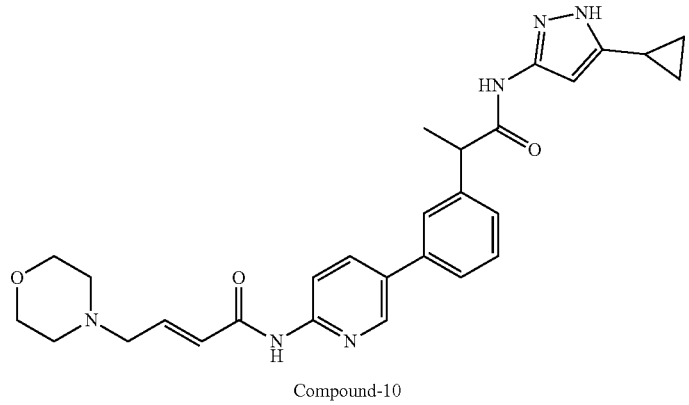

Compound-10

Step-i: Synthesis of tert-butyl 5-cyclopropyl-3-(2-(3-(4,4,5,5-tetramethyl-1,3,2-dioxaborolan-2-yl)phenyl)propanamido)-1H-pyrazole-1-carboxylate To a degassed solution of tert-butyl 3-(2-(3-bromophenyl)propanamido)-5-cyclopropyl-1H-pyrazole-1-carboxylate (5.0 g, 11.52 mmol) and 4,4,4',4',5,5,5',5'-octamethyl-2,2'-bi(1,3,2-dioxaborolane) (3.5 g, 13.8 mmol) in 1,4-dioxane (50 mL) was added potassium acetate (3.3 g, 34.5 mmol). The reaction mass was allowed to stir for 10 minutes with degassing at RT and added PdCl$_2$(dppf).DCM complex (0.046 g, 0.057 mmol). The reaction mass was heated for 12 h at 100° C. in a sealed tube, cooled the reaction mass and diluted with water and ethyl acetate. The aqueous layer was separated and re-extracted with ethyl acetate (2×25 mL). The combined organic layer was dried over anhydrous sodium sulfate and concentrated under vacuum. The crude material was purified by silica gel column chromatography by eluting with 20% ethyl acetate in hexane to afford the title compound (4.0 g, 60%), LCMS: m/z=482.2 (M+H)$^+$.

Step-ii: Synthesis of (E)-N-(5-(3-(1-((5-cyclopropyl-1H-pyrazol-3-yl)amino)-1-oxopropan-2-yl)phenyl)pyridin-2-yl)-4-morpholinobut-2-enamide To a degassed solution of tert-butyl-5-cyclopropyl-3-(2-(3-(4,4,5,5-tetramethyl-1,3,2-dioxaborolan-2-yl)phenyl)propanamido)-1H-pyrazole-1-carboxylate (0.5 g, 1.04 mmol) and (E)-N-(5-bromopyridin-2-yl)-4-morpholinobut-2-enamide (0.27 g, 0.83 mmol) in 1,4-dioxane (20 mL) and water (5 mL) was added Cs$_2$CO$_3$ (0.84 g, 2.6 mmol). The reaction mass was allowed to stir for 10 minutes with degassing and added PdCl$_2$(dppf).DCM complex (0.06 g, 0.07 mmol), heated the reaction mass for 12 h at 100° C. in a a sealed tube. The reaction mass was cooled and diluted with water and ethyl acetate. The aqueous layer was separated and re-extracted with ethyl acetate (2×25 mL). The combined organic layer was dried over anhydrous sodium sulfate and concentrated under vacuum. The crude material was purified by silica gel column chromatography by eluting with 10% methanol in DCM, further purified by preparative HPLC (Method: Column: Gemini NX C18 (21.2 mm×150 mm, 5 micron), Mobile phase: 0.01% NH$_4$OH in Water, Acetonitrile:Methanol (1:1)) to afford the title compound (0.2 g, 40%). $^1$HNMR (DMSO-d$_6$, 400 MHz): δ 12.02 (s, 1H), 10.76 (s, 1H), 10.41 (s, 1H), 8.61 (s, 1H), 8.26 (d, 1H), 8.05 (d, 1H), 7.69 (s, 1H), 7.55 (d, 1H), 7.42-7.34 (m, 2H), 6.82-6.75 (m, 1H), 6.47 (d, 1H), 6.12 (s, 1H), 3.91-3.86 (m, 1H), 3.60-3.58 (m, 4H), 3.13 (d, 2H), 2.37 (s, 4H), 1.83-1.76 (m, 1H), 1.41 (d, 3H), 0.87-0.85 (d, 2H), 0.60-0.59 (m, 2H); LCMS: m/z=501.10 (M+H)$^+$; HPLC: 97.63%, rt: 4.27 min.

Racemic (E)-N-(5-(3-(1-((5-cyclopropyl-1H-pyrazol-3-yl)amino)-1-oxopropan-2-yl)-phenyl)pyridin-2-yl)-4-morpholinobut-2-enamide was separated by using chiral preparative HPLC column (Method: Column: Chiral Pak IA(20 mm×250 mm, 5 micron), Elution: isocratic (50:50), A=ACN, B=MeOH, Flow: 20 mL/min) to afford the pure Isomer-1 and Isomer-2.

Isomer-1 (Compound-11): $^1$HNMR (DMSO-d$_6$, 400 MHz): δ 12.02 (s, 1H), 10.77 (s, 1H), 10.43 (s, 1H), 8.62-8.61 (m, 1H), 8.27 (d, 1H), 8.06 (d, 1H), 7.69 (s, 1H), 7.56 (d, 1H), 7.43-7.34 (m, 2H), 6.82-6.75 (m, 1H), 6.47 (d, 1H), 6.11 (s, 1H), 3.86 (m, 1H), 3.60-3.58 (m, 4H), 3.12 (d, 2H), 2.38 (s, 4H), 1.83-1.76 (m, 1H), 1.41 (d, 3H), 0.89-0.84 (m, 2H), 0.62-0.58 (m, 2H); LCMS: m/z=501.3 (M+H)$^+$; HPLC: 99.26%, rt: 3.45 min.; Chiral HPLC: 97.58%, rt: 7.54 min.

Isomer-2 (Compound-12): $^1$HNMR (DMSO-d$_6$, 400 MHz): δ 12.02 (s, 1H), 10.75 (s, 1H), 10.41 (s, 1H), 8.61-8.60 (m, 1H), 8.27-8.20 (m, 1H), 8.05 (d, 1H), 7.68 (s, 1H), 7.55 (d, 1H), 7.42-7.33 (m, 2H), 6.81-6.74 (m, 1H), 6.47 (d, 1H), 6.10 (s, 1H), 3.89-3.87 (m, 1H), 3.59-3.57 (m, 4H), 3.10 (d, 2H), 2.31 (s, 4H), 1.81-1.77 (m, 1H), 1.40 (d, 3H), 0.87-0.85 (m, 2H), 0.61-0.57 (m, 2H); LCMS: m/z=501.2 (M+H)$^+$; HPLC: 99.04%, rt: 3.44 min.; Chiral HPLC: 95.42%, rt: 9.07 min.

The compounds listed in the below table-2 were prepared by a procedure similar to the one described in Example-2 with appropriate variations in reactants, quantities of reagents, protections and deprotections, solvents and reaction conditions. The characterization data of the compounds are also summarized herein the table-2.

TABLE 2

| Comp. No. | Structure | Characterization Data |
|---|---|---|
| 13 | 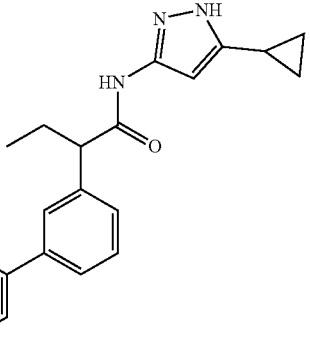 | $^1$HNMR (DMSO-$d_6$, 400 MHz): δ 11.99 (s, 1H), 10.41 (s, 1H), 10.13 (m, 1H), 7.73-7.71 (m, 2H), 7.60 (s, 1H), 7.60-7.54 (m, 2H), 7.46-7.44 (d, 1H), 7.35-7.31 (m, 1H), 7.27-7.25 (m, 1H), 6.74-6.67 (m, 1H), 6.27-6.23 (m, 1H), 6.11 (s, 1H), 3.62-3.58 (m, 1H), 3.02 (d, 2H), 2.14 (s, 6H), 2.06-1.99 (m, 1H), 1.78-1.73 (m, 1H), 1.70-1.63 (m, 1H), 0.84-0.79 (m, 5H), 0.58-0.57 (m, 2H); LCMS: m/z = 472.5 (M + H)$^+$; HPLC: 94.51%, rt: 6.18 min. |
| 14 | 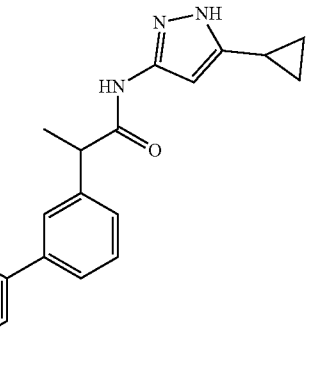 | $^1$HNMR (DMSO-$d_6$, 400 MHz): δ 12.02 (s, 1H), 10.42 (s, 1H), 9.91 (s, 1H), 8.09-8.05 (m, 1H), 7.65 (s, 1H), 7.65-7.51 (m, 2H), 7.44 (d, 1H), 7.42-7.28 (m, 2H), 6.76-6.68 (m, 1H), 6.45 (d, 1H), 6.08 (s, 1H), 3.86-3.82 (m, 1H), 3.05 (d, 2H), 2.13 (s, 6H), 1.77-1.75 (m, 1H), 1.38 (d, 3H), 0.83 (m, 2H), 0.57 (m, 2H); LCMS: m/z = 476.1 (M + H)$^+$; HPLC: 95.68%, rt: 6.12 min. |
| 15 | 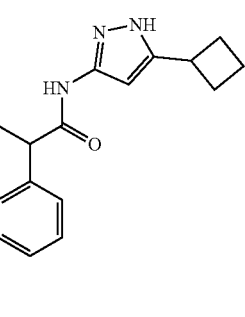 | $^1$HNMR (DMSO-$d_6$, 400 MHz): δ 12.02 (s, 1H), 10.46 (s, 1H), 10.18 (s, 1H), 7.76 (d, 2H), 7.65 (s, 1H), 7.60 (d, 2H), 7.49 (d, 1H), 7.39-7.30 (m, 2H), 6.78-6.71 (m, 1H), 6.32-6.27 (m, 2H), 3.93-3.88 (m, 1H), 3.07-3.05 (m, 2H), 2.22-2.19 (m, 8H), 2.07-2.05 (m, 2H), 1.97-1.87 (m, 3H), 1.42 (d, 3H); LCMS: m/z = 472.2 (M + H)$^+$; HPLC: 98.85%, rt: 3.71 min. |
| 16 | 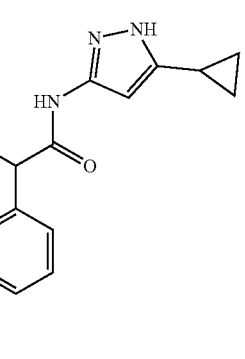 | $^1$HNMR (DMSO-$d_6$, 400 MHz): δ 12.05 (s, 1H), 10.47 (d, 2H), 8.86 (d, 1H), 8.23-8.21 (m, 1H), 8.10 (s, 1H), 7.91 (d, 1H), 7.87-7.85 (m, 1H), 7.40-7.39 (m, 2H), 6.81-6.77 (m, 1H), 6.32 (d, 1H), 6.14 (s, 1H), 3.93-3.91 (m, 1H), 3.09-3.07 (m, 2H), 2.41 (s, 6H), 1.81-1.79 (m, 1H), 1.42 (d, 3H), 0.86 (m, 2H), 0.61 (m, 2H); LCMS: m/z = 459 (M + H)$^+$; HPLC: 95.54%, rt: 5.79 min. |

TABLE 2-continued

| Comp. No. | Structure | Characterization Data |
|---|---|---|
| 17 | 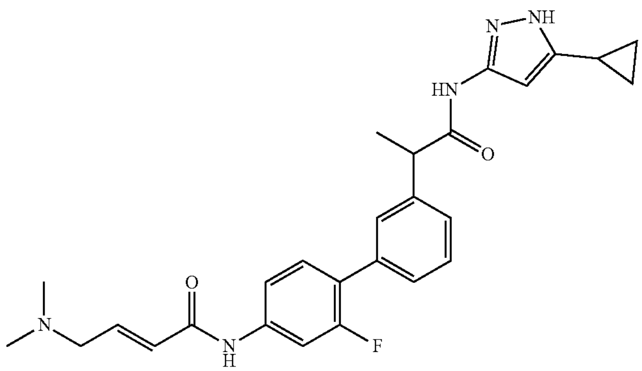 [SMILES: CC(C(=O)Nc1cc(C2CC2)[nH]n1)c1cccc(-c2ccc(NC(=O)/C=C/CN(C)C)cc2F)c1] | $^1$HNMR (DMSO-d$_6$, 400 MHz): δ 12.02 (s, 1H), 10.43 (s, 1H), 10.36 (s, 1H), 7.80-7.76 (d, 1H), 7.53 (s, 1H), 7.48-7.34 (m, 5H), 6.79-6.74 (m, 1H), 6.29 (d, 1H), 6.13 (s, 1H), 3.91-3.86 (m, 1H), 3.05 (d, 2H), 2.18 (s, 6H), 1.78 (m, 1H), 1.38 (d, 3H), 0.83-0.81 (m, 2H), 0.60-0.58 (m, 2H); LCMS: m/z = 476.2 (M + H)$^+$; HPLC: 99.40%, rt: 3.44 min. |
| 18 | 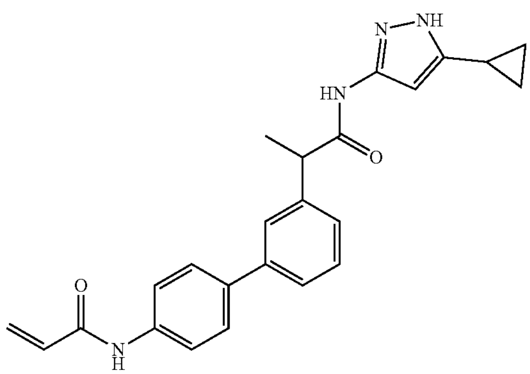 [SMILES: C=CC(=O)Nc1ccc(-c2cccc(C(C)C(=O)Nc3cc(C4CC4)[nH]n3)c2)cc1] | $^1$HNMR (DMSO-d$_6$, 400 MHz): δ 12.05 (s, 1H), 10.41 (s, 1H), 10.25 (m, 1H), 7.77 (d, 2H), 7.64-7.59 (m, 3H), 7.50 (d, 1H), 7.39-7.31 (m, 2H), 6.48-6.46 (m, 1H), 6.29 (d, 1H), 6.13 (s, 1H), 5.75 (d, 1H), 3.88 (s, 1H), 1.79 (m, 1H), 1.40 (d, 3H), 0.85 (d, 2H), 0.61 (d, 2H); LCMS: m/z = 400.8 (M + H)$^+$; HPLC: 97.91%, rt: 4.47 min. |
| 19 | 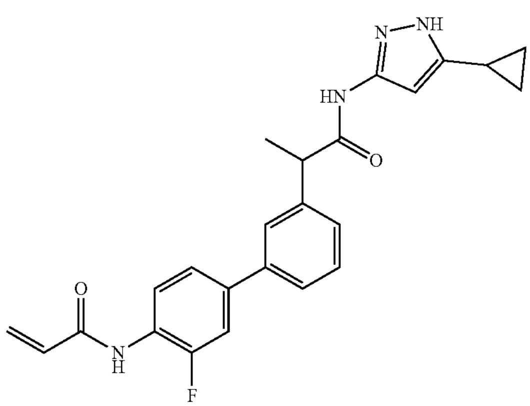 [SMILES: C=CC(=O)Nc1ccc(-c2cccc(C(C)C(=O)Nc3cc(C4CC4)[nH]n3)c2)cc1F] | $^1$HNMR (DMSO-d$_6$, 400 MHz): δ 12.03 (s, 1H), 10.41 (s, 1H), 10.05 (s, 1H), 8.13 (t, 1H), 7.70 (s, 1H), 7.60-7.55 (m, 2H), 7.49 (d, 1H), 7.42-7.34 (m, 2H), 6.68-6.62 (m, 1H), 6.32-6.28 (m, 1H), 6.13 (s, 1H), 5.81-5.78 (m, 1H), 3.92-3.87 (m, 1H), 1.84-1.78 (m, 1H), 1.42 (d, 3H), 0.88-0.86 (m, 2H), 0.63-0.61 (m, 2H); LCMS: m/z = 419.1 (M + H)$^+$; HPLC: 98.28%, rt: 7.07 min. |
| 20 | 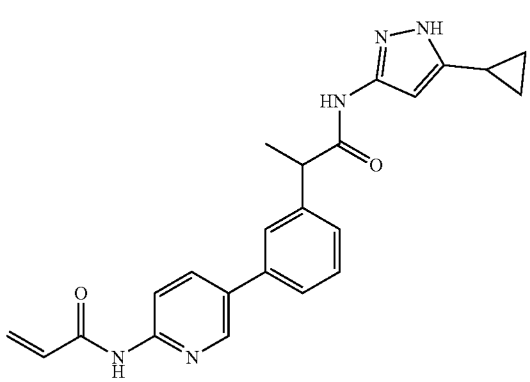 [SMILES: C=CC(=O)Nc1ccc(-c2cccc(C(C)C(=O)Nc3cc(C4CC4)[nH]n3)c2)cn1] | $^1$HNMR (DMSO-d$_6$, 400 MHz): δ 12.05 (s, 1H), 10.95 (s, 1H), 10.41 (s, 1H), 8.63 (s, 1H), 8.29 (d, 1H), 8.09 (d, 1H), 7.70 (s, 1H), 7.57 (d, 1H), 7.44-7.35 (m, 2H), 6.67-6.54 (m, 1H), 6.35-6.30 (d, 1H), 6.13 (s, 1H), 5.78 (d, 1H), 3.91-3.89 (m, 1H), 1.80-1.78 (m, 1H), 1.45 (d, 3H), 0.88-0.86 (m, 2H), 0.60-0.62 (m, 2H); LCMS: m/z = 402.2 (M + H)$^+$; HPLC: 99.41%, rt: 3.84 min. |

TABLE 2-continued

| Comp. No. | Structure | Characterization Data |
|---|---|---|
| 21 | 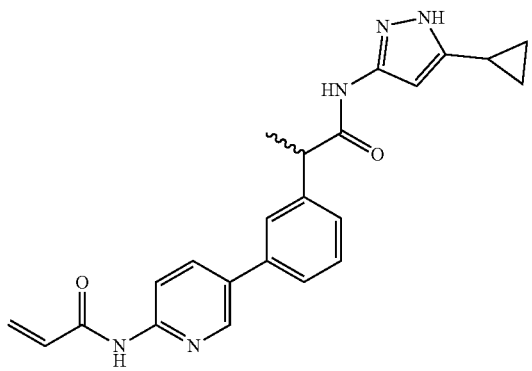 [SMILES: C=CC(=O)Nc1ccc(-c2cccc(C(C)C(=O)Nc3cc(C4CC4)[nH]n3)c2)cn1] | ¹HNMR (DMSO-d₆, 400 MHz): δ 12.05 (s, 1H), 10.95 (s, 1H), 10.41 (s, 1H), 8.63 (s, 1H), 8.29 (d, 1H), 8.09 (d, 1H), 7.70 (s, 1H), 7.57 (d, 1H), 7.44-7.35 (m, 2H), 6.67-6.54 (m, 1H), 6.35-6.30 (d, 1H), 6.13 (s, 1H), 5.78 (d, 1H), 3.91-3.89 (m, 1H), 1.80-1.78 (m, 1H), 1.45 (d, 3H), 0.88-0.86 (m, 2H), 0.60-0.62 (m, 2H); LCMS: m/z = 402.2 (M + H)⁺; HPLC: 97.74%, rt: 6.12 min.; Chiral HPLC: 96.78%, rt: 6.57 min. (Isomer-1 of compound-20) |
| 22 | 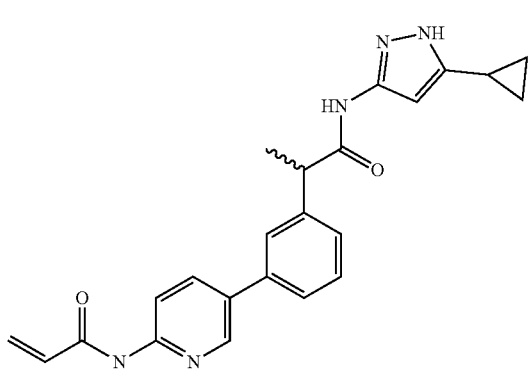 | ¹HNMR (DMSO-d₆, 400 MHz): δ 12.05 (s, 1H), 10.95 (s, 1H), 10.41 (s, 1H), 8.63 (s, 1H), 8.29 (d, 1H), 8.09 (d, 1H), 7.70 (s, 1H), 7.57 (d, 1H), 7.44-7.35 (m, 2H), 6.67-6.54 (m, 1H), 6.35-6.30 (d, 1H), 6.13 (s, 1H), 5.78 (d, 1H), 3.91-3.89 (m, 1H), 1.80-1.78 (m, 1H), 1.45 (d, 3H), 0.88-0.86 (m, 2H), 0.60-0.62 (m, 2H); LCMS: m/z = 402.2 (M + H)⁺; HPLC: 95.96%, rt: 6.11 min; Chiral HPLC: 98.55%, rt: 12.37 min. (Isomer-2 of compound-20) |
| 23 | 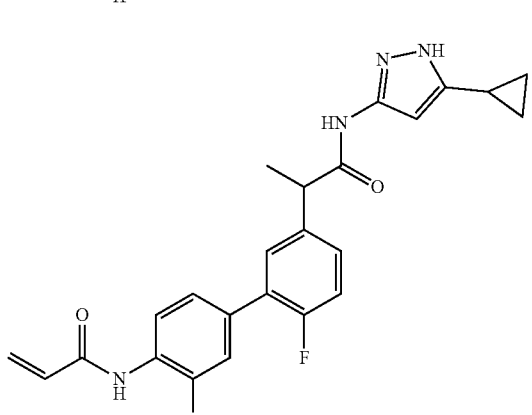 | ¹HNMR (DMSO-d₆, 400 MHz): δ 12.03 (s, 1H), 10.42 (s, 1H), 10.09 (s, 1H), 8.15 (t, 1H), 7.55 (d, 1H), 7.47 (d, 1H), 7.37 (d, 2H), 7.28 (t, 1H), 6.66-6.54 (m, 1H), 6.32-6.27 (d, 1H), 6.13 (s, 1H), 5.79 (d, 1H), 3.88 (d, 1H), 1.80-1.78 (m, 1H), 1.40 (d, 3H), 0.88-0.86 (m, 2H), 0.61-0.60 (m, 2H); LCMS: m/z = 436.9 (M + H)⁺; HPLC: 96.49%, rt: 4.21 min. |
| 24 | 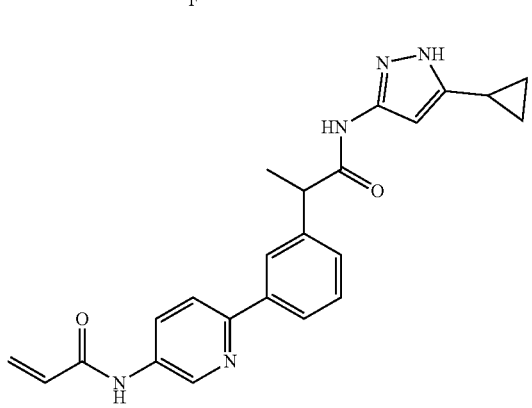 | ¹HNMR (DMSO-d₆, 400 MHz): δ 12.02 (s, 1H), 10.49-10.46 (d, 2H), 8.88 (s, 1H), 8.28 (d, 1H), 8.10 (s, 1H), 7.93-7.86 (m, 2H), 7.44-7.39 (m, 2H), 6.47-6.43 (m, 1H), 6.33-6.29 (d, 1H), 6.14 (s, 1H), 5.84 (d, 1H), 3.95-3.89 (m, 1H), 1.81-1.78 (m, 1H), 1.42 (d, 3H), 0.88-0.86 (d, 2H), 0.62-0.60 (d, 2H); LCMS: m/z = 402.2 (M + H)⁺; HPLC: 99.66%, rt: 3.54 min. |

TABLE 2-continued

| Comp. No. | Structure | Characterization Data |
|---|---|---|
| 25 | 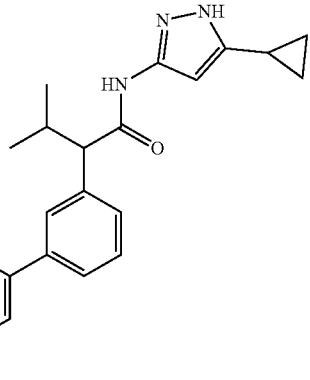 | ¹HNMR (DMSO-d₆, 400 MHz): δ 12.05-11.95 (brs, 1H), 10.7 (s, 1H), 10.06 (s, 1H), 8.14 (t, 1H), 7.69 (s, 1H), 7.58-7.55 (m, 2H), 7.48 (d, 1H), 7.42-7.35 (m, 2H), 6.65 (dd, 1H), 6.35 (d, 1H), 6.18 (s, 1H), 5.80 (d, 1H), 3.45-3.35 (m, 1H), 1.81-1.78 (m, 1H), 1.24 (s, 1H), 0.98 (d, 3H), 0.86 (d, 2H), 0.67 (d, 3H), 0.61 (d, 2H); LCMS: m/z = 447.0 (M + H)⁺; HPLC: 98.63%, rt: 4.63 min. |
| 26 | 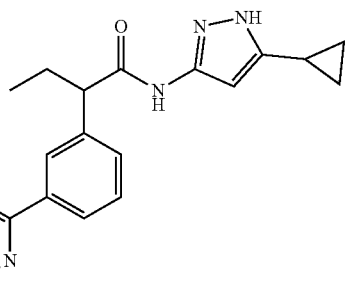 | ¹HNMR (DMSO-d₆, 400 MHz): δ 12.02 (s, 1H), 10.42 (s, 2H), 8.92 (s, 1H), 8.36 (s, 1H), 8.22 (s, 1H), 7.44 (d, 2H), 7.37 (d, 2H), 6.51 (s, 1H), 6.35-6.31 (m, 1H), 6.26 (d, 1H), 5.75 (d, 1H), 3.83-3.89 (m, 1H), 2.05-1.99 (m, 1H), 1.80-1.67 (m, 2H), 0.86-0.84 (m, 5H), 0.59-0.57 (m, 2H); LCMS: m/z = 416.30 (M + H)⁺; HPLC: 97.41%, rt: 7.99 min. |
| 27 | 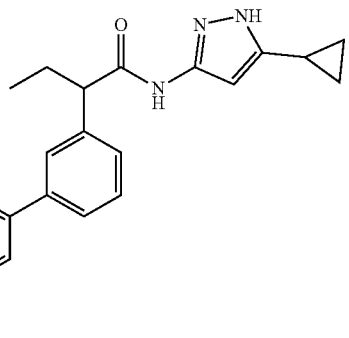 | ¹HNMR (DMSO-d₆, 400 MHz): δ 12.02 (s, 1H), 10.42 (s, 1H), 10.01 (s, 1H), 8.12 (t, 1H), 7.65 (s, 1H), 7.53 (d, 2H), 7.44 (d, 1H), 7.37 (d, 2H), 6.65-6.51 (m, 1H), 6.27 (d, 1H), 6.09 (s, 1H), 5.75 (d, 1H), 3.63-3.59 (m, 1H), 2.05-1.99 (m, 1H), 1.83-1.69 (m, 2H), 0.86-0.84 (m, 5H), 0.62-0.61 (m, 2H); LCMS: m/z = 433.3 (M + H)⁺; HPLC: 97.21%, rt: 4.33 min. |
| 28 | 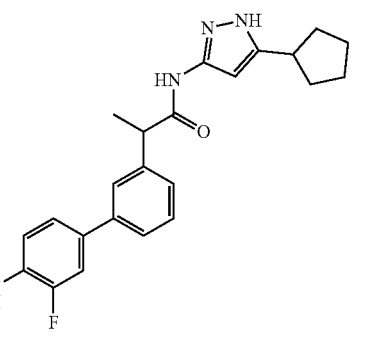 | ¹HNMR (DMSO-d₆, 400 MHz): δ 11.99 (s, 1H), 10.42 (s, 1H), 9.93 (s, 1H), 8.10 (t, 1H), 7.69 (s, 1H), 7.59 (d, 2H), 7.45-7.35 (m, 1H), 7.35-7.33 (m, 2H), 6.79-6.80 (m, 1H), 6.46 (d, 1H), 6.25 (s, 1H), 3.92-3.87 (m, 1H), 3.06 (d, 2H), 2.91-2.99 (m, 1H), 2.16 (s, 6H), 1.93 (s, 2H), 1.66-1.49 (m, 6H), 1.42-1.41 (m 3H); LCMS: m/z = 504.55 (M + H)⁺; HPLC: 96.66%, rt: 4.66 min. |

TABLE 2-continued

| Comp. No. | Structure | Characterization Data |
|---|---|---|
| 29 | 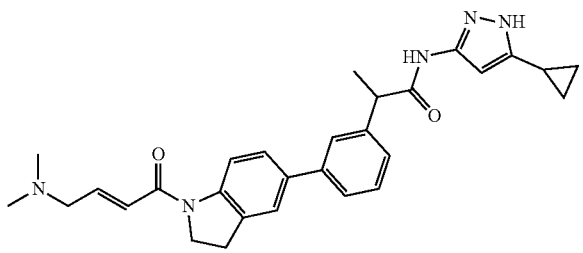 [SMILES: CC(C(=O)Nc1cc(C2CC2)[nH]n1)c1cccc(-c2ccc3c(c2)CCN3C(=O)/C=C/CN(C)C)c1] | ¹HNMR (DMSO-d₆, 400 MHz): δ 12.02 (s, 1H), 10.41 (s, 1H), 8.20 (d, 1H), 7.64 (s, 1H), 7.51-7.43 (m, 3H), 7.37-7.35 (m, 1H), 7.37-7.27 (m, 1H), 6.83-6.78 (m, 1H), 6.76 (d, 1H), 6.11 (s, 1H), 4.26-4.21 (m, 2H), 3.88-3.33 (m, 1H), 3.22-3.20 (m, 2H), 3.10-3.08 (m, 2H), 2.18 (s, 6H), 1.83-1.77 (m, 1H), 1.37 (d, 3H), 0.84-0.82 (m, 2H), 0.62-0.57 (m, 2H); LCMS: m/z = 484.4 (M + H)⁺; HPLC: 95.47%, rt: 4.25 min. |
| 30 | 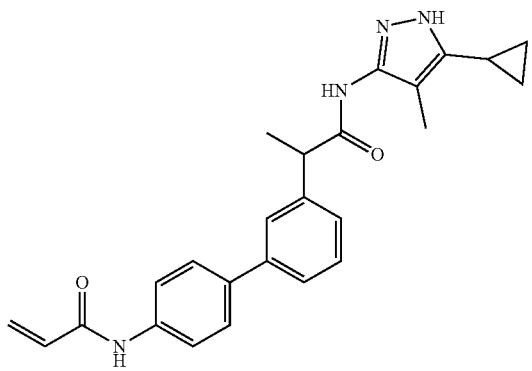 [SMILES: C=CC(=O)Nc1ccc(-c2cccc(C(C)C(=O)Nc3n[nH]c(C4CC4)c3C)c2)cc1] | ¹HNMR (DMSO-d₆, 400 MHz): δ 11.85 (s, 1H), 10.3 (s, 1H), 9.64 (s, 1H), 7.78-7.76 (m, 2H), 7.66-7.61 (m, 3H), 7.51 (d, 1H), 7.40-7.34 (m, 2H), 6.45 (dd, 1H), 6.25 (dd, 1H), 5.77 (dd, 1H), 3.87-3.86 (brs, 1H), 1.72-1.69 (m, 4H), 1.43-1.42 (m, 3H), 0.82 (d, 2H), 0.67 (d, 2H); LCMS: m/z = 415.3 (M + H)⁺; HPLC: 97.49, rt: 5.03 min. |
| 31 | 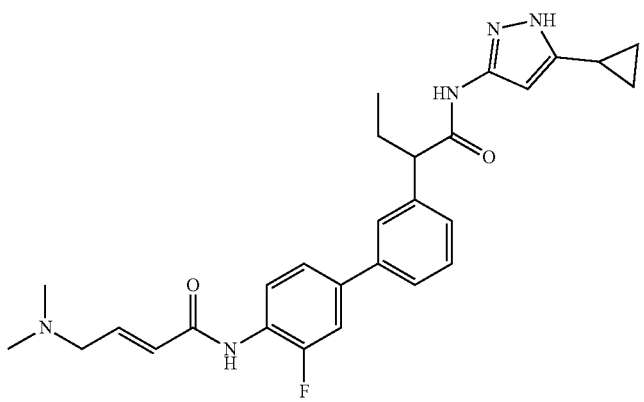 [SMILES: CCC(C(=O)Nc1cc(C2CC2)[nH]n1)c1cccc(-c2ccc(NC(=O)/C=C/CN(C)C)c(F)c2)c1] | ¹HNMR (DMSO-d₆, 400 MHz): δ 12.02 (s, 1H), 10.43 (s, 1H), 9.93 (s, 1H), 8.11 (t, 1H), 7.67 (s, 1H), 7.53 (d, 2H), 7.44 (d, 1H), 7.37 (d, 1H), 7.17 (s, 1H), 6.79-6.75 (m, 1H), 6.49-6.45 (m, 1H), 6.18 (s, 1H), 3.66-3.63 (m, 1H), 3.07-3.06 (m, 2H), 2.18 (s, 6H), 2.08-2.08 (m, 1H), 1.82-1.80 (m, 1H), 1.69-1.68 (m, 1H), 0.87-0.84 (m, 5H), 0.62 (s, 2H); LCMS: m/z = 490.1 (M + H)⁺; HPLC: 98.55%, rt: 4.54 min. |
| 32 | 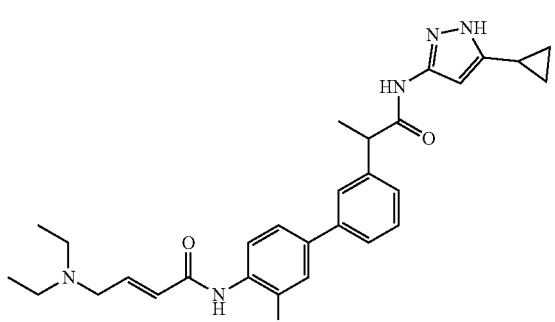 | ¹HNMR (DMSO-d₆, 400 MHz): δ 12.01 (s, 1H), 10.40 (s, 1H), 9.91 (s, 1H), 8.09 (t, 1H), 7.68 (s, 1H), 7.56-7.47 (m, 2H), 7.46 (d, 1H), 7.38-7.32 (m, 2H), 6.83-6.76 (m, 1H), 6.52 (d, 1H), 6.13 (s, 1H), 3.89-3.87 (m, 1H), 3.20 (d, 2H), 2.49-2.44 (m, 4H), 1.82-1.78 (m, 1H), 1.41 (d, 3H), 0.99-0.96 (m, 6H), 0.86 (d, 2H), 0.62 (d, 2H); LCMS: m/z = 504.40 (M + H)⁺; HPLC: 98.75%, rt: 4.47 min. |

TABLE 2-continued

| Comp. No. | Structure | Characterization Data |
|---|---|---|
| 33 | 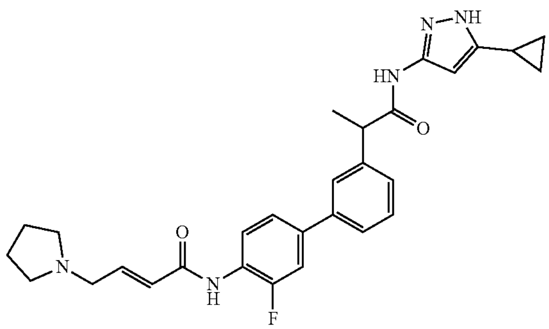 [SMILES: CC(C(=O)Nc1cc(C2CC2)[nH]n1)c1cccc(-c2ccc(NC(=O)/C=C/CN3CCCC3)c(F)c2)c1] | $^1$HNMR (DMSO-d$_6$, 400 MHz): δ 12.01 (s, 1H), 10.40 (s, 1H), 9.92 (s, 1H), 8.12-8.08 (m, 1H), 7.68 (s, 1H), 7.56-7.53 (m, 2H), 7.46 (d, 1H), 7.40-7.32 (m, 2H), 6.83-6.77 (m, 1H), 6.46 (d, 1H), 6.11 (s, 1H), 3.91-3.85 (m, 1H), 3.22 (d, 2H), 2.49-2.47 (m, 4H), 1.82-1.76 (m, 1H), 1.70 (d, 4H), 1.41 (d, 3H), 0.85 (d, 2H), 0.62-0.58 (m, 2H); LCMS: m/z = 502.40 (M + H)$^+$; HPLC: 95.31%, rt: 4.43 min. |
| 34 | 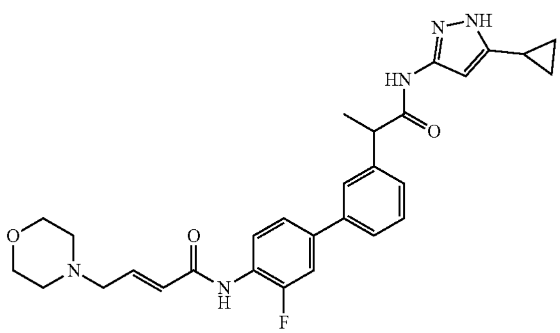 [SMILES: CC(C(=O)Nc1cc(C2CC2)[nH]n1)c1cccc(-c2ccc(NC(=O)/C=C/CN3CCOCC3)c(F)c2)c1] | $^1$HNMR (DMSO-d$_6$, 400 MHz): δ 12.01 (s, 1H), 10.41 (s, 1H), 9.94 (s, 1H), 8.10 (t, 1H), 7.68 (s, 1H), 7.56-7.53 (m, 2H), 7.46 (d, 1H), 7.40-7.32 (m, 2H), 6.78-6.72 (m, 1H), 6.48 (d, 1H), 6.11 (s, 1H), 3.91-3.85 (m, 1H), 3.60 (d, 4H), 3.10 (d, 2H), 2.38 (s, 4H), 1.83-1.74 (m, 1H), 1.41 (d, 3H), 0.88-0.85 (m, 2H), 0.61-0.58 (m, 2H); LCMS: m/z = 518.40 (M + H)$^+$; HPLC: 98.37%, rt: 4.23 min. |
| 35 | 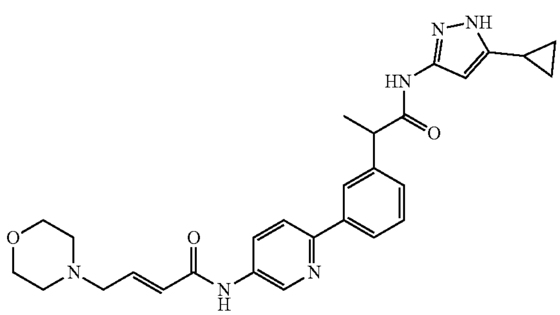 [SMILES: CC(C(=O)Nc1cc(C2CC2)[nH]n1)c1cccc(-c2ccc(NC(=O)/C=C/CN3CCOCC3)cn2)c1] | $^1$HNMR (DMSO-d$_6$, 400 MHz): δ 12.01 (s, 1H), 10.41 (s, 2H), 8.85 (s, 1H), 8.21 (d, 1H), 8.08 (s, 1H), 7.91-7.83 (m, 2H), 7.41-7.37 (m, 2H), 6.81-6.74 (m, 1H), 6.31 (d, 1H), 6.12 (s, 1H), 3.93-3.88 (m, 1H), 3.60 (t, 4H), 3.16-3.13 (m, 2H), 2.39 (s, 4H), 1.83-1.76 (m, 1H), 1.40 (d, 3H), 0.87-0.84 (d, 2H), 0.62-0.60 (m, 2H); LCMS: m/z = 501.40 (M + H)$^+$; HPLC: 97.02%, rt: 4.17 min. |
| 36 | 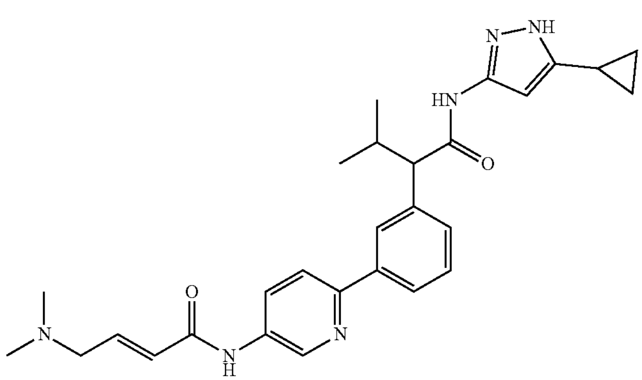 [SMILES: CC(C)C(C(=O)Nc1cc(C2CC2)[nH]n1)c1cccc(-c2ccc(NC(=O)/C=C/CN(C)C)cn2)c1] | $^1$HNMR (DMSO-d$_6$, 400 MHz): δ 12.02 (s, 1H), 10.49 (s, 1H), 10.40 (s, 1H), 8.87-8.86 (m, 1H), 8.23-8.20 (m, 1H), 8.10 (s, 1H), 7.90-7.84 (m, 2H), 7.42-7.38 (m, 2H), 6.82-6.75 (m, 1H), 6.32-6.28 (m, 1H), 6.14 (s, 1H), 3.40-3.37 (m, 1H), 3.08 (d, 2H), 2.41-2.35 (m, 1H), 2.19 (s, 6H), 1.81-1.77 (m, 1H), 0.98 (d, 3H), 0.86 (d, 2H), 0.66 (m, 3H), 0.61 (s, 2H); LCMS: m/z = 487.4 (M + H)$^+$; HPLC: 96.73%, rt: 6.05 min. |

TABLE 2-continued

| Comp. No. | Structure | Characterization Data |
|---|---|---|
| 37 | 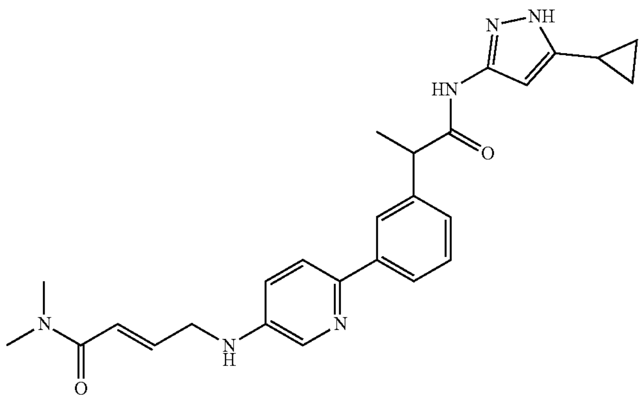 [SMILES: CC(C(=O)Nc1cc(C2CC2)[nH]n1)c1cccc(-c2ccc(NC/C=C/C(=O)N(C)C)cn2)c1] | $^1$HNMR (DMSO-d$_6$, 400 MHz): δ 12.00 (s, 1H), 10.42 (s, 1H), 8.07 (s, 1H), 7.97 (s, 1H), 7.73 (d, 1H), 7.64 (d, 1H), 7.33-7.25 (m, 2H), 7.02-6.99 (m, 1H), 6.67-6.61 (m, 2H), 6.40 (t, 1H), 6.12 (s, 1H), 3.94-3.84 (m, 3H), 2.97 (s, 3H), 2.95 (s, 3H), 1.82-1.78 (m, 1H), 1.38 (d, 3H), 0.86 (d, 2H), 0.61-0.59 (m, 2H); LCMS: m/z = 459.30 (M + H)$^+$; HPLC: 90.11%, rt: 4.01 min. |
| 38 | 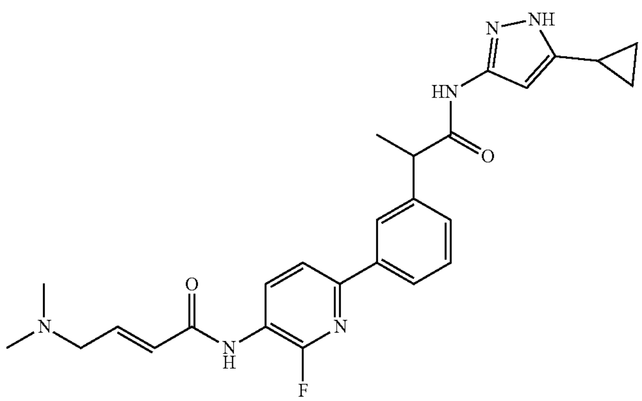 | $^1$HNMR (DMSO-d$_6$, 400 MHz): δ 12.02 (s, 1H), 10.46 (s, 1H), 10.15 (s, 1H), 8.66-8.61 (m, 1H), 8.03 (s, 1H), 7.89-7.84 (m, 2H), 7.41-7.40 (m, 2H), 6.82-6.75 (m, 1H), 6.53-6.47 (m, 1H), 6.12 (s, 1H), 3.92-3.90 (m, 1H), 3.06-3.04 (d, 2H), 2.18 (s, 6H), 1.81 (m, 1H), 1.40 (d, 3H), 0.87-0.85 (m, 2H), 0.61-0.60 (m, 2H); LCMS: m/z = 477.5 (M + H)$^+$; HPLC: 97.38%, rt: 5.77 min. |
| 39 | 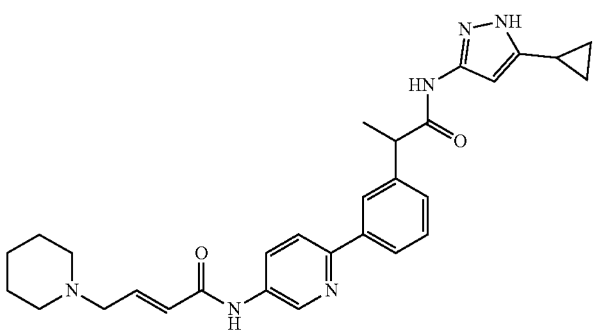 [SMILES: CC(C(=O)Nc1cc(C2CC2)[nH]n1)c1cccc(-c2ccc(NC(=O)/C=C/CN3CCCCC3)cn2)c1] | $^1$HNMR (DMSO-d$_6$, 400 MHz): δ 12.01 (s, 1H), 10.44 (s, 1H), 10.37 (s, 1H), 8.85-8.84 (s, 1H), 8.20 (d, 1H), 8.08 (s, 1H), 7.89 (d, 1H), 7.86-7.83 (m, 1H), 7.41-7.36 (m, 2H), 6.81-6.74 (m, 1H), 6.26 (d, 1H), 6.13 (s, 1H), 3.91-3.90 (m, 1H), 3.16-3.10 (m, 2H), 2.34 (s, 4H), 1.81-1.77 (m, 1H), 1.54-1.51 (m, 4H), 1.41-1.39 (m, 5H), 0.85 (d, 2H), 0.62-0.59 (m, 2H); LCMS: m/z = 499.60 (M + H)$^+$; HPLC: 98.43%, rt: 5.75 min. |
| 40 | 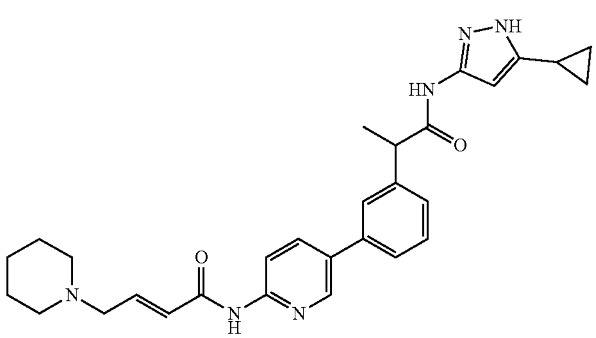 [SMILES: CC(C(=O)Nc1cc(C2CC2)[nH]n1)c1cccc(-c2ccc(NC(=O)/C=C/CN3CCCCC3)nc2)c1] | $^1$HNMR (DMSO-d$_6$, 400 MHz): δ 12.01 (s, 1H), 10.74 (s, 1H), 10.40 (s, 1H), 8.61 (d, 1H), 8.27 (d, 1H), 8.05 (d, 1H), 7.69 (s, 1H), 7.55 (d, 1H), 7.42-7.34 (m, 2H), 6.83-6.76 (m, 1H), 6.43 (d, 1H), 6.12 (s, 1H), 3.90-3.86 (m, 1H), 3.07-3.05 (d, 2H), 2.32 (s, 4H), 1.82-1.77 (m, 1H), 1.53-1.48 (m, 4H), 1.42-1.37 (m, 5H), 0.87-0.85 (d, 2H), 0.60-0.59 (m, 2H); LCMS: m/z = 499.70 (M + H)$^+$; HPLC: 97.36%, rt: 5.90 min. |

TABLE 2-continued

| Comp. No. | Structure | Characterization Data |
|---|---|---|
| 41 | 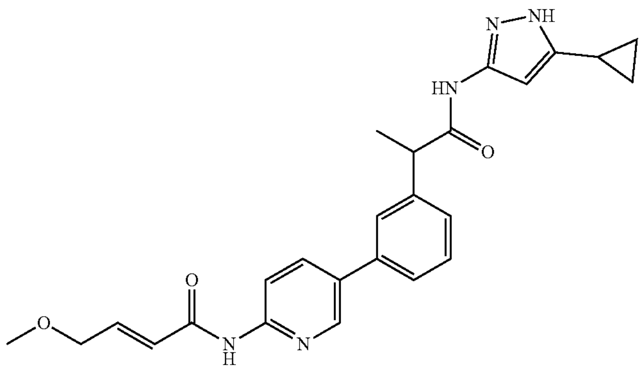 [SMILES: COC/C=C/C(=O)Nc1ccc(-c2cccc(C(C)C(=O)Nc3cc(C4CC4)[nH]n3)c2)cn1] | $^1$HNMR (DMSO-d$_6$, 400 MHz): δ 12.00 (s, 1H), 10.81 (s, 1H), 10.43 (s, 1H), 8.61 (d, 1H), 8.27 (d, 1H), 8.08-8.05 (m, 1H), 7.68 (s, 1H), 7.55 (d, 1H), 7.43-7.34 (m, 2H), 6.89-6.83 (m, 1H), 6.53-6.48 (m, 1H), 6.10 (s, 1H), 4.10-4.09 (m, 2H), 3.96-3.90 (m, 1H), 3.31 (s, 3H), 1.80-1.78 (m, 1H), 1.41-1.39 (d, 3H), 0.86-0.83 (m, 2H), 0.60-0.58 (m, 2H); LCMS: m/z = 446.4 (M + H)$^+$; HPLC: 95.99%, rt: 4.05 min. |
| 42 | 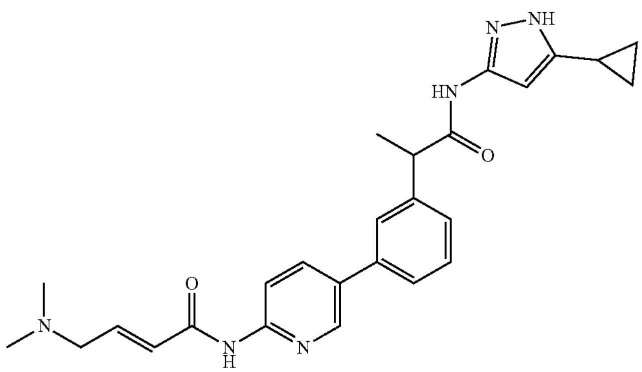 [SMILES: CC(C(=O)Nc1cc(C2CC2)[nH]n1)c1cccc(-c2ccc(NC(=O)/C=C/CN(C)C)nc2)c1] | $^1$HNMR (DMSO-d$_6$, 400 MHz): δ 12.05 (s, 1H), 10.75 (s, 1H), 10.41 (d, 1H), 8.61 (s, 1H), 8.28-8.26 (d, 1H), 8.07-8.05 (m, 1H), 7.69 (s, 1H), 7.55 (d, 1H), 7.42-7.34 (m, 2H), 6.83-6.76 (m, 1H), 6.44 (d, 1H), 6.11 (s, 1H), 3.89-3.87 (m, 1H), 3.06-3.04 (d, 2H), 2.15 (s, 6H), 1.78-1.76 (m, 1H), 1.42-1.40 (d, 3H), 0.87-0.84 (m, 2H), 0.61-0.59 (m, 2H); LCMS: m/z = 459.4 (M + H)$^+$; HPLC: 96.38%, rt: 4.26 min. |
| 43 | 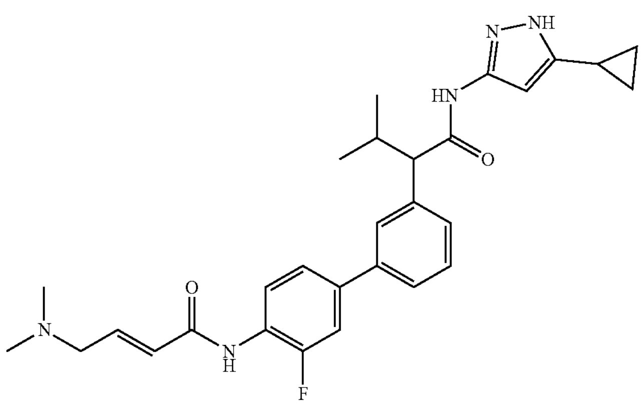 [SMILES: CC(C)C(C(=O)Nc1cc(C2CC2)[nH]n1)c1cccc(-c2ccc(NC(=O)/C=C/CN(C)C)c(F)c2)c1] | $^1$HNMR (DMSO-d$_6$, 400 MHz): δ 12.02 (s, 1H), 10.43 (s, 1H), 9.94 (s, 1H), 8.13-8.09 (m, 1H), 7.67 (s, 1H), 7.55-7.52 (m, 2H), 7.46-7.44 (m, 1H), 7.40-7.33 (m, 2H), 6.79-6.72 (m, 1H), 6.49-6.45 (m, 1H), 6.13 (s, 1H), 3.34-3.31 (m, 1H), 3.09-3.07 (d, 2H), 2.40-2.36 (m, 1H), 2.17 (s, 6H), 1.81-1.76 (m, 1H), 0.97 (d, 3H), 0.85 (d, 2H), 0.66 (m, 3H), 0.61 (s, 2H); LCMS: m/z = 504.4 (M + H)$^+$; HPLC: 98.59%, rt: 4.42 min. |
| 44 | 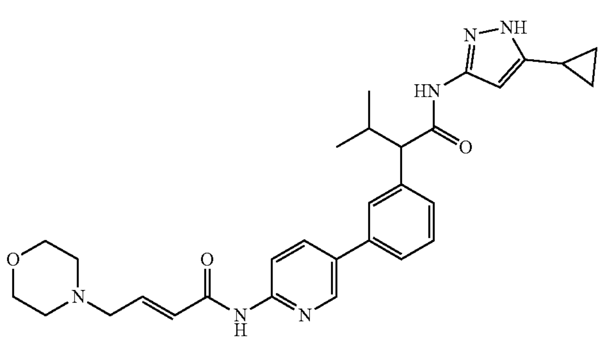 [SMILES: CC(C)C(C(=O)Nc1cc(C2CC2)[nH]n1)c1cccc(-c2ccc(NC(=O)/C=C/CN3CCOCC3)nc2)c1] | $^1$HNMR (DMSO-d$_6$, 400 MHz): δ 12.02 (s, 1H), 10.77 (s, 1H), 10.44 (s, 1H), 8.60 (s, 1H), 8.27 (d, 1H), 8.05 (d, 1H), 7.67 (s, 1H), 7.56 (d, 1H), 7.41-7.35 (m, 2H), 6.81-6.77 (m, 1H), 6.47 (d, 1H), 6.13 (s, 1H), 3.60-3.58 (m, 5H), 3.11 (d, 2H), 2.67-2.66 (m, 1H), 2.38 (s, 4H), 1.81-1.79 (m, 1H), 0.97 (d, 3H), 0.86 (d, 2H), 0.67 (d, 3H), 0.60 (s, 2H); LCMS: m/z = 529.40 (M + H)$^+$; HPLC: 95.50%, rt: 4.56 min. |

TABLE 2-continued

| Comp. No. | Structure | Characterization Data |
|---|---|---|
| 45 | 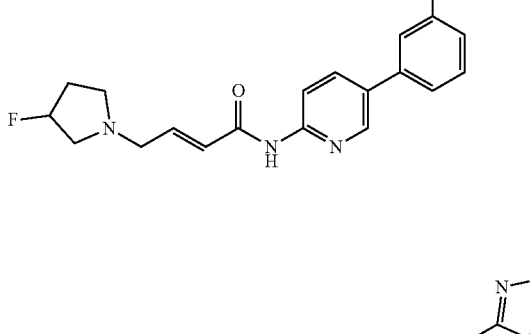 | ¹HNMR (DMSO-d₆, 400 MHz): δ 12.02-11.98 (brs, 1H), 10.77 (s, 1H), 10.43 (s, 1H), 8.62 (s, 1H), 8.27 (d, 1H), 8.16 (s, 1H), 8.07 (d, 1H), 7.69 (s, 1H), 7.56 (d, 1H), 7.43-7.35 (m, 1H), 6.85-6.80 (m, 1H), 6.48 (d, 1H), 6.11 (s, 1H), 5.30-5.10 (m, 1H), 3.90-3.89 (m, 1H), 2.88-2.79 (m, 2H), 2.70-2.59 (m, 2H), 2.33-2.32 (m, 1H), 2.21-2.09 (m, 2H), 1.82-1.78 (m, 2H), 1.41 (d, 3H), 0.88-0.86 (m, 2H), 0.62-0.59 (m, 2H); LCMS: m/z = 503.60 (M + H)⁺; HPLC: 92.66%, rt: 4.11 min. |
| 46 | 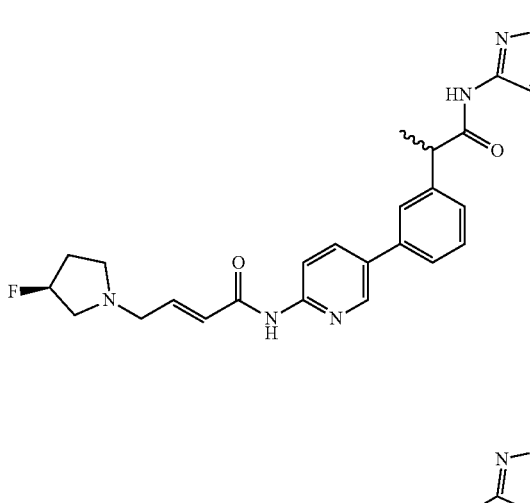 | ¹HNMR (DMSO-d₆, 400 MHz): δ 12.02-11.98 (brs, 1H), 10.77 (s, 1H), 10.43 (s, 1H), 8.62 (s, 1H), 8.27 (d, 1H), 8.16 (s, 1H), 8.07 (d, 1H), 7.69 (s, 1H), 7.56 (d, 1H), 7.43-7.35 (m, 1H), 6.85-6.80 (m, 1H), 6.48 (d, 1H), 6.11 (s, 1H), 5.30-5.10 (m, 1H), 3.90-3.89 (m, 1H), 2.88-2.79 (m, 2H), 2.70-2.59 (m, 2H), 2.33-2.32 (m, 1H), 2.21-2.09 (m, 2H), 1.82-1.78 (m, 2H), 1.41 (d, 3H), 0.88-0.86 (m, 2H), 0.62-0.59 (m, 2H); LCMS: m/z = 503.30 (M + H)⁺; HPLC: 95.38%, rt: 5.41 min. |
| 47 | 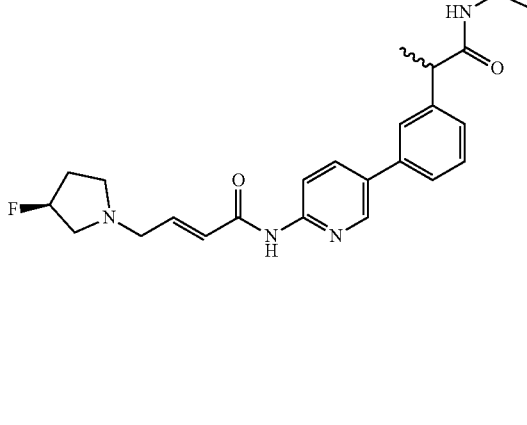 | ¹HNMR (DMSO-d₆, 400 MHz): δ 12.02-11.98 (brs, 1H), 10.77 (s, 1H), 10.43 (s, 1H), 8.62 (s, 1H), 8.27 (d, 1H), 8.16 (s, 1H), 8.07 (d, 1H), 7.69 (s, 1H), 7.56 (d, 1H), 7.43-7.35 (m, 1H), 6.85-6.80 (m, 1H), 6.48 (d, 1H), 6.11 (s, 1H), 5.30-5.10 (m, 1H), 3.90-3.89 (m, 1H), 2.88-2.79 (m, 2H), 2.70-2.59 (m, 2H), 2.33-2.32 (m, 1H), 2.21-2.09 (m, 2H), 1.82-1.78 (m, 2H), 1.41 (d, 3H), 0.88-0.86 (m, 2H), 0.62-0.59 (m, 2H); LCMS: m/z = 503.30 (M + H)⁺; HPLC: 97.79%, rt: 5.94 min.; Chiral HPLC: 98.06%, rt: 10.20 min. (Isomer-1 of compound-46) |
| 48 | 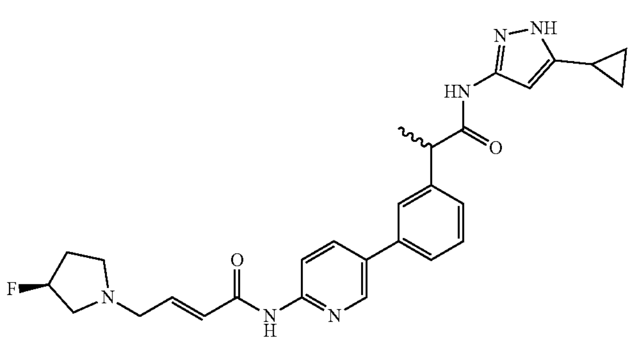 [SMILES: CC(C(=O)Nc1cc(C2CC2)[nH]n1)c1cccc(-c2ccc(NC(=O)/C=C/CN3CC[C@H](F)C3)nc2)c1] | ¹HNMR (DMSO-d₆, 400 MHz): δ 12.02-11.98 (brs, 1H), 10.77 (s, 1H), 10.43 (s, 1H), 8.62 (s, 1H), 8.27 (d, 1H), 8.16 (s, 1H), 8.07 (d, 1H), 7.69 (s, 1H), 7.56 (d, 1H), 7.43-7.35 (m, 1H), 6.85-6.80 (m, 1H), 6.48 (d, 1H), 6.11 (s, 1H), 5.30-5.10 (m, 1H), 3.90-3.89 (m, 1H), 2.88-2.79 (m, 2H), 2.70-2.59 (m, 2H), 2.33-2.32 (m, 1H), 2.21-2.09 (m, 2H), 1.82-1.78 (m, 2H), 1.41 (d, 3H), 0.88-0.86 (m, 2H), 0.62-0.59 (m, 2H); LCMS: m/z = 503.30 (M + H)⁺; HPLC: 95.92%, rt: 5.94 min.; Chiral HPLC: 97.74%, rt: 15.18 min. (Isomer-2 of compound-46) |

TABLE 2-continued

| Comp. No. | Structure | Characterization Data |
|---|---|---|
| 49 | 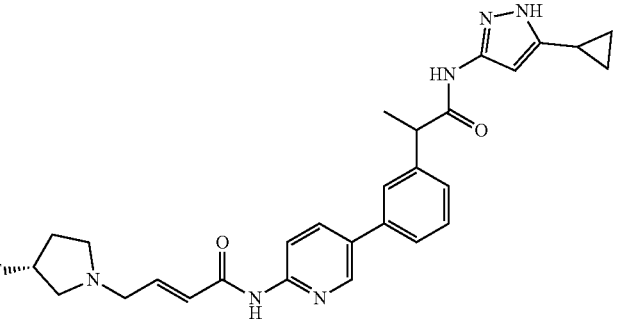 | ¹HNMR (DMSO-d$_6$, 400 MHz): δ 12.02-11.98 (brs, 1H), 10.77 (s, 1H), 10.43 (s, 1H), 8.62 (s, 1H), 8.27 (d, 1H), 8.16 (s, 1H), 8.07 (d, 1H), 7.69 (s, 1H), 7.56 (d, 1H), 7.43-7.35 (m, 1H), 6.85-6.80 (m, 1H), 6.48 (d, 1H), 6.11 (s, 1H), 5.30-5.10 (m, 1H), 3.90-3.89 (m, 1H), 2.88-2.79 (m, 2H), 2.70-2.59 (m, 2H), 2.33-2.32 (m, 1H), 2.21-2.09 (m, 2H), 1.82-1.78 (m, 2H), 1.41 (d, 3H), 0.88-0.86 (m, 2H), 0.62-0.59 (m, 2H); LCMS: m/z = 503.30 (M + H)⁺; HPLC: 97.79%, rt: 5.94 min. |
| 50 | 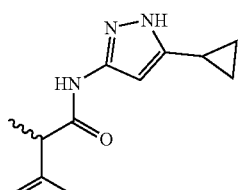 | ¹HNMR (DMSO-d$_6$, 400 MHz): δ 12.02-11.98 (brs, 1H), 10.77 (s, 1H), 10.43 (s, 1H), 8.62 (s, 1H), 8.27 (d, 1H), 8.16 (s, 1H), 8.07 (d, 1H), 7.69 (s, 1H), 7.56 (d, 1H), 7.43-7.35 (m, 1H), 6.85-6.80 (m, 1H), 6.48 (d, 1H), 6.11 (s, 1H), 5.30-5.10 (m, 1H), 3.90-3.89 (m, 1H), 2.88-2.79 (m, 2H), 2.70-2.59 (m, 2H), 2.33-2.32 (m, 1H), 2.21-2.09 (m, 2H), 1.82-1.78 (m, 2H), 1.41 (d, 3H), 0.88-0.86 (m, 2H), 0.62-0.59 (m, 2H); LCMS: m/z = 503.30 (M + H)⁺; HPLC: 98.31%, rt: 5.97 min; Chiral HPLC: 98.56%, rt: 10.44 min. (Isomer-1 of compound-49) |
| 51 | 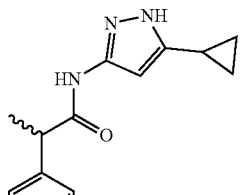 | ¹HNMR (DMSO-d$_6$, 400 MHz): δ 12.02-11.98 (brs, 1H), 10.77 (s, 1H), 10.43 (s, 1H), 8.62 (s, 1H), 8.27 (d, 1H), 8.16 (s, 1H), 8.07 (d, 1H), 7.69 (s, 1H), 7.56 (d, 1H), 7.43-7.35 (m, 1H), 6.85-6.80 (m, 1H), 6.48 (d, 1H), 6.11 (s, 1H), 5.30-5.10 (m, 1H), 3.90-3.89 (m, 1H), 2.88-2.79 (m, 2H), 2.70-2.59 (m, 2H), 2.33-2.32 (m, 1H), 2.21-2.09 (m, 2H), 1.82-1.78 (m, 2H), 1.41 (d, 3H), 0.88-0.86 (m, 2H), 0.62-0.59 (m, 2H); LCMS: m/z = 503.60 (M + H)⁺; HPLC: 97.48%, rt: 5.48 min. Chiral HPLC: 97.95%, rt: 20.50 min. (Isomer-2 of compound-49) |
| 52 | 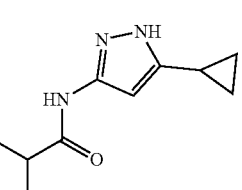 | ¹HNMR (DMSO-d$_6$, 400 MHz): δ 12.03 (s, 1H), 10.74 (s, 1H), 10.42 (s, 1H), 8.62 (s, 1H), 8.27 (d, 1H), 8.07 (d, 1H), 7.69 (s, 1H), 7.56 (d, 1H), 7.43-7.35 (m, 2H), 6.88-6.81 (m, 1H), 6.50 (d, 1H), 6.13 (s, 1H), 3.90-3.87 (m, 1H), 3.24 (s, 2H), 2.50 (m, 4H), 1.82-1.77 (m, 1H), 1.70 (m, 4H), 1.41 (d, 3H), 0.87-0.85 (d, 2H), 0.61-0.60 (d, 2H); LCMS: m/z = 485.64 (M + H)⁺; HPLC: 96.15%, rt: 8.45 min. |

TABLE 2-continued

| Comp. No. | Structure | Characterization Data |
|---|---|---|
| 53 | 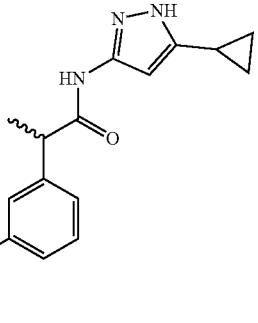 | ¹HNMR (DMSO-d₆, 400 MHz): δ 12.03 (s, 1H), 10.74 (s, 1H), 10.42 (s, 1H), 8.62 (s, 1H), 8.27 (d, 1H), 8.07 (d, 1H), 7.69 (s, 1H), 7.56 (d, 1H), 7.43-7.35 (m, 2H), 6.88-6.81 (m, 1H), 6.50 (d, 1H), 6.13 (s, 1H), 3.90-3.87 (m, 1H), 3.24 (s, 2H), 2.50 (m, 4H), 1.82-1.77 (m, 1H), 1.70 (m, 4H), 1.41 (d, 3H), 0.87-0.85 (d, 2H), 0.61-0.60 (d, 2H); LCMS: m/z = 485.64 (M + H)⁺; HPLC: 94.40%, rt: 5.95 min.; Chiral HPLC: 97.27%, rt: 13.51 min. (Isomer-1 of compound-52) |
| 54 | 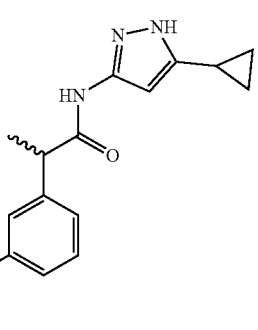 | ¹HNMR (DMSO-d₆, 400 MHz): δ 12.03 (s, 1H), 10.74 (s, 1H), 10.42 (s, 1H), 8.62 (s, 1H), 8.27-8.24 (d, 1H), 8.07-8.02 (d, 1H), 7.69 (s, 1H), 7.57-7.55 (d, 1H), 7.43-7.35 (m, 2H), 6.89-6.82 (m, 1H), 6.50 (d, 1H), 6.13 (s, 1H), 3.91-3.88 (m, 1H), 3.24 (s, 2H), 2.50 (m, 4H), 1.82-1.77 (m, 1H), 1.70 (m, 4H), 1.41-1.40 (d, 3H), 0.87-0.85 (d, 2H), 0.61-0.60 (d, 2H); LCMS: m/z = 485.64 (M + H)⁺; HPLC: 94.04%, rt: 5.97 min.; Chiral HPLC: 95.43%, rt: 16.67 min. (Isomer-2 of compound-52) |
| 55 | 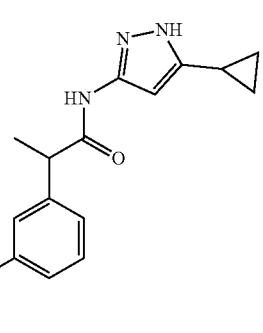 | ¹HNMR (DMSO-d₆, 400 MHz): δ 10.77 (s, 1H), 10.43 (s, 1H), 8.62 (s, 1H), 8.28 (d, 1H), 8.15 (m, 1H), 8.06 (d, 1H), 7.69 (s, 1H), 7.56 (d, 1H), 7.43-7.35 (m, 2H), 6.85-6.80 (m, 1H), 6.47 (d, 1H), 6.13 (s, 1H), 3.91-3.87 (m, 1H), 3.25 (d, 2H), 2.52-2.32 (m, 4H), 1.82-1.78 (m, 1H), 1.41 (d, 3H), 0.99-0.97 (m, 6H), 0.86 (d, 2H), 0.62-0.60 (m, 2H); LCMS: m/z = 487.6 (M + H)⁺; HPLC: 97.05%, rt: 4.10 min. |
| 56 | 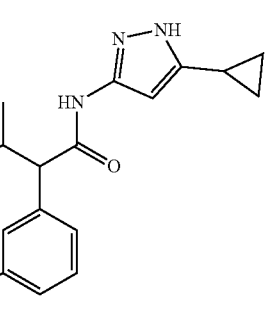 | ¹HNMR (DMSO-d₆, 400 MHz): δ 12.02 (s, 1H), 10.77 (s, 1H), 10.46 (s, 1H), 8.61 (s, 1H), 8.29-8.21 (m, 1H), 8.06 (d, 1H), 7.68 (s, 1H), 7.57 (d, 1H), 7.44-7.36 (m, 2H), 6.84-6.77 (m, 1H), 6.44 (d, 1H), 6.13 (s, 1H), 3.06 (d, 2H), 2.33 (s, 1H), 2.17 (s, 6H), 1.81-1.78 (m, 1H), 0.99-0.97 (d, 3H), 0.86 (d, 2H), 0.67 (d, 3H), 0.62-0.59 (m, 2H); LCMS: m/z = 487.6 (M + H)⁺; HPLC: 95.92%, rt: 4.35 min. |

TABLE 2-continued

| Comp. No. | Structure | Characterization Data |
|---|---|---|
| 57 | 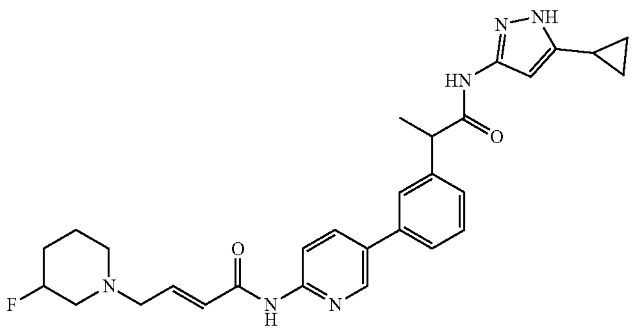 [SMILES: CC(C(=O)Nc1cc(C2CC2)[nH]n1)c1cccc(-c2ccc(NC(=O)/C=C/CN3CCCC(F)C3)nc2)c1] | ¹HNMR (DMSO-d$_6$, 400 MHz): δ 12.02 (s, 1H), 10.78 (s, 1H), 10.43 (s, 1H), 8.63 (d, 1H), 8.28 (d, 1H), 8.08 (dd, 1H), 7.70 (s, 1H), 7.57 (d, 1H), 7.44-7.40 (m, 1H), 7.38-7.36 (m, 1H), 6.84-6.77 (m, 1H), 6.56-6.45 (m, 1H), 6.14 (s, 1H), 4.73-4.59 (m, 1H), 3.93-3.88 (m, 1H), 3.17-3.16 (m, 2H), 2.78-2.67 (m, 2H), 2.45-2.25 (m, 2H), 1.85-1.78 (m, 3H), 1.74-1.46 (m, 2H), 1.42 (d, 3H), 0.87 (d, 2H), 0.61 (d, 2H); LCMS: m/z = 517.6 (M + H)⁺; HPLC: 99.22%, rt: 3.40 min. |
| 58 | 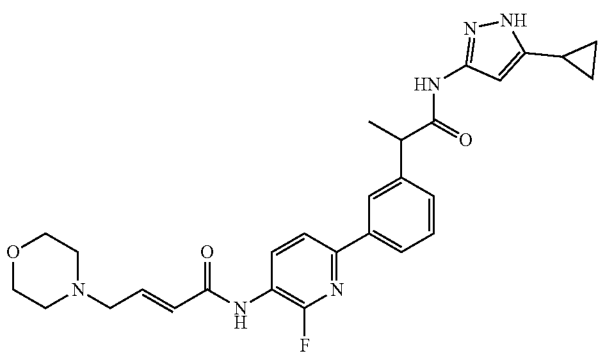 [SMILES: CC(C(=O)Nc1cc(C2CC2)[nH]n1)c1cccc(-c2ccc(NC(=O)/C=C/CN3CCOCC3)c(F)n2)c1] | ¹HNMR (DMSO-d$_6$, 400 MHz): δ 12.02 (s, 1H), 10.48 (s, 1H), 10.17 (s, 1H), 8.65 (d, 1H), 8.05 (s, 1H), 7.91-7.85 (m, 2H), 7.43-7.42 (m, 2H), 6.81-6.76 (m, 1H), 6.55-6.52 (m, 1H), 6.14 (s, 1H), 3.94-3.92 (m, 1H), 3.62-3.60 (m, 4H), 3.16-3.13 (m, 2H), 2.40 (s, 4H), 1.82-1.79 (m, 1H), 1.43 (d, 3H), 0.87 (d, 2H), 0.62 (d, 2H); LCMS: m/z = 519.2 (M + H)⁺; HPLC: 98.82%, rt: 5.92 min. |
| 59 | 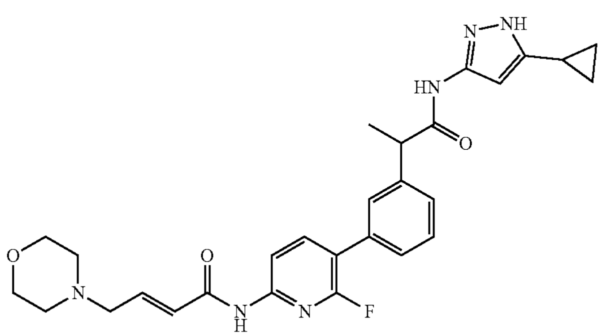 [SMILES: CC(C(=O)Nc1cc(C2CC2)[nH]n1)c1cccc(-c2ccc(NC(=O)/C=C/CN3CCOCC3)nc2F)c1] | ¹HNMR (DMSO-d$_6$, 400 MHz): δ 12.02 (s, 1H), 10.43 (s, 1H), 10.36 (s, 1H), 8.21-8.18 (d, 1H), 8.12-8.07 (m, 1H), 7.59-7.58 (m, 1H), 7.44-7.38 (m, 3H), 6.85-6.78 (m, 1H), 6.46-6.42 (d, 1H), 6.11 (s, 1H), 3.90-3.87 (m, 1H), 3.61-3.58 (m, 4H), 3.16-3.11 (m, 2H), 2.38-2.32 (m, 4H), 1.88-1.77 (m, 1H), 1.41-1.39 (m, 3H), 0.89-0.84 (m, 2H), 0.62-0.58 (m, 2H); LCMS: m/z = 519 (M + H)⁺; HPLC: 98.28%, rt: 3.82 min. |
| 60 | 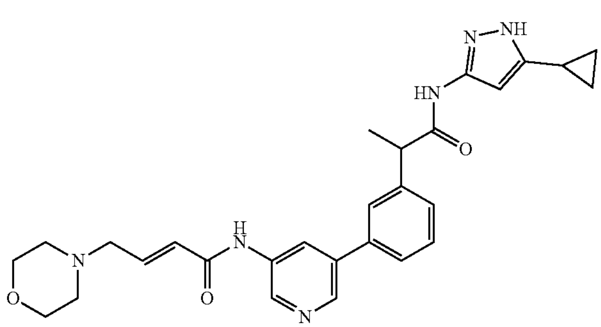 [SMILES: CC(C(=O)Nc1cc(C2CC2)[nH]n1)c1cccc(-c2cncc(NC(=O)/C=C/CN3CCOCC3)c2)c1] | ¹HNMR (DMSO-d$_6$, 400 MHz): δ 12.02 (s, 1H), 10.43 (s, 1H), 10.36 (s, 1H), 8.21-8.18 (d, 1H), 8.55-8.54 (m, 1H), 8.35 (s, 1H), 7.66 (s, 1H), 7.55-7.53 (m, 1H), 7.47-7.40 (m, 2H), 6.83-6.76 (m, 1H), 6.34-6.30 (d, 1H), 6.15 (s, 1H), 3.95-3.93 (m, 1H), 3.61-3.58 (m, 4H), 3.16-3.11 (m, 2H), 2.38-2.32 (m, 4H), 1.88-1.77 (m, 1H), 1.41-1.39 (m, 3H), 0.89-0.84 (m, 2H), 0.62-0.58 (m, 2H); LCMS: m/z = 501.1 (M + H)⁺; HPLC: 95.28%, rt: 5.61 min. |

TABLE 2-continued

| Comp. No. | Structure | Characterization Data |
|---|---|---|
| 61 | 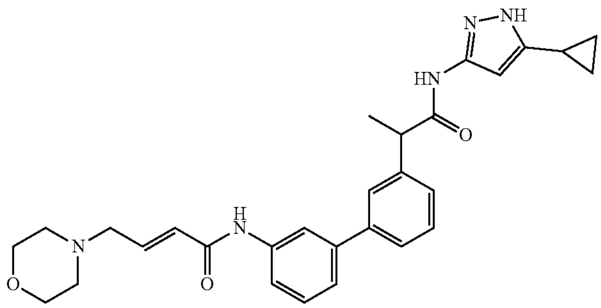 [SMILES: CC(C(=O)Nc1cc(C2CC2)[nH]n1)c1cccc(-c2cccc(NC(=O)/C=C/CN3CCOCC3)c2)c1] | ¹HNMR (DMSO-d$_6$, 400 MHz): 12.02 (s, 1H), 10.43 (s, 1H), 10.36 (s, 1H), 7.93 (s, 1H), 7.68-7.66 (d, 1H), 7.62 (s, 1H), 7.47-7.35 (m, 4H), 7.31-7.29 (d, 1H), 6.78-6.71 (m, 1H), 6.32-6.28 (d, 1H), 6.14 (s, 1H), 3.91-3.88 (m, 1H), 3.61-3.58 (m, 4H), 3.17-3.11 (m, 2H), 2.39-2.32 (m, 4H), 1.82-1.75 (m, 1H), 1.41-1.36 (m, 3H), 0.88-0.86 (m, 2H), 0.61-0.60 (m, 2H); LCMS: m/z = 500.1 (M + H)⁺; HPLC: 95.40%, rt: 6.08 min. |
| 62 | 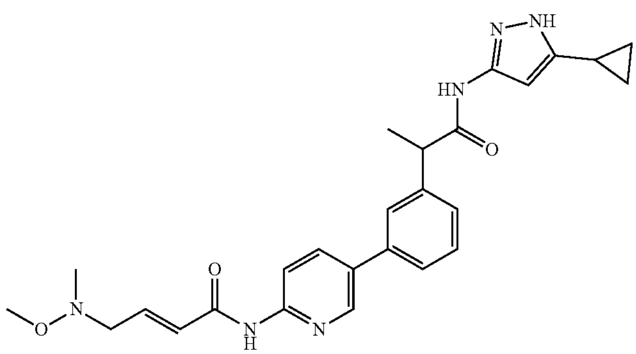 [SMILES: CON(C)C/C=C/C(=O)Nc1ccc(-c2cccc(C(C)C(=O)Nc3cc(C4CC4)[nH]n3)c2)cn1] | ¹HNMR (DMSO-d$_6$, 400 MHz): 12.02 (s, 1H), 10.82 (s, 1H), 10.42 (s, 1H), 8.64-8.63 (d, 1H), 8.31-8.29 (d, 1H), 8.10-8.08 (m, 1H), 7.71 (s, 1H), 7.59-7.57 (d, 1H), 7.45-7.41 (m, 1H), 7.38-7.36 (d, 1H), 6.92-6.85 (m, 1H), 6.49-6.45 (d, 1H), 6.13 (s, 1H), 3.92-3.90 (m, 1H), 3.44 (s, 5H), 2.55 (s, 3H), 1.84-1.80 (m, 1H), 1.44-1.42 (m, 3H), 0.89-0.86 (m, 2H), 0.64-0.60 (m, 2H); LCMS: m/z = 475.6 (M + H)⁺; HPLC: 95.10%, rt: 4.01 min. |
| 63 | 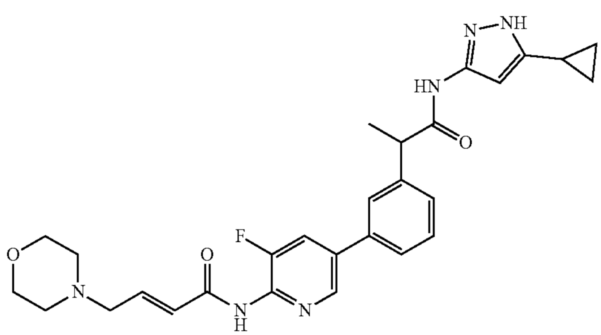 [SMILES: CC(C(=O)Nc1cc(C2CC2)[nH]n1)c1cccc(-c2cnc(NC(=O)/C=C/CN3CCOCC3)c(F)c2)c1] | ¹HNMR (DMSO-d$_6$, 400 MHz): δ 12.02 (s, 1H), 10.48 (s, 1H), 10.41 (s, 1H), 8.56 (s, 1H), 8.09-8.06 (m, 1H), 7.76 (s, 1H), 7.64-7.63 (d, 1H), 7.46-7.39 (m, 2H), 6.81-6.74 (m, 1H), 6.38-6.34 (d, 1H), 6.14 (s, 1H), 3.95-3.88 (m, 1H), 3.61-3.59 (m, 4H), 3.16-3.13 (m, 2H), 2.40 (s, 4H), 1.84-1.79 (m, 1H), 1.43-1.42 (d, 3H), 0.88-0.86 (m, 2H), 0.62-0.60 (m, 2H); LCMS: m/z = 519.60 (M + H)⁺; HPLC: 95.10%, rt: 5.79 min. |
| 64 | 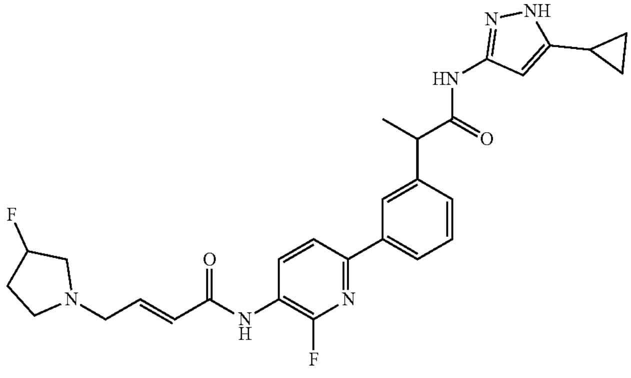 [SMILES: CC(C(=O)Nc1cc(C2CC2)[nH]n1)c1cccc(-c2ccc(NC(=O)/C=C/CN3CCC(F)C3)c(F)n2)c1] | ¹HNMR (DMSO-d$_6$, 400 MHz): δ 12.02 (s, 1H), 10.48 (s, 1H), 10.21 (s, 1H), 8.68-8.63 (m, 1H), 8.04 (s, 1H), 7.90-7.86 (m, 2H), 7.88-7.85 (m, 2H), 7.42-7.41 (d, 2H), 6.85-6.81 (m, 1H), 6.55-6.52 (d, 1H), 6.14 (s, 1H), 5.61-5.21 (m, 1H), 3.93-3.91 (m, 1H), 2.85-2.81 (m, 2H), 2.26-2.21 (m, 2H), 2.01-1.80 (m, 3H), 1.42-1.40 (d, 3H), 0.88-0.86 (m, 2H), 0.61-0.60 (m, 2H); LCMS: m/z = 520.30 (M + H)⁺; HPLC: 95.27%, rt: 6.29 min. |

TABLE 2-continued

| Comp. No. | Structure | Characterization Data |
|---|---|---|
| 65 | 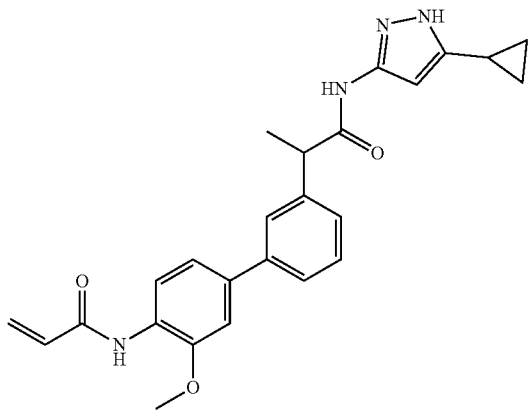 [SMILES: C=CC(=O)Nc1ccc(-c2cccc(C(C)C(=O)Nc3cc(C4CC4)[nH]n3)c2)cc1OC] | ¹HNMR (DMSO-d₆, 400 MHz): δ 12.01 (s, 1H), 10.41 (s, 1H), 9.47 (s, 1H), 8.17-8.15 (d, 1H), 7.60 (s, 1H), 7.55-7.53 (d, 1H), 7.41-7.37 (m, 1H), 7.33-7.32 (m, 1H), 7.25-7.21 (d, 1H), 7.20-7.18 (d, 1H), 6.80-6.72 (m, 1H), 6.27-6.22 (d, 1H), 6.13 (s, 1H), 5.74-5.71 (d, 1H), 3.93-3.86 (m, 3H), 2.61-2.35 (m, 1H), 1.86-1.72 (m, 1H), 1.46 (d, 3H), 0.88-0.86 (m, 2H), 0.62-0.64 (m, 2H), LCMS: m/z = 431.5 (M + H)⁺; HPLC: 95.38%, rt: 4.20 min. |
| 66 | 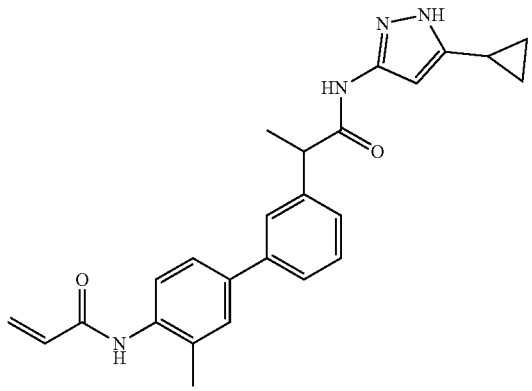 [SMILES: C=CC(=O)Nc1ccc(-c2cccc(C(C)C(=O)Nc3cc(C4CC4)[nH]n3)c2)cc1C] | ¹HNMR (DMSO-d₆, 400 MHz): δ 12.01 (s, 1H), 10.4 (s, 1H), 9.53 (s, 1H), 7.65-7.61 (m, 2H), 7.51-7.49 (d, 2H), 7.47-7.43 (d, 1H), 7.41-7.38 (m, 1H), 7.36-7.33 (d, 1H), 6.62-6.53 (m, 1H), 6.28-6.24 (s, 1H), 6.10 (s, 1H), 5.77-5.74 (d, 1H), 3.91-3.85 (m, 1H), 2.32-2.29 (s, 3H), 1.82-1.78 (m, 1H), 1.42-1.40 (d, 3H), 0.88-0.86 (m, 2H), 0.62-0.60 (m, 2H), LCMS: m/z = 415.1 (M + H)⁺; HPLC: 95.38%, rt: 4.47 min. |
| 67 | 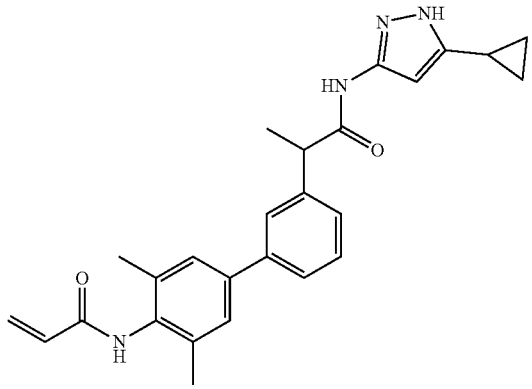 [SMILES: C=CC(=O)Nc1c(C)cc(-c2cccc(C(C)C(=O)Nc3cc(C4CC4)[nH]n3)c2)cc1C] | ¹HNMR (DMSO-d₆, 400 MHz): δ 12.10 (s, 1H), 10.41 (s, 1H), 9.51 (s, 1H), 7.60 (s, 1H), 7.51-7.42 (d, 1H), 7.38-7.32 (m, 4H), 6.62 (s, 1H), 6.65-653 (m, 1H), 6.14-6.13 (d, 1H), 5.76-5.73 (m, 1H), 3.32-3.22 (m, 1H) 2.62-2.51 (s, 3H), 2.53-2.24 (s, 3H), 1.81-1.70 (m, 1H), 1.47 (d, 3H), 0.88-0.86 (m, 2H), 0.62-0.64 (m, 2H), LCMS: m/z = 429.2 (M + H)⁺; HPLC: 99.38%, rt: 4.48 min. |
| 68 | 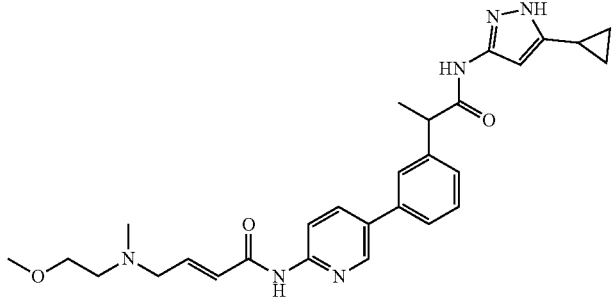 [SMILES: COCCN(C)C/C=C/C(=O)Nc1ccc(-c2cccc(C(C)C(=O)Nc3cc(C4CC4)[nH]n3)c2)cn1] | ¹HNMR (DMSO-d₆, 400 MHz): δ 12.10 (s, 1H), 10.82 (s, 1H), 10.41 (s, 1H), 8.62-8.61 (d, 1H), 8.29-8.27 (d, 1H), 8.08-8.05 (m, 1H), 7.70 (s, 1H), 7.57-7.55 (d, 1H), 7.43-7.35 (m, 2H), 6.87-6.80 (m, 1H), 6.51-6.47 (d, 1H), 6.13 (s, 1H), 3.91-3.89 (m, 1H), 3.45-3.42 (d, 2H), 3.24 (s, 3H), 3.18-3.15 (d, 2H), 2.53-2.51 (d, 2H), 2.20 (s, 3H), 1.82-179 (m, 1H), 1.43-1.41 (d, 3H), 0.86-0.85 (m, 2H), 0.62-0.61 (m, 2H) LCMS: m/z = 503.30 (M + H)⁺; HPLC: 97.87%, rt: 7.07 min. |

TABLE 2-continued

| Comp. No. | Structure | Characterization Data |
|---|---|---|
| 69 | 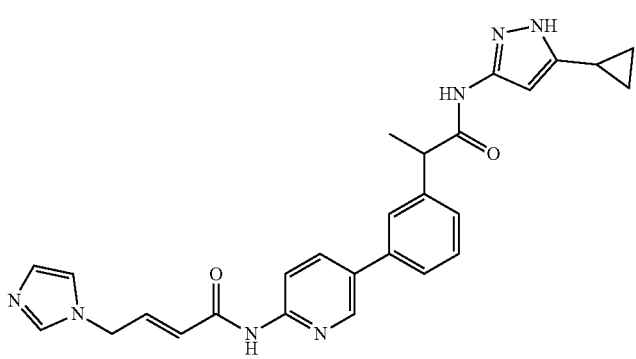 [SMILES: CC(C(=O)Nc1cc(C2CC2)[nH]n1)c1cccc(-c2ccc(NC(=O)/C=C/Cn3ccnc3)nc2)c1] | ¹HNMR (DMSO-d₆, 400 MHz): δ 12.10 (s, 1H), 11.79 (s, 1H), 10.41 (s, 1H), 8.60-8.59 (m, 1H), 8.17-8.15 (d, 1H), 8.06-8.04 (m, 1H), 7.09 (s, 1H), 7.67 (s, 1H), 7.57-7.53 (m, 2H), 7.42-7.33 (m, 2H), 7.10-7.07 (d, 1H), 6.96 (s, 1H), 6.14-6.07 (m, 2H), 3.91-3.84 (m, 1H), 3.31-3.29 (d, 2H), 1.80-1.40 (m, 1H), 1.40-1.39 (d, 3H), 0.87-0.81 (m, 2H), 0.59-0.56 (m, 2H) LCMS: m/z = 482.23 (M + H)⁺; HPLC: 99.21%, rt: 5.91 min. |
| 70 | 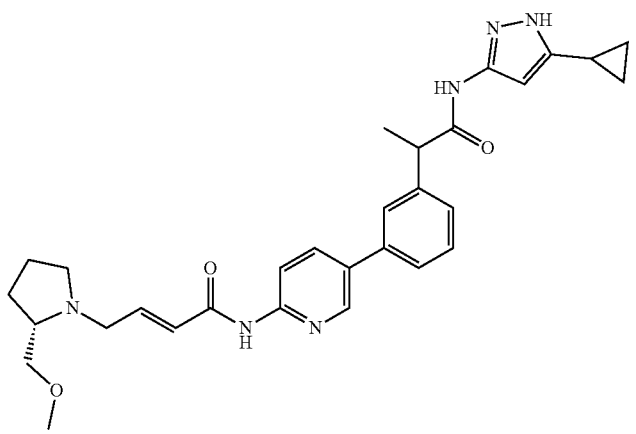 [SMILES: COC[C@@H]1CCCN1C/C=C/C(=O)Nc1ccc(-c2cccc(C(C)C(=O)Nc3cc(C4CC4)[nH]n3)c2)cn1] | ¹HNMR (DMSO-d₆, 400 MHz): δ 12.10 (s, 1H), 10.78 (s, 1H), 10.41 (s, 1H), 8.62-8.61 (d, 1H), 8.29-8.27 (d, 1H), 8.08-8.05 (m, 1H), 7.69 (s, 1H), 7.57-7.55 (d, 1H), 7.43-7.39 (m, 1H), 7.40-7.35 (d, 1H), 6.87-6.83 (m, 1H), 6.47-6.43 (d, 1H), 6.13 (s, 1H), 3.91-3.89 (m, 1H), 3.67-3.64 (m, 1H), 3.34 (s, 3H), 3.28-3.12 (m, 2H), 3.07-2.98 (m, 1H), 2.64-2.52 (m, 2H), 2.19-2.17 (m, 1H), 1.85-180 (m, 2H), 1.67-1.64 (m, 2H), 1.50-1.48 (m, 1H), 1.43-1.41 (d, 3H), 0.86-0.85 (m, 2H), 0.62-0.61 (m, 2H) LCMS: m/z = 529.35 (M + H)⁺; HPLC: 98.94%, rt: 6.06 min. |
| 71 | 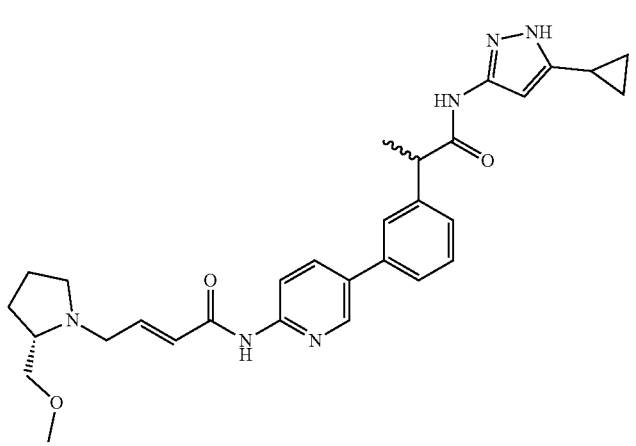 [SMILES: COC[C@@H]1CCCN1C/C=C/C(=O)Nc1ccc(-c2cccc(C(C)C(=O)Nc3cc(C4CC4)[nH]n3)c2)cn1] | ¹HNMR (DMSO-d₆, 400 MHz): δ 11.01 (s, 1H), 10.53 (s, 1H), 9.93 (s, 1H), 8.65-8.64 (d, 1H), 8.29-8.27 (d, 1H), 8.12-8.09 (m, 1H), 7.70 (s, 1H), 7.58-7.56 (d, 1H), 7.44-7.36 (m, 2H), 6.89-6.85 (m, 1H), 6.66-6.62 (d, 1H), 6.11 (s, 1H), 3.99-3.97 (m, 1H), 3.94-3.90 (m, 2H), 3.71 (s, 1H), 3.66-3.56 (m, 2H), 3.52-3.50 (m, 1H), 3.34 (s, 3H), 3.16-3.14 (m, 1H), 2.13-2.01 (m, 1H), 2.00-1.88 (m, 1H), 1.86-1.80 (m, 3H), 1.43-1.42 (d, 3H), 0.89-0.84 (m, 2H), 0.62-0.58 (m, 2H); LCMS: m/z = 529.30 (M + H)⁺; HPLC: 95.22%, rt: 5.36 min. (Isomer-1 of compound-70) |

TABLE 2-continued

| Comp. No. | Structure | Characterization Data |
|---|---|---|
| 72 | 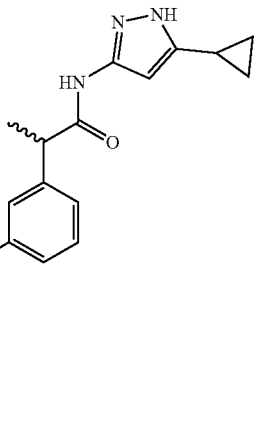 | ¹HNMR (DMSO-d₆, 400 MHz): δ 11.01 (s, 1H), 10.53 (s, 1H), 9.93 (s, 1H), 8.65-8.64 (d, 1H), 8.29-8.27 (d, 1H), 8.12-8.09 (m, 1H), 7.70 (s, 1H), 7.58-7.56 (d, 1H), 7.44-7.36 (m, 2H), 6.89-6.85 (m, 1H), 6.66-6.62 (d, 1H), 6.11 (s, 1H), 3.99-3.97 (m, 1H), 3.94-3.90 (m, 2H), 3.71 (s, 1H), 3.66-3.56 (m, 2H), 3.52-3.50 (m, 1H), 3.34 (s, 3H), 3.16-3.14 (m, 1H), 2.13-2.01 (m, 1H), 2.00-1.88 (m, 1H), 1.86-1.80 (m, 3H), 1.43-1.42 (d, 3H), 0.89-0.84 (m, 2H), 0.62-0.58 (m, 2H); LCMS: m/z = 529.30 (M + H)⁺; HPLC: 95.02%, rt: 5.61 min. (Isomer-2 of compound-70) |
| 73 | 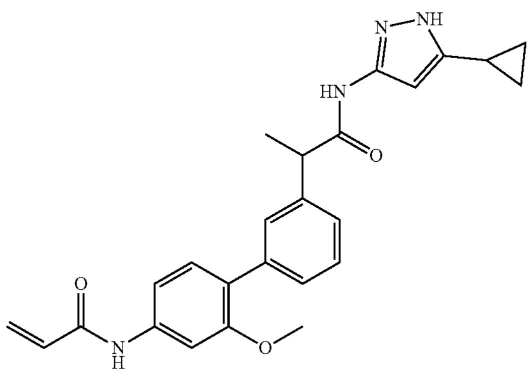 [SMILES: C=CC(=O)Nc1ccc(-c2cccc(C(C)C(=O)Nc3cc(C4CC4)[nH]n3)c2)c(OC)c1] | ¹HNMR (DMSO-d₆, 400 MHz): δ 12.01 (s, 1H), 10.40 (s, 1H), 10.26 (s, 1H), 7.54 (s, 1H), 7.42 (s, 1H), 7.31-7.22 (m, 5H), 6.48-6.42 (m, 1H), 6.30-6.25 (d, 1H), 6.13 (s, 1H), 5.74-5.71 (d, 1H), 3.86-3.84 (m, 1H), 3.72-3.70 (d, 3H), 2.61-2.35 (m, 1H), 1.39-1.23 (d, 3H), 0.88-0.86 (m, 2H), 0.62-0.64 (m, 2H), LCMS: m/z = 430.51 (M + H)⁺; HPLC: 95.75%, rt: 4.07 min. |
| 74 | 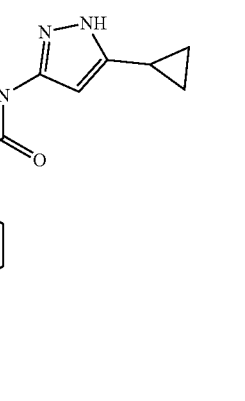 | ¹HNMR (DMSO-d₆, 400 MHz): δ 12.05 (s, 1H), 10.45 (s, 1H), 8.78-8.77 (m, 2H), 8.02-8.00 (m, 1H), 7.68 (s, 1H), 7.57-7.55 (m, 1H), 7.45-7.37 (m, 3H), 6.38-6.31 (m, 1H), 6.16-6.12 (m, 2H), 5.66-5.63 (m, 1H), 4.49-4.48 (m, 2H), 3.92-3.90 (m, 1H), 1.82-1.78 (m, 1H), 1.42-1.41 (m, 3H), 0.88-0.86 (m, 2H), 0.61-0.60 (m, 2H); LCMS: m/z = 416.3 (M + H)⁺; HPLC: 95.62%, rt: 3.80 min. |
| 75 | 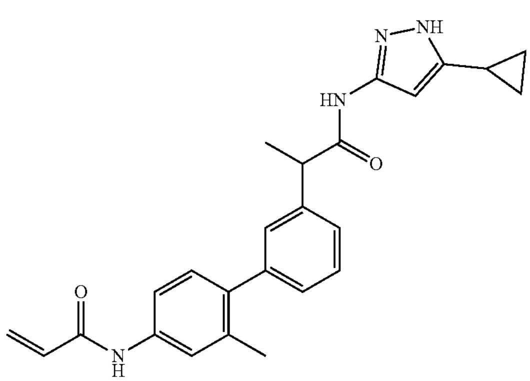 [SMILES: C=CC(=O)Nc1ccc(-c2cccc(C(C)C(=O)Nc3cc(C4CC4)[nH]n3)c2)c(C)c1] | ¹HNMR (DMSO-d₆, 400 MHz): δ 12.01 (s, 1H), 10.41 (s, 1H), 9.52 (s, 1H), 7.53 (s, 2H), 7.34-7.32 (m, 3H), 7.16-7.13 (d, 2H), 6.61-6.52 (m, 1H), 6.28-6.24 (d, 1H), 6.10 (s, 1H), 5.77-5.74 (d, 1H), 3.90-3.81 (m, 1H), 2.20 (s, 3H), 1.80-1.70 (m, 1H), 1.39-138 (d, 3H), 0.88-0.86 (m, 2H), 0.62-0.64 (m, 2H), LCMS: m/z = 414.5 (M + H)⁺; HPLC: 97.6%, rt: 9.68 min. |

TABLE 2-continued

| Comp. No. | Structure | Characterization Data |
|---|---|---|
| 76 | 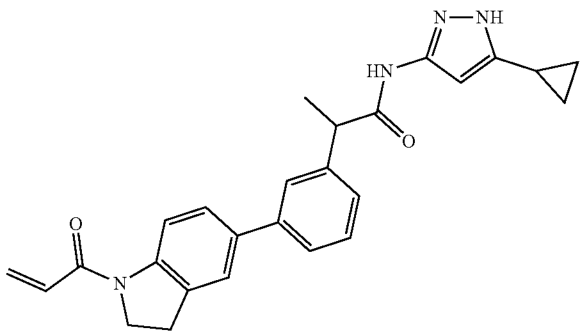 [SMILES: C=CC(=O)N1CCc2cc(-c3cccc(C(C)C(=O)Nc4cc(C5CC5)[nH]n4)c3)ccc21] | ¹HNMR (DMSO-d₆, 400 MHz): δ 12.01 (s, 1H), 10.41 (s, 1H), 8.22-8.20 (d, 2H), 7.64 (s, 1H), 7.53 (s, 1H), 7.50-7.46 (m, 1H), 7.38-7.35 (m, 1H), 7.31-7.29 (d, 1H), 6.80-6.74 (m, 1H), 6.34-6.29 (d, 1H), 6.13 (s, 1H), 5.85-5.82 (d, 1H), 4.29-4.24 (m, 2H), 3.89-3.87 (m, 1H), 3.33-3.15 (m, 2H), 1.82-1.78 (m, 1H), 1.41-1.40 (d, 3H), 0.88-0.86 (m, 2H), 0.62-0.64 (m, 2H), LCMS: m/z = 427.15 (M + H)⁺; HPLC: 97.60%, rt: 4.53 min. |
| 77 | 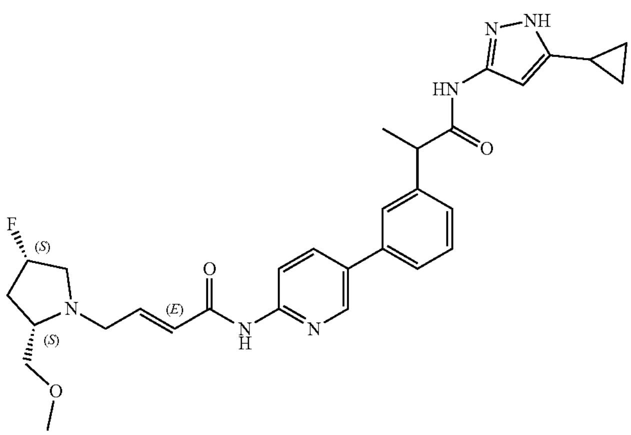 | ¹HNMR (DMSO-d₆, 400 MHz): δ 12.01 (s, 1H), 11.89 (s, 1H), 10.43 (s, 1H), 8.62-8.61 (d, 1H), 8.31-8.27 (m, 1H), 8.08-8.05 (m, 1H), 7.70 (s, 1H), 7.58-7.56 (d, 1H), 7.44-7.36 (m, 2H), 6.89-6.85 (m, 1H), 6.48-6.44 (d, 1H), 6.11 (s, 1H), 3.99-3.87 (m, 1H), 3.71-3.66 (m, 1H), 3.47-3.43 (m, 1H), 3.34 (s, 3H), 3.20-3.15 (m, 2H), 3.09-3.05 (m, 2H), 2.72-2.67 (m, 1H), 2.37-2.33 (m, 2H), 1.80-1.75 (m, 2H), 1.43-1.41 (m, 3H), 0.89-0.84 (m, 2H), 0.62-0.58 (m, 2H); LCMS: m/z = 547.30 (M + H)⁺; HPLC: 95.24%, rt: 6.08 min. |
| 78 | 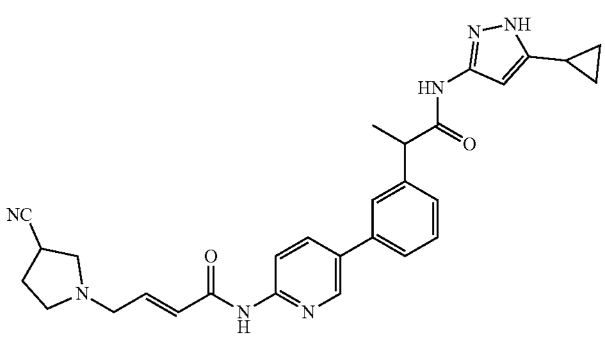 [SMILES: CC(C(=O)Nc1cc(C2CC2)[nH]n1)c1cccc(-c2ccc(NC(=O)/C=C/CN3CCC(C#N)C3)nc2)c1] | ¹HNMR (DMSO-d₆, 400 MHz): δ 12.01 (s, 1H), 11.89 (s, 1H), 10.43 (s, 1H), 8.62-8.61 (d, 1H), 8.31-8.27 (d, 1H), 8.08-8.05 (m, 1H), 7.70 (s, 1H), 7.58-7.56 (d, 1H), 7.44-7.36 (m, 2H), 6.89-6.79 (m, 1H), 6.48-6.44 (d, 1H), 6.11 (s, 1H), 3.99-3.87 (m, 1H), 3.43-3.40 (m, 3H), 2.76-2.66 (m, 4H), 2.32 (s, 1H), 1.97-1.92 (m, 1H), 1.83-1.78 (m, 1H), 1.43-1.41 (m, 3H), 0.89-0.84 (m, 2H), 0.62-0.58 (m, 2H); LCMS: m/z = 510.20 (M + H)⁺; HPLC: 95.16%, rt: 5.96 min. |
| 79 | 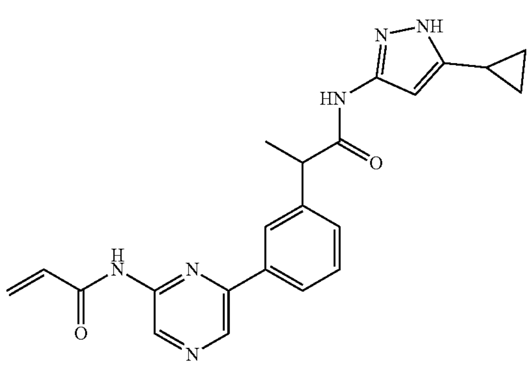 [SMILES: C=CC(=O)Nc1cncc(-c2cccc(C(C)C(=O)Nc3cc(C4CC4)[nH]n3)c2)n1] | ¹HNMR (DMSO-d₆, 400 MHz): δ 12.01 (s, 1H), 11.04 (s, 1H), 10.32 (s, 1H), 9.40 (s, 1H), 8.92 (s, 1H), 8.10 (s, 1H), 7.97-7.98 (d, 1H), 7.46-7.46 (m, 2H), 6.89-6.79 (m, 1H), 6.48-6.44 (d, 1H), 6.11 (s, 1H), 5.88-5.85 (d, 1H), 3.99-3.87 (m, 1H), 2.08-1.78 (m, 1H), 1.43-1.41 (m, 3H), 0.89-0.84 (m, 2H), 0.62-0.58 (m, 2H); LCMS: m/z = 402.80 (M + H)⁺; HPLC: 95.62%, rt: 3.46 min. |

TABLE 2-continued

| Comp. No. | Structure | Characterization Data |
|---|---|---|
| 80 | 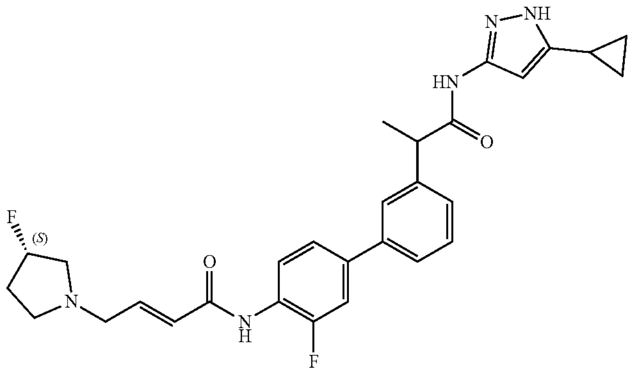 | ¹HNMR (DMSO-d₆, 400 MHz): δ 12.01 (s, 1H), 10.41 (s, 1H), 9.96 (s, 1H), 8.14-8.10 (m, 1H), 7.69 (s, 1H), 7.57-7.54 (m, 2H), 7.48-7.47 (d, 1H), 7.46-7.33 (m, 2H), 6.89-6.79 (m, 1H), 6.48-6.44 (d, 1H), 6.11 (s, 1H), 5.28-5.14 (m, 1H), 3.99-3.87 (m, 1H), 3.28-3.26 (m, 2H), 2.90-2.80 (m, 2H), 2.70-2.66 (m, 1H), 2.35-2.32 (m, 2H), 2.20-2.08 (m, 1H), 1.83-1.78 (m, 2H), 1.43-1.41 (m, 3H), 0.89-0.84 (m, 2H), 0.62-0.58 (m, 2H); LCMS: m/z = 520.31 (M + H)⁺; HPLC: 91.57%, rt: 6.11 min. |
| 81 | 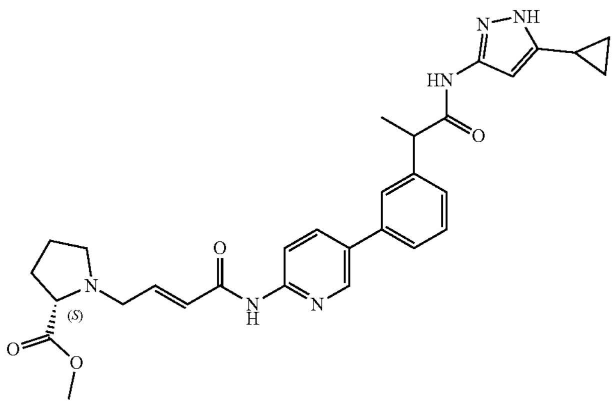 | ¹HNMR (DMSO-d₆, 400 MHz): δ 12.01 (s, 1H), 11.89 (s, 1H), 10.43 (s, 1H), 8.62-8.61 (d, 1H), 8.29-8.27 (d, 1H), 8.08-8.05 (m, 1H), 7.70 (s, 1H), 7.58-7.56 (d, 1H), 7.44-7.36 (m, 2H), 6.89-6.85 (m, 1H), 6.48-6.44 (d, 1H), 6.11 (s, 1H), 4.44 (s, 4H), 4.15-4.01 (m, 3H), 3.96-3.93 (m, 1H), 3.92 (s, 3H), 3.60-3.43 (m, 1H), 2.09-2.05 (m, 1H), 1.82-1.43 (m, 1H), 1.43-1.41 (m, 3H), 0.89-0.84 (m, 2H), 0.62-0.58 (m, 2H); LCMS: m/z = 543.25 (M + H)⁺; HPLC: 95.52%, rt: 6.07 min. |
| 82 | 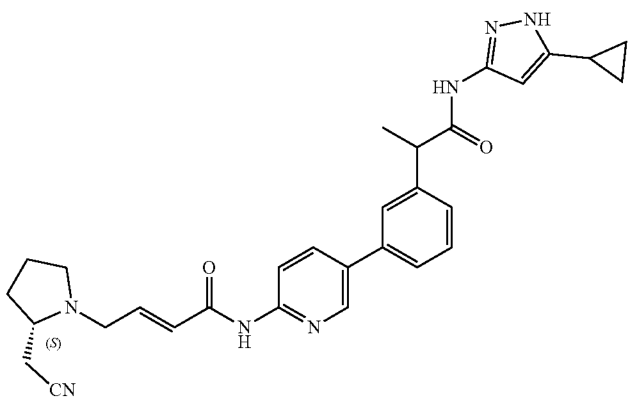 | ¹HNMR (DMSO-d₆, 400 MHz): δ 12.01 (s, 1H), 11.89 (s, 1H), 10.43 (s, 1H), 8.62-8.61 (d, 1H), 8.31-8.27 (d, 1H), 8.08-8.05 (m, 1H), 7.70 (s, 1H), 7.58-7.56 (d, 1H), 7.44-7.36 (m, 2H), 6.89-6.79 (m, 1H), 6.48-6.44 (d, 1H), 6.11 (s, 1H), 3.99-3.87 (m, 1H), 3.64-3.61 (m, 1H), 3.10-3.02 (m, 2H), 2.74-2.68 (m, 1H), 2.67-2.62 (m, 2H), 2.28-2.22 (m, 1H), 2.01-1.94 (m, 1H), 1.84-1.68 (m, 3H), 1.61-1.60 (m, 1H), 1.43-1.41 (d, 3H), 0.89-0.84 (m, 2H), 0.62-0.58 (m, 2H); LCMS: m/z = 524.21 (M + H)⁺; HPLC: 93.58%, rt: 6.07 min. |

Example-3: Synthesis of 4-acrylamido-N-(3-((5-ethyl-1H-pyrazol-3-yl)amino)phenyl)-benzamide (Compound-83)

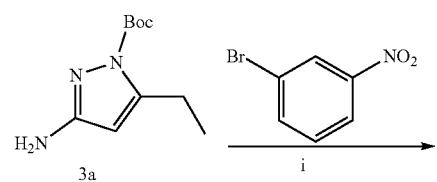

-continued

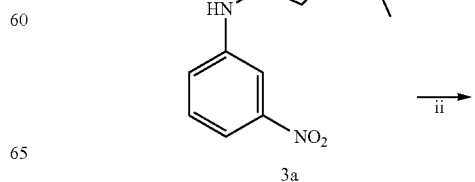

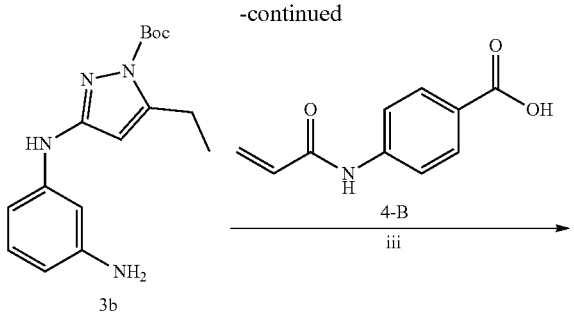

Step-i: Synthesis of tert-butyl 5-ethyl-3-((3-nitrophenyl)amino)-1H-pyrazole-1-carboxylate To a degassed solution of tert-butyl 3-amino-5-ethyl-1H-pyrazole-1-carboxylate (synthesized similar to intermediate-1-A) (0.5 g, 2.36 mmol) and 1-bromo-3-nitrobenzene (0.571 g, 2.84 mmol) in 1,4-dioxane (20 mL) added Cs$_2$CO$_3$ (1.91 g, 5.92 mmol), stirred the reaction mass for 10 minutes at RT and degassed further for 10 min and added Xantphos (0.136 g, 0.236.mmol) and Pd$_2$(dba)$_3$ (0.108 g, 0.118 mmol). The reaction mass was heated for 4 h at 100° C. in a sealed tube. The reaction mass was cooled and diluted with water and ethyl acetate. The organic layer was separated and the aqueous layer was extracted again with ethyl acetate (2×20 mL). The combined organic layer was dried over anhydrous sodium sulphate and concentrated under vacuum. The crude compound was purified by silica gel column chromatography by eluting with 15% ethyl acetate-hexane to afford the title compound (0.2 g, 35%). LCMS: m/z=333.10 (M+H)$^+$.

Step-ii: Synthesis of tert-butyl 3-((3-aminophenyl)amino)-5-ethyl-1H-pyrazole-1-carboxylate tert-butyl-5-ethyl-3-((3-nitrophenyl)amino)-1H-pyrazole-1-carboxylate (0.2 g, 0.60 mmol) was taken in ethanol, 10% Pd/C (0.05 g) was added and reaction mass was stirred at RT under H$_2$ pressure (40 Psi) for 4 h in a Parr shaker. Reaction mixture was filtered on a celite bed, washed with ethanol and the filtrate was concentrated under vacuum to get the title compound. (0.13 g, 49%) LCMS: m/z=302.8 (M+H)$^+$.

Step-iii: Synthesis of tert-butyl 3-((3-(4-acrylamidobenzamido)phenyl)amino)-5-ethyl-1H-pyrazole-1-carboxylate To a solution of 4-acrylamidobenzoic acid (0.098 g (intermediate-11), 0.52 mmol) in DMF (4 mL), was added HATU (0.245 g, 0.64 mmol) followed by DIPEA (0.2 mL, 1.05 mmol) and finally added tert-butyl 3-((3-aminophenyl)amino)-5-ethyl-1H-pyrazole-1-carboxylate (0.13 g, 0.430 mmol). The reaction mixture was stirred for 12 h at room temperature. The reaction mixture was quenched with ice-water and diluted with ethyl acetate. The aqueous layer was separated and extracted with ethyl acetate (2×25 mL). The combined organic phase was washed with brine, dried over Na$_2$SO$_4$, filtered and concentrated. (0.13 g, 90%). LCMS: m/z=476.2 (M+H)$^+$.

Step-iv: Synthesis of 4-acrylamido-N-(3-((5-ethyl-1H-pyrazol-3-yl)amino)phenyl)benzamide To a solution of tert-butyl-3-((3-(4-acrylamidobenzamido)phenyl)amino)-5-ethyl-1H-pyrazole-1-carboxylate (0.13 g, 0.33 mmol) in DCM (3 mL), TFA (1 mL) was added at 0° C. The reaction mass was stirred at room temperature for 2 h. The reaction mass was concentrated under vacuum to afford crude compound. The crude compound was purified by silica gel column chromatography by eluting with 10% methanol-DCM, further purified by Preparative HPLC (Method: Column: X-BRIDGE PREP C18 5 MICRON OBD (19 mm×150 mm), Mobile phase: 0.01% NH$_4$OH: Acetonitrile) to afford the title compound (0.030 g, 25%). $^1$HNMR (DMSO-d$_6$, 400 MHz): δ 11.5 (s, 1H), 10.38 (s, 1H), 9.93 (s, 3H), 8.23 (s, 1H), 7.91 (d, 1H), 7.76 (d, 1H), 7.64 (s, 1H), 7.05-6.98 (m, 3H), 6.46-6.40 (m, 1H), 6.29-6.24 (d, 1H), 5.78 (d, 1H), 5.62 (s, 1H), 2.52-2.50 (m, 2H), 1.16-1.12 (t, 3H); LCMS: m/z=376.10 (M+H)$^+$; HPLC: 92.00%, rt: 3.28 min.

Example-4: Synthesis of (E)-N-(5-cyclopropyl-1H-pyrazol-3-yl)-2-(3-(1-(4-(dimethylamino)-but-2-enoyl)-1,2,3,6-tetrahydropyridin-4-yl)phenyl)propanamide (Compound-84)

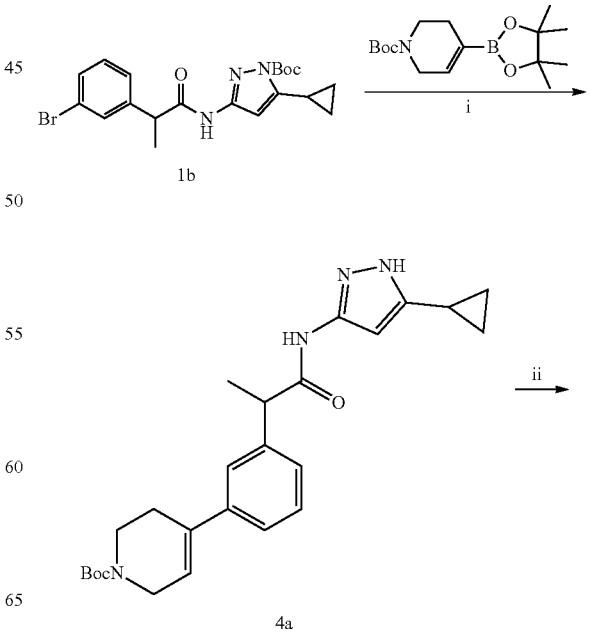

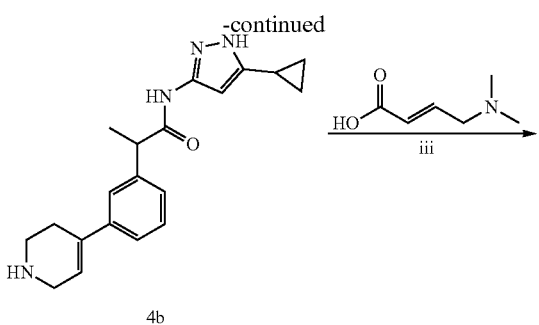

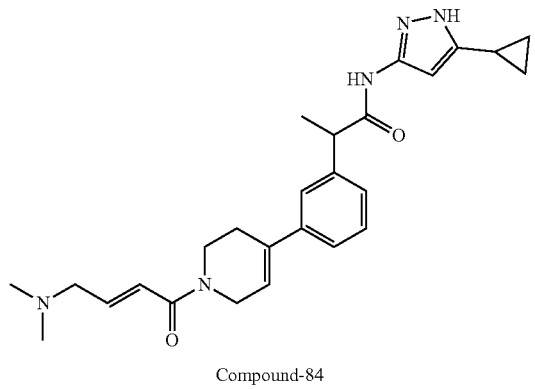

Compound-84

Step-i: Synthesis of tert-butyl 4-(3-(1-((5-cyclopropyl-1H-pyrazol-3-yl)amino)-1-oxopropan-2-yl)phenyl)-3,6-dihydropyridine-1 (2H)-carboxylate To a degassed solution of tert-butyl 3-(2-(3-bromophenyl)propanamido)-5-cyclopropyl-1H-pyrazole-1-carboxylate (0.45 g, 1.03 mmol) and tert-butyl 4-(4,4,5,5-tetramethyl-1,3,2-dioxaborolan-2-yl)-3,6-dihydropyridine-1(2H)-carboxylate (0.42 g, 1.37 mmol) in 1,4-dioxane (20 mL) and water (1 mL) $K_2CO_3$ (0.45 g, 3.26 mmol) was added. The reaction mass was stirred for 10 minutes and degassed further for 10 min and added $PdCl_2$(dppf).DCM (0.044 g, 0.05 mmol). The reaction mass was heated for 5 h at 100° C. in a sealed tube. The reaction mass was cooled to room temperature and diluted with water and ethyl acetate. The separated organic layer was dried over anhydrous sodium sulphate and concentrated under reduced pressure, purified the compound by combi flash column by eluting with 70% ethyl acetate-hexane system to afford the title compound (0.3 g, 66%) LCMS: m/z=437.2 $(M+H)^+$.

Step-ii: Synthesis of N-(5-cyclopropyl-1H-pyrazol-3-yl)-2-(3-(1,2,3,6-tetrahydropyridin-4-yl)phenyl)propanamide TFA (1 mL) was slowly added to a stirred solution of tert-butyl 4-(3-(1-((5-cyclopropyl-1H-pyrazol-3-yl)amino)-1-oxopropan-2-yl)phenyl)-3,6-dihydropyridine-1(2H)-carboxylate (0.1 g, 0.22 mmol) in dry DCM (10 mL) under argon atmosphere at 0° C. The resulting reaction mixture was allowed to warm to room temperature and stirred for 1 h. After completion of the reaction, excess solvents were removed under reduced pressure to dryness to afford the title compound (0.13 g title compound as TFA salt). LCMS: m/z=337.1 $(M+H)^+$.

Step-iii: Synthesis of (E)-N-(5-cyclopropyl-1H-pyrazol-3-yl)-2-(3-(1-(4-(dimethylamino)but-2-enoyl)-1,2,3,6-tetrahydropyridin-4-yl)phenyl)propanamide To a solution of (E)-4-(dimethylamino)but-2-enoic acid (0.063 g, 0.37 mmol) in DMF (5 mL) was added HATU (0.21 g, 0.55 mmol) at 0° C. followed by DIPEA (0.14 mL, 1.11 mmol) and finally added N-(5-cyclopropyl-1H-pyrazol-3-yl)-2-(3-(1,2,3,6-tetrahydropyridin-4-yl)phenyl)propanamide (0.17 g, 0.37 mmol). The reaction mass was stirred for 1 h at room temperature. The reaction mixture was quenched with ice-water and diluted with ethyl acetate. The aqueous layer was separated and extracted with ethyl acetate (2×25 mL). The combined organic phase was washed with brine, dried over $Na_2SO_4$, filtered and concentrated under reduced pressure and further purified by preparative HPLC condition (Column: X-bridge prep C18 5 u OBD (19*150 mm), Mobile phase: Ammonia-water) to afford the title compound as free base (0.02 g, 12%); $^1$HNMR (DMSO-$d_6$, 400 MHz): δ 12.02 (s, 1H), 10.38 (s, 1H), 7.44 (s, 1H), 7.24-7.27 (m, 3H), 6.59-6.66 (m, 2H), 6.13 (s, 2H), 4.15-4.25 (m, 2H), 3.81-3.83 (d, 2H), 3.73-3.74 (m, 2H), 3.4 (s, 1H), 3.03 (s, 2H), 2.14 (s, 6H), 1.79-1.82 (m, 1H), 1.36 (d, 3H), 0.87 (d, 2H), 0.6 (d, 2H). LCMS: m/z=448.2 $(M+H)^+$; HPLC: 98.28%, rt: 5.92 min.

Example-5: Synthesis of (E)-N-(5-cyclopropyl-1H-pyrazol-3-yl)-2-(3-(1-(4-(dimethylamino)but-2-enoyl)piperidin-4-yl)phenyl)propanamide (Compound-85)

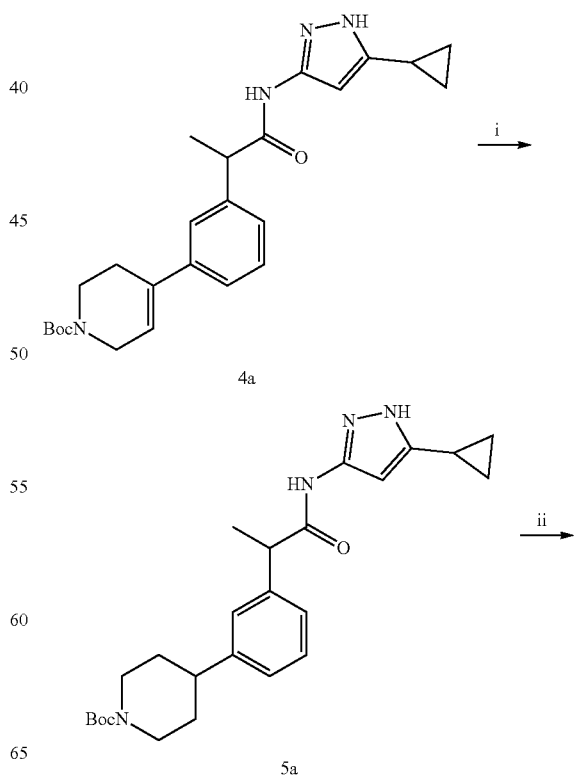

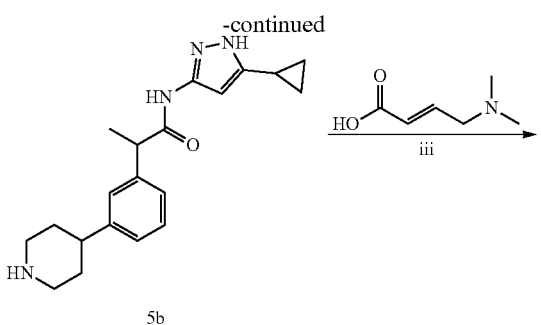

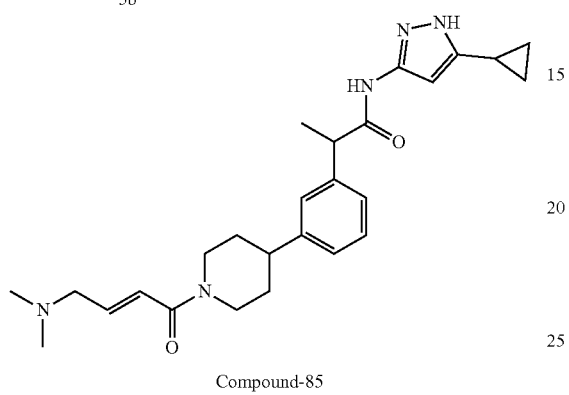

Compound-85

Step-i: Synthesis of tert-butyl 4-(3-(1-((5-cyclopropyl-1H-pyrazol-3-yl)amino)-1-oxopropan-2-yl)phenyl)piperidine-1-carboxylate 10% Pd/C was added to a degassed solution of tert-butyl 4-(3-(1-((5-cyclopropyl-1H-pyrazol-3-yl)amino)-1-oxopropan-2-yl)phenyl)-3,6-dihydropyridine-1(2H)-carboxylate (0.12 g, 0.28 mmol) in methanol (10 mL). The reaction mixture was subjected to hydrogenation at 45 PSi in Parr shaker for 40 minutes. The reaction mass was filtered through celite bed and washed the celite bed with methanol. The filtrate was concentrated under reduced pressure to afford the title compound (0.11 g, 87%). LCMS: m/z=439.1 (M+H)$^+$.

Step-ii: Synthesis of N-(5-cyclopropyl-1H-pyrazol-3-yl)-2-(3-(piperidin-4-yl)phenyl)-propanamide TFA (1 mL) was slowly added to a stirred solution of tert-butyl 4-(3-(1-((5-cyclopropyl-1H-pyrazol-3-yl)amino)-1-oxopropan-2-yl)phenyl)piperidine-1-carboxylate (0.11 g, 0.25 mmol) in dry DCM (5 mL) under argon atmosphere at 0° C. The resulting reaction mixture was allowed to warm to room temperature and stirred for 1 h. After completion of the reaction, excess solvents were removed under reduced pressure to dryness to afford the title compound (0.12 g title compound as TFA salt). LCMS: m/z=339.25 (M+H)$^+$.

Step-iii: Synthesis of (E)-N-(5-cyclopropyl-1H-pyrazol-3-yl)-2-(3-(1-(4-(dimethylamino)but-2-enoyl)piperidin-4-yl)phenyl)propanamide To a solution of (E)-4-(dimethylamino)but-2-enoic acid (0.063 g, 0.37 mmol) in DMF (5 mL) was added HATU (0.21 g, 0.55 mmol) at 0° C. followed by DIPEA (0.14 g, 1.11 mmol) and finally added N-(5-cyclopropyl-1H-pyrazol-3-yl)-2-(3-(piperidin-4-yl)phenyl)propanamide (0.17 g, 0.37 mmol). The reaction mass was stirred for 1 h at room temperature. The reaction mixture was quenched with ice-water and diluted with ethyl acetate. The aqueous layer was separated and extracted with ethyl acetate (2×25 mL). The combined organic phase was washed with brine, dried over Na$_2$SO$_4$, filtered and concentrated under reduced pressure and purified by prep HPLC (X bridge C18 (21.2*150 mm), ammonium hydroxide/water—acetonitrile) to afford the title compound (0.021 g, 9.3%). $^1$HNMR (DMSO-d$_6$, 400 MHz): δ 11.98 (s, 1H), 10.33 (s, 1H), 7.13-7.21 (m, 3H), 7.05 (d, 1H), 6.51-6.62 (m, 2H), 6.09 (s, 1H), 4.53 (d, 1H), 4.11 (d, 1H), 3.75 (d, 1H), 3.09 (t, 1H), 2.98 (d, 2H), 2.63-2.75 (m, 2H), 2.11 (s, 6H), 1.75-1.77 (m, 3H), 1.44-1.47 (m, 2H), 1.30 (d, 3H), 0.84 (d, 2H), 0.57 (d, 2H); LCMS: m/z=450.0 (M+H)$^+$; HPLC: 98.00%, rt: 6.44 min.

Example-6: Synthesis of N-(3'-(2-((5-Methyl-1H-pyrazol-3-yl)amino)-2-oxoethyl)-[1,1'-biphenyl]-4-yl)acrylamide (Compound-86)

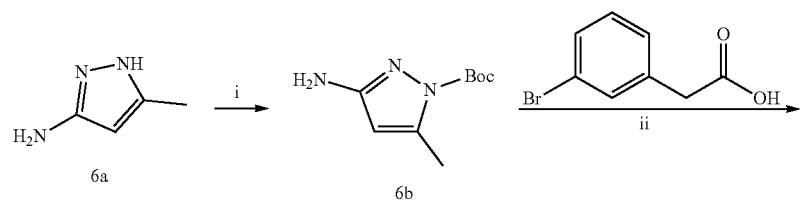

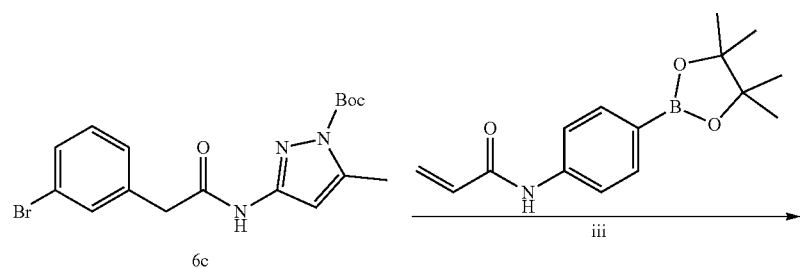

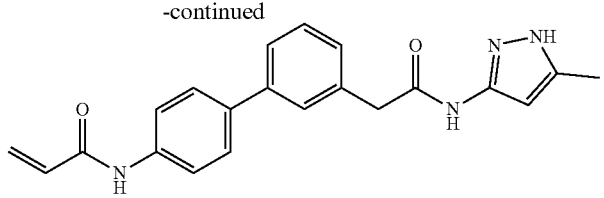

Compound-86

Step i: Synthesis of tert-butyl 3-amino-5-methyl-1H-pyrazole-1-carboxylate

60% NaH (0.5 g, 20.6 mmol) was added to a stirred solution of 5-methyl-1H-pyrazol-3-amine (2 g, 20.6 mmol) in THF (50 mL) at 0° C. over a period of 10 min followed by the addition of Boc anhydride (4.5 mL, 20.6 mmol). The reaction mass was stirred at room temperature over a period of 2 h. The reaction mass was diluted with ethyl acetate and water. The separated organic layer was dried over anhydrous sodium sulphate and concentrated under reduced pressure, the residue was purified by combiflash by eluting with 30% ethyl acetate-hexane system to afford the title compound (1.8 g, 80%) LCMS: m/z=198.0 (M+H)$^+$.

Step-ii: Synthesis of tert-butyl 3-(2-(3-bromophenyl)acetamido)-5-methyl-1H-pyrazole-1-carboxylate To a solution of 2-(3-bromophenyl)acetic acid (0.5 g, 2.32 mmol) in DCM (20 mL) was added EDCI (0.88 g, 0.4.65 mmol) at 0° C. followed by DIPEA (1.12 mL, 6.97 mmol) and finally added tert-butyl 3-amino-5-methyl-1H-pyrazole-1-carboxylate (0.4 g, 2.09 mmol). The reaction mass was stirred for 12 h at room temperature. The reaction mixture was quenched with ice-water and diluted with DCM. The aqueous layer was separated and extracted with ethyl acetate (2×25 mL). The combined organic phase was washed with brine, dried over Na$_2$SO$_4$, filtered and concentrated under reduced pressure and purified by eluting with 20% ethyl acetate-hexane in combiflash to afford the title compound (0.3 g, 60%). LCMS: m/z=395.9 (M+H)$^+$.

Step-iii: Synthesis of N-(3'-(2-((5-Methyl-1H-pyrazol-3-yl)amino)-2-oxoethyl)-[1,1'-biphenyl]-4-yl)acrylamide To a degassed solution of tert-butyl 3-(2-(3-bromophenyl)acetamido)-5-methyl-1H-pyrazole-1-carboxylate (0.2 g, 0.5 mmol) and N-(4-(4,4,5,5-tetramethyl-1,3,2-dioxaborolan-2-yl)phenyl)acrylamide (0.166 g, 0.6 mmol) in DMF (2.5 mL) and water (0.5 mL), K$_2$CO$_3$ (0.12 g, 0.81 mmol) was added. The reaction mass was stirred for 10 minutes and degassed further for 10 min and added Bis(triphenylphosphine) palladium(II) dichloride (0.017 g, 0.025 mmol). The reaction mass was heated for 5 h at 100° C. in a sealed tube. The reaction mass was cooled and diluted with water and ethyl acetate. The separated organic layer was dried over anhydrous sodium sulphate and concentrated under reduced pressure and purified by preparative HPLC (Condition: Kinetex Evo, A: 0.1% formic acid in H$_2$O, B: Acetonitrile-methanol) to afford the title compound (0.018 g, 20%). $^1$HNMR (DMSO-d$_6$, 400 MHz): δ 11.78 (s, 1H), 10.14 (s, 1H), 10.04 (s, 1H), 7.811 (d, 2H), 7.789 (t, 3H), 7.55 (d, 1H), 7.438 (t, 1H), 7.33 (d, 1H), 6.53-6.47 (m, 1H), 6.34 (d, 1H), 6.29 (s, 1H), 5.80 (d, 1H), 3.71 (s, 2H), 2.22 (s, 3H); LCMS: m/z=361.1 (M+H)$^+$; HPLC: 96.04%, rt: 3.39 min.

The compounds listed in the below table-3 were prepared by procedure similar to the one described in Example-6 with appropriate variations in reactants, quantities of reagents, protections and deprotections, solvents and reaction conditions. The characterization data of the compounds are also summarized herein the table-3.

TABLE 3

| Compound No. | Structure | Characterization data |
|---|---|---|
| 87 | 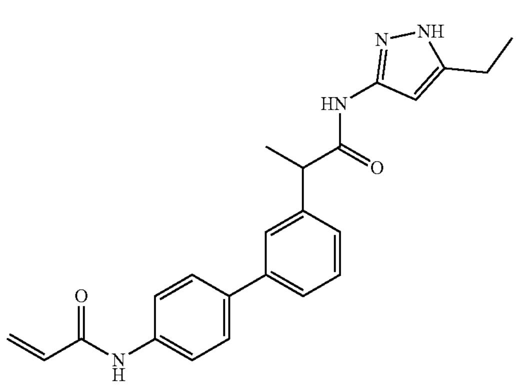 [SMILES: C=CC(=O)Nc1ccc(-c2cccc(C(C)C(=O)Nc3cc(CC)[nH]n3)c2)cc1] | $^1$HNMR (DMSO-d$_6$, 400 MHz): δ 11.99 (s, 1H), 10.43 (s, 1H), 10.27 (s, 1H), 7.77 (d, 2H), 7.66-7.60 (m, 3H), 7.50 (d, 1H), 7.38 (t, 1H), 7.32 (d, 1H), 6.49-6.42 (m, 1H), 6.30-6.25 (m, 2H), 5.77 (dd, 1H), 3.90 (dd, 1H), 2.5 (q, 2H), 1.42 (d, 3H), 1.13 (t, 3H); LCMS: m/z = 389.20 (M + H)$^+$; HPLC: 95.10%, rt: 12.02 min. |

TABLE 3-continued
| Compound No. | Structure | Characterization data |
|---|---|---|
| 88 | 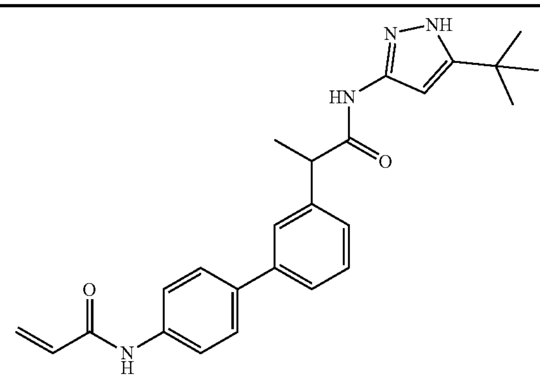 | $^1$HNMR (DMSO-$d_6$, 400 MHz): δ 12.06 (s, 1H), 10.45 (s, 1H), 10.26 (s, 1H), 7.78 (d, 2H), 7.76 (t, 3H), 7.51 (d, 1H), 7.40-7.31 (m, 2H), 6.46-6.42 (m, 1H), 6.30-6.25 (m, 2H), 5.77 (dd, 1H), 3.91 (d, 1H), 1.43 (d, 3H), 1.22 (s, 9H); LCMS: m/z = 417.1 (M + H)$^+$; HPLC: 97.51%, rt: 4.38 min. |
Example-7: Synthesis of (E)-N-(3-((1H-Indazol-3-yl)amino)phenyl)-4-(4-(dimethylamino)-but-2-enamido)benzamide (Compound-89)
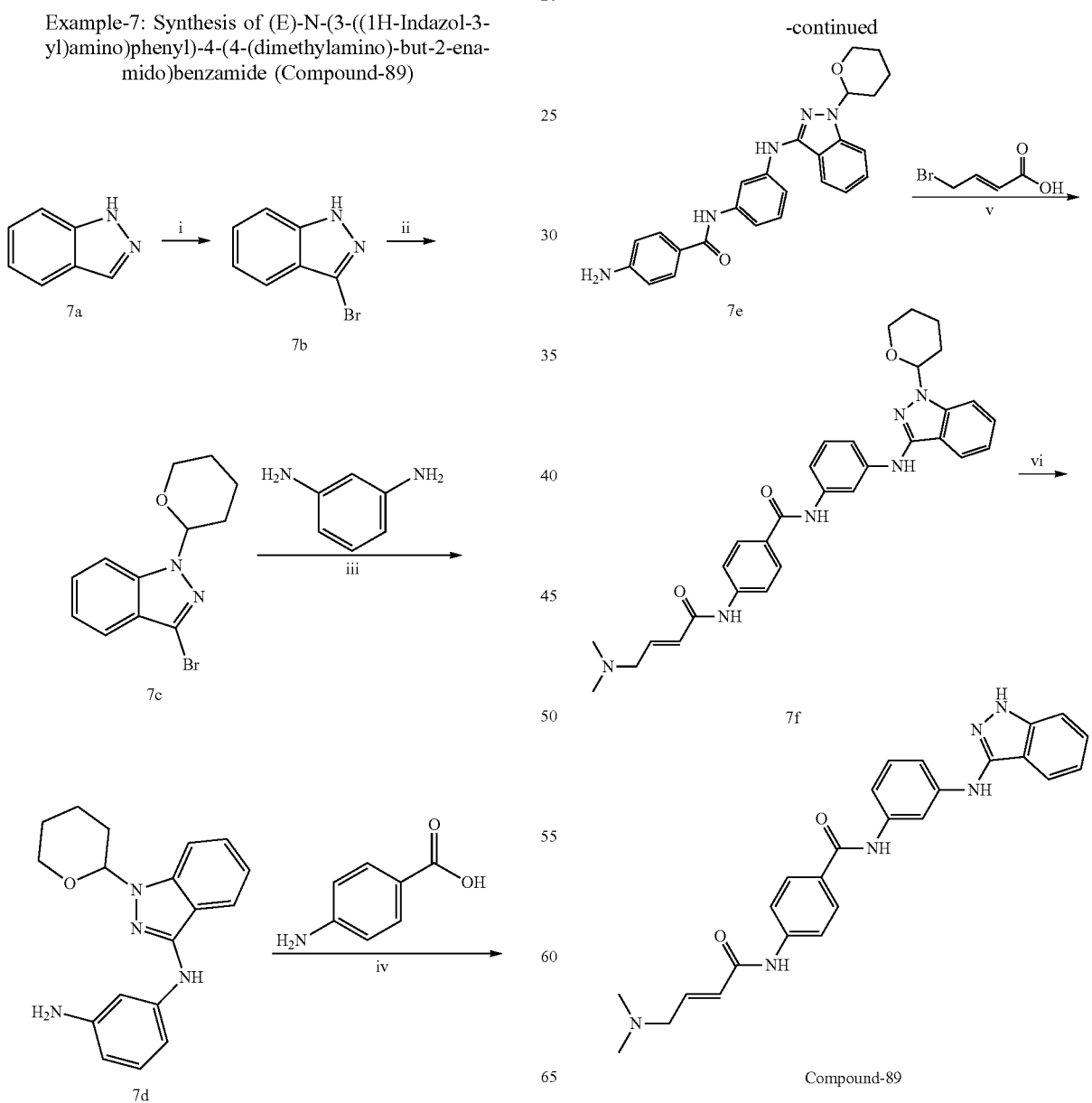
Compound-89

Step-i: Synthesis of 3-bromo-1H-indazole

Bromine (1.5 g, 9.4 mmol) in 2M NaOH solution (10 mL) was added drop wise to a suspension of indazole (1.5 g, 12.7 mmol) in 2M NaOH solution (23 mL) at ambient temperature. Stirred the reaction mass for 3 h at room temperature and added sodium bisulfate (0.05 g) followed by the addition of 2N HCl. The solid precipitated was filtered out and washed with water, suction dried followed by in Rotavap under reduced pressure to afford the title compound (2g, 80%). LCMS: m/z=197.1 (M+H)$^+$.

Step-ii: Synthesis of 3-bromo-1-(tetrahydro-2H-pyran-2-yl)-1H-indazole 3,4-dihydro-2H-Pyrane (0.42 g, 5 mmol) was added to a solution of 3-bromo-1H-indazole (0.5 g, 2.5 mmol) in ethyl acetate (10 mL) with catalytic amount of PTSA (0.05 g). The resulting reaction mass was stirred and heated to reflux for 5 h. The reaction mass was neutralized with aq. ammonia and diluted with ethyl acetate. The separated organic layer was dried over anhydrous sodium sulphate and concentrated under reduced pressure and purified by silica gel column chromatography by eluting with 5% ethyl acetate-hexane to afford the title compound (0.4 g, 51%) LCMS: m/z=283 (M+3).

Step-iii: Synthesis of N$^1$-(1-(tetrahydro-2H-pyran-2-yl)-1H-indazol-3-yl)benzene-1,3-diamine Benzene-1,3-diamine (0.02 g, 0.21 mmol) and 3-bromo-1-(tetrahydro-2H-pyran-2-yl)-1H-indazole (0.05 g, 0.17 mmol) were taken in toluene (15 mL) in a seal tube at room temperature and argon gas was purged for 5-10 min. Then sodium tert-butoxide (0.032 g, 0.34 mmol) and BINAP (0.01 g, 0.017 mmol) were added and the resulting reaction mixture was purged with argon gas for 5 min. followed by the addition of Pd$_2$(dba)$_3$ (0.003 g, 0.003 mmol). The argon gas purging was continued for additional 15 min. before sealing the reaction vial. Then the reaction mixture was heated at 110° C. for 8 h. After completion of the reaction by TLC, reaction mass was filtered through celite and the filtrate was evaporated, the residue was purified by combi-flash by eluting with 0-40% ethyl acetate-hexane to afford the desired compound (0.025 g, 56%); LCMS: m/z=309.2 (M+H)$^+$.

Step-iv: Synthesis of 4-amino-N-(3-((1-(tetrahydro-2H-pyran-2-yl)-1H-indazol-3-yl)amino)phenyl)benzamide To a solution of 4-aminobenzoic acid (0.052 g, 0.78 mmol) in DMF (10 mL) was added HATU (0.15 g, 0.41 mmol) at 0° C. followed by DIPEA (0.12 mL, 0.96 mmol) and finally added N$^1$-(1-(tetrahydro-2H-pyran-2-yl)-1H-indazol-3-yl)benzene-1,3-diamine (0.1 g, 0.32 mmol). The reaction mass was stirred for 12 h at room temperature. The reaction mixture was quenched with ice-water and diluted with ethyl acetate. The aqueous layer was separated and extracted with ethyl acetate (2×25 mL). The combined organic phase was washed with brine, dried over Na$_2$SO$_4$, filtered and concentrated under reduced pressure and purified with silica gelcolumn chromatography by eluting with 40% ethyl acetate-hexane to afford the title compound (0.07 g, 50%). LCMS: m/z=428.2 (M+H)$^+$.

Step-v: Synthesis of (E)-4-(4-(dimethylamino)but-2-enamido)-N-(3-((1-(tetrahydro-2H-pyran-2-yl)-1H-indazol-3-yl)amino)phenyl)benzamide (E)-4-bromobut-2-enoic acid (0.32 g, 1.99 mmol) was taken in DCM (20 mL) with catalytic amount of DMF followed by the addition of oxalyl chloride (0.27 g, 2.17 mmol). The reaction mass was stirred for 2 h, concentrated the reaction mass under reduced pressure to residue. Re dissolved the residue in DCM (2 mL) and was added at −5° C. to a mixture of 4-amino-N-(3-((1-(tetrahydro-2H-pyran-2-yl)-1H-indazol-3-yl)amino)phenyl)benzamide (0.42 g, 0.99 mmol) in acetonitrile (10 mL) and DIPEA (0.7 mL, 3.96 mmol). The resulting reaction mixture was stirred for 10 minutes at −5° C. and after completion of the reaction, a solution of N, N-dimethylamine (2M in THF, 1.5 mL, 2.97 mmol) was added and then allowed to stir at room temperature for 12 h. The reaction mixture was quenched with saturated NaHCO$_3$ solution and diluted with DCM. The aqueous layer was separated and extracted with DCM (2×25 mL). The combined organic phase was washed with brine, dried over Na$_2$SO$_4$, filtered and concentrated under reduced pressure and purified the residue with silica gelcolumn chromatography by eluting with 10% methanol-DCM to afford the title compound (0.12 g, 20%). LCMS: m/z=539.3 (M+H)$^+$.

Step-vi: Synthesis of (E)-N-(3-((1H-indazol-3-yl)amino)phenyl)-4-(4-(dimethylamino)but-2-enamido)benzamide Methanolic HCl (0.3 mL) was added to a solution of (E)-4-(4-(dimethylamino)but-2-enamido)-N-(3-((1-(tetrahydro-2H-pyran-2-yl)-1H-indazol-3-yl)amino)phenyl)benzamide (0.12 g, 0.20 mmol) in DCM (4 mL) at room temperature and stirred for 2 h, concentrated the reaction mass under reduced pressure. The residue was dissolved in DCM and basified with NaHCO$_3$ solution. The separated organic phase was washed with brine, dried over Na$_2$SO$_4$, filtered and concentrated under reduced pressure and purified using prep. TLC by eluting with 10% methanol-DCM and triturated the resulting compound with ether to afford the title compound (0.012 g, 16%). $^1$HNMR (DMSO-d$_6$, 400 MHz): δ 11.98 (s, 1H), 10.34 (s, 1H), 10.04 (s, 1H), 8.86 (s, 1H), 8.11 (s, 1H), 7.97 (t, 3H), 7.78 (d, 2H), 7.47 (d, 1H), 7.32-7.38 (m, 2H), 7.19 (t, 1H), 7.11 (d, 1H), 7.02 (t, 1H), 6.76-6.80 (m, 1H), 6.30-6.34 (m, 1H), 3.12-3.14 (m, 2H), 2.08 (s, 6H); LCMS: m/z=455.3 (M+H)$^+$; HPLC: 95.93%, rt: 6.14 min.

Example-8: Synthesis of N-(3'-(1-((1H-indazol-3-yl)amino)-1-oxopropan-2-yl)-[1,1'-biphenyl]-4-yl)acrylamide (Compound-90)

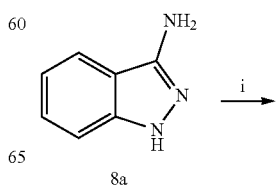

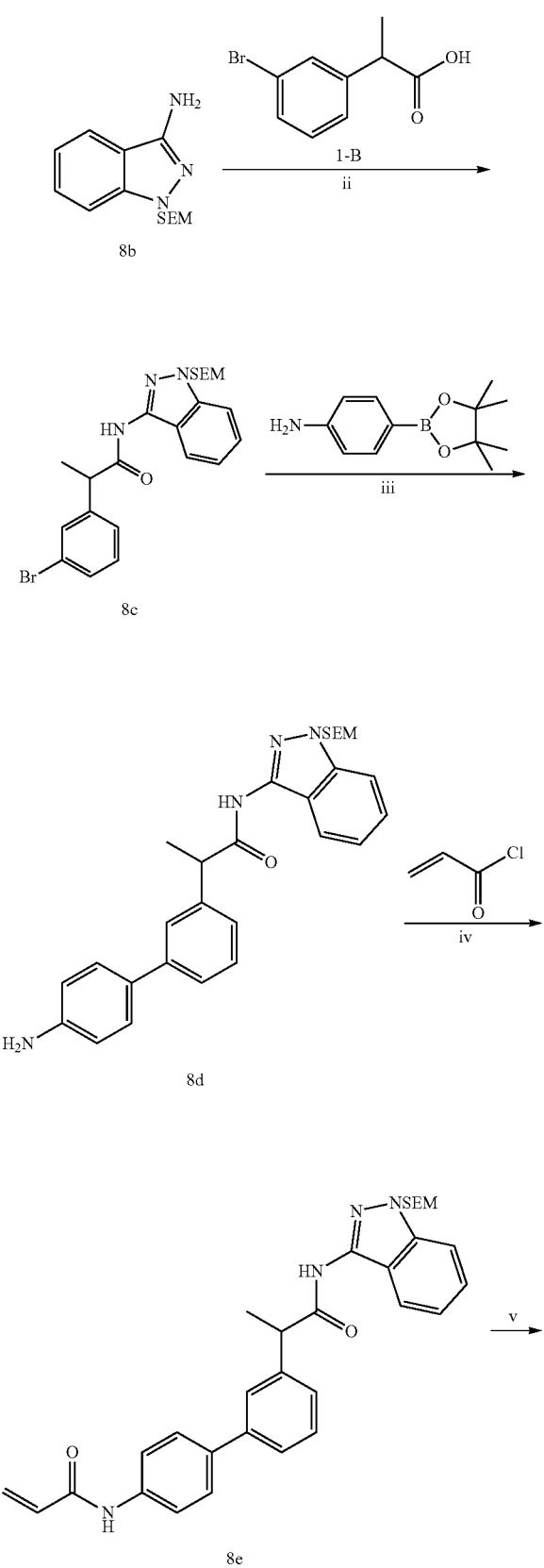

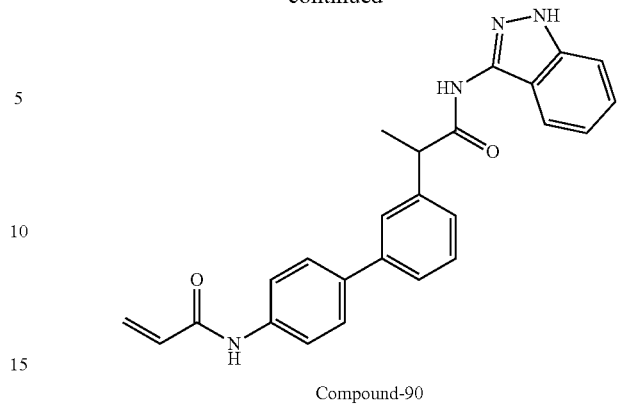

Compound-90

Step-i: Synthesis of 1-((2-(trimethylsilyl)ethoxy)methyl)-1H-indazol-3-amine

NaH (0.89 g, 22.3 mmol) was added lot wise to a stirred solution of 3-amino indazole (2.5 g, 18.6 mmol) in DMF at 0° C., the reaction mass was stirred for 15 min followed by the addition of SEM chloride. The reaction mass was stirred at ambient temperature for 2 h and was quenched with ethyl acetate and ice cold water. The ethyl acetate layer was separated, washed with water followed by brine, dried and concentrated under reduced pressure, purified the crudeby combiflash to afford the desired title compound (2.5 g, 50%) LCMS: m/z=264.1 (M+H)$^+$.

Step-ii: Synthesis of 2-(3-bromophenyl)-N-(1-((2-(trimethylsilyl)ethoxy)methyl)-1H-indazol-3-yl)propanamide To a solution of 2-(3-bromophenyl)propanoic acid (1.2 g, 5.2 mmol) in DCM (15 mL) was added oxalyl chloride (1.1 mL, 13.1 mmol) dropwise at 0° C. followed by the addition of one drop of DMF. The reaction mass was stirred for 1 h and concentrated under reduced pressure. The resulting crude residue was redissolved in DCM (5 mL) and added to a stirred solution of 1-((2-(trimethylsilyl)ethoxy)methyl)-1H-indazol-3-amine (1.38 g, 5.2 mmol) in pyridine (15 mL) and DCM (15 mL) at 0° C. The resulting reaction mass was stirred at ambient temperature for 1 h. The reaction mass was diluted with ethyl acetate and water. The separated organic layer was dried over anhydrous sodium sulphate and concentrated under reduced pressure, the residue was purified by combiflash by eluting with 20% ethyl acetate-hexane system to afford the title compound (1.3 g, 54%) LCMS: m/z=474.4 (M+H)$^+$.

Step-iii: Synthesis of 2-(4'-amino-[1,1'-biphenyl]-3-yl)-N-(1-((2-(trimethylsilyl)ethoxy)-methyl)-1H-indazol-3-yl)propanamide To a degassed solution of 2-(3-bromophenyl)-N-(1-((2-(trimethylsilyl)ethoxy)methyl)-1H-indazol-3-yl)propanamide (1.3 g, 2.7 mmol) and N-(4-(4,4,5,5-tetramethyl-1,3,2-dioxaborolan-2-yl)phenyl)acrylamide (0.92 g, 4.1 mmol) in 1,4-dioxane (15 mL) and water (4 mL), Cs$_2$CO$_3$ (2.72 g, 8.3 mmol) was added. The reaction mass was stirred for 10 minutes and degassed further for 10 minutes and added PdCl$_2$(dppf)$_2$.DCM (0.11 g, 0.13 mmol). The reaction mass was heated for 12 h at 110° C. in a sealed tube. The reaction mass was cooled and diluted with water and ethyl acetate. The separated organic layer was dried over anhydrous sodium sulphate and concentrated under reduced pressure, purified the compound by silica gel column chromatography by eluting with 40% ethyl acetate-hexane system to afford the title compound (1g, 78%) LCMS: m/z=487.4 (M+H)⁺.

Step-iv: Synthesis of N-(3'-(1-oxo-1-((1-((2-(trimethylsilyl)ethoxy)methyl)-1H-indazol-3-yl)amino)propan-2-yl)-[1,1'-biphenyl]-4-yl)acrylamide TEA (0.34 mL, 2.4 mmol) was added to a solution of 2-(4'-amino-[1,1'-biphenyl]-3-yl)-N-(1-((2-(trimethylsilyl)ethoxy)methyl)-1H-indazol-3-yl)propanamide (0.4 g, 0.8 mmol) in DCM (8 mL) at 0° C. The reaction mass was stirred for 5 minutes and added acryloyl chloride (0.088 g, 0.9 mmol) in DCM (1 mL). The resultant reaction mass was stirred for 20 minutes at 0° C., quenched the reaction mass with ice cold water and DCM. The separated organic layer was washed with water followed by brine, dried and concentrated under reduced pressure to afford the title compound (0.4 g crude) LCMS: m/z=541.2 (M+H)⁺.

Step-v: Synthesis of N-(3'-(1-((1H-indazol-3-yl)amino)-1-oxopropan-2-yl)-[1,1'-biphenyl]-4-yl)acrylamide TFA (5 mL) was slowly added to a stirred solution of N-(3'-(1-oxo-1-((1-((2-(trimethylsilyl)ethoxy)methyl)-1H-indazol-3-yl)amino)propan-2-yl)-[1,1'-biphenyl]-4-yl)acrylamide (0.4 g, 0.7 mmol) in dry DCM (5 mL) under argon atmosphere at 0° C. The resulting reaction mixture was allowed to warm to room temperature and stirred for 12 h. After completion of the reaction, excess solvents were removed under reduced pressure. The resulting residue was stirred with aqueous NH₃ solution (10 mL) for 1 h. The solid separated was filtered and washed with ether and hexane and further purified by preparative HPLC condition (Column: Zorbax C18 (21.2*150 mm), Mobile phase: Acetonitrile-water) to afford the title compound as free base (0.04 g, 13%). ¹HNMR (DMSO-d₆, 400 MHz): δ 12.65 (s, 1H), 10.53 (s, 1H), 10.26 (s, 1H), 7.78 (d, 2H), 7.73 (s, 1H), 7.65 (t, 3H), 7.54 (d, 1H), 7.39-7.45 (m, 3H), 7.29 (t, 1H), 7.0 (t, 1H), 6.42-6.49 (m, 1H), 6.26 (dd, 1H), 5.77 (dd, 1H), 4.03 (dd, 1H), 1.50 (d, 3H). LCMS: m/z=411.1 (M+H)⁺; HPLC: 98.43%, rt: 3.95 min.

Example-9: Synthesis of (E)-N-(3'-(1-((1H-indazol-3-yl)amino)-1-oxopropan-2-yl)-[1,1'-biphenyl]-4-yl)-4-(dimethylamino)but-2-enamide (Compound-91)

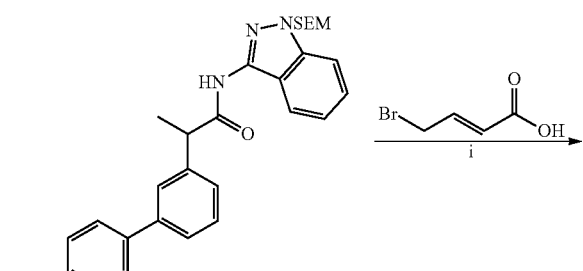

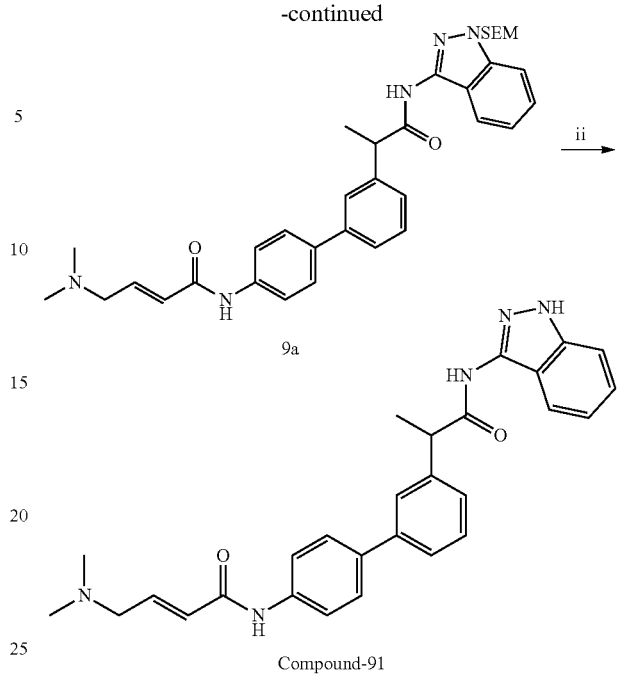

Step-i: Synthesis of (E)-4-(dimethylamino)-N-(3'-(1-oxo-1-((1-((2-(trimethylsilyl)ethoxy)-methyl)-1H-indazol-3-yl)amino)propan-2-yl)-[1,1'-biphenyl]-4-yl)but-2-enamide To a solution of (E)-4-bromobut-2-enoic acid (0.35 g, 2.1 mmol) in DCM (8 mL) was added oxalyl chloride (0.27 mL 2.3 mmol) drop wise at 0° C. followed by the addition of one drop of DMF, stirred the reaction mass for 1.5 h and concentrated under reduced pressure. The resulting crude residue redissolved in DCM (2 mL) and added to a stirred solution of 2-(4'-amino-[1,1'-biphenyl]-3-yl)-N-(1-((2-(trimethylsilyl)ethoxy)methyl)-1H-indazol-3-yl)propanamide (0.51 g, 1 mmol) in DIPEA (0.94 mL, 5.3 mmol) and acetonitrile (10 mL) at 0° C. for 20 minutes followed by the addition of 2M N,N-dimethylamine solution in THF (1.3 mL) at 0° C. The resulting reaction mass was stirred at ambient temperature for 12 h. The reaction mass was diluted with DCM and water. The separated organic layer was dried over anhydrous sodium sulphate and concentrated under reduced pressure, the residue was purified by combiflash by eluting with 8% methanol-chloroform system to afford the title compound (0.3 g, 48%). LCMS: m/z=598.1 (M+H)⁺.

Step-ii: Synthesis of (E)-N-(3'-(1-((1H-indazol-3-yl)amino)-1-oxopropan-2-yl)-[1,1'-biphenyl]-4-yl)-4-(dimethylamino)but-2-enamide TFA (5 mL) was slowly added to a stirred solution of (E)-4-(dimethylamino)-N-(3'-(1-oxo-1-((1-((2-(trimethylsilyl)ethoxy)methyl)-1H-indazol-3-yl)amino)propan-2-yl)-[1,1'-biphenyl]-4-yl)but-2-enamide (0.3 g, 0.5 mmol) in dry DCM (5 mL) under argon atmosphere at 0° C. The resulting reaction mixture was allowed to warm to room temperature and stirred for 12 h. After completion of the reaction, excess solvents were removed under reduced pressure. The crude was purified by preparative HPLC condition (Column: Xbridge C18 (19*150 mm), Mobile phase: Ammonium acetate-Acetonitrile-water) to afford the title compound as free base (0.01 g, 4.2%). ¹HNMR (DMSO-d₆, 400 MHz): δ

12.64 (s, 1H), 10.52 (s, 1H), 10.17 (s, 1H), 7.75 (t, 3H), 7.62-7.67 (m, 4H), 7.53 (d, 1H), 7.39-7.45 (m, 3H), 7.30 (t, 1H), 6.71-6.76 (m, 1H), 6.28 (d, 1H), 4.03 (d, 1H), 3.06 (d, 2H), 2.18 (s, 6H), 1.51 (d, 3H). LCMS: m/z=468.1 (M+H)+; HPLC: 90.40%, rt: 6.25 min.

Example-10: Synthesis of (E)-N-(6-(3-(1-((5-cyclopropyl-1H-pyrazol-3-yl)amino)-1-oxopropan-2-yl)phenyl)pyrazin-2-yl)-4-(pyrrolidin-1-yl)but-2-enamide (Compound-92)

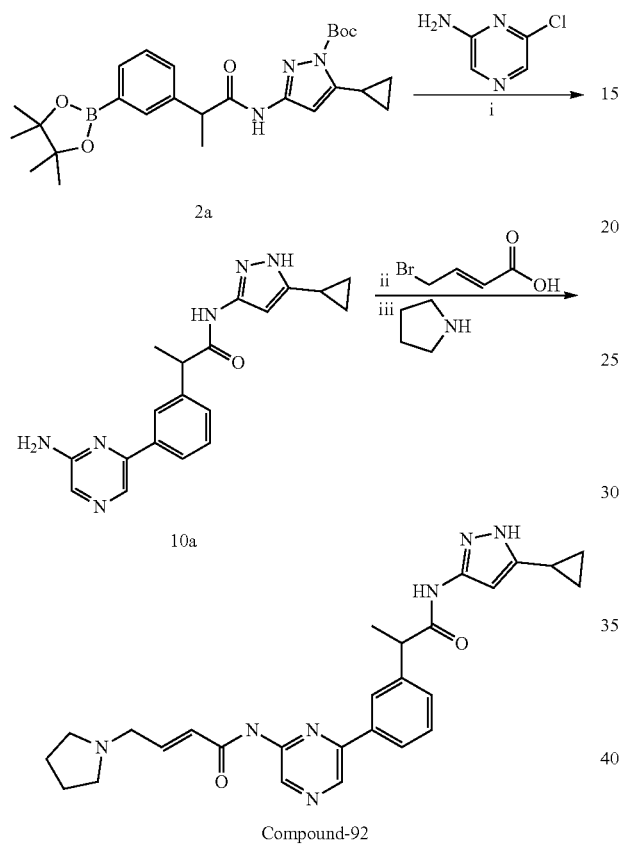

Step-: Synthesis of 2-(3-(6-aminopyrazin-2-yl)phenyl)-N-(5-cyclopropyl-1H-pyrazol-3-yl)propanamide To a degassed solution of tert-butyl 5-cyclopropyl-3-(2-(3-(4,4,5,5-tetramethyl-1,3,2-dioxaborolan-2-yl)phenyl)propanamido)-1H-pyrazole-1-carboxylate (1.5 g, 3.11 mmol) and 6-chloropyrazin-2-amine (0.32 g, 2.49 mmol) in 1,4-dioxane (40 mL) and water (10 mL), Cs₂CO₃ (2.5 g, 7.69 mmol) was added. The reaction mass was stirred for 10 minutes and degassed further for 10 min and added PdCl₂(dppf).DCM (0.17 g, 0.218 mmol). The reaction mass was heated for 12 h at 100° C. in a sealed tube. The reaction mass was cooled to room temperature and diluted with water and ethyl acetate. The separated organic layer was dried over anhydrous sodium sulphate and concentrated under reduced pressure. The residue was purified by silica gel column chromatography by eluting with 15% ethyl acetate-hexane to afford the title compound (1g, 50%) LCMS: m/z=349.2 (M+H)+.

Step-ii: Synthesis of (E)-N-(6-(3-(1-((5-cyclopropyl-1H-pyrazol-3-yl)amino)-1-oxopropan-2-yl)phenyl)pyrazin-2-yl)-4-(pyrrolidin-1-yl)but-2-enamide (E)-4-bromobut-2-enoic acid (Intermediate-1d, 0.227 g, 1.31 mmol) was taken in DCM (5 mL) with catalytic amount of DMF followed by the addition of oxalyl chloride (0.121 g, 0.95 mmol). The reaction mass was stirred for 1.5 h, concentrated the reaction mass under reduced pressure to residue. Re dissolved the reaction mass in DCM (2 mL) and was added at 0° C. to a mixture of 2-(3-(6-aminopyrazin-2-yl)phenyl)-N-(5-cyclopropyl-1H-pyrazol-3-yl)propanamide (0.30 g, 0.86 mmol) in acetonitrile (5 mL) and DIPEA (0.37 mL, 2.16 mmol). The resulting reaction mixture was stirred for 10 minutes at 0° C. and after completion of the reaction, a solution of pyrrolidine (0.086 g, 1.2 mmol) was added and then allowed to stir at room temperature for 12 h. The reaction mixture was quenched with saturated NaHCO₃ solution and diluted with DCM. The aqueous layer was separated and extracted with DCM (2×25 mL). The combined organic phase was washed with brine, dried over Na₂SO₄, filtered and concentrated under reduced pressure and purified the residue with silica gelcolumn chromatography by eluting with 10% methanol-DCM to afford the title compound (0.01 g, 10%). ¹HNMR (DMSO-d₆, 400 MHz): δ 12.10 (s, 1H), 11.25 (s, 1H), 10.49 (s, 1H), 9.93 (s, 1H), 9.39 (s, 1H), 8.95 (m, 1H), 8.09 (s, 1H), 7.97-7.95 (d, 1H), 7.53-7.47 (m, 1H), 6.91-6.84 (m, 1H), 6.71-6.67 (d, 1H), 6.11 (s, 1H), 4.09-4.06 (m, 2H), 3.94-3.93 (m, 1H), 3.61-3.55 (m, 2H), 2.79-2.77 (m, 2H), 2.08-1.88 (m, 2H), 1.82-1.77 (m, 3H), 1.44-1.43 (m, 3H), 0.88-0.85 (m, 2H), 0.64-0.62 (m, 2H), LCMS: m/z=485.2 (M+H)+, HPLC: 95.04%, rt: 7.07 min.

Example-11: Synthesis of (S,E)-N-(5-(3-(1-((5-cyclopropyl-1H-pyrazol-3-yl)amino)-1-oxopropan-2-yl)phenyl)pyridin-2-yl)-4-morpholinobut-2-enamide (Compound-93)

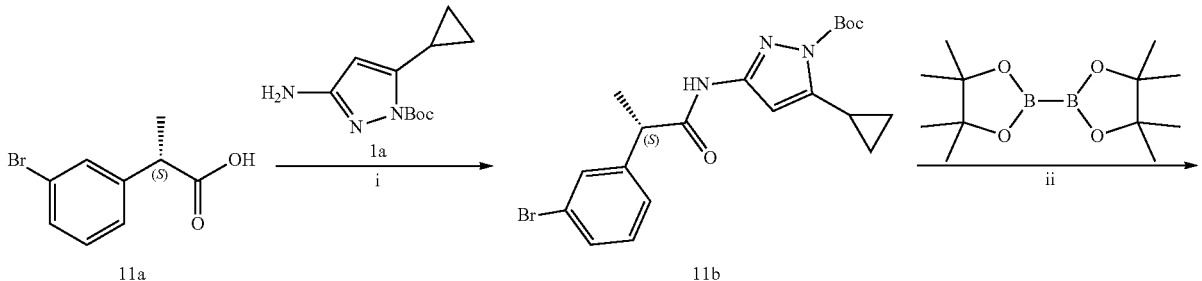

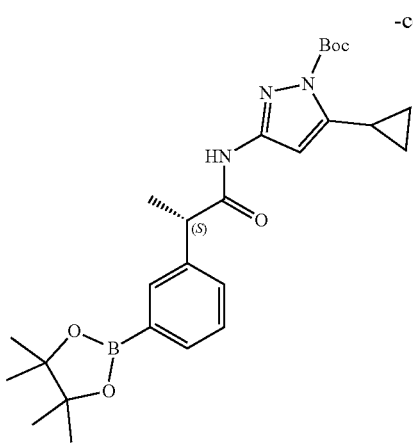

11c

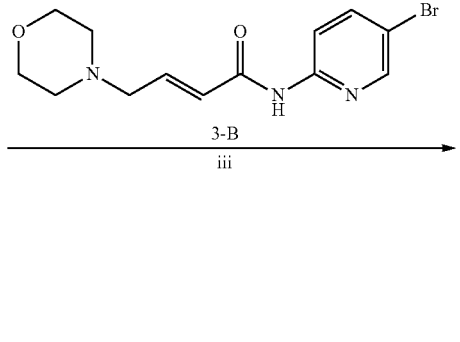

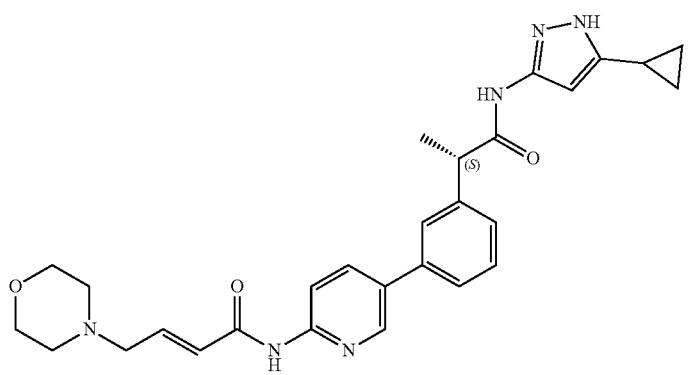

Compound-93

Step-i: Synthesis of tert-butyl (S)-3-(2-(3-bromophenyl)propanamido)-5-cyclopropyl-1H-pyrazole-1-carboxylate (S)-2-(3-bromophenyl)propanoic acid (0.08 g, 0.34 mmol) (synthesis carried out as described in reference WO2014/201073 A1) was taken in 2 mL DCM at 0° C. with catalytic amount of DMF and added oxalyl chloride (0.42 g, 0.34 mmol), allowed to stir the reaction mass at room temperature for 1.5 h. The reaction mass was concentrated under vacuum, and the residue was dissolved in 2 mL of dry DCM and added to a cooled solution of tert-butyl 3-amino-5-cyclopropyl-1H-pyrazole-1-carboxylate (0.078 g, 0.34 mmol) in 2 mL of DCM and TEA (0.086 g, 0.1 mL) at 0° C. The resultant reaction mass was stirred at room temperature for 1 h, after 1 h, the reaction mixture was diluted with DCM then washed with saturated NaHCO$_3$ solution followed by brine solution. The organic layer was dried over anhydrous sodium sulfate, concentrated under vacuum and purified by silica gel column chromatography by eluting with 15% ethyl acetate in hexane to afford the title compound (0.1 g, 53%). LCMS: m/z=436.1 (M+H)$^+$.

Step-ii: Synthesis of tert-butyl (S)-5-cyclopropyl-3-(2-(3-(4,4,5,5-tetramethyl-1,3,2-dioxaborolan-2-yl)phenyl)propanamido)-1H-pyrazole-1-carboxylate To a degassed solution of tert-butyl (S)-3-(2-(3-bromophenyl)propanamido)-5-cyclopropyl-1H-pyrazole-1-carboxylate (0.1 g 0.23 mmol) and 4,4,4',4',5,5,5',5'-octamethyl-2,2'-bi(1,3,2-dioxaborolane) (0.087 g, 0.34 mmol) in 1,4-dioxane (5 mL) was added potassium acetate (0.045 g, 0.46 mmol). The reaction mass was allowed to stir for 10 minutes with degassing at RT and added PdCl$_2$(dppf).DCM complex (0.010 g, 0.011 mmol). The reaction mass was heated for 12 h at 100° C. in a sealed tube, cooled the reaction mass and diluted with water and ethyl acetate. The aqueous layer was separated and re-extracted with ethyl acetate (2×5 mL). The combined organic layer was dried over anhydrous sodium sulfate and concentrated under vacuum. The crude was purified by silica gel column chromatography by eluting with 20% ethyl acetate in hexane to afford the title compound (0.065 g, 58%), LCMS: m/z=482.2 (M+H)$^+$.

Step-iii: Synthesis of (S, E)-N-(5-(3-(1-((5-cyclopropyl-1H-pyrazol-3-yl)amino)-1-oxopropan-2-yl)phenyl)pyridin-2-yl)-4-morpholinobut-2-enamide To a degassed solution of tert-butyl (S)-5-cyclopropyl-3-(2-(3-(4,4,5,5-tetramethyl-1,3,2-dioxaborolan-2-yl)phenyl)propanamido)-1H-pyrazole-1-carboxylate (0.065 g, 0.13 mmol) and (E)-N-(5-bromopyridin-2-yl)-4-morpholinobut-2-enamide (0.044 g, 0.13 mmol) in 1,4-dioxane (2 mL) and water (0.1 mL) was added Cs$_2$CO$_3$ (0.084 g, 0.26 mmol). The reaction mass was allowed to stir for 10 minutes with degassing and added PdCl$_2$(dppf).DCM complex (0.005 g, 0.007 mmol), heated the reaction mass for 12 h at 100° C. in a a sealed tube. The reaction mass was cooled and diluted with water and ethyl acetate. The aqueous layer was separated and re-extracted with ethyl acetate (2×5 mL). The combined organic layer was dried over anhydrous sodium sulfate and concentrated under vacuum. The crude was purified by silica gel column chromatography by eluting with 10% methanol in DCM (further purified by Preparative HPLC, Column: GEMINI NX C18:21.2 mm*150 mm, A:0.01% Ammonia, B:ACN/MeOH) to afford the title compound (0.006 g, 8%). $^1$HNMR (CD$_3$OD-d$_6$, 400 MHz):δ 8.57-8.56 (d, 1H), 8.26-8.24 (d, 1H), 8.04-8.02 (m, 1H), 7.65 (s, 1H), 7.53-7.50 (m, 1H), 7.44-7.39 (m, 2H), 7.00-6.93 (m, 1H), 6.43-6.39 (d, 1H), 6.13 (s, 1H), 3.89-3.88 (m, 1H), 3.73-3.70 (m, 4H), 3.23-3.21 (m, 2H), 2.51-2.48 (m, 4H), 1.86-1.81 (m, 1H), 1.54-1.39 (d, 3H), 0.94-0.92 (m, 2H), 0.68-0.62 (m, 2H); LCMS: m/z=501.1 (M+H)$^+$; HPLC: 96.27%, rt: 5.88 min., Chiral HPLC: 90.84%, rt: 8.87 min.

Example-12: Synthesis of (E)-N-(5-cyclopropyl-1H-pyrazol-3-yl)-1-(3-(6-(4-(pyrrolidin-1-yl)but-2-enamido)pyridin-3-yl)phenyl)cyclopropane-1-carboxamide (Compound-94)

Step-i: Synthesis of tert-butyl 3-(1-(3-bromophenyl)cyclopropane-1-carboxamido)-5-cyclopropyl-1H-pyrazole-1-carboxylate To a solution of 1-(3-bromophenyl)cyclopropane-1-carboxylic acid (0.4 g, 1.66 mmol) (synthesis carried out as described in references EP1206446 B1; and WO2005/19161A1) in DMF (5 mL) was added HATU (0.94 g, 2.49 mmol) followed by DIPEA (0.86 mL, 4.98 mmol) at 0° C. and finally added tert-butyl 3-amino-5-cyclopropyl-1H-pyrazole-1-carboxylate (0.37 g, 1.66 mmol). The reaction mass was stirred for 15 h at room temperature. The reaction mixture was quenched with ice-water and diluted with ethyl acetate. The aqueous layer was separated and extracted with ethyl acetate (2×25 mL). The combined organic phase was washed with brine, dried over Na$_2$SO$_4$, filtered and concentrated the crude residue was purified by 100-200 silica gel column chromatography to afford desired title compound (0.4 g, 54%). LCMS: m/z=448.0 (M+H)$^+$.

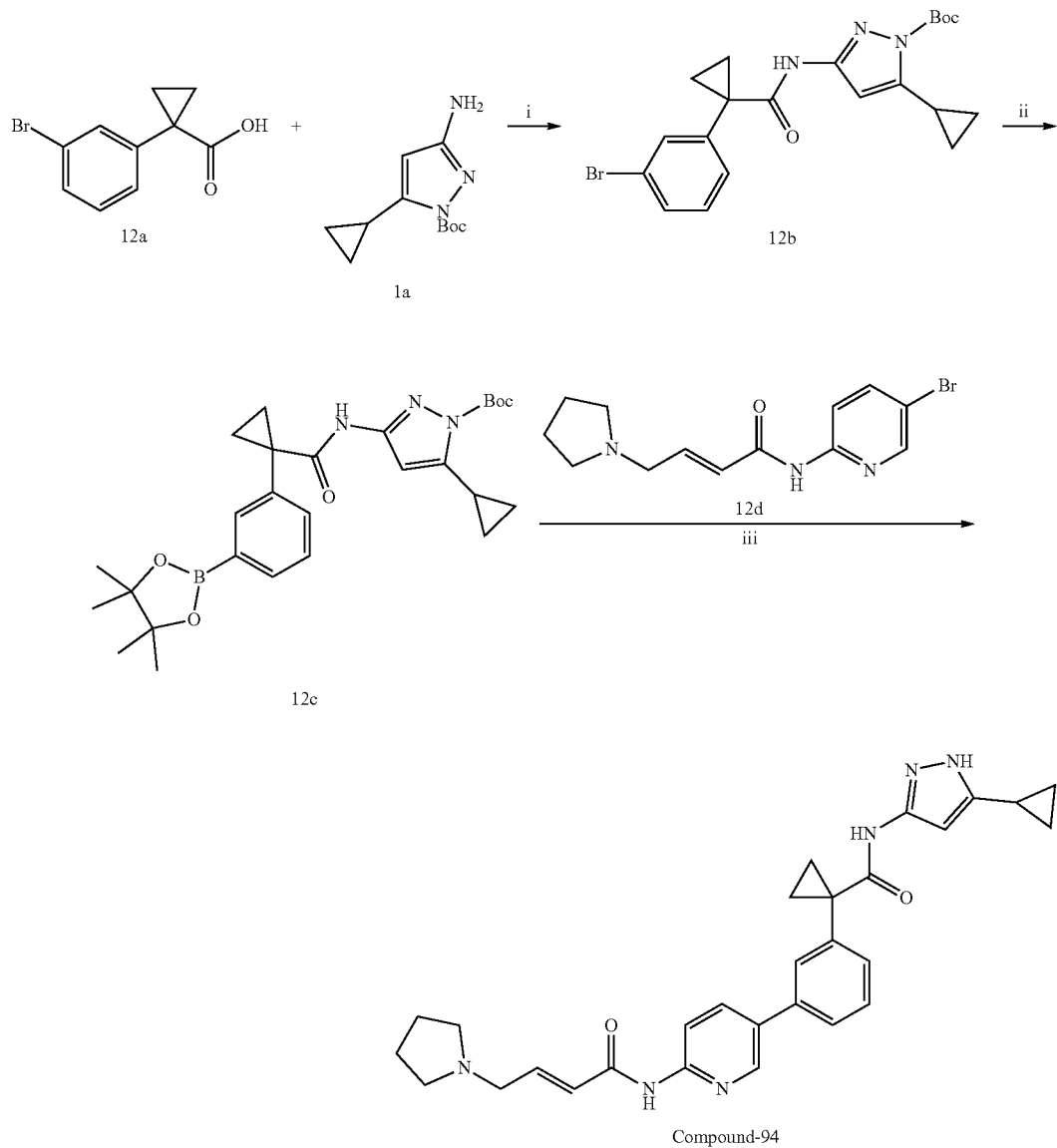

Step-ii: Synthesis of tert-butyl 5-cyclopropyl-3-(1-(3-(4,4,5,5-tetramethyl-1,3,2-dioxaborolan-2-yl)phenyl)cyclopropane-1-carboxamido)-1H-pyrazole-1-carboxylate To a degassed solution of tert-butyl 3-(1-(3-bromophenyl)cyclopropane-1-carboxamido)-5-cyclopropyl-1H-pyrazole-1-carboxylate (0.2 g, 0.45 mmol) and 4,4,4',4',5,5,5',5'-octamethyl-2,2'-bi(1,3,2-dioxaborolane) (0.25 g, 0.54 mmol) in 1,4-dioxane (10 mL) was added KOAc (0.13 g, 1.35 mmol). The reaction mass was stirred for 10 minutes and degassed further for 10 minutes with argon and added PdCl$_2$(dppf).DCM (0.036 g, 0.045 mmol). The reaction mass was heated for 15 h at 110° C. in a sealed tube. Then the reaction mass was cooled to room temperature and diluted with water and ethyl acetate. The separated organic layer was dried over anhydrous sodium sulphate and concentrated under vacuum and purified by silica gel column chromatography by eluting with 15% ethyl acetate-hexane to afford the title compound (0.2 g, crude) LCMS: m/z=494.2 (M+H)$^+$.

Step-iii: Synthesis of (E)-N-(5-cyclopropyl-1H-pyrazol-3-yl)-1-(3-(6-(4-(pyrrolidin-1-yl)but-2-enamido)pyridin-3-yl)phenyl)cyclopropane-1-carboxamide To a degassed solution of tert-butyl 5-cyclopropyl-3-(1-(3-(4,4,5,5-tetramethyl-1,3,2-dioxaborolan-2-yl)phenyl)cyclopropane-1-carboxamido)-1H-pyrazole-1-carboxylate (0.2 g, 0.4 mmol) and (E)-N-(5-bromopyridin-2-yl)-4-(pyrrolidin-1-yl)but-2-enamide (0.1 g, 0.33 mmol) (synthesised similer to intermediate 3-B) in 1,4-dioxane (10 mL) and water (2 mL) Cs$_2$CO$_3$ (0.26 g, 0.81 mmol) was added. The reaction mass was stirred for 10 minutes and degassed further for 10 min with argon and added PdCl$_2$(dppf).DCM (0.033 g, 0.04 mmol). Then the reaction mass was heated for 15 h at 110° C. in a sealed tube. The reaction mass was cooled to room temperature and diluted with water and ethyl acetate. The separated organic layer was dried over anhydrous sodium sulphate and concentrated under vacuum and purified by silica gel column chromatography by eluting with 0-5% MeOH-DCM and further purified by preparative HPLC (Method: A: 0.005% TFA in water, B: ACN-MeOH, Column: Kinetex 5μ (150 mm×19.0 mm) to afford the title compound (0.02 g, 10%). $^1$HNMR (DMSO-d, 400 MHz): δ 12.01 (s, 1H), 10.90 (s, 1H), 10.85 (brs, 1H), 8.69-8.68 (d, 1H), 8.28-8.26 (m, 1H), 8.16-8.13 (m, 1H), 7.75 (s, 1H), 7.67-7.65 (m, 1H), 7.50-7.42 (m, 2H), 6.88-6.81 (m, 1H), 6.49-6.45 (m, 1H), 6.05 (s, 1H), 3.21-3.18 (m, 2H), 2.55-2.45 (m, 4H), 1.82-1.70 (m, 1H), 1.70-1.68 (m, 4H), 1.45-1.42 (m, 2H), 1.16-1.12 (m, 2H), 0.89-0.84 (m, 2H), 0.62-0.58 (m, 2H); LCMS: m/z=497.3 (M+H)$^+$; HPLC: 93.65%, rt: 4.52 min.

Example-13: Synthesis of (E)-N-(5-(3-(1-((5-cyclopropyl-1H-pyrazol-3-yl)amino)-2-methyl-1-oxopropan-2-yl)phenyl)pyridin-2-yl)-4-(pyrrolidin-1-yl)but-2-enamide (Compound-95)

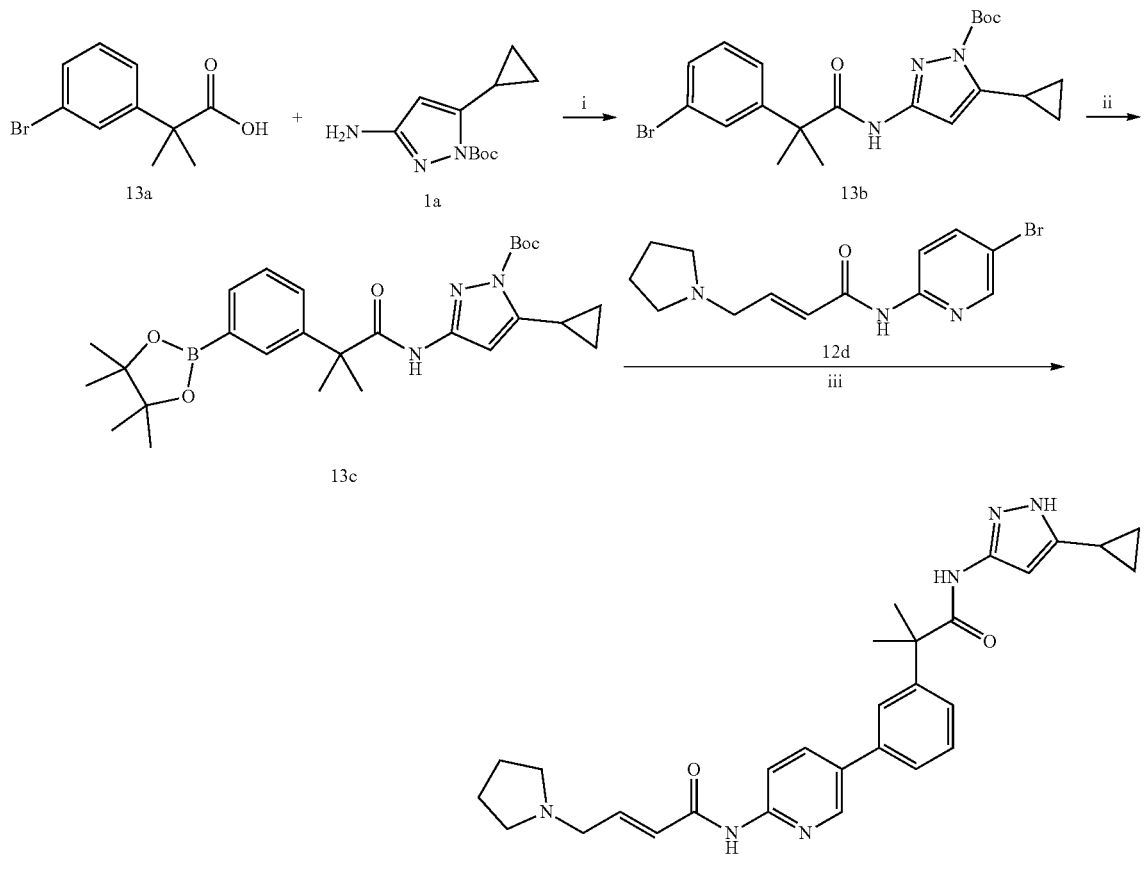

Compound-95

Step-i: Synthesis of tert-butyl 3-(2-(3-bromophenyl)-2-methylpropanamido)-5-cyclopropyl-1H-pyrazole-1-carboxylate To the solution of 2-(3-bromophenyl)-2-methylpropanoic acid (0.4 g, 1.66 mmol)(synthesis carried out as described in reference US2008/194600A1) in DMF (5 mL) was added HATU (0.94 g, 2.49 mmol) followed by DIPEA (0.86 mL, 4.98 mmol) at 0° C. and finally added tert-butyl 3-amino-5-cyclopropyl-1H-pyrazole-1-carboxylate (0.37 g, 1.66 mmol). The reaction mass was stirred for 15 h at room temperature. The reaction mixture was quenched with ice-water and diluted with ethyl acetate. The aqueous layer was separated and extracted with ethyl acetate (2×25 mL). The combined organic phase was washed with brine, dried over $Na_2SO_4$, filtered and concentrated the crude residue was purified by 100-200 silica gel column chromatography to afford desired compound (0.15 g, 20%). LCMS: m/z=450.0 $(M+H)^+$.

Step-ii: Synthesis of tert-butyl 5-cyclopropyl-3-(2-methyl-2-(3-(4,4,5,5-tetramethyl-1,3,2-dioxaborolan-2-yl)phenyl)propanamido)-1H-pyrazole-1-carboxylate To a degassed solution of tert-butyl 3-(2-(3-bromophenyl)-2-methylpropanamido)-5-cyclopropyl-1H-pyrazole-1-carboxylate (0.15 g, 0.45 mmol) and 4,4,4',4',5,5,5',5'-octamethyl-2,2'-bi(1,3,2-dioxaborolane) (0.1 g, 0.4 mmol) in 1,4-dioxane (10 mL) was added KOAc (0.1 g, 1.0 mmol). The reaction mass was stirred for 10 minutes and degassed further for 10 minutes with argon and added $PdCl_2(dppf)$.DCM (0.027 g, 0.033 mmol). The reaction mass was heated for 15 h at 110° C. in a sealed tube. Cooled the reaction mass and diluted with water and ethyl acetate. The separated organic layer was dried over anhydrous sodium sulphate and concentrated under vacuum and purified by silica gel column chromatography by eluting with 15% ethyl acetate-hexane to afford the title compound (0.15 g, 92%) LCMS: m/z=496.3 $(M+H)^+$.

Step-iii: Sythesis of (E)-N-(5-(3-(1-((5-cyclopropyl-1H-pyrazol-3-yl)amino)-2-methyl-1-oxopropan-2-yl)phenyl)pyridin-2-yl)-4-(pyrrolidin-1-yl)but-2-enamide To a degassed solution of tert-butyl 5-cyclopropyl-3-(2-methyl-2-(3-(4,4,5,5-tetramethyl-1,3,2-dioxaborolan-2-yl)phenyl)propanamido)-1H-pyrazole-1-carboxylate (0.14 g, 0.28 mmol) and (E)-N-(5-bromopyridin-2-yl)-4-(pyrrolidin-1-yl)but-2-enamide (0.09 g, 0.28 mmol) in 1,4-dioxane (10 mL) and water (2 mL) added $Cs_2CO_3$ (0.17 g, 0.56 mmol). The reaction mass was stirred for 10 minutes and degassed further for 10 min with argon and added $PdCl_2(dppf)$.DCM (0.023 g, 0.028 mmol), then heated for 15 h at 110° C. in a sealed tube. The reaction mass was cooled to room temperature and diluted with water and ethyl acetate. The separated organic layer was dried over anhydrous sodium sulphate and concentrated under vacuum and the residue was purified by silica gel column chromatography by eluting with 0-5% MeOH-DCM and further purified by preparative HPLC (Method: A: 0.005% TFA in water, B: ACN-MeOH, Column: Kinetex 5 p (150 mm×19.0 mm) to afford the title compound (0.004 g, 2.85%). $^1$HNMR (DMSO-$d_6$, 400 MHz): δ 11.05 (s, 1H), 9.89 (brs, 1H), 9.49 (s, 1H), 8.68-8.67 (m, 1H), 8.28-8.26 (m, 1H), 8.15-8.12 (m, 1H), 7.65 (s, 1H), 7.659-7.57 (m, 1H), 7.46-7.42 (m, 1H), 7.34-7.32 (m, 1H), 6.85-6.79 (m, 1H), 6.66-6.62 (m, 1H), 6.12 (s, 1H), 3.07-3.05 (m, 2H), 2.5 (s, 4H), 2.00-1.80 (m, 5H), 1.60 (s, 6H), 0.90-0.87 (m, 2H), 0.64-0.60 (m, 2H); LCMS: m/z=499.3 $(M+H)^+$; HPLC: 95.03%, rt: 6.16 min.

Although the present invention has been illustrated by certain of the preceding examples, it is not to be construed as being limited thereby; but rather, the present invention encompasses the generic area as hereinbefore disclosed. Various modifications and embodiments can be made without departing from the spirit and scope thereof. For example, the compounds in the table-4 below which can be prepared by following similar procedure as described in above Schemes/Examples with suitable modifications known to the one ordinary skilled in the art are also included in the scope of the present invention:

TABLE 4

| Compound. No. | Structure |
|---|---|
| 96. | 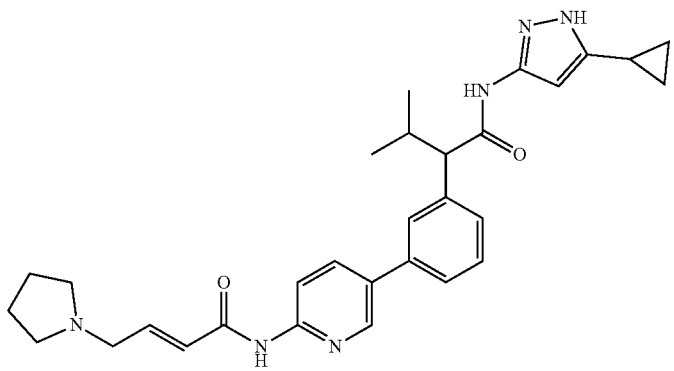 [SMILES: CC(C)C(C(=O)Nc1cc(C2CC2)[nH]n1)c1cccc(-c2ccc(NC(=O)/C=C/CN3CCCC3)nc2)c1] |

TABLE 4-continued
| Compound. No. | Structure |
|---|---|
| 97. | 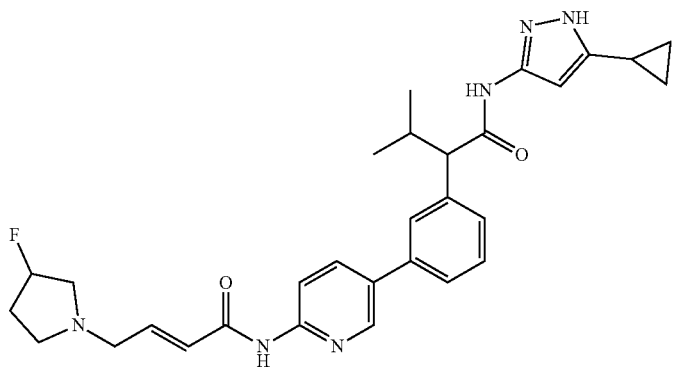 [SMILES: CC(C)C(C(=O)Nc1cc(C2CC2)[nH]n1)c1cccc(-c2ccc(NC(=O)/C=C/CN3CCC(F)C3)nc2)c1] |
| 98. | 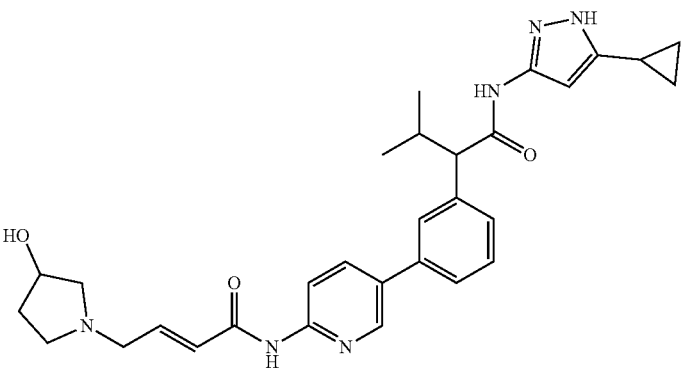 [SMILES: CC(C)C(C(=O)Nc1cc(C2CC2)[nH]n1)c1cccc(-c2ccc(NC(=O)/C=C/CN3CCC(O)C3)nc2)c1] |
| 99. | 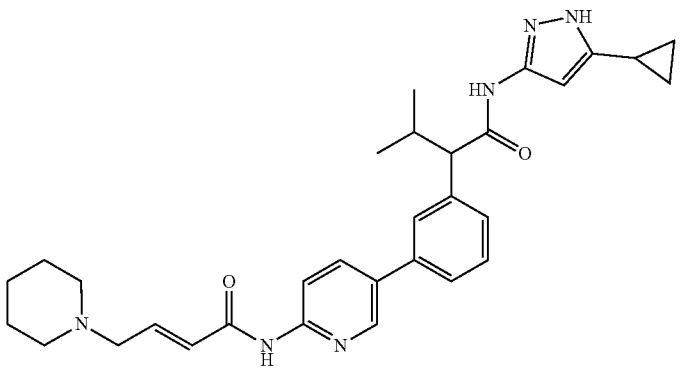 [SMILES: CC(C)C(C(=O)Nc1cc(C2CC2)[nH]n1)c1cccc(-c2ccc(NC(=O)/C=C/CN3CCCCC3)nc2)c1] |
| 100. | 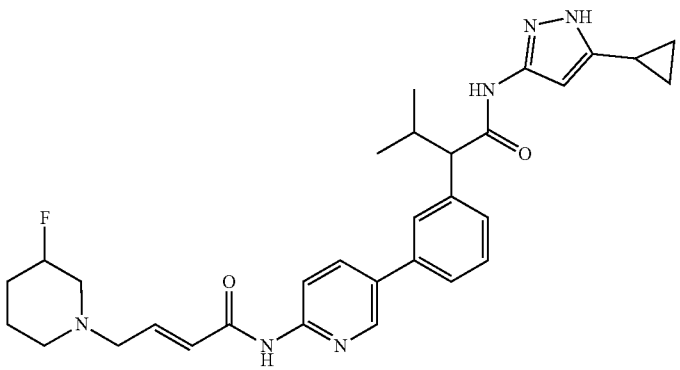 [SMILES: CC(C)C(C(=O)Nc1cc(C2CC2)[nH]n1)c1cccc(-c2ccc(NC(=O)/C=C/CN3CCCC(F)C3)nc2)c1] |

TABLE 4-continued
| Compound. No. | Structure |
|---|---|
| 101. | 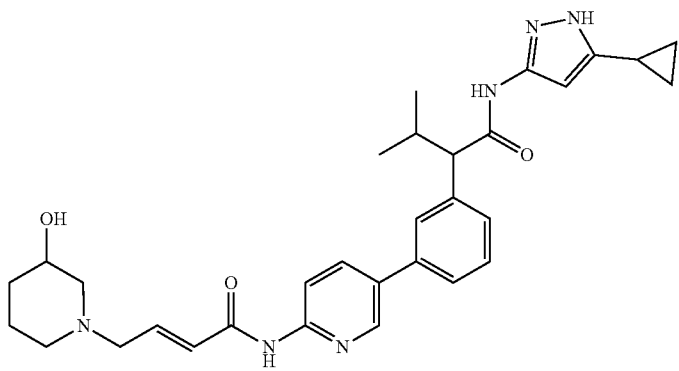 [SMILES: CC(C)C(C(=O)Nc1cc(C2CC2)[nH]n1)c1cccc(-c2ccc(NC(=O)/C=C/CN3CCCC(O)C3)nc2)c1] |
| 102. | 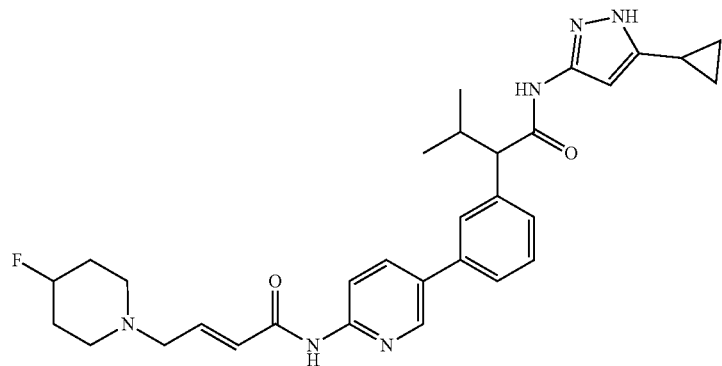 [SMILES: CC(C)C(C(=O)Nc1cc(C2CC2)[nH]n1)c1cccc(-c2ccc(NC(=O)/C=C/CN3CCC(F)CC3)nc2)c1] |
| 103. | 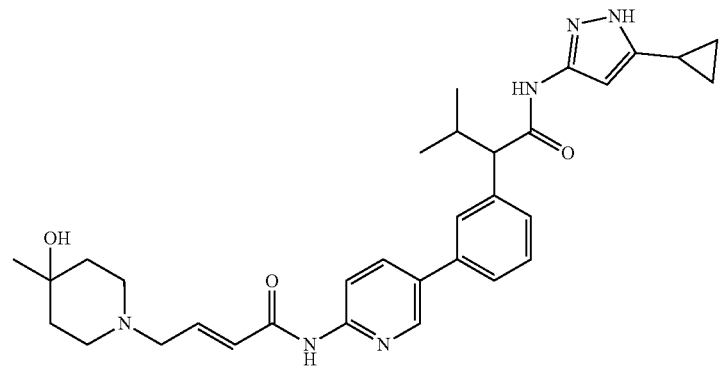 [SMILES: CC(C)C(C(=O)Nc1cc(C2CC2)[nH]n1)c1cccc(-c2ccc(NC(=O)/C=C/CN3CCC(C)(O)CC3)nc2)c1] |
| 104. | 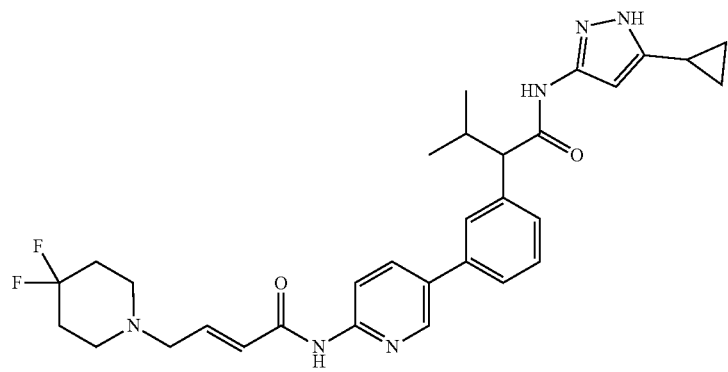 [SMILES: CC(C)C(C(=O)Nc1cc(C2CC2)[nH]n1)c1cccc(-c2ccc(NC(=O)/C=C/CN3CCC(F)(F)CC3)nc2)c1] |

… TABLE 4-continued
| Compound. No. | Structure |
|---|---|
| 105. | 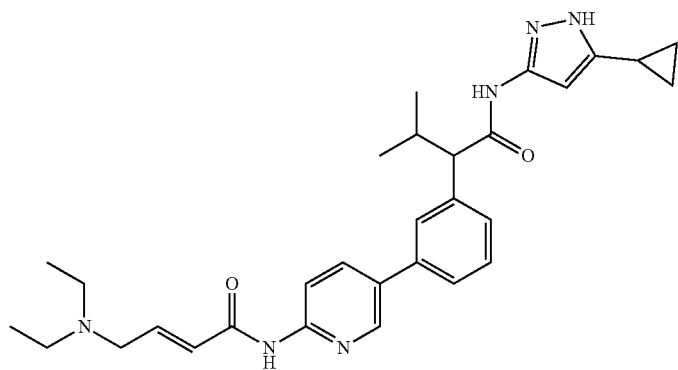 [SMILES: CCN(CC)C/C=C/C(=O)Nc1ccc(-c2cccc(C(C(=O)Nc3cc(C4CC4)[nH]n3)C(C)C)c2)cn1] |
| 106. | 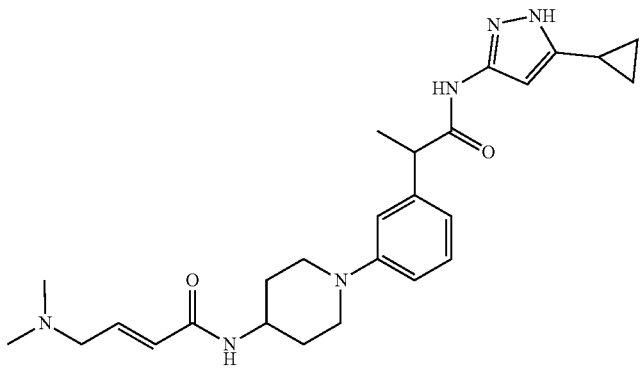 [SMILES: CC(C(=O)Nc1cc(C2CC2)[nH]n1)c1cccc(N2CCC(NC(=O)/C=C/CN(C)C)CC2)c1] |
| 107. | 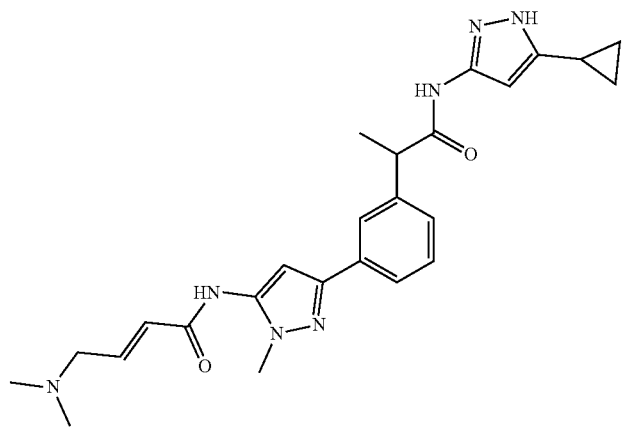 [SMILES: CC(C(=O)Nc1cc(C2CC2)[nH]n1)c1cccc(-c2cc(NC(=O)/C=C/CN(C)C)n(C)n2)c1] |

TABLE 4-continued
| Compound. No. | Structure |
|---|---|
| 108. | 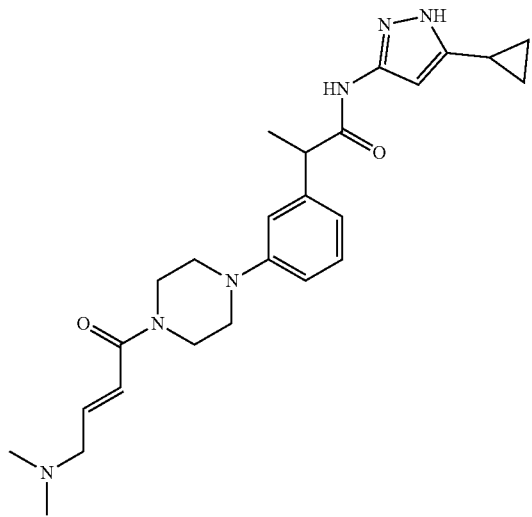 [SMILES: CC(C(=O)Nc1cc(C2CC2)[nH]n1)c1cccc(N2CCN(C(=O)/C=C/CN(C)C)CC2)c1] |
| 109. | 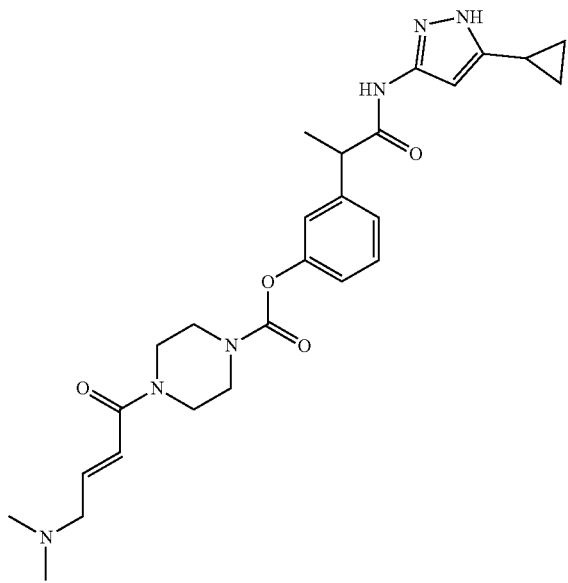 [SMILES: CC(C(=O)Nc1cc(C2CC2)[nH]n1)c1cccc(OC(=O)N2CCN(C(=O)/C=C/CN(C)C)CC2)c1] |
| 110. | 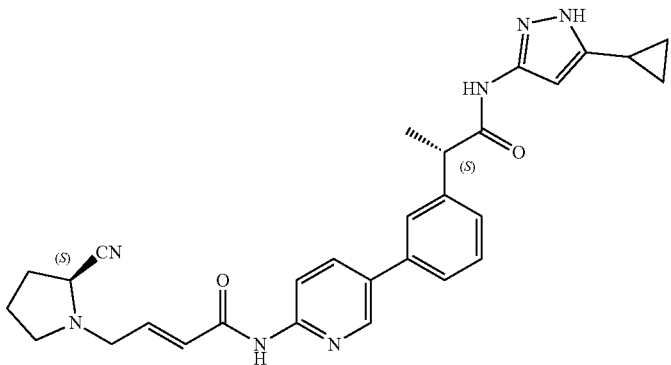 |

TABLE 4-continued
| Compound. No. | Structure |
|---|---|
| 111. | 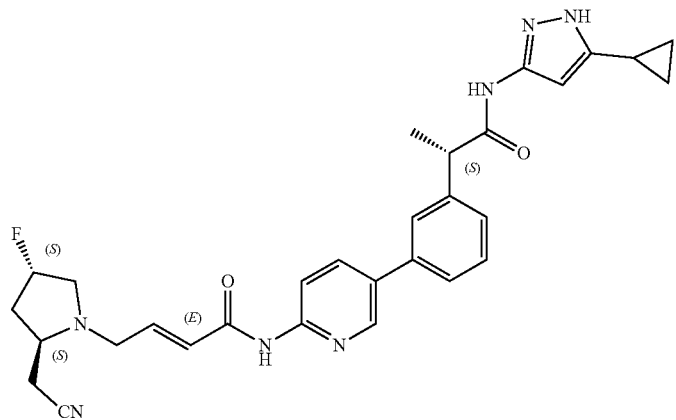 |
| 112. | 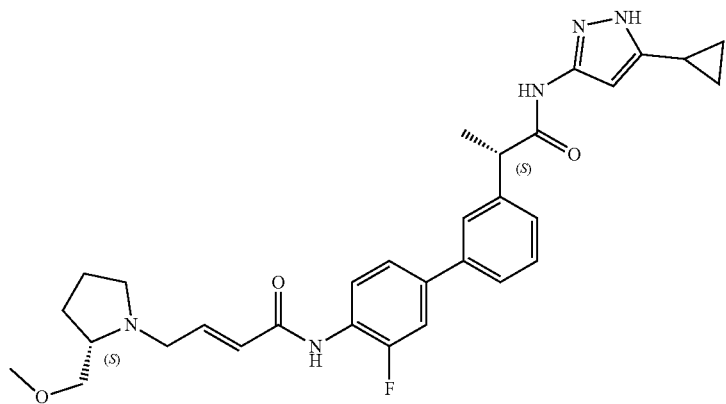 |
| 113. | 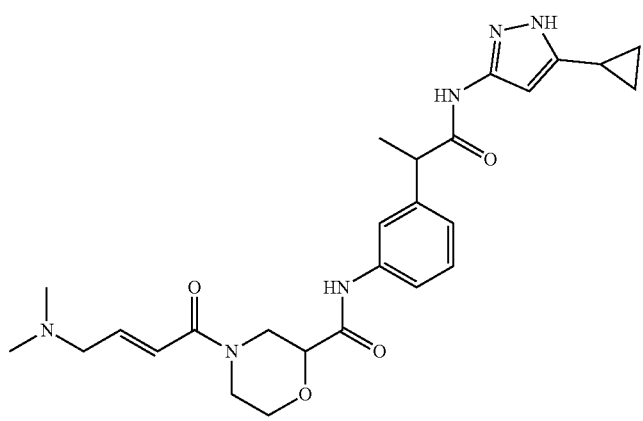 [SMILES: CC(C(=O)Nc1cc(C2CC2)[nH]n1)c1cccc(NC(=O)C2CN(C(=O)/C=C/CN(C)C)CCO2)c1] |

TABLE 4-continued
| Compound. No. | Structure |
|---|---|
| 114. | 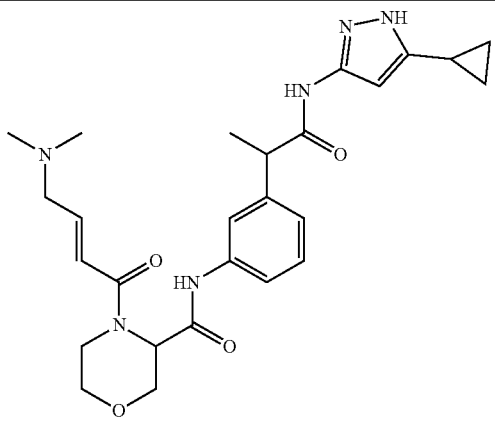 |
| 115. | 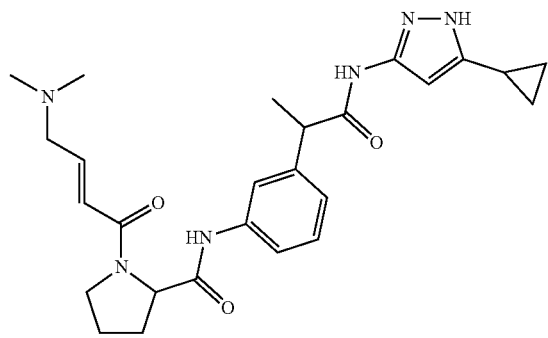 [SMILES: CC(C(=O)Nc1cc(C2CC2)[nH]n1)c1cccc(NC(=O)C2CCCN2C(=O)/C=C/CN(C)C)c1] |
| 116. | 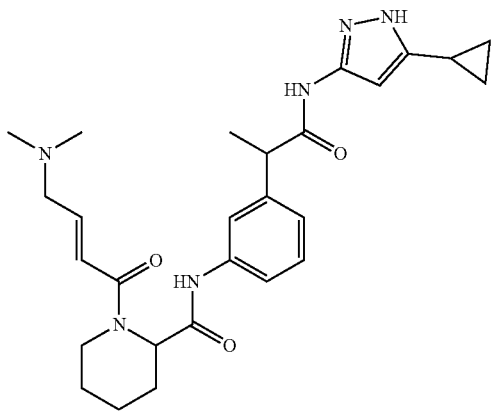 [SMILES: CC(C(=O)Nc1cc(C2CC2)[nH]n1)c1cccc(NC(=O)C2CCCCN2C(=O)/C=C/CN(C)C)c1] |
| 117. | 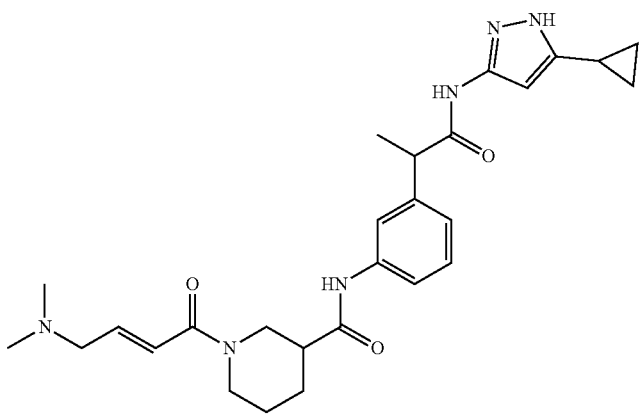 [SMILES: CC(C(=O)Nc1cc(C2CC2)[nH]n1)c1cccc(NC(=O)C2CCCN(C(=O)/C=C/CN(C)C)C2)c1] |

TABLE 4-continued
| Compound. No. | Structure |
|---|---|
| 118. | 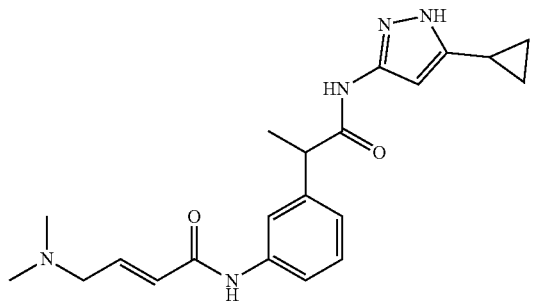 [SMILES: CC(C(=O)Nc1cc(C2CC2)[nH]n1)c1cccc(NC(=O)/C=C/CN(C)C)c1] |
| 119. | 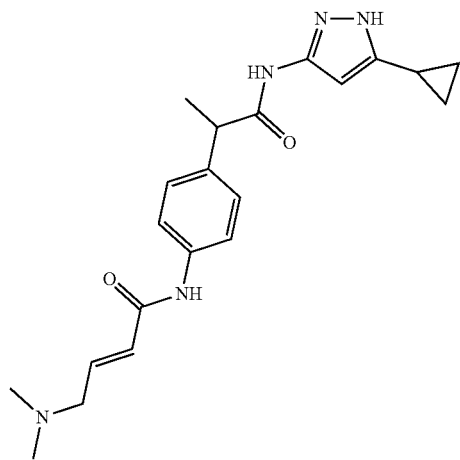 [SMILES: CC(C(=O)Nc1cc(C2CC2)[nH]n1)c1ccc(NC(=O)/C=C/CN(C)C)cc1] |
| 120. | 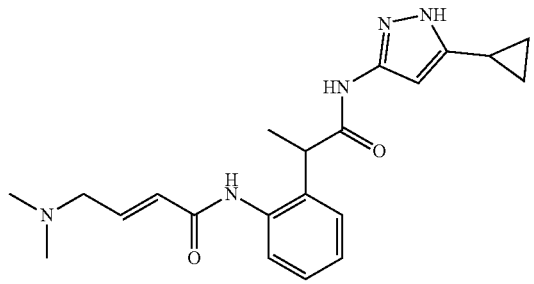 [SMILES: CC(C(=O)Nc1cc(C2CC2)[nH]n1)c1ccccc1NC(=O)/C=C/CN(C)C] |
| 121. | 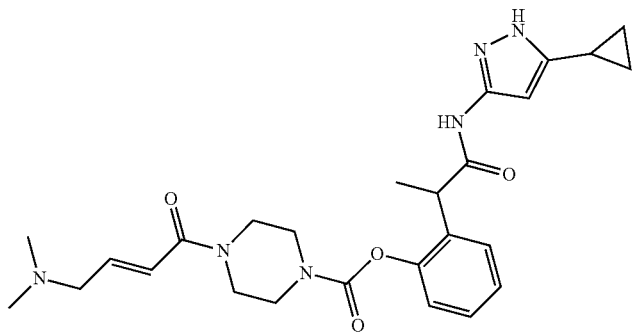 [SMILES: CC(C(=O)Nc1cc(C2CC2)[nH]n1)c1ccccc1OC(=O)N1CCN(C(=O)/C=C/CN(C)C)CC1] |

TABLE 4-continued
| Compound. No. | Structure |
|---|---|
| 122. | 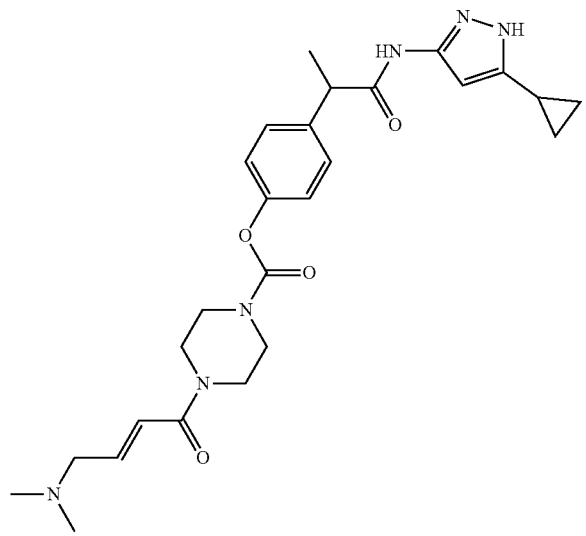 [SMILES: CC(C(=O)Nc1cc(C2CC2)[nH]n1)c1ccc(OC(=O)N2CCN(C(=O)/C=C/CN(C)C)CC2)cc1] |
| 123. | 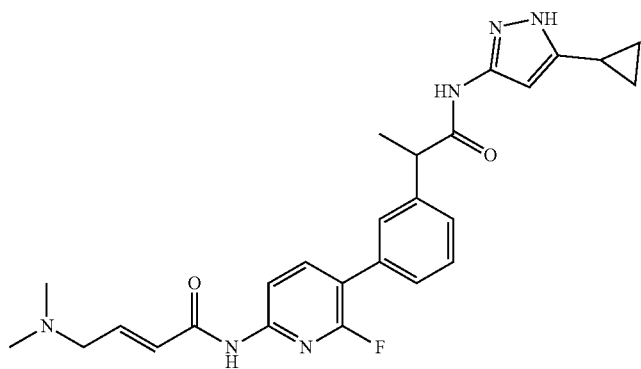 |
| 124. | 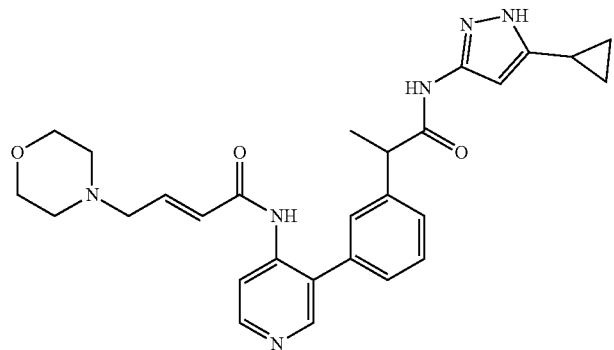 [SMILES: CC(C(=O)Nc1cc(C2CC2)[nH]n1)c1cccc(-c2cnccc2NC(=O)/C=C/CN2CCOCC2)c1] |

TABLE 4-continued
| Compound. No. | Structure |
|---|---|
| 125. | 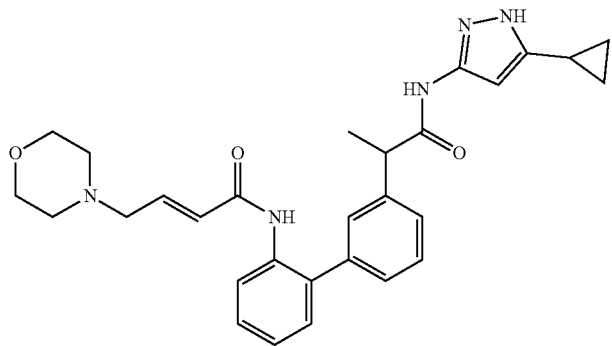 [SMILES: CC(C(=O)Nc1cc(C2CC2)[nH]n1)c1cccc(-c2ccccc2NC(=O)/C=C/CN2CCOCC2)c1] |
| 126. | 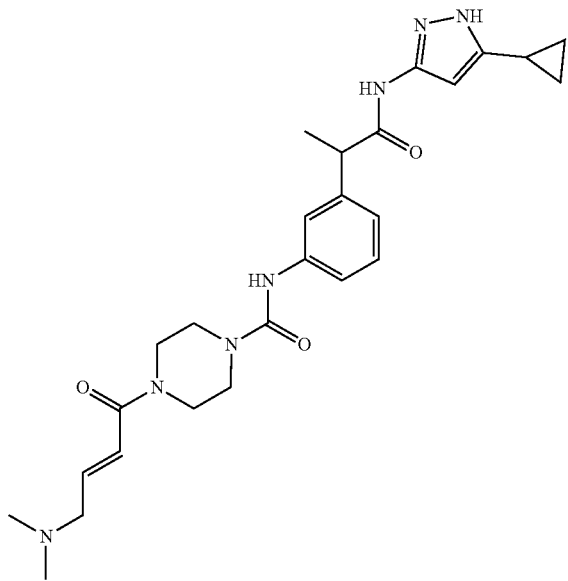 [SMILES: CC(C(=O)Nc1cc(C2CC2)[nH]n1)c1cccc(NC(=O)N2CCN(C(=O)/C=C/CN(C)C)CC2)c1] |
| 127. | 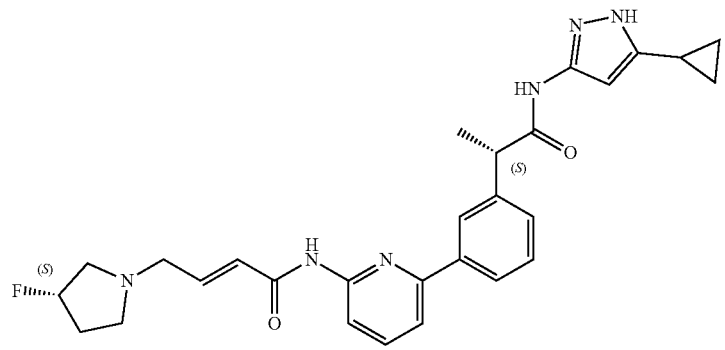 |

TABLE 4-continued

| Compound. No. | Structure |
|---|---|
| 128. | 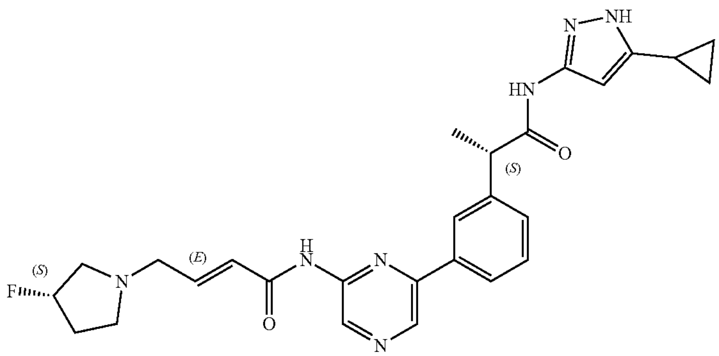 |
| 129. | 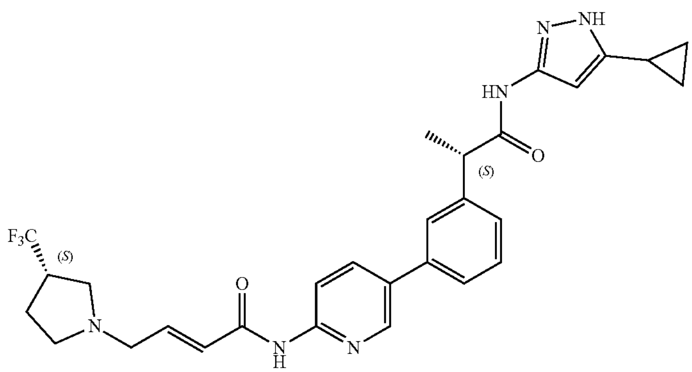 |
| 130. | 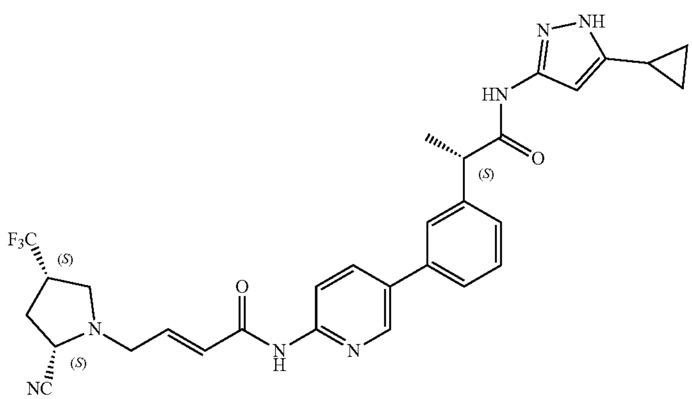 |
| 131. | 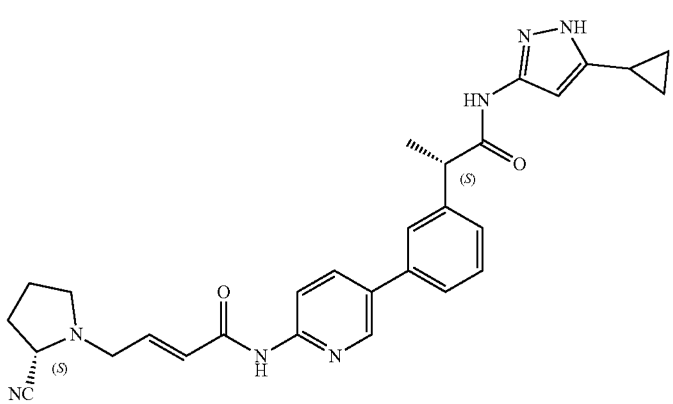 |

TABLE 4-continued

| Compound. No. | Structure |
|---|---|
| 132. | (structure: N-(5-cyclopropyl-1H-pyrazol-3-yl) (S)-2-aryl propanamide, aryl = biphenyl with 3-fluoro-4-[(E)-4-(diethylamino)but-2-enamido] substituent) |
| 133. | (structure: 3-[(5-cyclopropyl-1H-pyrazol-3-yl)amino]-4-methylisoquinoline substituted at 6-position with 4-[(E)-4-(dimethylamino)but-2-enamido]phenyl) |
| 134. | (structure: N-(5-cyclopropyl-1H-pyrazol-3-yl)-2-[2-(4-{(E)-4-(dimethylamino)but-2-enamido}phenyl)pyridin-4-yl]propanamide) |
| 135. | (structure: N-(5-cyclopropyl-1H-pyrazol-3-yl)-2-{3-[4-((E)-4-(dimethylamino)but-2-enamido)cyclohexyl]phenyl}propanamide) |

TABLE 4-continued
| Compound. No. | Structure |
|---|---|
| 136. | 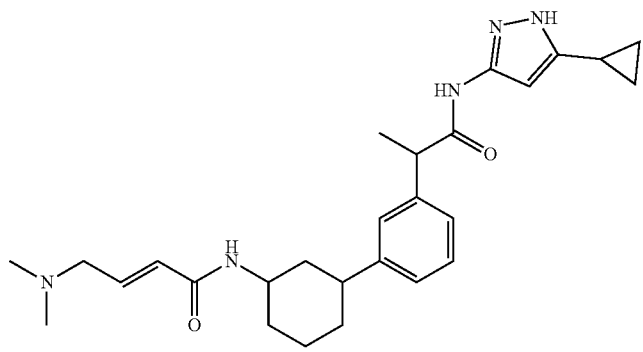 [SMILES: CC(C(=O)Nc1cc(C2CC2)[nH]n1)c1cccc(C2CCCC(NC(=O)/C=C/CN(C)C)C2)c1] |
| 137. | 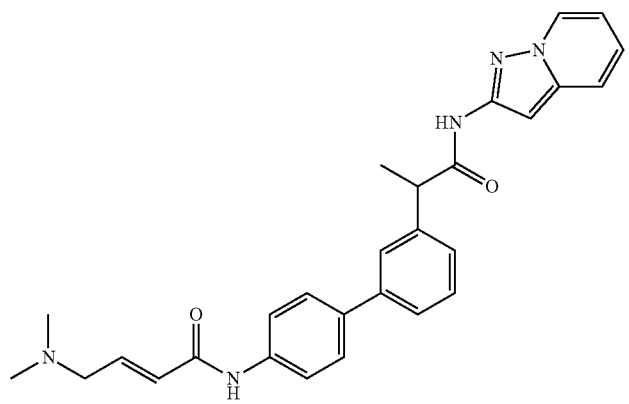 [SMILES: CC(C(=O)Nc1cc2ccccn2n1)c1cccc(-c2ccc(NC(=O)/C=C/CN(C)C)cc2)c1] |
| 138. | 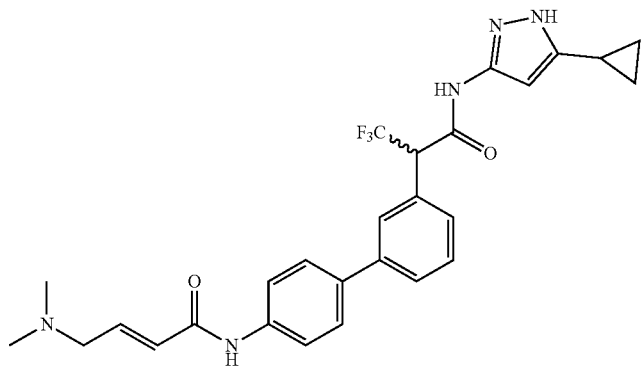 [SMILES: CN(C)C/C=C/C(=O)Nc1ccc(-c2cccc(C(C(=O)Nc3cc(C4CC4)[nH]n3)C(F)(F)F)c2)cc1] |
| 139. | 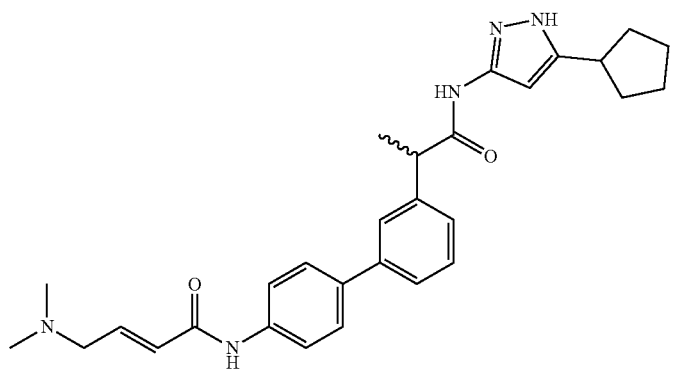 [SMILES: CC(C(=O)Nc1cc(C2CCCC2)[nH]n1)c1cccc(-c2ccc(NC(=O)/C=C/CN(C)C)cc2)c1] |

TABLE 4-continued
| Compound. No. | Structure |
|---|---|
| 140. | 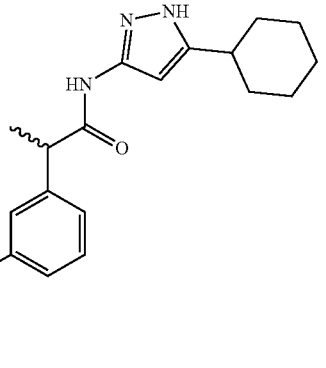 |
| 141. | 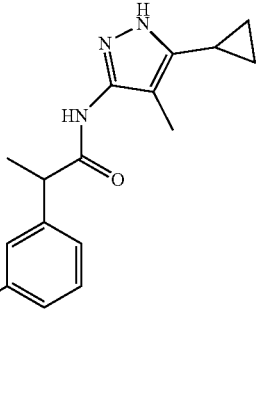 |
| 142. | 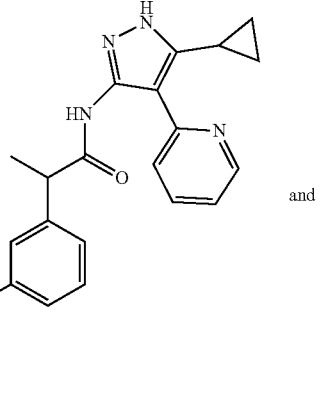 and |
| 143. | 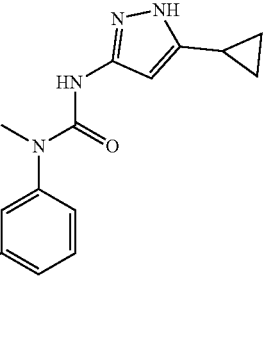 |

Biochemical Assay for CDK7:

The ability of compounds to inhibit CDK7 kinase activity was tested in a TR-FRET assay using 5 nM of CDK7/CycH/MNAT1 obtained from Invitrogen, USA. Test compounds were pre-incubated with the kinase at room temperature for 60 min. After the incubation, substrate mix [100 nM Ultralight MBP (Perkin Elmer, USA) and 1 mM ATP (Sigma)] was added. The above reaction was stopped by the addition of 40 mM EDTA after 60 minutes of kinase reaction. 1 nM Eu-labelled antiphospho-MBP antibody [Perkin Elmer, USA] was added, mixed well and the fluorescence emission at 615 nm and 665 nm [excitation at 340 nm] was measured. The final DMSO concentration in the assay was 1%. For $IC_{50}$ determination, appropriate concentrations were made by $\frac{1}{3}^{rd}$ serial dilutions of 10 mM DMSO stock solution of test compound. All the fluorescence measurements were made in a Victor 3 Multilabel Counter [Perkin Elmer, USA]. The $IC_{50}$ was determined by fitting the dose response data to sigmoidal curve fitting equation using GraphPad Prism software V5. To identify compounds that inhibit CDK7 irreversibly, time depended inhibition studies were carried by pre-incubating compound with the enzyme at three time points (20, 60 and 180 min) and carrying out assay as described above.

The compounds were screened by the above mentioned assay procedure. The % inhibitionat 10 μM concentration and the $IC_{50}$ values of the compounds are summarized in the table-5 below wherein "+++" refers to an $IC_{50}$ value less than 0.025 μM, "++" refers to $IC_{50}$ value in range of 0.025 μM to 0.1 μM and "+" refers to an $IC_{50}$ value greater than 0.1 μM.

TABLE 5

% inhibition and $IC_{50}$ values

| Compound No. | % inhibition @ 10 μM | $IC_{50}$ (μM) |
|---|---|---|
| 1 | 92% | ++ |
| 2 | 69% | + |
| 3 | 99% | ++ |
| 4 | 95% | + |
| 5 | 80% | + |
| 6 | 0% | − |
| 7 | 84% | + |
| 8 | 92% | + |
| 9 | 60% | + |
| 10 | 99% | +++ |
| 11 | 75% | + |
| 12 | 98% | +++ |
| 13 | 97% | ++ |
| 14 | 95% | + |
| 15 | 93% | +++ |
| 16 | 95% | ++ |
| 17 | 80% | + |
| 18 | 95% | + |
| 19 | 97% | ++ |
| 20 | 100% | +++ |
| 21 | 89% | + |
| 22 | 97% | +++ |
| 23 | 98% | ++ |
| 24 | 96% | ++ |
| 25 | 97% | ++ |
| 26 | 96% | +++ |
| 27 | 98% | +++ |
| 28 | 96% | ++ |
| 29 | 97% | +++ |
| 30 | 28% | + |
| 31 | 100% | +++ |
| 32 | 100% | +++ |
| 33 | 97% | ++ |
| 34 | 88% | + |
| 35 | 86% | + |
| 36 | 98% | +++ |
| 37 | 67% | + |
| 38 | 94% | + |
| 39 | 84% | + |
| 40 | 100% | +++ |
| 41 | 90% | + |
| 42 | 98% | +++ |
| 43 | 99% | +++ |
| 44 | 99% | +++ |
| 45 | 89% | +++ |
| 46 | 95% | +++ |
| 47 | 91% | +++ |
| 48 | 90% | ++ |
| 49 | 89% | +++ |
| 50 | 94% | +++ |
| 51 | 90% | + |
| 52 | 91% | +++ |
| 53 | 100% | +++ |
| 54 | 78% | +++ |
| 55 | 95% | +++ |
| 56 | 96% | +++ |
| 57 | 98% | +++ |
| 58 | 90% | + |
| 59 | 99% | ++ |
| 60 | 99% | ++ |
| 61 | 92% | + |
| 62 | 81% | + |
| 63 | 98% | ++ |
| 64 | 94% | ++ |
| 65 | 94% | + |
| 66 | 88% | + |
| 67 | 79% | + |
| 68 | 95% | +++ |
| 69 | 87% | ++ |
| 70 | 81% | ++ |
| 71 | 81% | + |
| 72 | 98% | +++ |
| 73 | 91% | + |
| 74 | 79% | + |
| 75 | 78% | + |
| 76 | 98% | +++ |
| 77 | 98% | ++ |
| 78 | 100% | ++ |
| 79 | 102% | +++ |
| 80 | 95% | ++ |
| 81 | 100% | ++ |
| 82 | 99% | ++ |
| 83 | 62% | + |
| 84 | 88% | + |
| 85 | 74% | + |
| 86 | 48% | − |
| 87 | 89% | + |
| 88 | 62% | + |
| 89 | 45% | − |
| 90 | 83% | + |
| 91 | 84% | + |
| 92 | 86% | ++ |
| 93 | 100% | +++ |
| 94 | 85% | + |
| 95 | 71% | + |

We claim:

1. A compound of formula (IB):

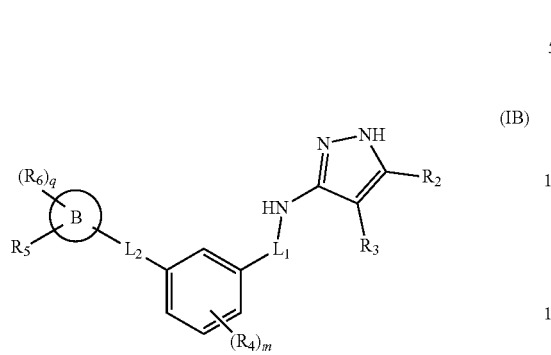

(IB)

or a pharmaceutically acceptable salt or a stereoisomer thereof;

wherein, ring B is phenyl, piperidinyl, pyridinyl, 1,2,3,6-tetrahydropyridinyl, piperazinyl, pyrazinyl, pyrazolyl, morpholinyl, indolinyl or pyrrolidinyl;

$R_2$ is $(C_1-C_6)$alkyl or $(C_3-C_{10})$cycloalkyl;

$R_3$ is hydrogen or $(C_1-C_6)$alkyl;

$R_4$ at each occurrence is halo;

$R_5$ is

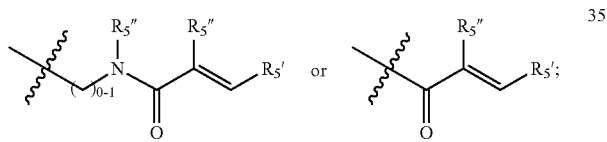

wherein $R_5'$ is hydrogen, halo, methoxymethyl or —CH$_2$—NR$_a$R$_b$; $R_5''$ is H;

$R_a$ and $R_b$ are each independently $(C_1-C_6)$alkyl, $(C_1-C_6)$alkoxy or methoxyethyl; alternatively, $R_a$ and $R_b$ together with the nitrogen atom to which they are attached form an optionally substituted 5 to 6 membered ring containing 0-2 additional heteroatoms that are independently N, O or S; wherein the optional substituent is one or more halo, cyano, cyano($C_1$-$C_6$)alkyl, methoxymethyl or —COO-($C_1$-$C_6$)alkyl or a combination thereof;

$R_6$ at each occurrence is halo, $(C_1$-$C_6)$alkyl or $(C_1$-$C_6)$ alkoxy;

$L_1$ is *—CR$_c$R$_d$—C(O)— or absent; wherein * is point of attachment with phenyl ring;

$R_c$ and $R_d$ independently are hydrogen or $(C_1$-$C_6)$alkyl; alternatively, $R_c$ and $R_d$ together with the carbon atom to which they are attached form a $(C_3$-$C_{10})$cycloalkyl ring;

L2 is —C(O)NH— or absent;

m is 0 or 1; and q is 0 to 2.

2. The compound of claim 1, having formula (ID):

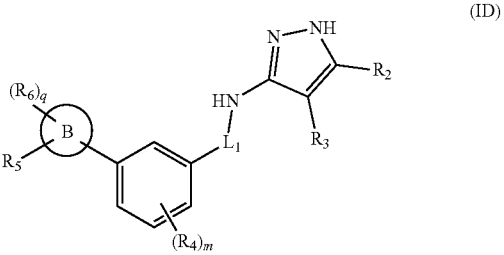

(ID)

or a pharmaceutically acceptable salt thereof or a stereoisomer thereof.

3. The compound of claim 1, having formula (IE):

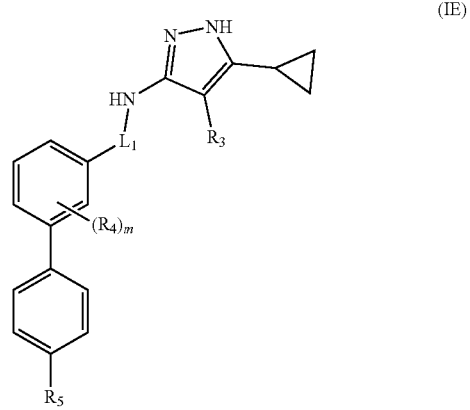

(IE)

or a pharmaceutically acceptable salt thereof or a stereoisomer thereof;

wherein, $L_1$ is *—CR$_c$R$_d$—C(O)—; wherein * is point of attachment with the phenyl ring.

4. The compound of claim 1, having a compound of formula (IF):

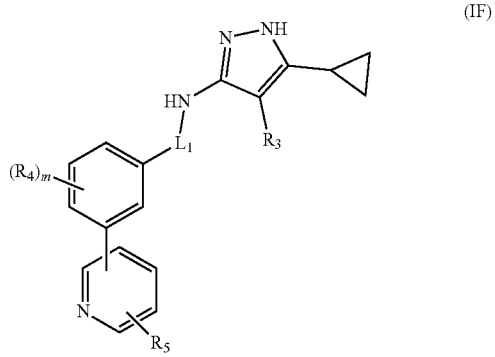

(IF)

or a pharmaceutically acceptable salt thereof or a stereoisomer thereof;

wherein,

R₃ is hydrogen;

R5 is

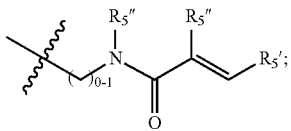

wherein R₅' is hydrogen, methoxymethyl or —(CH₂)—NR_aR_b; R₅" is H;

R_a and R_b are each independently (C₁-C₆)alkyl, (C₁-C₆) alkoxy or methoxyethyl;

alternatively, R_a and R_b together with the nitrogen atom to which they are attached form an optionally substituted 5 to 6 membered heterocyclic ring containing 0-2 additional heteroatoms that are independently N, O or S; wherein the optional substituent is one or more halo, cyano, cyano(C₁-C₆)alkyl, methoxymethyl or —COO-(C₁-C₆)alkyl or a combination thereof;

L₁ is *—CR_cR_d—C(O)—; wherein * is point of attachment with phenyl ring;

R_c and R_d independently are hydrogen or (C₁-C₆)alkyl; alternatively, R_c and R_d together with the carbon atom to which they are attached form a (C₃-C₁₀)cycloalkyl ring; and m is 0 and R4 is absent.

5. The compound according to claim 1, wherein ring B is phenyl or pyridinyl.

6. The compound according to claim 1, wherein R₂ is cyclopropyl.

7. The compound according to claim 1, wherein R₅ is

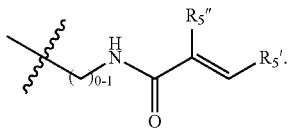

8. The compound according to claim 7, wherein R₅' is (CH₂)₂—NR_aR_b; wherein R_a and R_b are each independently (C₁-C₆)alkyl; alternatively, R_a and R_b together with the nitrogen atom to which they are attached form an optionally substituted 5 to 6 membered heterocyclic ring containing 0-2 additional heteroatoms that are independently O, S or N; wherein the optional substituent independently is one or more halo.

9. The compound according to claim 8, wherein R_a and R_b together with the nitrogen atom to which they are attached form a 5 to 6 membered heterocyclic ring containing 0-2 additional heteroatoms that are independently O, S or N.

10. The compound according to claim 1, wherein L₁ is *—CR_cR_d—C(O)—; wherein * is the point of attachment with the phenyl ring.

11. The compound according to claim 1, wherein L₂ is absent.

12. The compound of claim 1 selected from the group consisting of:

| Compound No. | IUPAC name |
|---|---|
| 1 | (E)-N-(3'-(1-((5-cyclopropyl-1H-pyrazol-3-yl)amino)-1-oxopropan-2-yl)-[1,1'-biphenyl]-4-yl)-4-(dimethylamino)but-2-enamide; |
| 2 | (E)-N-(3'-(1-((5-cyclopropyl-1H-pyrazol-3-yl)amino)-1-oxopropan-2-yl)-[1,1'-biphenyl]-4-yl)-4-(dimethylamino)but-2-enamide (Isomer-1 of compound-1); |
| 3 | (E)-N-(3'-(1-((5-cyclopropyl-1H-pyrazol-3-yl)amino)-1-oxopropan-2-yl)-[1,1'-biphenyl]-4-yl)-4-(dimethylamino)but-2-enamide (Isomer-2 of compound-1); |
| 4 | (E)-N-(5'-(1-((5-cyclopropyl-1H-pyrazol-3-yl)amino)-1-oxopropan-2-yl)-2'-fluoro-[1,1'-biphenyl]-4-yl)-4-(dimethylamino)but-2-enamide; |
| 5 | (E)-N-(3'-(1-((5-cyclopropyl-1H-pyrazol-3-yl)amino)-1-oxopropan-2-yl)-4'-fluoro-[1,1'-biphenyl]-4-yl)-4-(dimethylamino)but-2-enamide; |
| 7 | (E)-N-(3'-(2-((5-cyclopropyl-1H-pyrazol-3-yl)amino)-2-oxoethyl)-[1,1'-biphenyl]-4-yl)-4-(dimethylamino)but-2-enamide; |
| 8 | (E)-4-(dimethylamino)-N-(3'-(1-((5-ethyl-1H-pyrazol-3-yl)amino)-1-oxopropan-2-yl)-[1,1'-biphenyl]-4-yl)but-2-enamide; |
| 9 | (E)-N-(3'-(1-((5-(tert-butyl)-1H-pyrazol-3-yl)amino)-1-oxopropan-2-yl)-[1,1'-biphenyl]-4-yl)-4-(dimethylamino)but-2-enamide; |
| 13 | (E)-N-(3'-(1-((5-cyclopropyl-1H-pyrazol-3-yl)amino)-1-oxobutan-2-yl)-[1,1'-biphenyl]-4-yl)-4-(dimethylamino)but-2-enamide; |
| 14 | (E)-N-(3'-(1-((5-cyclopropyl-1H-pyrazol-3-yl)amino)-1-oxopropan-2-yl)-3-fluoro-[1,1'-biphenyl]-4-yl)-4-(dimethylamino)but-2-enamide; |
| 15 | (E)-N-(3'-(1-((5-cyclobutyl-1H-pyrazol-3-yl)amino)-1-oxopropan-2-yl)-[1,1'-biphenyl]-4-yl)-4-(dimethylamino)but-2-enamide; |
| 16 | (E)-N-(6-(3-(1-((5-cyclopropyl-1H-pyrazol-3-yl)amino)-1-oxopropan-2-yl)phenyl)pyridin-3-yl)-4-(dimethylamino)but-2-enamide; |
| 17 | (E)-N-(3'-(1-((5-cyclopropyl-1H-pyrazol-3-yl)amino)-1-oxopropan-2-yl)-2-fluoro-[1,1'-biphenyl]-4-yl)-4-(dimethylamino)but-2-enamide; |
| 18 | N-(3'-(1-((5-cyclopropyl-1H-pyrazol-3-yl)amino)-1-oxopropan-2-yl)-[1,1'-biphenyl]-4-yl)acrylamide; |
| 19 | N-(3'-(1-((5-cyclopropyl-1H-pyrazol-3-yl)amino)-1-oxopropan-2-yl)-3-fluoro-[1,1'-biphenyl]-4-yl)acrylamide; |
| 20 | N-(5-(3-(1-((5-cyclopropyl-1H-pyrazol-3-yl)amino)-1-oxopropan-2-yl)phenyl)pyridin-2-yl)acrylamide; |
| 21 | N-(5-(3-(1-((5-cyclopropyl-1H-pyrazol-3-yl)amino)-1-oxopropan-2-yl)phenyl)pyridin-2-yl)acrylamide (Isomer-1 of compound-20); |
| 22 | N-(5-(3-(1-((5-cyclopropyl-1H-pyrazol-3-yl)amino)-1-oxopropan-2-yl)phenyl)pyridin-2-yl)acrylamide (Isomer-2 of compound-20); |
| 23 | N-(5'-(1-((5-cyclopropyl-1H-pyrazol-3-yl)amino)-1-oxopropan-2-yl)-2',3-difluoro-[1,1'-biphenyl]-4-yl)acrylamide; |
| 24 | N-(6-(3-(1-((5-cyclopropyl-1H-pyrazol-3-yl)amino)-1-oxopropan-2-yl)phenyl)pyridin-3-yl)acrylamide; |
| 25 | 2-(4'-acrylamido-3'-fluoro-[1,1'-biphenyl]-3-yl)-N-(5-cyclopropyl-1H-pyrazol-3-yl)-3-methylbutanamide; |
| 26 | 2-(3-(5-acrylamidopyridin-2-yl)phenyl)-N-(5-cyclopropyl-1H-pyrazol-3-yl)butanamide; |
| 27 | 2-(4'-acrylamido-3'-fluoro-[1,1'-biphenyl]-3-yl)-N-(5-cyclopropyl-1H-pyrazol-3-yl)butanamide; |

| Compound No. | IUPAC name |
|---|---|
| 28 | (E)-N-(3'-(1-((5-cyclopentyl-1H-pyrazol-3-yl)amino)-1-oxopropan-2-yl)-3-fluoro-[1,1'-biphenyl]-4-yl)-4-(dimethylamino)but-2-enamide; |
| 29 | (E)-N-(5-cyclopropyl-1H-pyrazol-3-yl)-2-(3-(1-(4-(dimethylamino)but-2-enoyl)indolin-5-yl)phenyl)propanamide; |
| 30 | N-(3'-(1-((5-cyclopropyl-4-methyl-1H-pyrazol-3-yl)amino)-1-oxopropan-2-yl)-[1,1'-biphenyl]-4-yl)acrylamide; |
| 31 | (E)-N-(3'-(1-((5-cyclopropyl-1H-pyrazol-3-yl)amino)-1-oxobutan-2-yl)-3-fluoro-[1,1'-biphenyl]-4-yl)-4-(dimethylamino)but-2-enamide; |
| 32 | (E)-N-(3'-(1-((5-cyclopropyl-1H-pyrazol-3-yl)amino)-1-oxopropan-2-yl)-3-fluoro-[1,1'-biphenyl]-4-yl)-4-(diethylamino)but-2-enamide; |
| 33 | (E)-N-(3'-(1-((5-cyclopropyl-1H-pyrazol-3-yl)amino)-1-oxopropan-2-yl)-3-fluoro-[1,1'-biphenyl]-4-yl)-4-(pyrrolidin-1-yl)but-2-enamide; |
| 34 | (E)-N-(3'-(1-((5-cyclopropyl-1H-pyrazol-3-yl)amino)-1-oxopropan-2-yl)-3-fluoro-[1,1'-biphenyl]-4-yl)-4-morpholinobut-2-enamide; |
| 35 | (E)-N-(6-(3-(1-((5-cyclopropyl-1H-pyrazol-3-yl)amino)-1-oxopropan-2-yl)phenyl)pyridin-3-yl)-4-morpholinobut-2-enamide; |
| 36 | (E)-N-(6-(3-(1-((5-cyclopropyl-1H-pyrazol-3-yl)amino)-3-methyl-1-oxobutan-2-yl)phenyl)pyridin-3-yl)-4-(dimethylamino)but-2-enamide; |
| 37 | (E)-4-((6-(3-(1-((5-cyclopropyl-1H-pyrazol-3-yl)amino)-1-oxopropan-2-yl)phenyl)pyridin-3-yl)amino)-N,N-dimethylbut-2-enamide; |
| 38 | (E)-N-(6-(3-(1-((5-cyclopropyl-1H-pyrazol-3-yl)amino)-1-oxopropan-2-yl)phenyl)-2-fluoropyridin-3-yl)-4-(dimethylamino)but-2-enamide; |
| 39 | (E)-N-(6-(3-(1-((5-cyclopropyl-1H-pyrazol-3-yl)amino)-1-oxopropan-2-yl)phenyl)pyridin-3-yl)-4-(piperidin-1-yl)but-2-enamide; |
| 40 | (E)-N-(5-(3-(1-((5-cyclopropyl-1H-pyrazol-3-yl)amino)-1-oxopropan-2-yl)phenyl)pyridin-2-yl)-4-(piperidin-1-yl)but-2-enamide; |
| 41 | (E)-N-(5-(3-(1-((5-cyclopropyl-1H-pyrazol-3-yl)amino)-1-oxopropan-2-yl)phenyl)pyridin-2-yl)-4-methoxybut-2-enamide; |
| 42 | (E)-N-(5-(3-(1-((5-cyclopropyl-1H-pyrazol-3-yl)amino)-1-oxopropan-2-yl)phenyl)pyridin-2-yl)-4-(dimethylamino)but-2-enamide; |
| 43 | (E)-N-(3'-(1-((5-cyclopropyl-1H-pyrazol-3-yl)amino)-3-methyl-1-oxobutan-2-yl)-3-fluoro-[1,1'-biphenyl]-4-yl)-4-(dimethylamino)but-2-enamide; |
| 45 | (E)-N-(5-(3-(1-((5-cyclopropyl-1H-pyrazol-3-yl)amino)-1-oxopropan-2-yl)phenyl)pyridin-2-yl)-4-(3-fluoropyrrolidin-1-yl)but-2-enamide; |
| 46 | (E)-N-(5-(3-(1-((5-cyclopropyl-1H-pyrazol-3-yl)amino)-1-oxopropan-2-yl)phenyl)pyridin-2-yl)-4-((S)-3-fluoropyrrolidin-1-yl)but-2-enamide; |
| 47 | (E)-N-(5-(3-(1-((5-cyclopropyl-1H-pyrazol-3-yl)amino)-1-oxopropan-2-yl)phenyl)pyridin-2-yl)-4-((S)-3-fluoropyrrolidin-1-yl)but-2-enamide (Isomer-1 of compound-46); |
| 48 | E)-N-(5-(3-(1-((5-cyclopropyl-1H-pyrazol-3-yl)amino)-1-oxopropan-2-yl)phenyl)pyridin-2-yl)-4-((S)-3-fluoropyrrolidin-1-yl)but-2-enamide (Isomer-2 of compound-46); |
| 49 | (E)-N-(5-(3-(1-((5-cyclopropyl-1H-pyrazol-3-yl)amino)-1-oxopropan-2-yl)phenyl)pyridin-2-yl)-4-((R)-3-fluoropyrrolidin-1-yl)but-2-enamide |
| 50 | (E)-N-(5-(3-(1-((5-cyclopropyl-1H-pyrazol-3-yl)amino)-1-oxopropan-2-yl)phenyl)pyridin-2-yl)-4-((R)-3-fluoropyrrolidin-1-yl)but-2-enamide (Isomer-1 of compound-49); |
| 51 | (E)-N-(5-(3-(1-((5-cyclopropyl-1H-pyrazol-3-yl)amino)-1-oxopropan-2-yl)phenyl)pyridin-2-yl)-4-((R)-3-fluoropyrrolidin-1-yl)but-2-enamide (Isomer-2 of compound-49); |
| 55 | (E)-N-(5-(3-(1-((5-cyclopropyl-1H-pyrazol-3-yl)amino)-1-oxopropan-2-yl)phenyl)pyridin-2-yl)-4-(diethylamino)but-2-enamide; |
| 56 | (E)-N-(5-(3-(1-((5-cyclopropyl-1H-pyrazol-3-yl)amino)-3-methyl-1-oxobutan-2-yl)phenyl)pyridin-2-yl)-4-(dimethylamino)but-2-enamide; |
| 57 | (E)-N-(5-(3-(1-((5-cyclopropyl-1H-pyrazol-3-yl)amino)-1-oxopropan-2-yl)phenyl)pyridin-2-yl)-4-(3-fluoropiperidin-1-yl)but-2-enamide; |
| 58 | (E)-N-(6-(3-(1-((5-cyclopropyl-1H-pyrazol-3-yl)amino)-1-oxopropan-2-yl)phenyl)-2-fluoropyridin-3-yl)-4-morpholinobut-2-enamide; |
| 59 | (E)-N-(5-(3-(1-((5-cyclopropyl-1H-pyrazol-3-yl)amino)-1-oxopropan-2-yl)phenyl)-6-fluoropyridin-2-yl)-4-morpholinobut-2-enamide; |
| 60 | (E)-N-(5-(3-(1-((5-cyclopropyl-1H-pyrazol-3-yl)amino)-1-oxopropan-2-yl)phenyl)pyridin-2-yl)-4-morpholinobut-2-enamide; |
| 61 | (E)-N-(3'-(1-((5-cyclopropyl-1H-pyrazol-3-yl)amino)-1-oxopropan-2-yl)-[1,1'-biphenyl]-3-yl)-4-morpholinobut-2-enamide; |
| 62 | (E)-N-(5-(3-(1-((5-cyclopropyl-1H-pyrazol-3-yl)amino)-1-oxopropan-2-yl)phenyl)pyridin-2-yl)-4-(methoxy(methyl)amino)but-2-enamide; |
| 63 | (E)-N-(5-(3-(1-((5-cyclopropyl-1H-pyrazol-3-yl)amino)-1-oxopropan-2-yl)phenyl)-3-fluoropyridin-2-yl)-4-morpholinobut-2-enamide; |
| 64 | (E)-N-(6-(3-(1-((5-cyclopropyl-1H-pyrazol-3-yl)amino)-1-oxopropan-2-yl)phenyl)-2-fluoropyridin-3-yl)-4-(3-fluoropyrrolidin-1-yl)but-2-enamide; |
| 65 | N-(3'-(1-((5-cyclopropyl-1H-pyrazol-3-yl)amino)-1-oxopropan-2-yl)-3-methoxy-[1,1'-biphenyl]-4-yl)acrylamide; |
| 66 | N-(3'-(1-((5-cyclopropyl-1H-pyrazol-3-yl)amino)-1-oxopropan-2-yl)-3-methyl-[1,1'-biphenyl]-4-yl)acrylamide; |
| 67 | N-(3'-(1-((5-cyclopropyl-1H-pyrazol-3-yl)amino)-1-oxopropan-2-yl)-3,5-dimethyl-[1,1'-biphenyl]-4-yl)acrylamide; |
| 68 | (E)-N-(5-(3-(1-((5-cyclopropyl-1H-pyrazol-3-yl)amino)-1-oxopropan-2-yl)phenyl)pyridin-2-yl)-4-((2-methoxyethyl)(methyl)amino)but-2-enamide; |
| 69 | (E)-N-(5-(3-(1-((5-cyclopropyl-1H-pyrazol-3-yl)amino)-1-oxopropan-2-yl)phenyl)pyridin-2-yl)-4-(1H-imidazol-1-yl)but-2-enamide; |
| 70 | (E)-N-(5-(3-(1-((5-cyclopropyl-1H-pyrazol-3-yl)amino)-1-oxopropan-2-yl)phenyl)pyridin-2-yl)-4-((S)-2-(methoxymethyl)pyrrolidin-1-yl)but-2-enamide; |
| 71 | (E)-N-(5-(3-(1-((5-cyclopropyl-1H-pyrazol-3-yl)amino)-1-oxopropan-2-yl)phenyl)pyridin-2-yl)-4-((S)-2-(methoxymethyl)pyrrolidin-1-yl)but-2-enamide (Isomer-1 of compound-70); |

| Compound No. | IUPAC name |
|---|---|
| 72 | (E)-N-(5-(3-(1-((5-cyclopropyl-1H-pyrazol-3-yl)amino)-1-oxopropan-2-yl)phenyl)pyridin-2-yl)-4-((S)-2-(methoxymethyl)pyrrolidin-1-yl)but-2-enamide (Isomer-2 of compound-70); |
| 73 | N-(3'-(1-((5-cyclopropyl-1H-pyrazol-3-yl)amino)-1-oxopropan-2-yl)-2-methoxy-[1,1'-biphenyl]-4-yl)acrylamide; |
| 74 | N-((5-(3-(1-((5-cyclopropyl-1H-pyrazol-3-yl)amino)-1-oxopropan-2-yl)phenyl)pyridin-2-yl)methyl)acrylamide; |
| 75 | N-(3'-(1-((5-cyclopropyl-1H-pyrazol-3-yl)amino)-1-oxopropan-2-yl)-2-methyl-[1,1'-biphenyl]-4-yl)acrylamide; |
| 76 | 2-(3-(1-acryloylindolin-5-yl)phenyl)-N-(5-cyclopropyl-1H-pyrazol-3-yl)propanamide; |
| 77 | (E)-N-(5-(3-(1-((5-cyclopropyl-1H-pyrazol-3-yl)amino)-1-oxopropan-2-yl)phenyl)pyridin-2-yl)-4-((2S,4S)-4-fluoro-2-(methoxymethyl)pyrrolidin-1-yl)but-2-enamide; |
| 78 | (E)-4-(3-cyanopyrrolidin-1-yl)-N-(5-(3-(1-((5-cyclopropyl-1H-pyrazol-3-yl)amino)-1-oxopropan-2-yl)phenyl)pyridin-2-yl)but-2-enamide; |
| 79 | N-(6-(3-(1-((5-cyclopropyl-1H-pyrazol-3-yl)amino)-1-oxopropan-2-yl)phenyl)pyrazin-2-yl)acrylamide; |
| 80 | (E)-N-(3'-(1-((5-cyclopropyl-1H-pyrazol-3-yl)amino)-1-oxopropan-2-yl)-3-fluoro-[1,1'-biphenyl]-4-yl)-4-((S)-3-fluoropyrrolidin-1-yl)but-2-enamide; |
| 81 | methyl ((E)-4-((5-(3-(1-((5-cyclopropyl-1H-pyrazol-3-yl)amino)-1-oxopropan-2-yl)phenyl)pyridin-2-yl)amino)-4-oxobut-2-en-1-yl)-L-prolinate; |
| 82 | (E)-4-((S)-2-(cyanomethyl)pyrrolidin-1-yl)-N-(5-(3-(1-((5-cyclopropyl-1H-pyrazol-3-yl)amino)-1-oxopropan-2-yl)phenyl)pyridin-2-yl)but-2-enamide; |
| 83 | 4-acrylamido-N-(3-((5-ethyl-1H-pyrazol-3-yl)amino)phenyl)benzamide; |
| 84 | (E)-N-(5-cyclopropyl-1H-pyrazol-3-yl)-2-(3-(1-(4-(dimethylamino)but-2-enoyl)-1,2,3,6-tetrahydropyridin-4-yl)phenyl)propanamide; |
| 85 | (E)-N-(5-cyclopropyl-1H-pyrazol-3-yl)-2-(3-(1-(4-(dimethylamino)but-2-enoyl)piperidin-4-yl)phenyl)propanamide; |
| 86 | N-(3'-(2-((5-methyl-1H-pyrazol-3-yl)amino)-2-oxoethyl)-[1,1'-biphenyl]-4-yl)acrylamide; |
| 87 | N-(3'-(1-((5-ethyl-1H-pyrazol-3-yl)amino)-1-oxopropan-2-yl)-[1,1'-biphenyl]-4-yl)acrylamide; |
| 88 | N-(3'-(1-((5-(tert-butyl)-1H-pyrazol-3-yl)amino)-1-oxopropan-2-yl)-[1,1'-biphenyl]-4-yl)acrylamide; |
| 89 | (E)-N-(3-((1H-indazol-3-yl)amino)phenyl)-4-(4-(dimethylamino)but-2-enamido)benzamide; |
| 90 | N-(3'-(1-((1H-indazol-3-yl)amino)-1-oxopropan-2-yl)-[1,1'-biphenyl]-4-yl)acrylamide; |
| 91 | (E)-N-(3'-(1-((1H-indazol-3-yl)amino)-1-oxopropan-2-yl)-[1,1'-biphenyl]-4-yl)-4-(dimethylamino)but-2-enamide; |
| 92 | (E)-N-(6-(3-(1-((5-cyclopropyl-1H-pyrazol-3-yl)amino)-1-oxopropan-2-yl)phenyl)pyrazin-2-yl)-4-(pyrrolidin-1-yl)but-2-enamide; |
| 93 | (S,E)-N-(5-(3-(1-((5-cyclopropyl-1H-pyrazol-3-yl)amino)-1-oxopropan-2-yl)phenyl)pyridin-2-yl)-4-morpholinobut-2-enamide; |
| 94 | (E)-N-(5-cyclopropyl-1H-pyrazol-3-yl)-1-(3-(6-(4-(pyrrolidin-1-yl)but-2-enamido)pyridin-3-yl)phenyl)cyclopropane-1-carboxamide; and |
| 95 | (E)-N-(5-(3-(1-((5-cyclopropyl-1H-pyrazol-3-yl)amino)-2-methyl-1-oxopropan-2-yl)phenyl)pyridin-2-yl)-4-(pyrrolidin-1-yl)but-2-enamide; | or a pharmaceutically acceptable salt or a stereoisomer thereof.

13. A pharmaceutical composition comprising the compound of claim 1, or a pharmaceutically acceptable salt or a stereoisomer thereof and at least one pharmaceutically acceptable carrier or excipient.

14. A pharmaceutical composition comprising the compound of claim 12, or pharmaceutically acceptable salt or a stereoisomer thereof, and at least one pharmaceutically acceptable carrier or excipient.

\* \* \* \* \*